(12) United States Patent
Miller et al.

(10) Patent No.: US 12,150,633 B2
(45) Date of Patent: *Nov. 26, 2024

(54) METHODS AND APPARATUS FOR FASTENING AND CLAMPING TISSUE

(71) Applicant: Amsel Medical Corporation, Cambridge, MA (US)

(72) Inventors: Arnold Miller, Cambridge, MA (US); Raanan Miller, Cambridge, MA (US); Nir Lilach, Kfar Yehoshua (IL); William Edelman, Sharon, MA (US)

(73) Assignee: AMSEL MEDICAL CORPORATION, Cambridge, MA (US)

( * ) Notice: Subject to any disclaimer, the term of this patent is extended or adjusted under 35 U.S.C. 154(b) by 346 days.

This patent is subject to a terminal disclaimer.

(21) Appl. No.: 16/835,011

(22) Filed: Mar. 30, 2020

(65) Prior Publication Data

US 2020/0289100 A1 Sep. 17, 2020

Related U.S. Application Data

(63) Continuation of application No. 15/906,763, filed on Feb. 27, 2018, now Pat. No. 10,820,895, which is a
(Continued)

(51) Int. Cl.
*A61B 17/122* (2006.01)
*A61B 17/00* (2006.01)
(Continued)

(52) U.S. Cl.
CPC ...... *A61B 17/0057* (2013.01); *A61B 17/0643* (2013.01); *A61B 17/068* (2013.01);
(Continued)

(58) Field of Classification Search
CPC .............. A61B 17/0057; A61B 17/064; A61B 17/0643; A61B 17/083; A61B 17/12;
(Continued)

(56) References Cited

U.S. PATENT DOCUMENTS 3,971,284 A 7/1976 Hasson
4,007,743 A 2/1977 Blake
(Continued)

FOREIGN PATENT DOCUMENTS

EP 1745750 1/2007
EP 1908419 A1 4/2008
(Continued)

*Primary Examiner* — Melanie R Tyson

(57) ABSTRACT

Apparatus and methods for occluding hollow body structures, such as blood vessels, and for attaching tissue layers and/or non-tissue layers together by providing implantable elements on opposite sides of the structure or layers and drawing the implants together to occlude the body structure and/or bring the layers together. The implants are deliverable in a low-profile configuration and self-expand to an enlarged configuration. The implantable elements are delivered by transfixing the body structure, then releasing the implants on opposite sides of the body structure and drawing the implants together to effect an occlusion or attachment. The implants are configured to apply oppositely directed forces to opposite surfaces of the tissue layers at alternate, circumferentially spaced locations and may constrain the tissue in a serpentine pattern or in a direct clamping pattern. The implants grip the tissue in a manner that defines a pressure zone about the transfixion aperture that prevents leakage from the aperture.

33 Claims, 124 Drawing Sheets

Related U.S. Application Data continuation-in-part of application No. 14/639,814, filed on Mar. 5, 2015, now Pat. No. 9,936,955, which is a continuation-in-part of application No. 14/272,304, filed on May 7, 2014, now Pat. No. 10,076,339, which is a continuation-in-part of application No. 13/857,424, filed on Apr. 5, 2013, now abandoned, which is a continuation-in-part of application No. 13/348,416, filed on Jan. 11, 2012, now abandoned.

(60) Provisional application No. 61/820,589, filed on May 7, 2013, provisional application No. 61/620,787, filed on Apr. 5, 2012, provisional application No. 61/431,609, filed on Jan. 11, 2011.

(51) Int. Cl.
*A61B 17/064* (2006.01)
*A61B 17/068* (2006.01)
*A61B 17/12* (2006.01)
*A61B 17/128* (2006.01)
*A61B 18/14* (2006.01)
*A61F 5/00* (2006.01)
*A61F 6/20* (2006.01)
*A61F 6/22* (2006.01)
*A61B 18/00* (2006.01)
*A61B 34/30* (2016.01)
*A61B 90/00* (2016.01)

(52) U.S. Cl.
CPC .. *A61B 17/12031* (2013.01); *A61B 17/12113* (2013.01); *A61B 17/122* (2013.01); *A61B 17/1285* (2013.01); *A61B 18/14* (2013.01); *A61F 5/0086* (2013.01); *A61F 6/206* (2013.01); *A61F 6/22* (2013.01); *A61B 17/00234* (2013.01); *A61B 2017/0046* (2013.01); *A61B 17/00491* (2013.01); *A61B 2017/0053* (2013.01); *A61B 2017/00584* (2013.01); *A61B 2017/00601* (2013.01); *A61B 2017/00606* (2013.01); *A61B 2017/00623* (2013.01); *A61B 2017/00628* (2013.01); *A61B 2017/00672* (2013.01); *A61B 2017/00734* (2013.01); *A61B 2017/00862* (2013.01); *A61B 2017/00867* (2013.01); *A61B 2017/00893* (2013.01); *A61B 2017/1205* (2013.01); *A61B 17/12109* (2013.01); *A61B 17/1222* (2013.01); *A61B 2018/00083* (2013.01); *A61B 2018/00345* (2013.01); *A61B 2018/00589* (2013.01); *A61B 2018/00595* (2013.01); *A61B 2018/0063* (2013.01); *A61B 34/30* (2016.02); *A61B 2034/301* (2016.02); *A61B 2090/376* (2016.02); *A61B 2090/378* (2016.02)

(58) Field of Classification Search
CPC ........ A61B 17/12031; A61B 17/12109; A61B 17/122; A61B 17/1227; A61B 2017/00575; A61B 2017/00584; A61B 2017/00592; A61B 2017/00606; A61B 2017/00619; A61B 2017/00646; A61B 2017/0645; A61F 5/0086; A61F 6/206
See application file for complete search history.

(56) References Cited

U.S. PATENT DOCUMENTS

| | | |
|---|---|---|
| 4,235,238 A | 11/1980 | Ogiu |
| 4,326,531 A | 4/1982 | Shimonaka |
| 4,532,926 A | 8/1985 | O'Holla |
| 4,548,202 A | 10/1985 | Duncan |
| 4,573,469 A | 3/1986 | Golden |
| 4,800,879 A | 1/1989 | Golyakhovsky |
| 5,026,379 A | 6/1991 | Yoon |
| 5,217,484 A | 6/1993 | Marks |
| 5,282,811 A | 2/1994 | Booker |
| 5,290,299 A | 3/1994 | Fain |
| 5,334,217 A | 8/1994 | Das |
| 5,536,275 A | 7/1996 | Neuss |
| 5,601,557 A | 2/1997 | Hayhurst |
| 5,709,224 A | 1/1998 | Behl |
| 5,865,791 A | 2/1999 | Whayne |
| 5,947,994 A | 9/1999 | Louw |
| 5,976,127 A | 11/1999 | Lax |
| 6,071,292 A | 6/2000 | Makower |
| 6,113,611 A | 9/2000 | Miller |
| 6,132,438 A | 10/2000 | Fleischman |
| 6,156,044 A | 12/2000 | Kammerer |
| 6,312,446 B1 | 11/2001 | Huebsch |
| 6,319,278 B1 | 11/2001 | Quinn |
| 6,387,104 B1 | 5/2002 | Pugsley |
| 6,458,153 B1 | 10/2002 | Bailey |
| 6,485,504 B1 | 11/2002 | Johnson |
| 6,491,707 B2 | 12/2002 | Makowerr |
| 6,540,782 B1 | 4/2003 | Snyders |
| 6,551,533 B1 | 4/2003 | Kuhn |
| 6,565,581 B1 | 5/2003 | Spence |
| 6,616,684 B1 | 9/2003 | Vidland |
| 6,645,242 B1 | 11/2003 | Quinn |
| 6,776,754 B1 | 8/2004 | Wilk |
| 6,827,736 B2 | 12/2004 | Perouse |
| 6,951,571 B1 | 4/2005 | Snvastava |
| 6,913,607 B2 | 7/2005 | Ainsworth |
| 6,960,220 B2 | 11/2005 | Marino |
| 7,041,132 B2 | 5/2006 | Quijano |
| 7,101,366 B2 | 9/2006 | Trout |
| 7,149,587 B2 | 12/2006 | Wardle |
| 7,220,274 B1 | 5/2007 | Quinn |
| 7,416,554 B2 | 8/2008 | Lam |
| 7,462,183 B2 | 12/2008 | Behl |
| 7,766,816 B2 | 8/2010 | Chin |
| 7,766,962 B1 | 8/2010 | Quinn |
| 7,798,953 B1 | 9/2010 | Wilk |
| 7,942,884 B2 | 5/2011 | Vahid |
| 8,133,242 B1 | 3/2012 | Quinn |
| 8,211,121 B1 | 7/2012 | Quinn |
| 8,257,389 B2 | 9/2012 | Chanduszko |
| 8,556,961 B2 | 10/2013 | Quinn |
| 8,579,935 B2 | 11/2013 | DeVries |
| 8,632,520 B2 | 1/2014 | Otley |
| 8,870,946 B1 | 10/2014 | Quinn |
| 9,173,712 B2 | 11/2015 | Annest |
| 10,076,339 B2 * | 9/2018 | Miller .............. A61B 17/12109 |
| 10,820,895 B2 * | 11/2020 | Miller ............... A61B 17/0057 |
| 2003/0004568 A1 | 1/2003 | Ken |
| 2003/0105473 A1 | 6/2003 | Miller |
| 2003/0120286 A1 | 6/2003 | Burbank |
| 2003/0139819 A1 | 7/2003 | De Beer |
| 2003/0171771 A1 | 9/2003 | Anderson |
| 2003/0199963 A1 | 10/2003 | Tower |
| 2003/0199972 A1 | 10/2003 | Zadno-Azizi |
| 2004/0044364 A1 | 3/2004 | DeVries |
| 2004/0116992 A1 | 6/2004 | Wardle |
| 2004/0138684 A1 | 7/2004 | Eton |
| 2004/0215339 A1 | 10/2004 | Drasler |
| 2005/0004652 A1 | 1/2005 | Van Der Burg |
| 2005/0038460 A1 | 2/2005 | Jayaraman |
| 2005/0137682 A1 | 6/2005 | Justino |
| 2005/0267524 A1 | 12/2005 | Chanduszko |
| 2005/0267529 A1 | 12/2005 | Crockett |
| 2005/0277966 A1 | 12/2005 | Ewers |
| 2005/0288786 A1 | 12/2005 | Chanduszko |
| 2006/0264987 A1 | 11/2006 | Sgro |
| 2006/0271103 A1 | 11/2006 | Ferrari |
| 2007/0027466 A1 | 2/2007 | Ortiz |
| 2007/0043349 A1 | 2/2007 | Swanson |
| 2007/0073337 A1 | 3/2007 | Abbott |
| 2007/0106328 A1 | 5/2007 | Wardle |
| 2007/0135826 A1 | 6/2007 | Zaver |

(56) References Cited

U.S. PATENT DOCUMENTS

| | | |
|---|---|---|
| 2007/0144539 A1 | 6/2007 | Van der Burg |
| 2007/0179527 A1 | 8/2007 | Eskuri |
| 2007/0265658 A1 | 11/2007 | Nelson |
| 2008/0004640 A1 | 1/2008 | Ellingwood |
| 2008/0077180 A1 | 3/2008 | Kladakis |
| 2008/0109066 A1 | 5/2008 | Quinn |
| 2008/0208226 A1 | 8/2008 | Seibold |
| 2008/0306495 A1 | 12/2008 | Thompson |
| 2009/0084386 A1 | 4/2009 | McClellan |
| 2009/0114233 A1 | 5/2009 | Edoga |
| 2009/0125038 A1 | 5/2009 | Ewers |
| 2009/0157174 A1 | 6/2009 | Yoganathan |
| 2010/0004740 A1 | 1/2010 | Seguin |
| 2010/0198254 A1 | 8/2010 | Schaeffer |
| 2010/0228269 A1 | 9/2010 | Gamson |
| 2010/0234880 A1 | 9/2010 | Abbott |
| 2011/0082495 A1 | 4/2011 | Ruiz |
| 2011/0108039 A1 | 5/2011 | Frigstad |
| 2011/0152902 A1 | 6/2011 | Kurrus |
| 2011/0295302 A1 | 12/2011 | Mohl |
| 2011/0319906 A1 | 12/2011 | Rudakov |
| 2012/0232569 A1 | 9/2012 | Wright |
| 2012/0283758 A1 | 11/2012 | Miller |
| 2013/0046331 A1 | 2/2013 | Christensen |
| 2013/0218259 A1 | 8/2013 | Quinn |
| 2013/0274857 A1 | 10/2013 | Quinn |
| 2014/0100460 A1 | 4/2014 | Otley |
| 2015/0094740 A1 | 4/2015 | Gagne |
| 2015/0201947 A1 | 7/2015 | Hill |

FOREIGN PATENT DOCUMENTS

| | | |
|---|---|---|
| EP | 2311381 | 4/2011 |
| JP | 2009291476 | 12/2009 |
| WO | WO200217771 | 7/2002 |
| WO | WO 2005/006990 | 1/2005 |
| WO | WO 2006/130836 | 7/2006 |
| WO | WO 2007/006286 | 1/2007 |
| WO | WO2007002307 | 4/2007 |
| WO | WO 2008/115922 | 9/2008 |
| WO | WO 2009/029914 | 3/2009 |
| WO | WO 2010/127083 | 11/2010 |

* cited by examiner

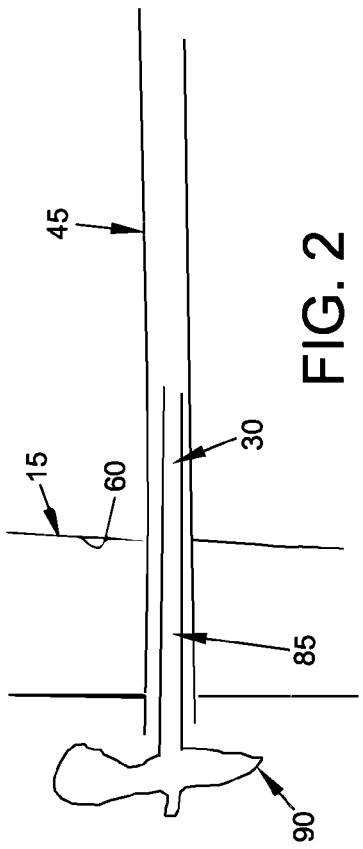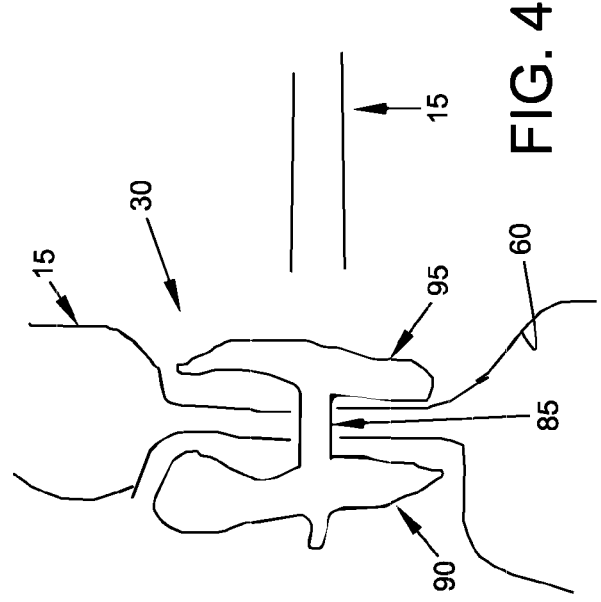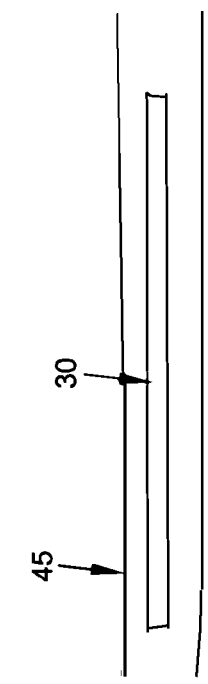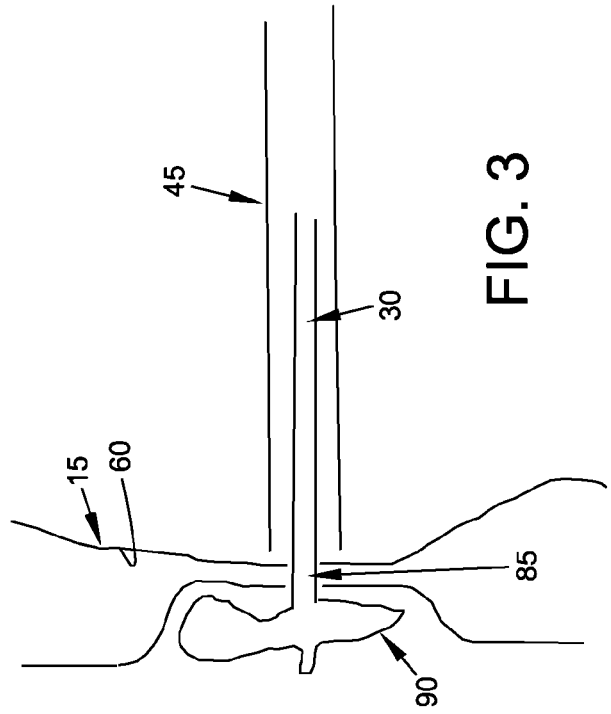

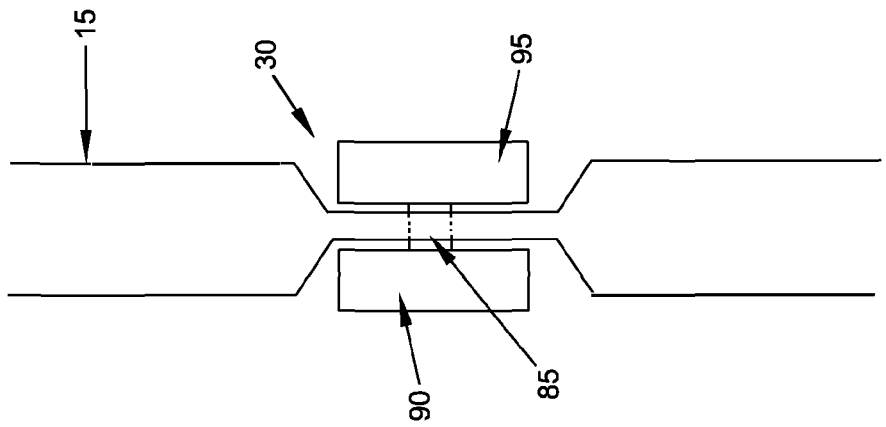
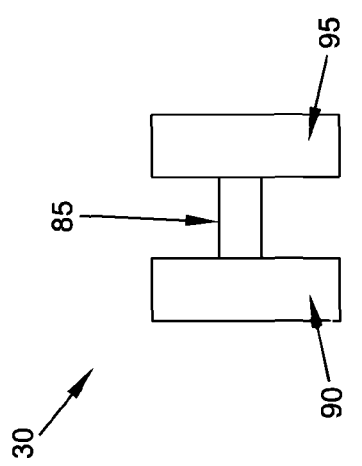
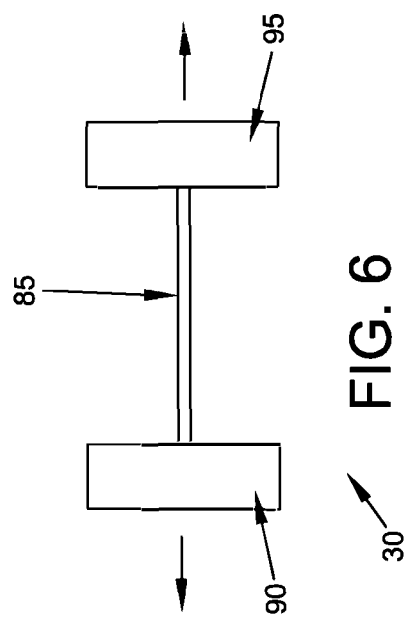

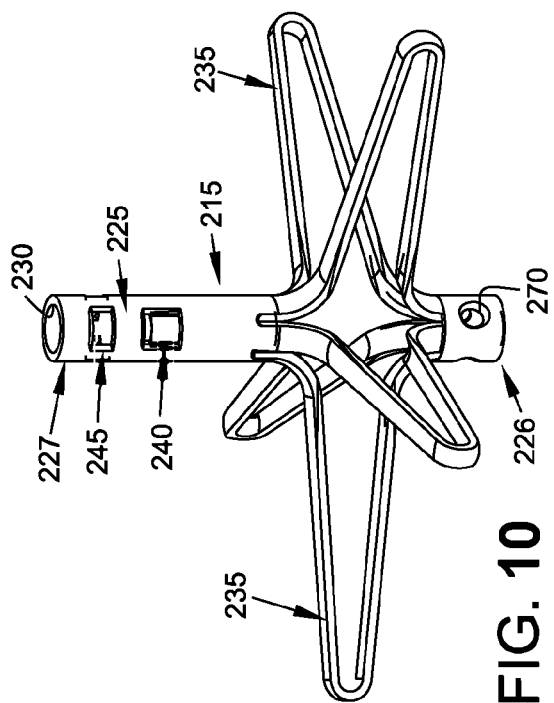
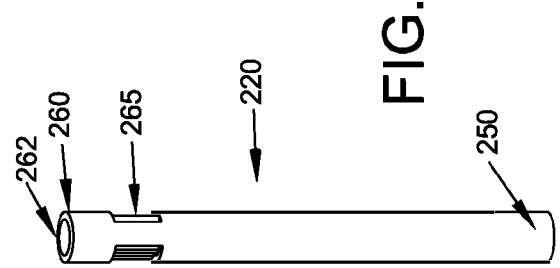
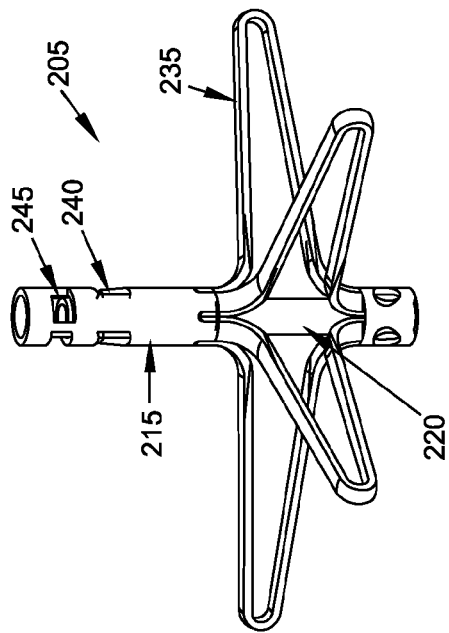

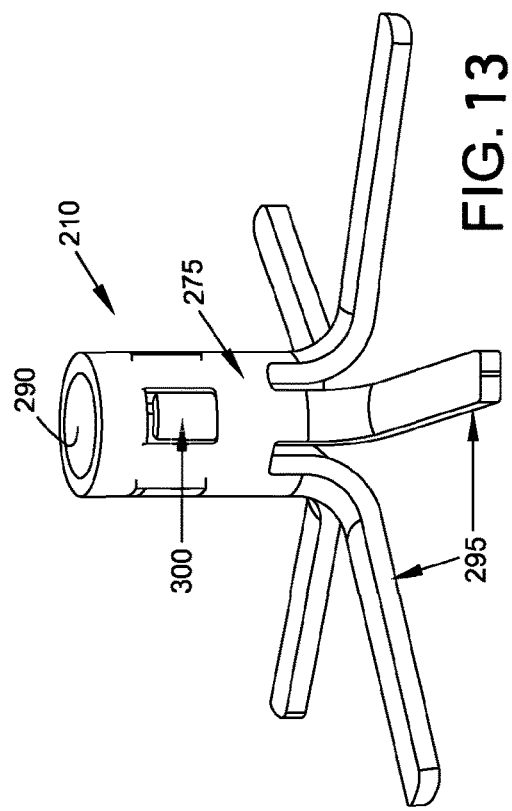
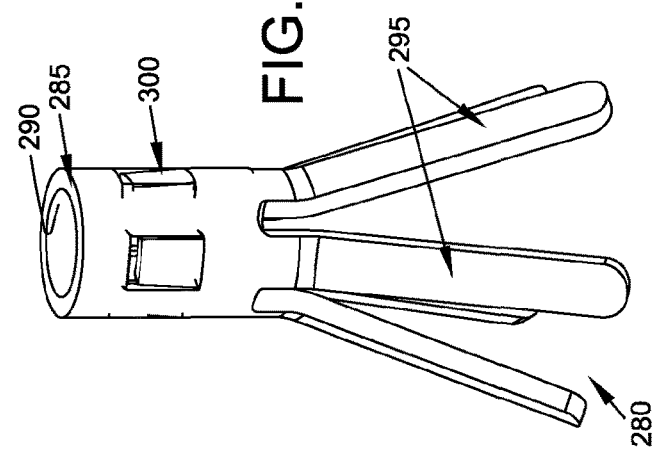
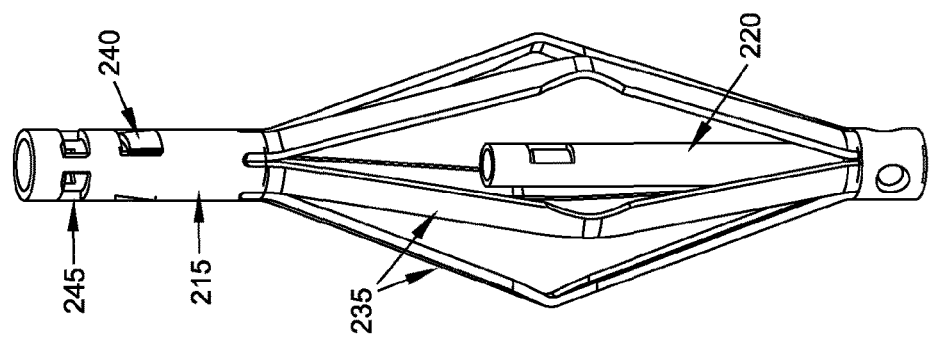

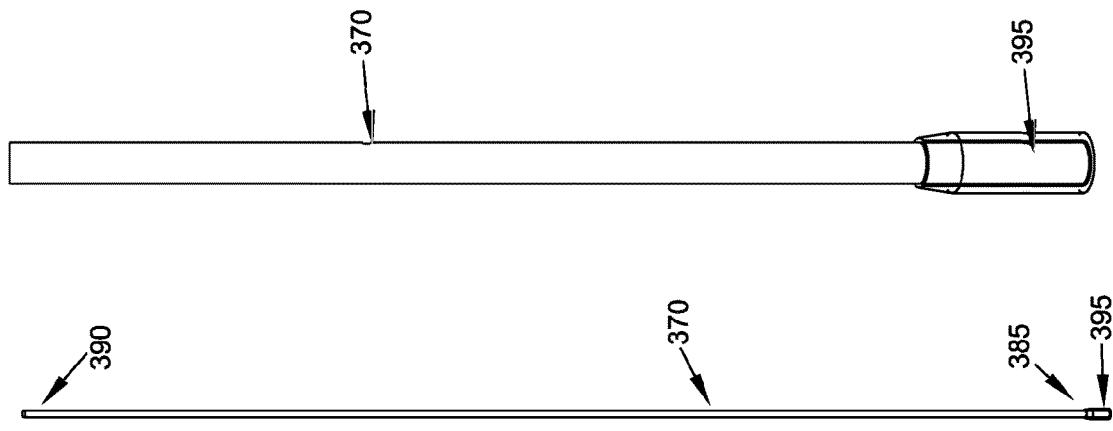
FIG. 24
FIG. 23
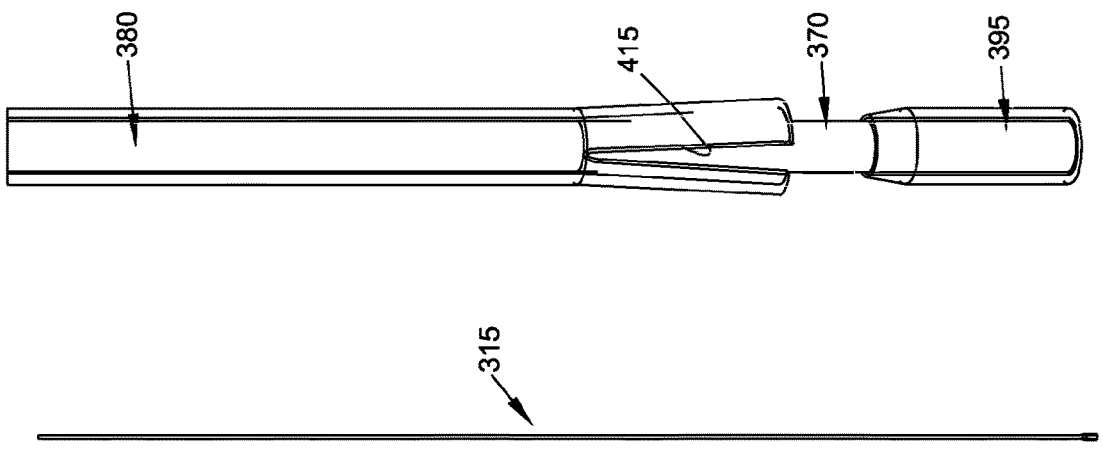
FIG. 22
FIG. 21

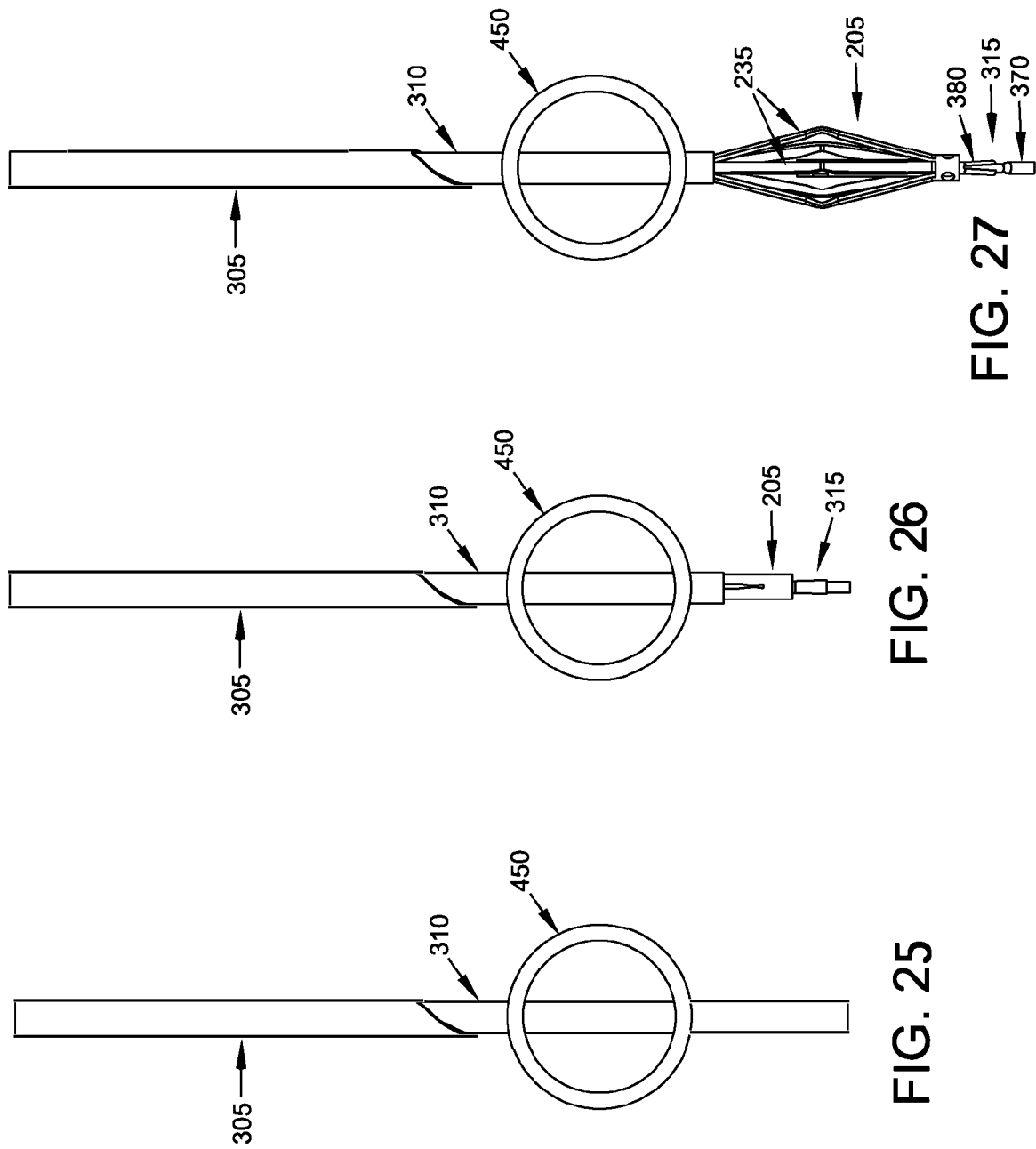

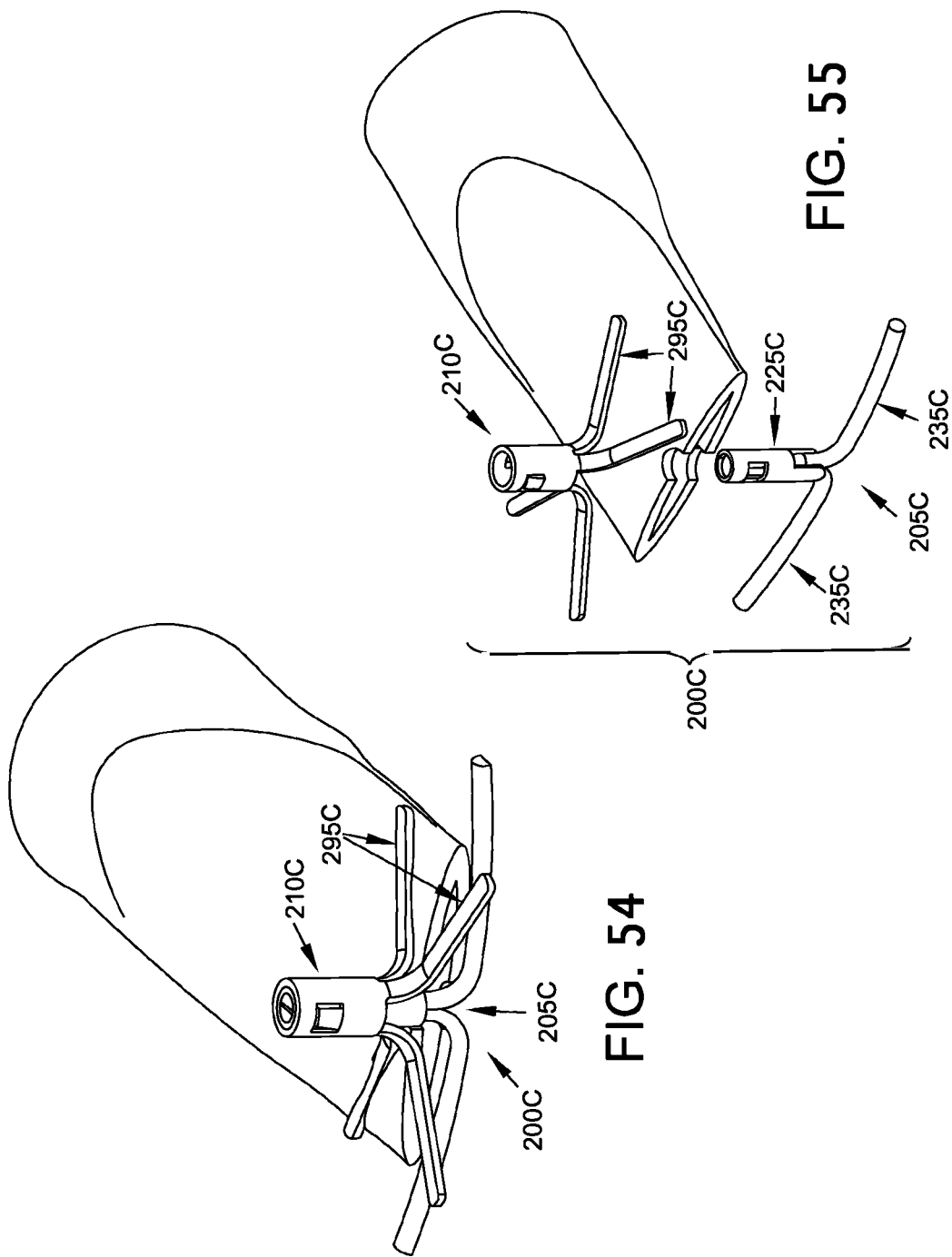

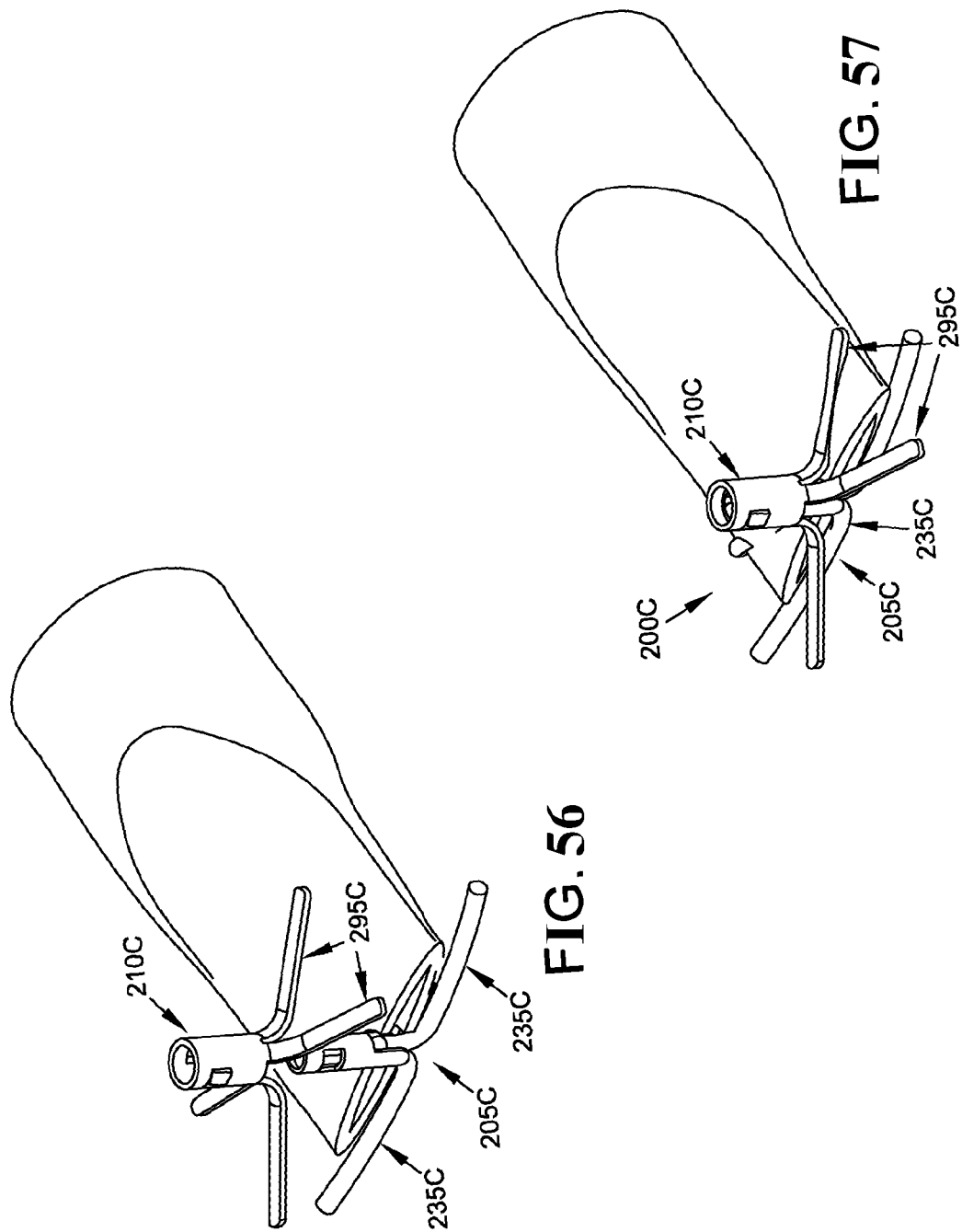

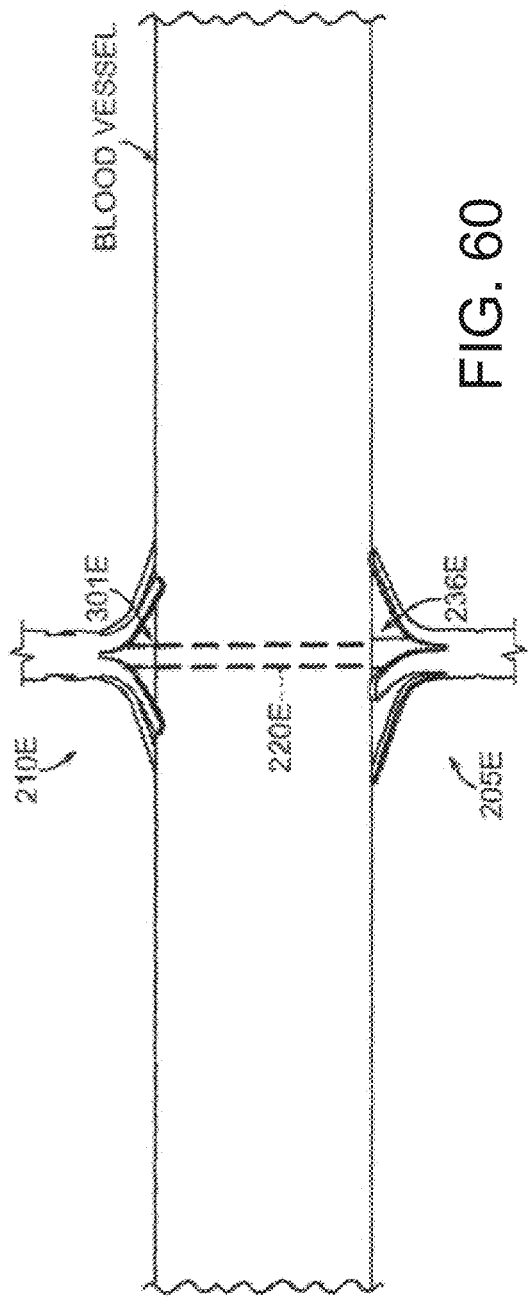
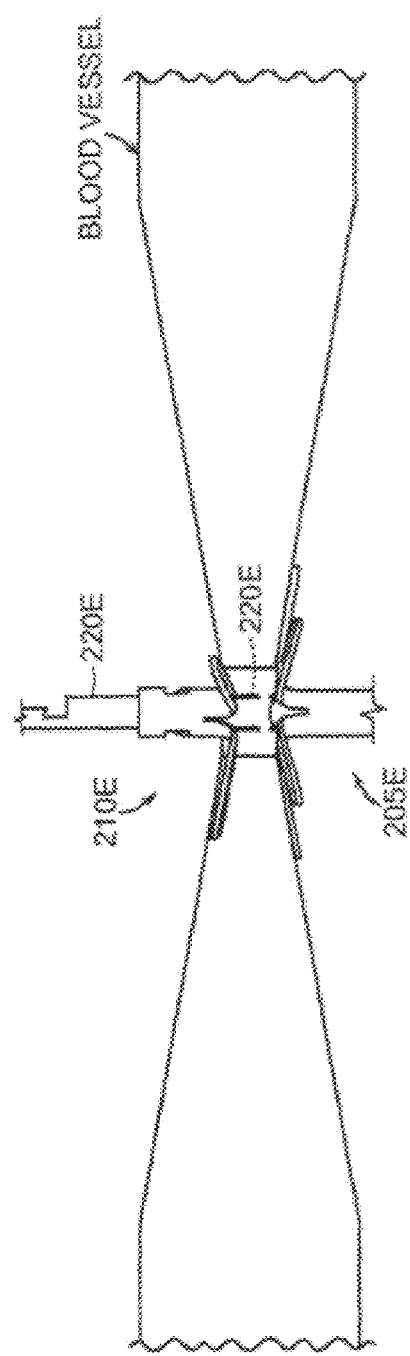

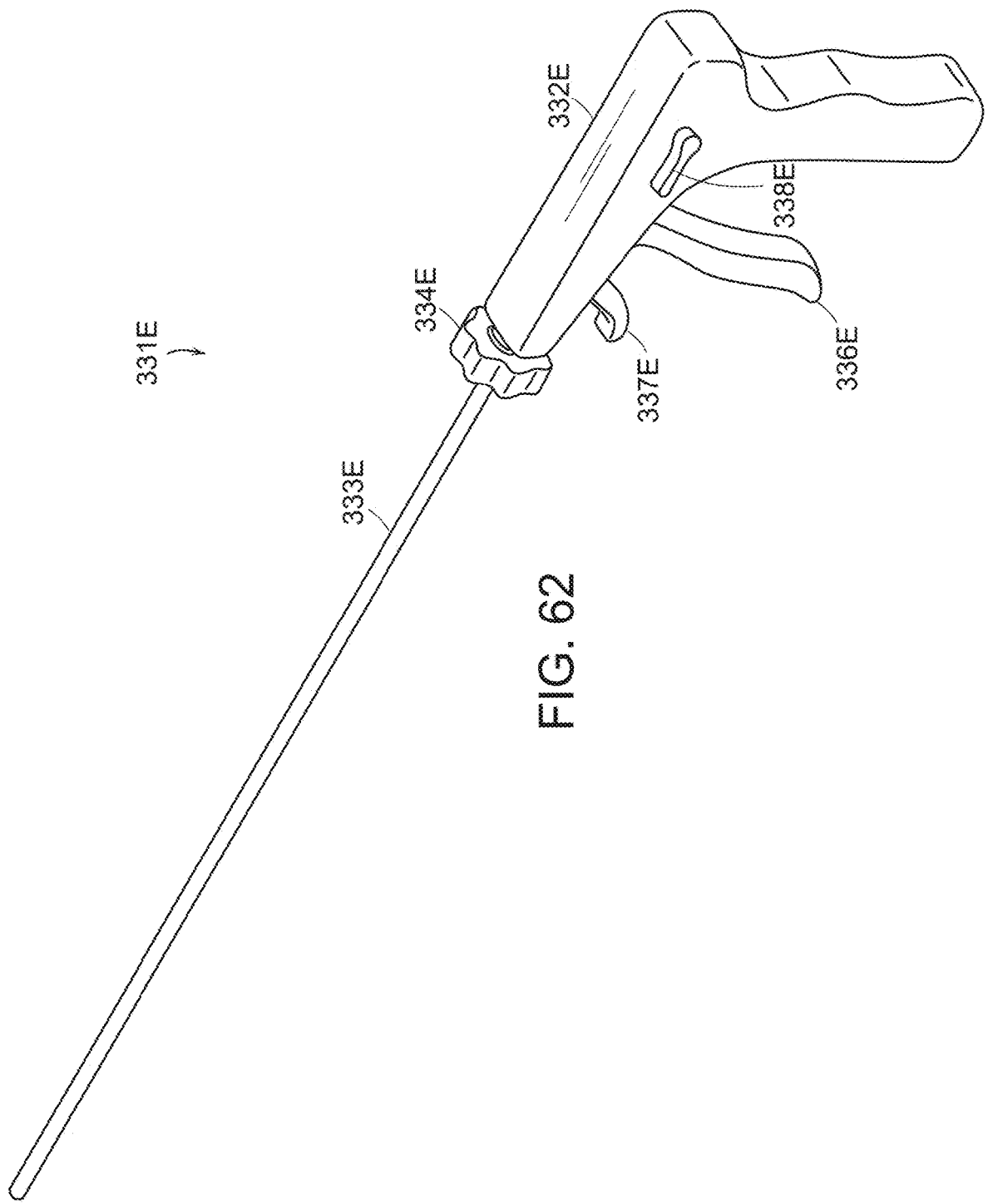

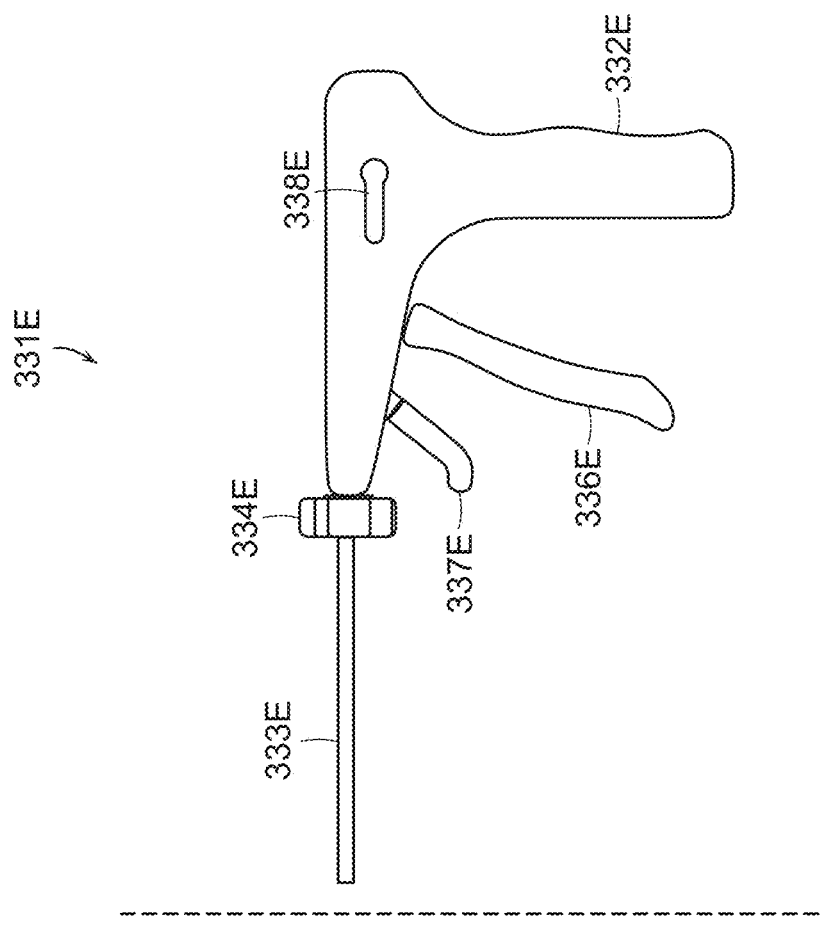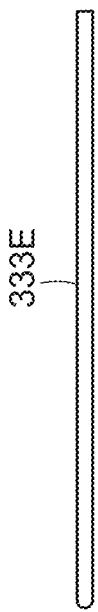
FIG. 64

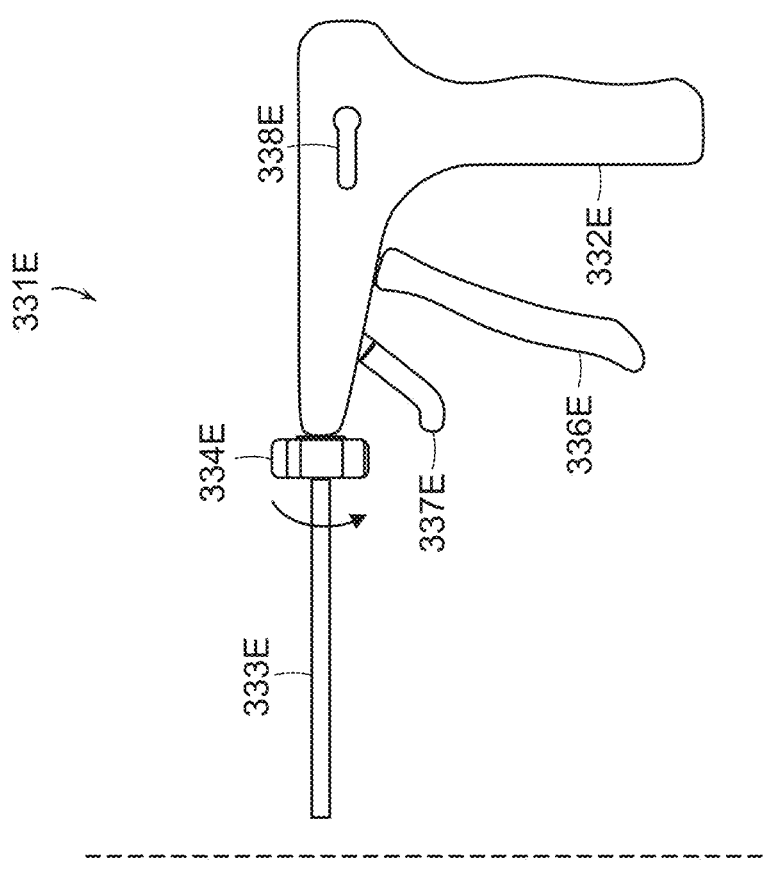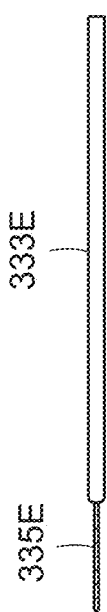
FIG. 65

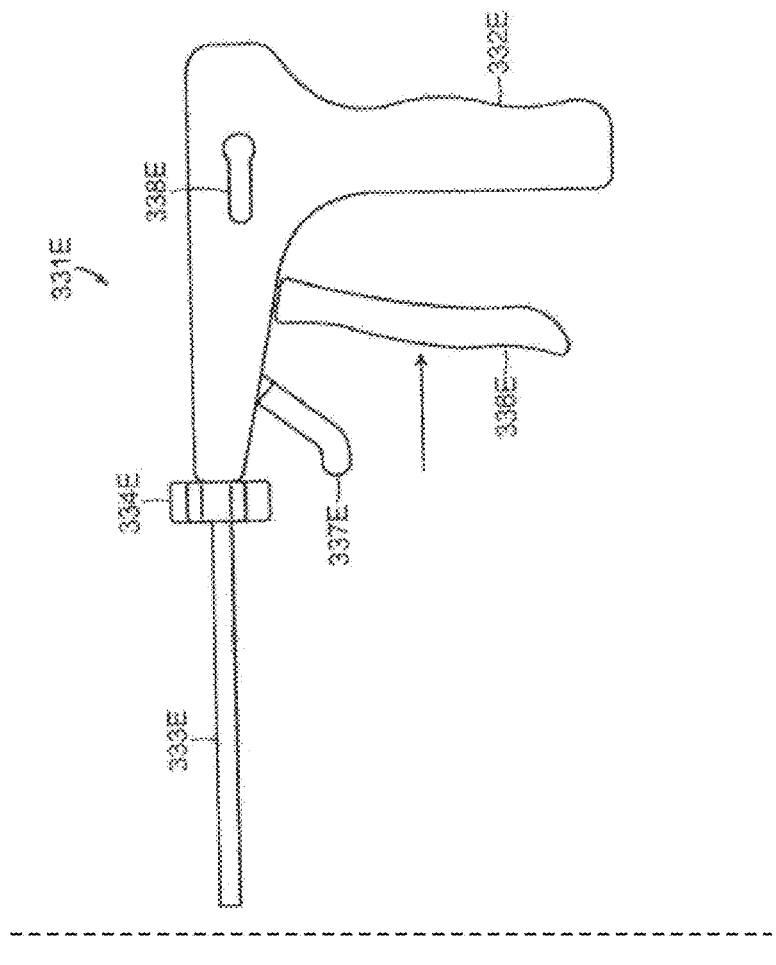
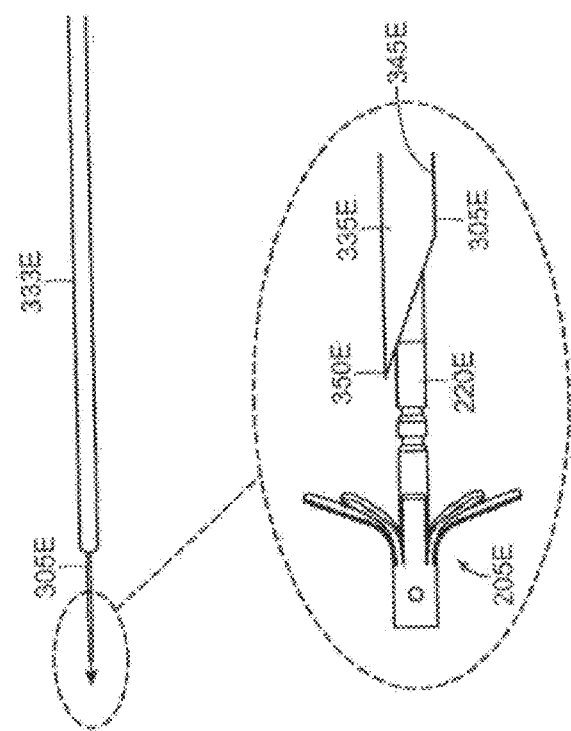
FIG. 66

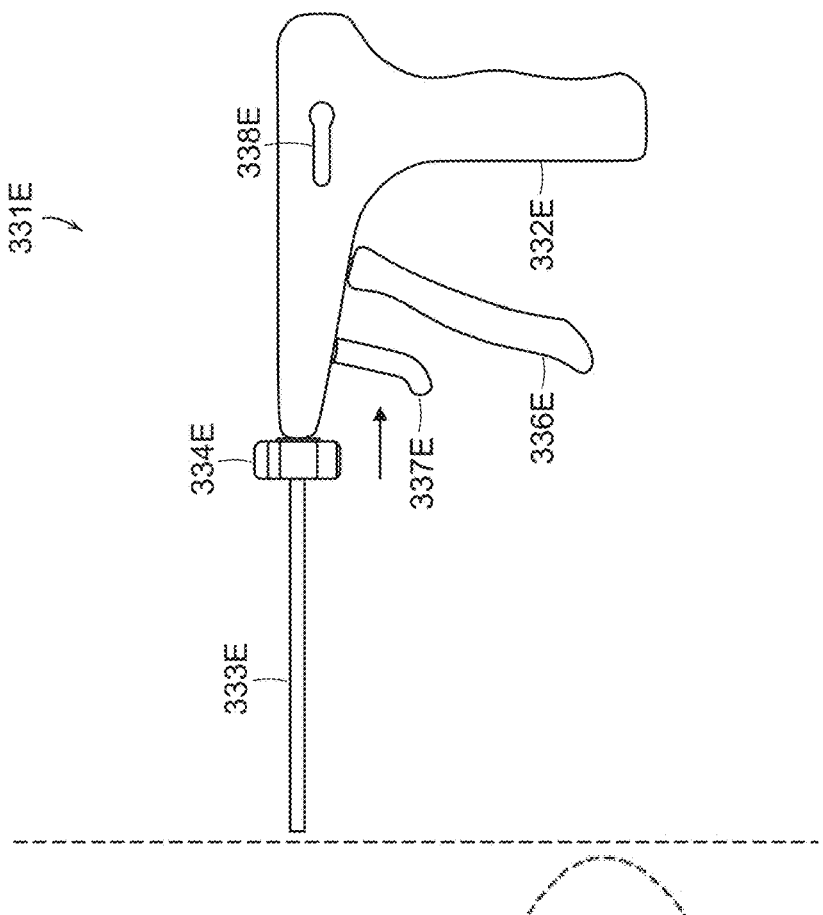
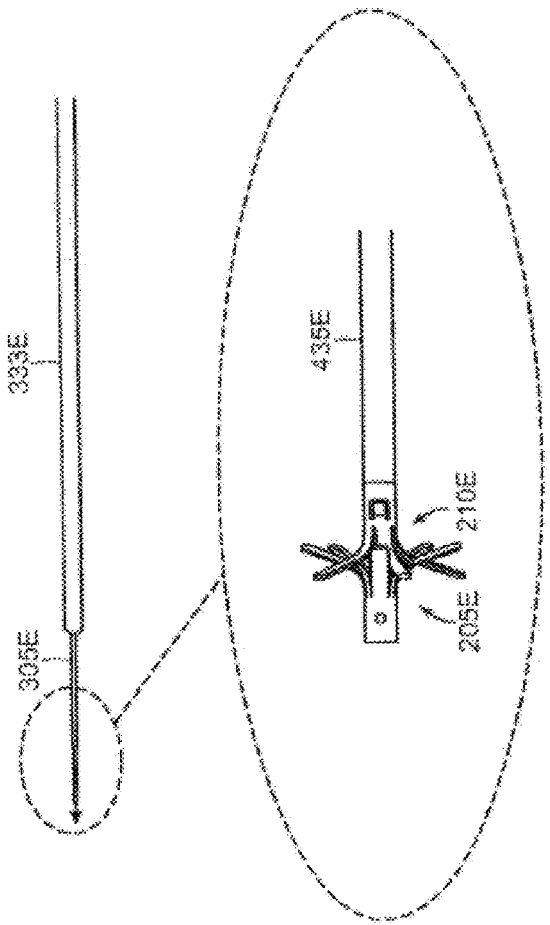
FIG. 68

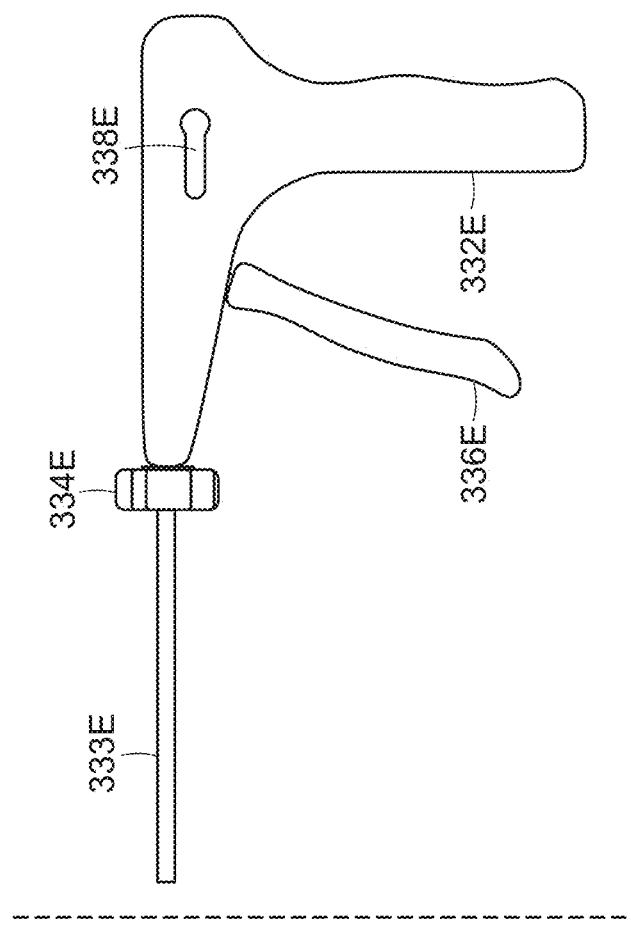
FIG. 72

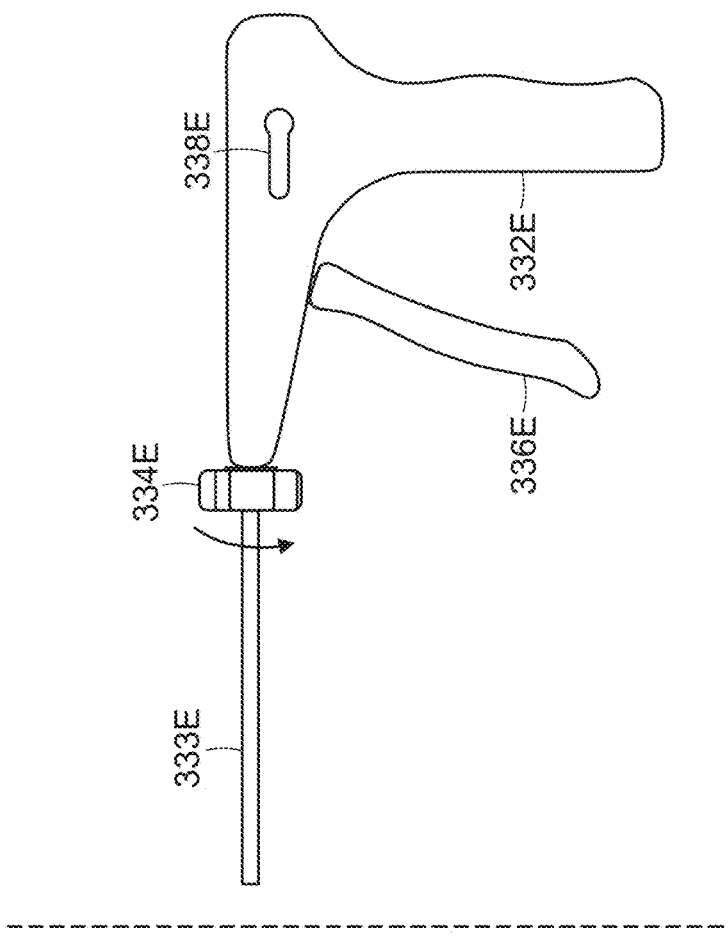
FIG. 73

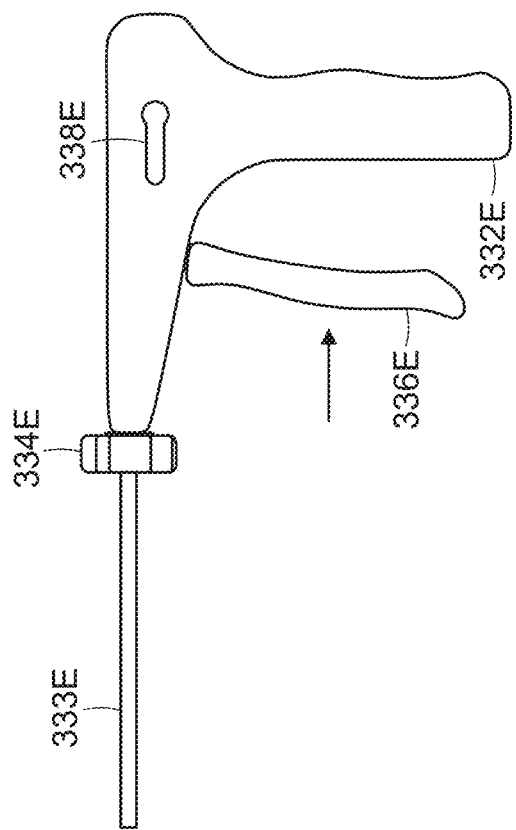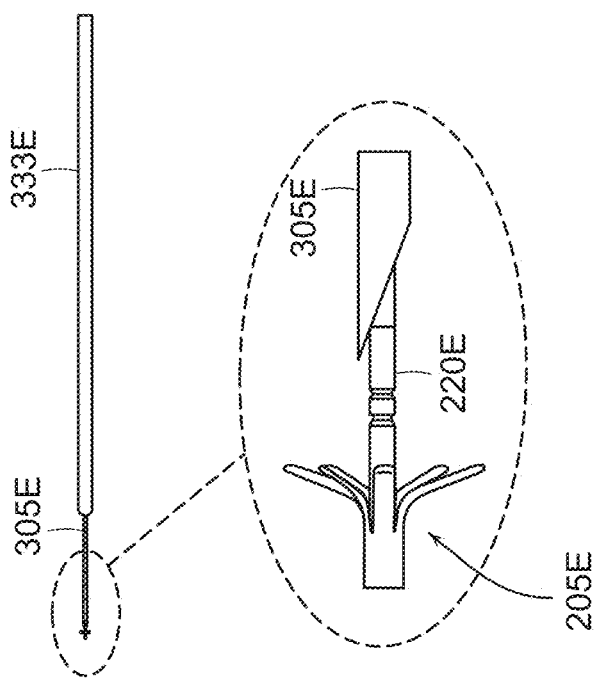
FIG. 74

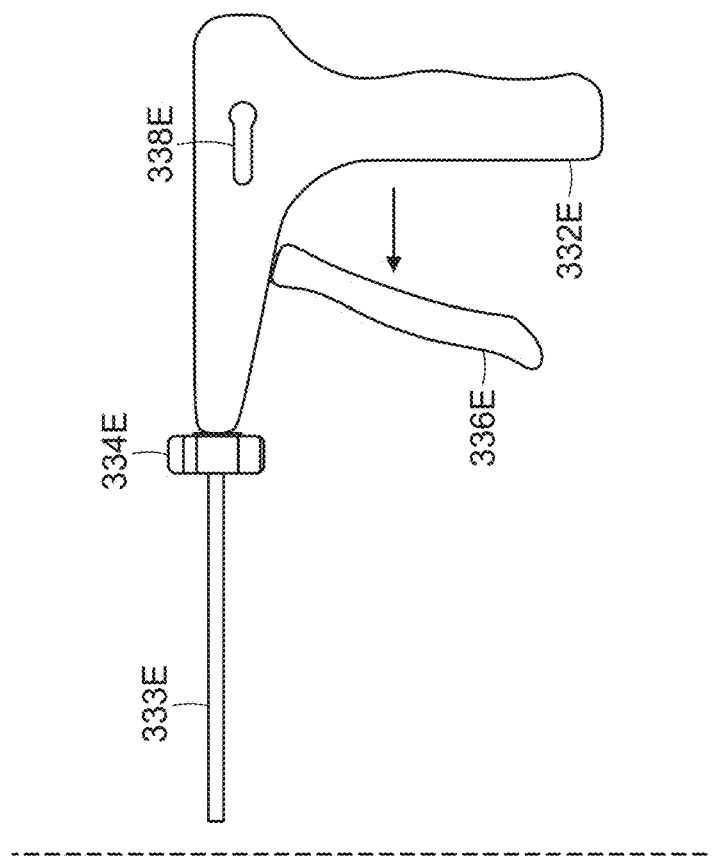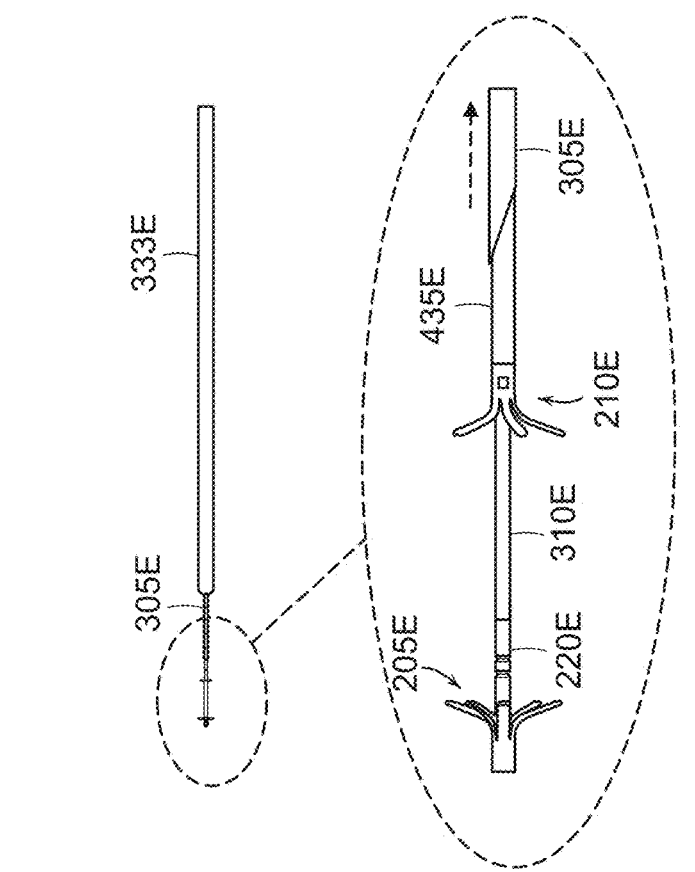
FIG. 75

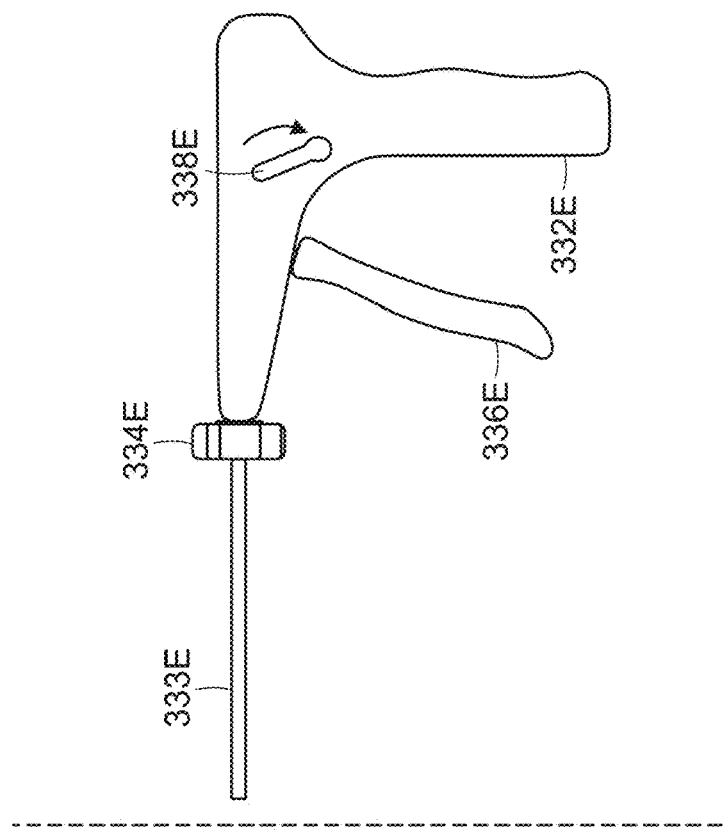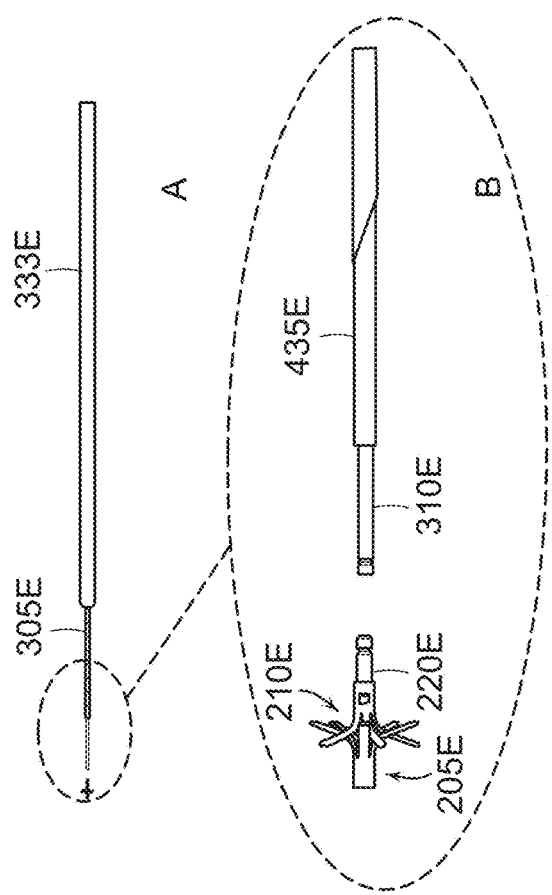
FIG. 77

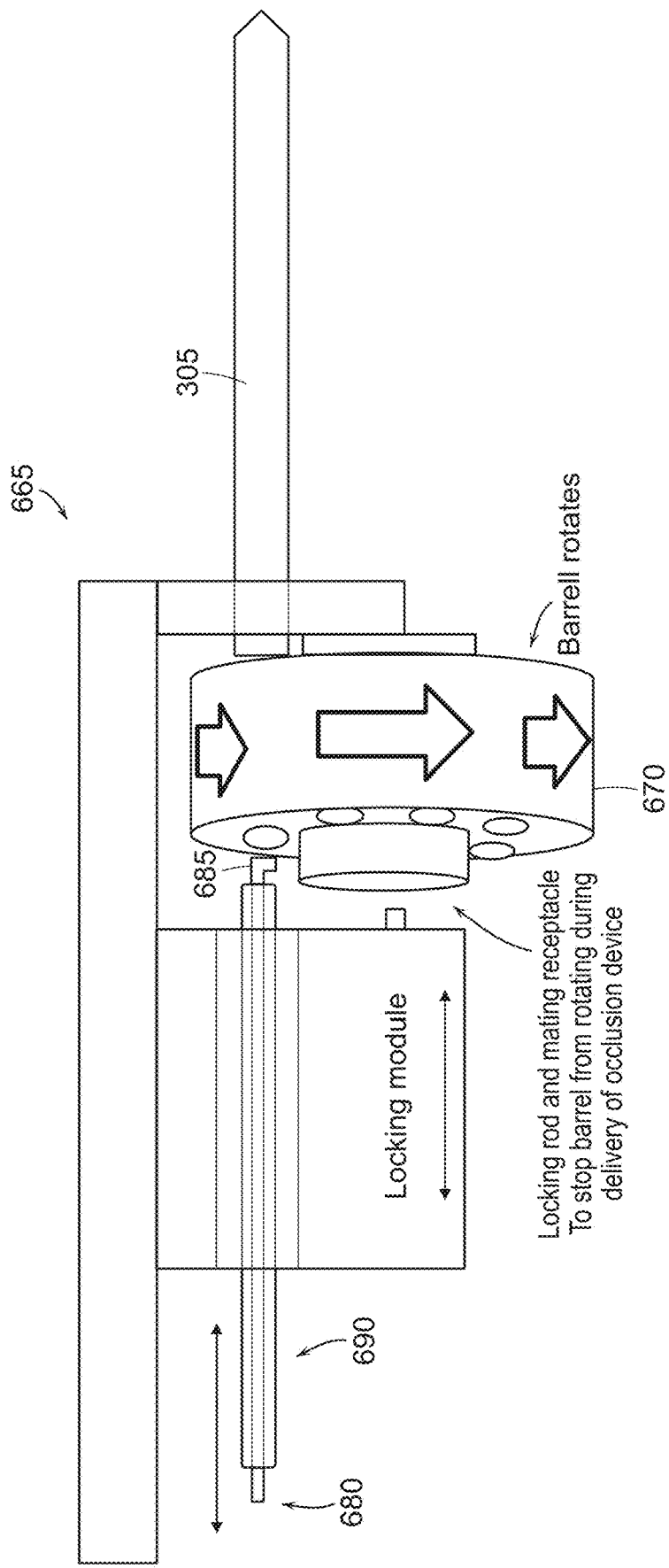

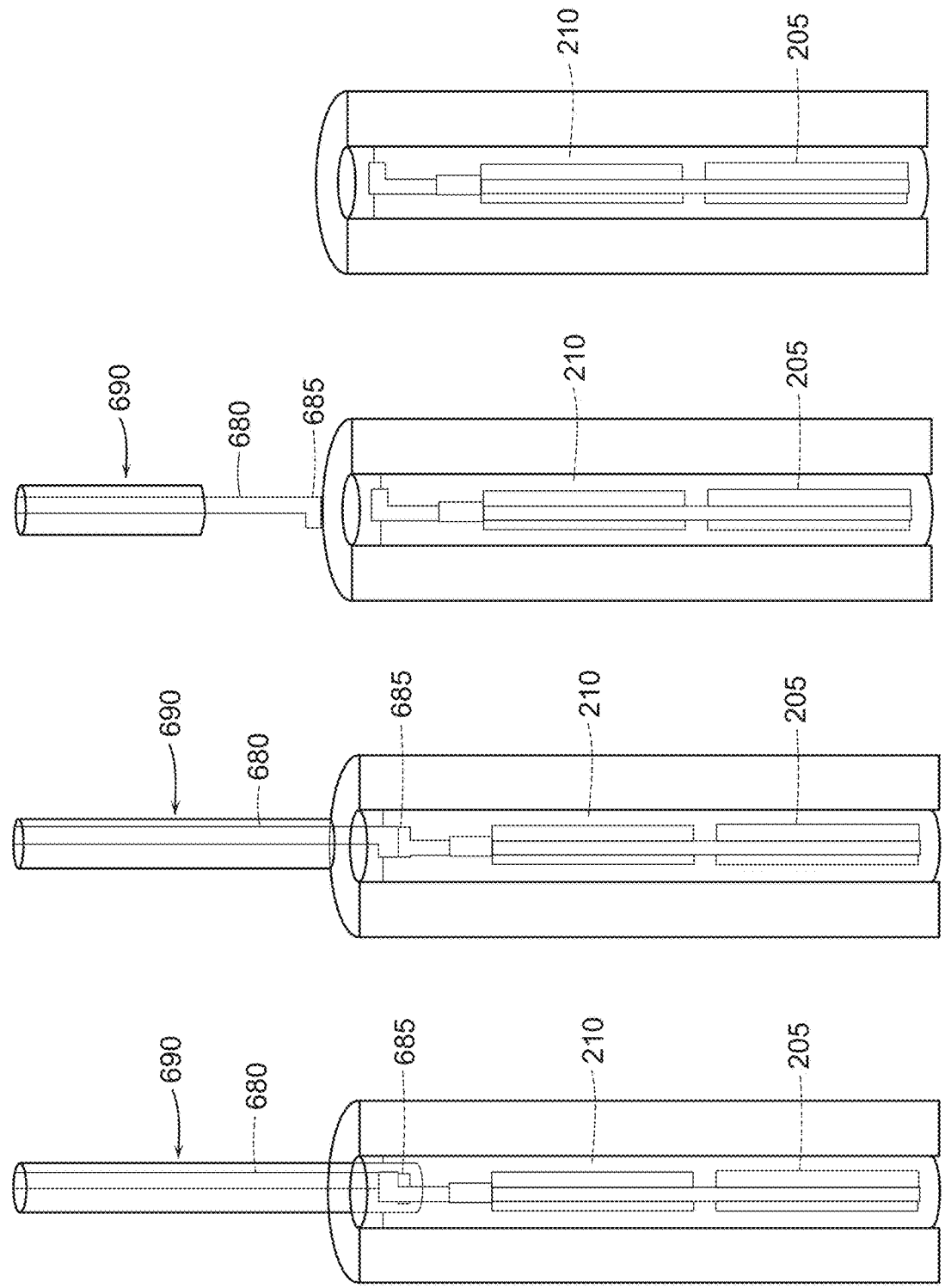

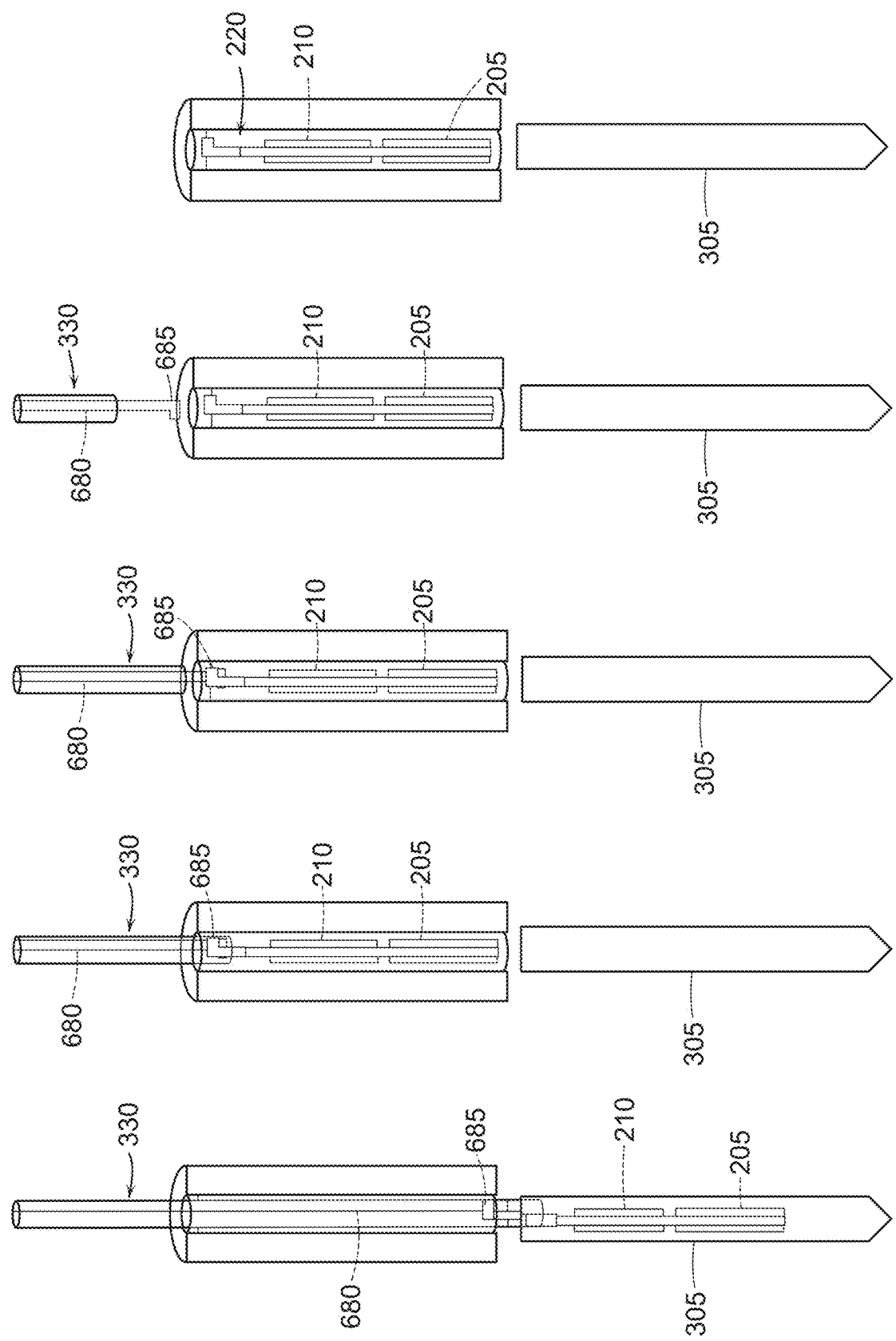

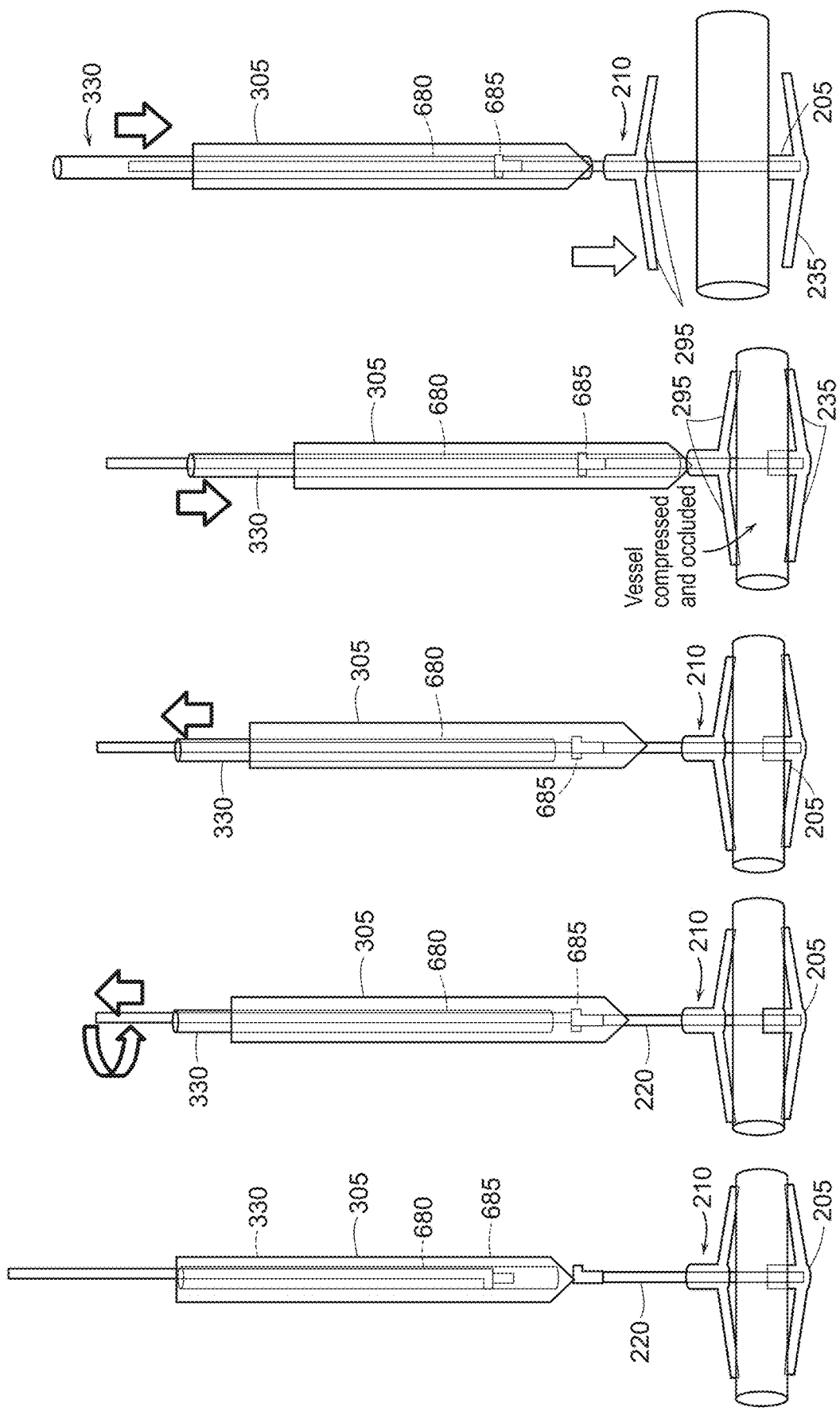

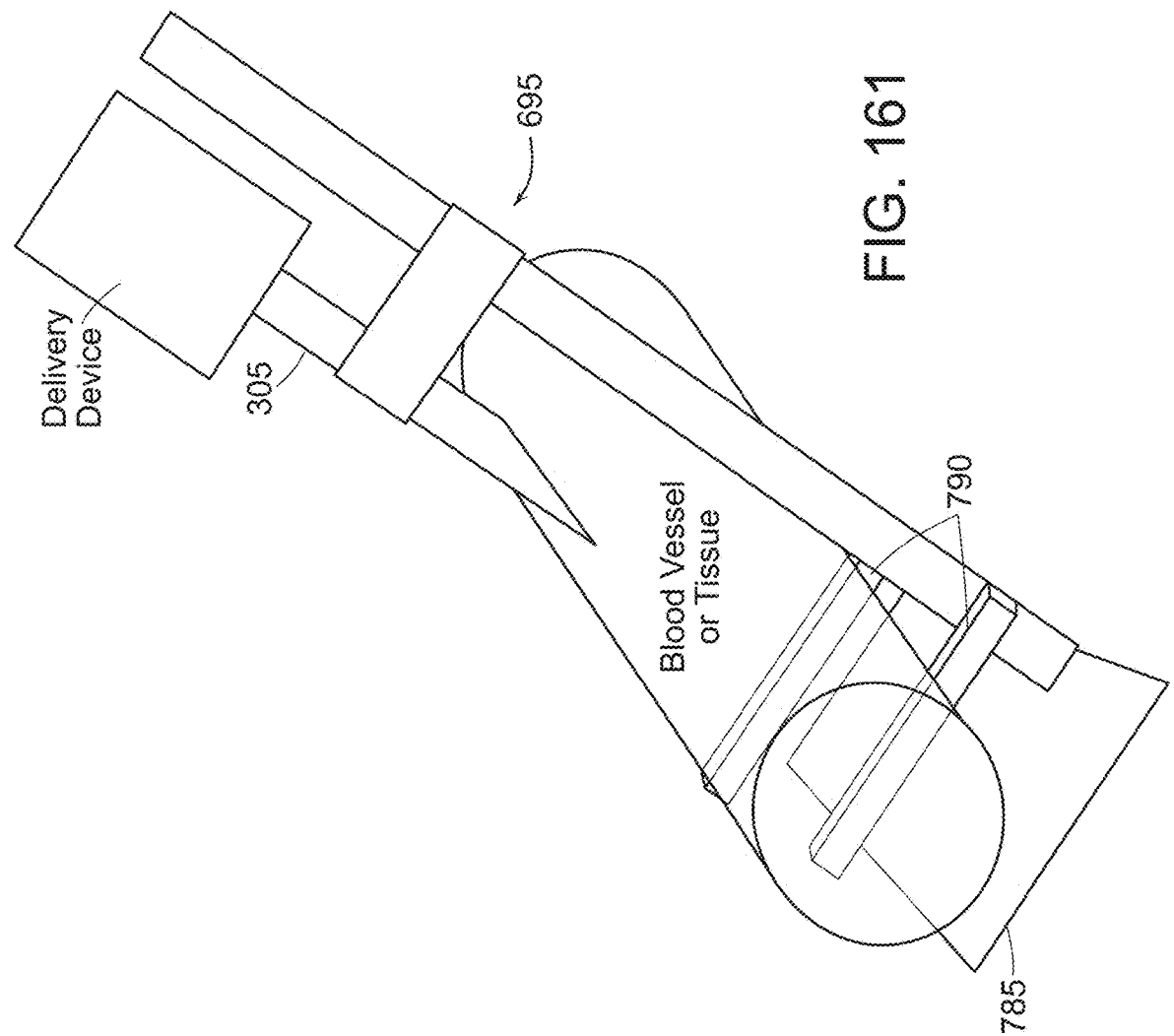

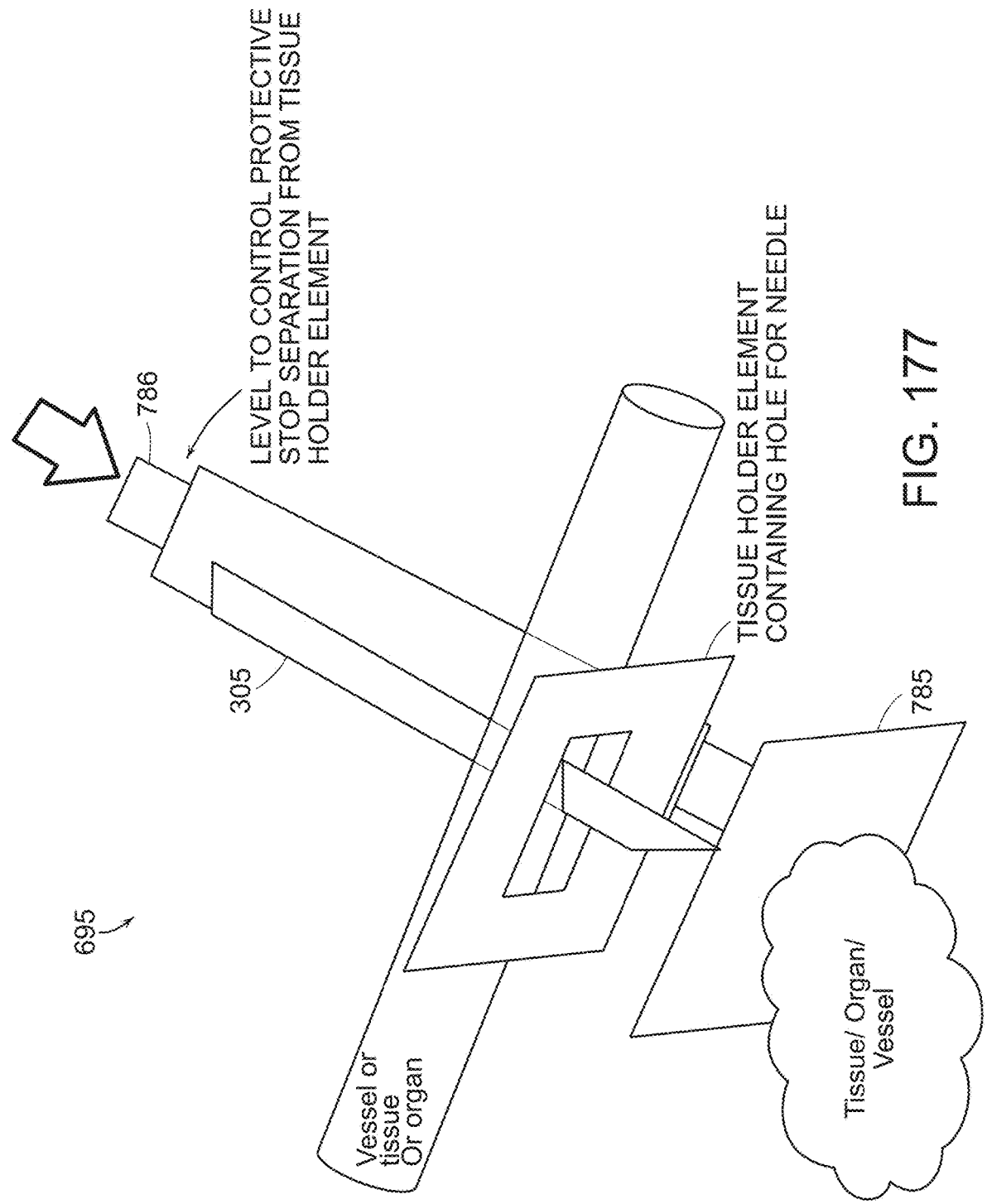

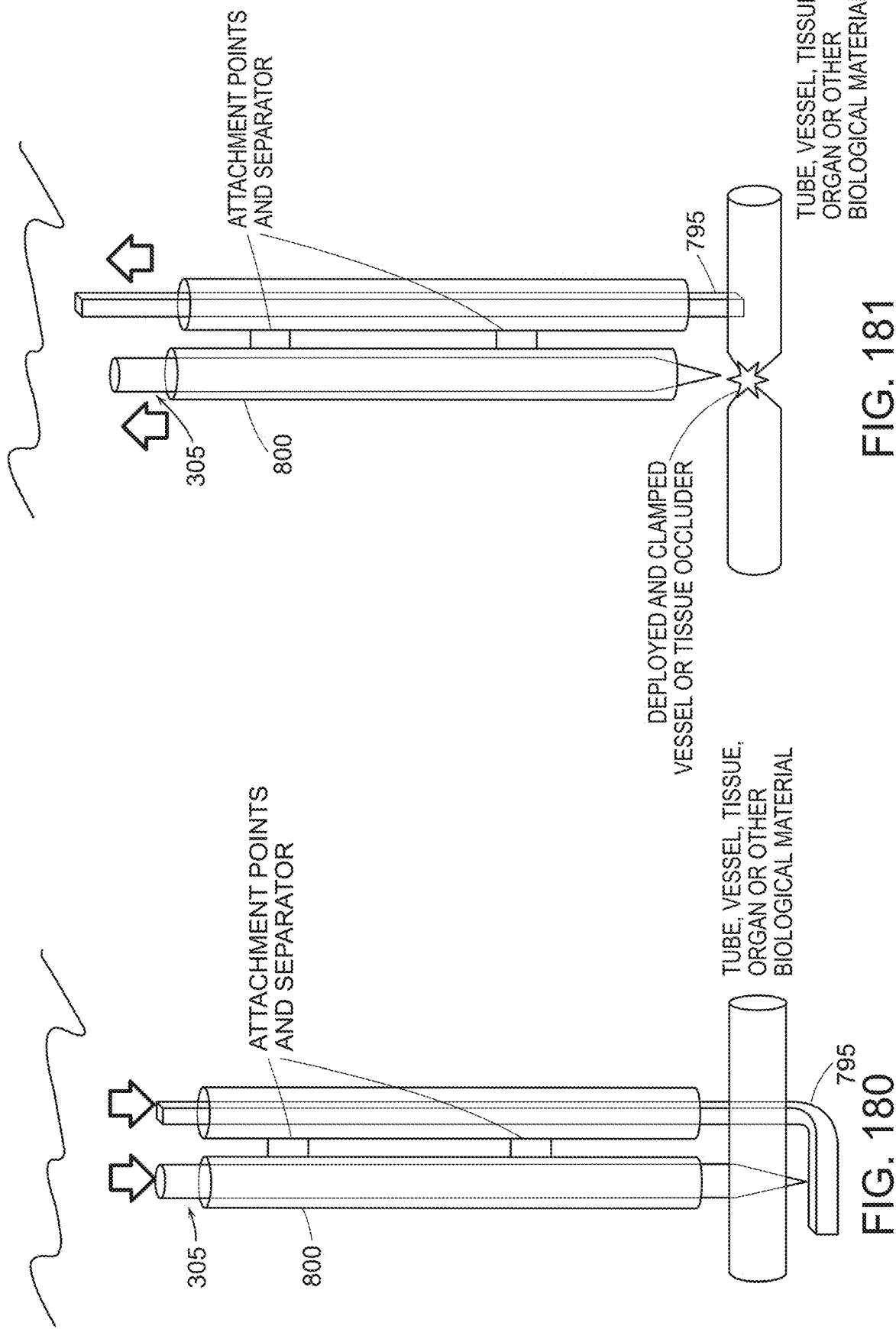

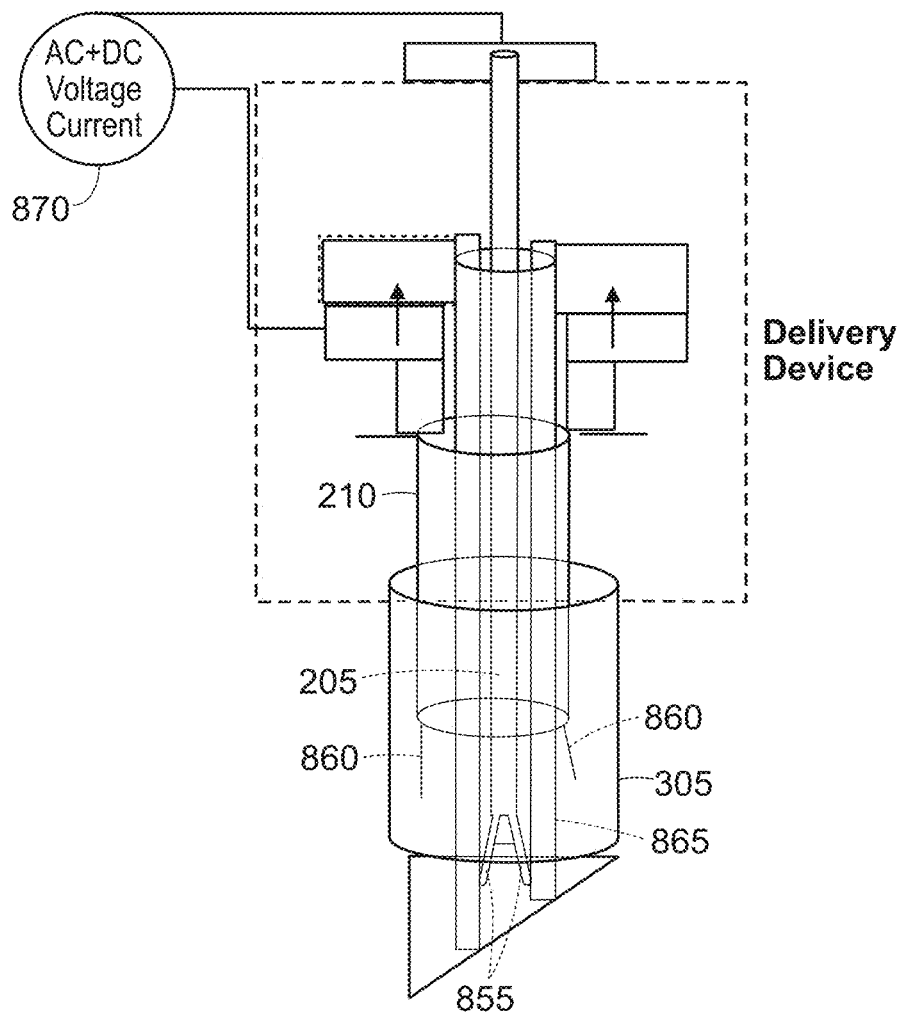
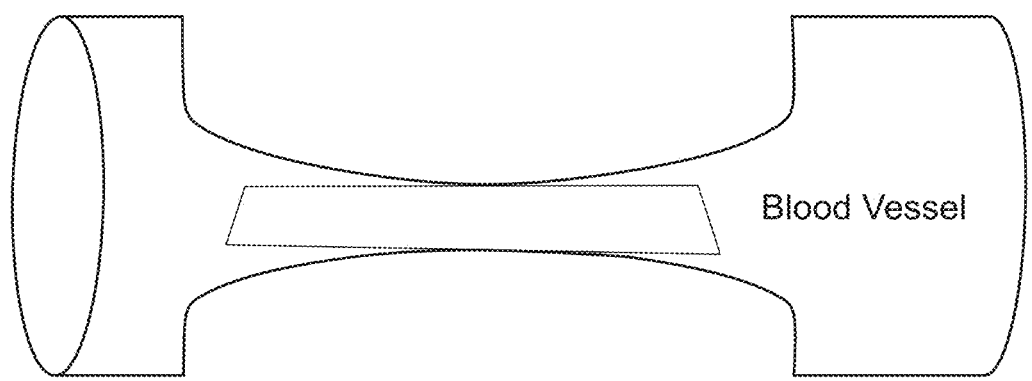
FIG. 207

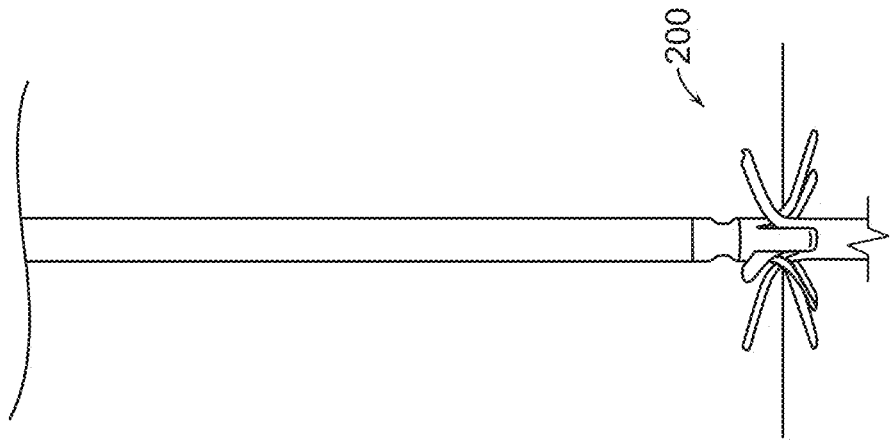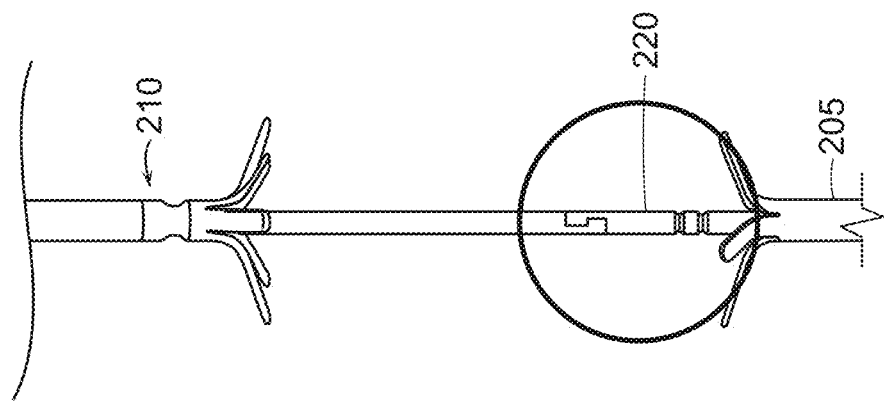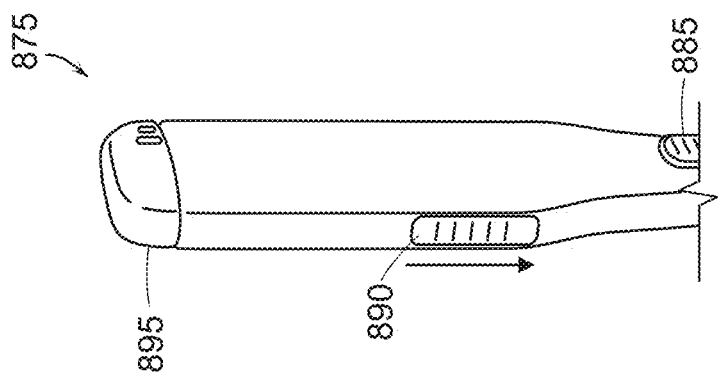
FIG. 210

METHODS AND APPARATUS FOR FASTENING AND CLAMPING TISSUE

REFERENCE TO PENDING PRIOR PATENT APPLICATIONS

This patent application is a continuation of pending prior U.S. patent application Ser. No. 15/906,763, filed Feb. 27, 2018 which is a continuation-in-part of pending prior U.S. patent application Ser. No. 14/639,814, filed Mar. 5, 2015 by Amsel Medical Corporation and Arnold Miller et al. for METHOD AND APPARATUS FOR OCCLUDING A BLOOD VESSEL AND/OR FOR OCCLUDING OTHER TUBULAR STRUCTURES AND/OR FOR CLOSING OPENINGS IN STRUCTURES AND/OR FOR SECURING AT LEAST TWO OBJECTS TOGETHER, which patent claims priority to prior applications as set forth in the accompanying Application Data Sheet filed herewith, all of which are hereby incorporated by reference, in their entireties.

FIELD OF THE INVENTION

This invention relates to surgical methods and apparatus in general, and more particularly to surgical methods and apparatus for fastening or clamping tissue layers together as well as for attaching non-tissue devices or prostheses to tissue and to occlude tubular body structures.

BACKGROUND OF THE INVENTION

Numerous techniques and devices have been employed by surgeons and clinicians to attach tissue to tissue, to occlude tubular body structures, to attach non-tissue prostheses and devices to tissue, to prevent excess bleeding after tissue resection and the like. A partial list would include sutures, staples, ligating clips, adhesives, clamps, cauterization, among others. The present inventions provide improved methods and devices for performing those and other like functions.

SUMMARY OF THE INVENTION

The present invention provides a new and improved approaches for fastening tissue to tissue, tissue to non-tissue, for clamping resected tissue and for occluding blood vessels and other tubular body structures.

In one aspect, the present invention comprises the provision and use of a novel tissue fastener (sometimes referred to as an "fastener") that can be used in numerous surgical environments to attach tissue to tissue or to non-tissue prostheses. Fastener may be deployed using a minimally-invasive approach (i.e., either percutaneously or endoluminally), with visualization being provided by ultrasound and/or other visualization apparatus (e.g., CT, MRI, X-ray etc.) or may be used under direct visualization (e.g., during "open" surgery) or under indirect visualization (e.g., during laparoscopic surgery where visualization is provided through the use of a scope, or during percutaneous surgery where visualization is provided through the use of imaging apparatus such as an ultrasound imager, an X-ray imager, etc.).

BRIEF DESCRIPTION OF THE DRAWINGS

The objects and features of the invention will be appreciated more fully from the following description of the illustrative embodiments, with reference to the accompanying drawings in which:

FIGS. 1-7 are diagrammatic representations of fasteners of the invention;

FIGS. 8-24 illustrate an embodiment of the fastener and installation apparatus which may be used to deploy the two-part fastener;

FIGS. 25-45 illustrate the sequential steps in deploying the embodiment of FIGS. 8-24;

FIGS. 54-57 are schematic views showing yet another two-part fastener formed in accordance with the present invention;

FIGS. 58-61 are schematic views showing another two-part occluder formed in accordance with the present invention;

FIGS. 62-70 are schematic views showing an installation apparatus for deploying the two-part occluder shown in FIGS. 58-61;

FIGS. 71-77 are schematic views showing another installation apparatus for deploying the two-part occluder shown in FIGS. 58-61;

FIGS. 134-137 are view showing a multiple fastener delivery device which may be used to deploy a plurality of fasteners;

FIGS. 138-157 illustrate the sequential deployment of fastener elements; are schematic views showing a two-part fastener having asymmetric legs;

FIGS. 161-181 are schematic views showing various constructions for separating the tissue to be occluded from the surrounding tissue, and/or for protecting the surrounding tissue from damage during delivery of the fastener;

FIGS. 193-208 are schematic views showing how the fastener may be combined with electrocautery;

FIGS. 209-212 are schematic views showing a handle for deploying a fastener.

DETAILED DESCRIPTION OF THE ILLUSTRATIVE EMBODIMENTS

Figure 8:
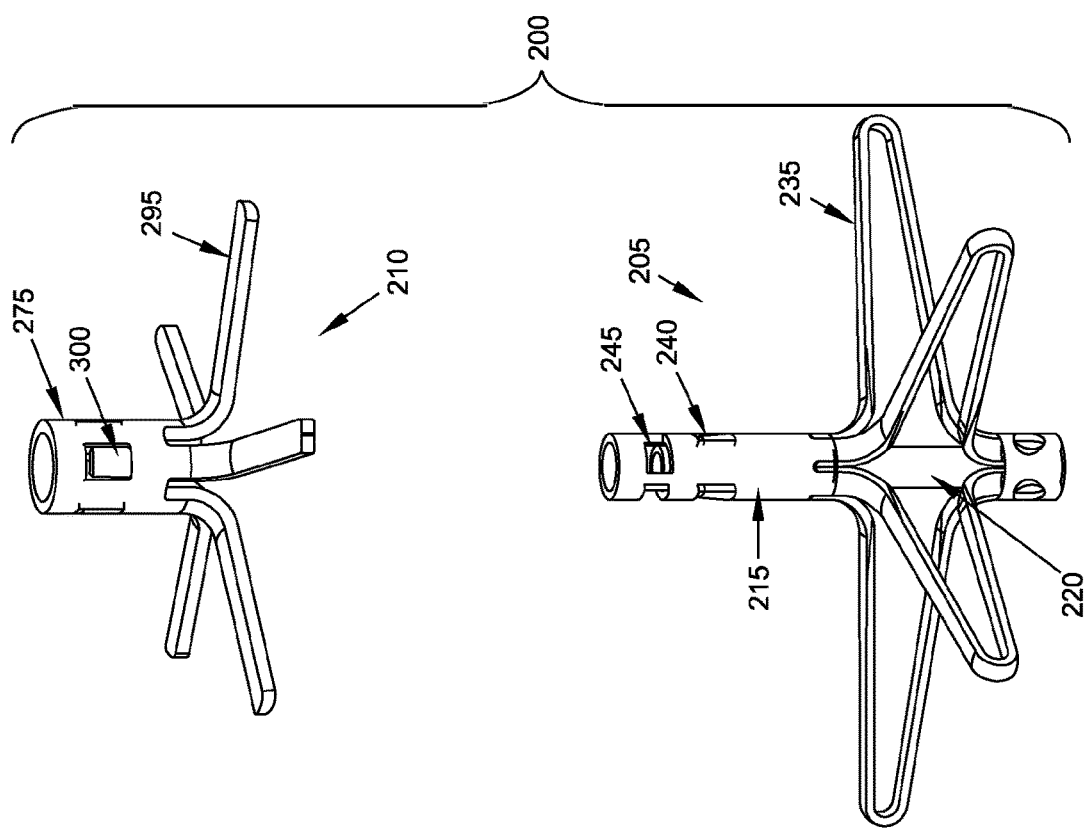

The present invention also provides new and improved surgical methods and apparatus for occluding other tubular structures and/or for closing openings in structures and/or for securing at least two objects together.

And the present invention provides new and improved surgical methods and apparatus for fastening mechanical structures to tissues or blood vessels, for example, for drug delivery.

More particularly, the present invention comprises the provision and use of a novel fastener which is used to occlude a vein (e.g., the proximal saphenous vein, the small saphenous vein, tributaries, the perforator veins, etc.) so as to restrict blood flow through the vein and thereby treat varicose veins below the point of occlusion. Significantly, the novel fastener is configured to be deployed using a minimally-invasive approach (i.e., either percutaneously or endoluminally), with visualization being provided by ultrasound and/or other visualization apparatus (e.g., CT, MRI, X-ray etc.). As a result, the novel treatment can be provided in a doctor's office, with minimal local anesthetic, and effectively no post-operative care.

FIGS. 1-4 show, diagrammatically, a form of fastener 30 that may comprise a transluminal section 85, a far side lateral projection 90 and a near side lateral projection 95, with the far side lateral projection 90 and the near side lateral projection 95 being held in opposition to one another so as to close down a lumen of a blood vessel or attach layers of tissue or non-tissue together. Such an arrangement may be provided by many different types of structures, e.g., such as the "double T-bar" structure shown in FIGS. 5-7 where the transluminal section 85 of the fastener 30 is formed out of an elastic material which draws the two opposing T-bars 90, 95 of the fastener together so as to provide clamping or vessel occlusion. By way of further example but not limitation, far side lateral projection 90 and near side lateral projection 95 may be connected together by a loop of suture, with the loop of suture being lockable in a reduced size configuration with a sliding locking knot.

Furthermore, multiple fasteners 30 may be used on tissue or to occlude a blood vessel more completely, or to occlude a blood vessel in multiple regions, or to attach a material (e.g., a drug or cellular delivery element) in multiple places to tissue or to a blood vessel. The fasteners may be coated with a drug-eluting compound, or the fasteners may be electrically charged to enhance or prevent clotting or to deliver a desired compound or agent to the blood vessel, etc. If desired, the location of the occluding or attachment element may be precisely controlled to deliver the desired compound or agent at a specific anatomical location.

Drug/Cellular Delivery Applications

The fastener 30 may be modified so as to allow drug/cellular delivery at fixed points within or adjacent to the vasculature or other hollow bodily structure. In this form the device may be provided with a drug/cellular delivery body 105 attached thereto, is advanced across a blood vessel 110 or attached to tissue Two-Part Fastener Looking next at FIG. 8, there is shown a two-part fastener 200 formed in accordance with the present invention. Two-part fastener 200 generally comprises a distal implant 205 and a proximal implant 210.

Distal implant 205 is shown in further detail in FIGS. 9-12. Distal implant 205 comprises a distal implant body 215 and a distal implant locking tube 220. Distal implant body 215 comprises a tube 225 having a distal end 226, a proximal end 227, and a lumen 230 extending therebetween. Tube 225 is slit intermediate its length so as to define a plurality of legs 235. A set of inwardly-projecting tangs 240 are formed in tube 225 between legs 235 and proximal end 227. A set of windows 245 are formed in tube 225 between inwardly-projecting tangs 240 and proximal end 227. Distal implant body 215 is preferably formed out of an elastic material (e.g., a shape memory material having superelastic properties such as Nitinol or superelastic polymers, including superelastic plastics) and constructed so that its legs 235 normally project laterally away from the longitudinal axis of tube 225 (e.g., in the manner shown in FIGS. 9 and 10, however, due to the elastic nature of the material used to form distal implant body 215, legs 235 can be constrained inwardly (e.g., within the lumen of a delivery needle, as will hereinafter be discussed) so that distal implant body 215 can assume a substantially linear disposition. See, for example, FIG. 12, which shows legs 235 moved inwardly relative to the position shown in FIGS. 9 and 10. However, when any such constraint is removed, the elastic nature of the material used to form distal implant body 215 causes legs 235 to return to the position shown in FIGS. 9 and 10.

Distal implant locking tube 220 (FIG. 11) comprises a generally tubular structure having a distal end 250, a proximal end 260 and a lumen 262 extending therebetween. A set of windows 265 are formed in the distal implant locking tube 220, with windows 265 being disposed distal to proximal end 260.

Distal implant locking tube 220 is disposed within lumen 230 of distal implant body 215. When distal implant 205 is in its aforementioned substantially linear condition (i.e., with legs 235 restrained in an in-line condition), distal implant locking tube 220 terminates well short of tangs 240 of distal implant body 215, so that the proximal end 227 of distal implant body 215 can move longitudinally relative to distal end 226 of distal implant body 215. However, when the proximal end 227 of distal implant body 215 is moved distally a sufficient distance to allow full radial expansion of legs 235 (see FIG. 8), locking tangs 240 of distal implant body 215 will be received within windows 265 of distal implant locking tube 220, whereby to lock distal implant 205 in its radially-expanded condition (i.e., with legs 235 projecting laterally away from the longitudinal axis of tube 225, e.g., in the manner shown in FIGS. 9 and 10). Spot welds applied via openings 270 formed in the distal end 226 of distal implant body 215 serve to lock distal implant locking tube 220 to distal implant body 215, whereby to form a singular structure (see FIGS. 9 and 12).

Looking next at FIGS. 13 and 14, proximal implant 210 comprises a tube 275 having a distal end 280, a proximal end 285, and a lumen 290 extending therebetween. Tube 275 is slit at its distal end so as to define a plurality of legs 295. A set of inwardly-projecting tangs 300 are formed in tube 275 between legs 295 and proximal end 285. Proximal implant 210 is preferably formed out of an elastic material (e.g., a shape memory material having superelastic properties such as Nitinol) and constructed so that its legs 295 normally project laterally away from the longitudinal axis of tube 275 (e.g., in the manner shown in FIG. 13), however, legs 295 can be constrained inwardly (e.g., within the lumen of a delivery tube, as will hereinafter be discussed) so that proximal implant 210 can assume a substantially linear disposition. See, for example, FIG. 14, which shows legs 295 moved inwardly relative to the position shown in FIG. 13. However, when any such constraint is removed, the elastic nature of the material used to form proximal implant 210 causes legs 295 to return to the position shown in FIG. 13.

Figure 45:
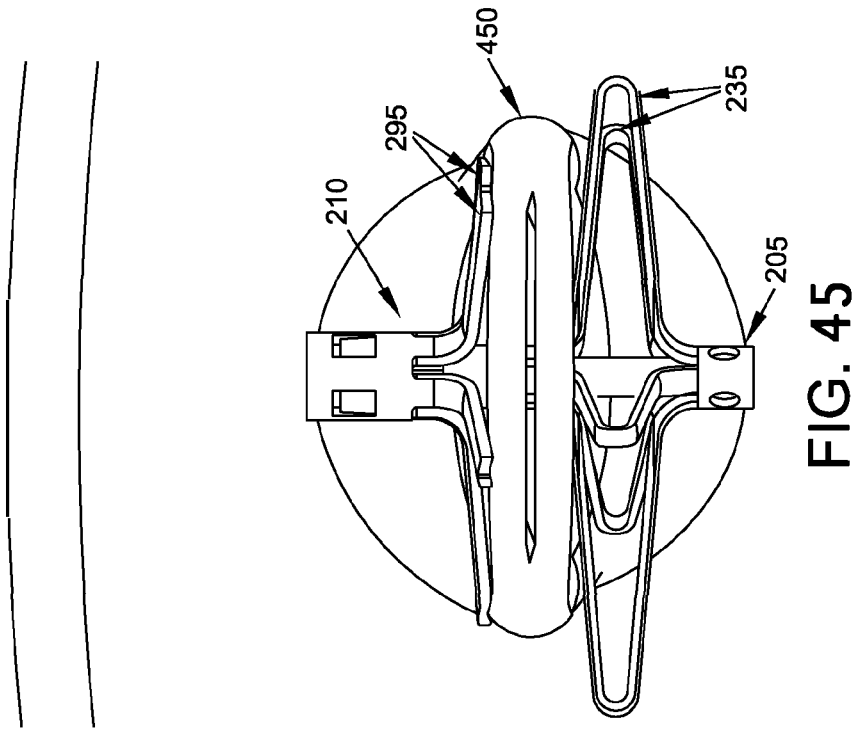

As will hereinafter be discussed, distal implant 205 and proximal implant 210 are configured and sized so that tube 225 of distal implant body 215 can be received in lumen 290 of proximal implant 210, with the expanded legs 235 of distal implant 205 opposing the expanded legs 295 of proximal implant 210 (see, for example, FIG. 45), whereby to impose a clamping action on the side wall of a blood vessel (e.g., vein) disposed therebetween and thereby occlude the blood vessel, as will hereinafter be discussed in further detail (or, as an alternative, the opposing expanded legs of the proximal and distal implants could interdigitate to impose the clamping action). Furthermore, distal implant 205 and proximal implant 210 are configured and sized so that they may be locked in this position, inasmuch as inwardly-projecting tangs 300 of proximal implant 210 will project into windows 245 of distal implant 205.

Figure 16:
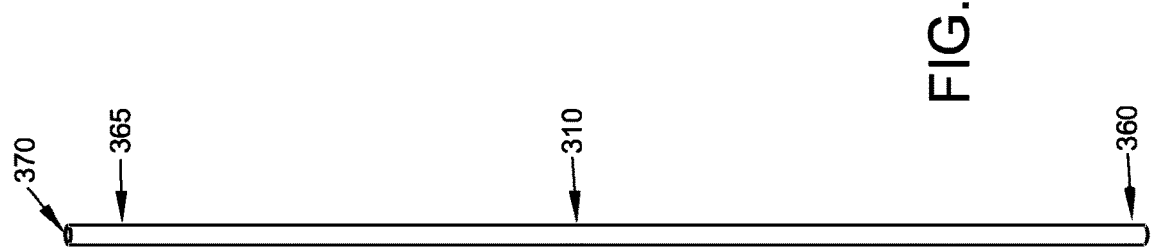
Figure 15:
Figure 17:
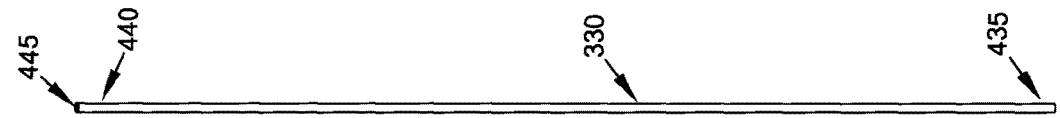
Figure 18:
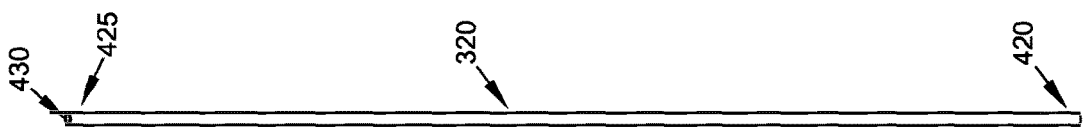
Figure 19:
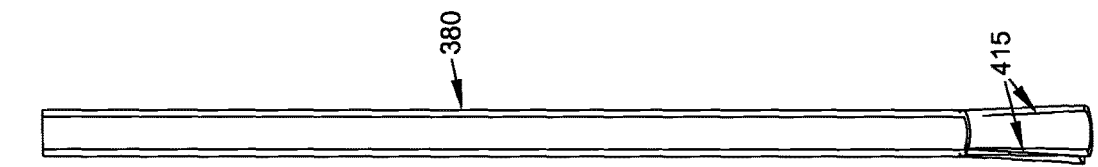
Figure 20:
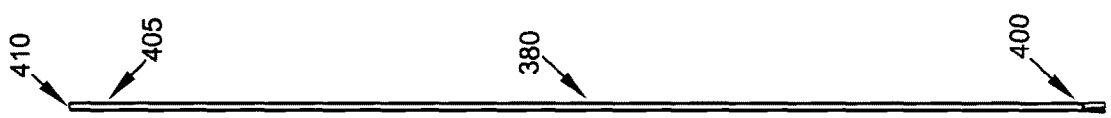

Two-part fastener 200 is intended to be deployed using associated installation apparatus. This associated installation apparatus preferably comprises a hollow needle 305 (FIG. 15) for penetrating tissue, a distal implant delivery tube 310 (FIG. 16) for delivering distal implant 205 through hollow needle 305 to the far side of the blood vessel which is to be occluded, a composite guidewire 315 (FIGS. 17-22) for supplying support to various components during delivery and deployment, a push rod 320 (FIG. 23) for delivering various components over composite guidewire 315, and a proximal implant delivery tube 330 (FIG. 24) for delivering proximal implant 210 for mating with distal implant 205, as will hereinafter be discussed.

Hollow needle 305 (FIG. 15) comprises a distal end 335, a proximal end 340 and a lumen 345 extending therebetween. Distal end 335 terminates in a sharp point 350. In one preferred form of the invention, hollow needle 305 comprises a side port 355 which communicates with lumen 345.

Distal implant delivery tube 310 (FIG. 16) comprises a distal end 360, a proximal end 365 and a lumen 370 extending therebetween.

Composite guidewire 315 (FIGS. 17-22) comprises a guidewire rod 370 and a guidewire sheath 380. Guidewire rod 370 comprises a distal end 385 and a proximal end 390. Distal end 385 terminates in an enlargement 395. Guidewire sheath 380 comprises a distal end 400, a proximal end 405 and a lumen 410 extending therebetween. The distal end 400 of guidewire sheath 380 comprises at least one, and preferably a plurality of, proximally-extending slits 415. Proximally-extending slits 415 open on the distal end of guidewire sheath 380 and allow the distal end of guidewire sheath 380 to radially expand somewhat. As will hereinafter be discussed, guidewire rod 370 and guidewire sheath 380 are configured and sized so that guidewire rod 370 can be received in lumen 410 of guidewire sheath 380. Further-more, when guidewire rod 370 is forced proximally relative to guidewire sheath 380, the proximally-extending slits 415 in guidewire sheath 380 allow the distal end of the guidewire sheath 380 to expand somewhat so as to receive at least some of the enlargement 395 formed on the distal end of guidewire rod 370. As this occurs, the distal end of guidewire sheath 380 will expand radially.

Push rod 320 (FIG. 23) comprises a distal end 420, a proximal end 425 and a lumen 430 extending therebetween.

Proximal implant delivery tube 330 (FIG. 24) comprises a distal end 435, a proximal end 440 and a lumen 445 extending therebetween.

Two-part fastener 200 and its associated installation apparatus are preferably used as follows.

First, hollow needle 305 (carrying distal implant delivery tube 310 therein, which in turn contains the composite guidewire 315 therein, upon which is mounted distal implant 205) is passed through the skin of the patient, through intervening tissue, and across the blood vessel (e.g., vein 450) which is to be occluded. See FIGS. 25-27. As this is done, any blood flowing out side port 355 can be monitored—excessive or pulsatile blood flow can indicate that hollow needle has accidentally struck an artery.

Next, hollow needle 305 is retracted, leaving distal implant delivery tube 310 extending across the blood vessel. See FIG. 25.

Then distal implant delivery tube 310 is retracted somewhat so as to expose the distal ends of composite guidewire, or rod, 315 and distal implant 205. See FIG. 26.

Figure 28:
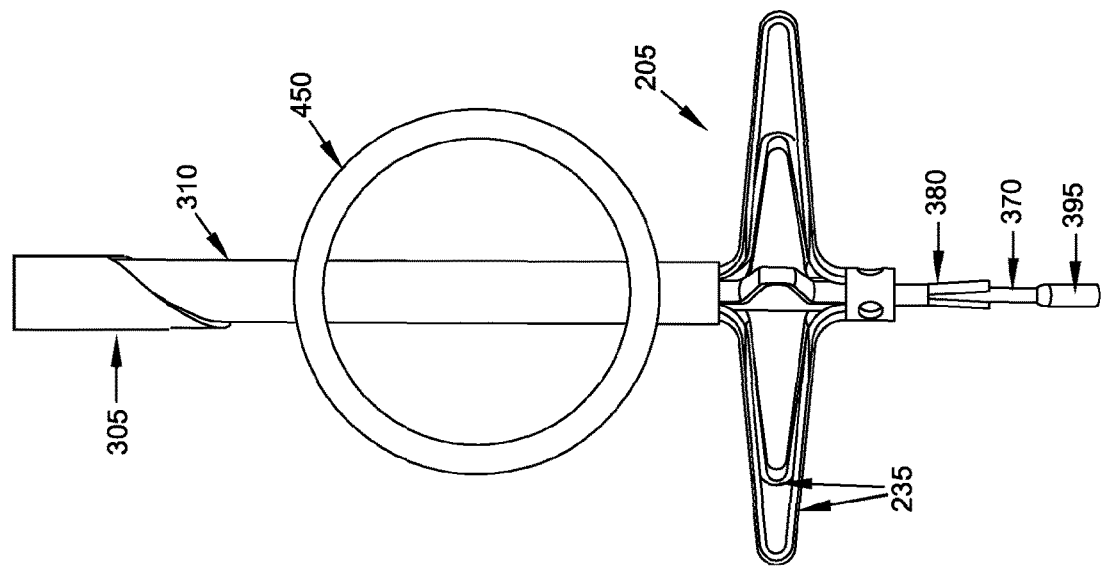

Next, composite guidewire 315, push rod 320 and distal implant 205 are all moved distally, so as to advance the distal ends of composite guidewire 315 and the distal implant 205 out of the distal end of distal implant delivery tube 310. As this occurs, legs 235 of distal implant 205 are released from the constraint of distal implant delivery tube 310 and expand radially. See FIGS. 27 and 28.

Figure 29:
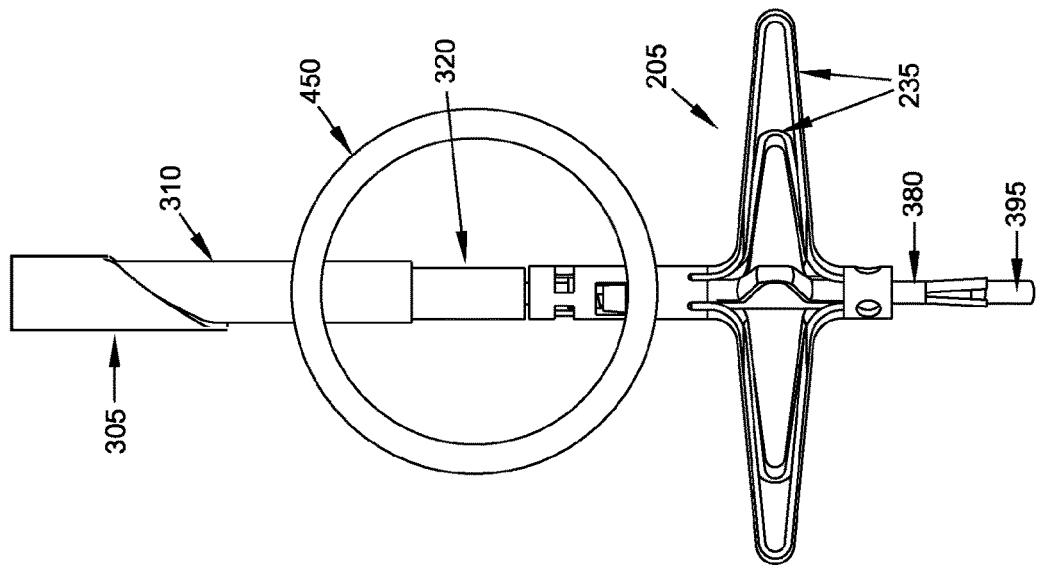

Then, with push rod 320 being held in place against the proximal end of distal implant 205, composite guidewire 315 is pulled proximally so as to bring the distal end of distal implant 205 toward the proximal end of distal implant 205, whereby to cause locking tangs 240 of distal implant body 215 to enter windows 265 of distal implant locking tube 220, whereby to lock legs 235 in their radially-expanded condition (see FIG. 29).

Figure 31:
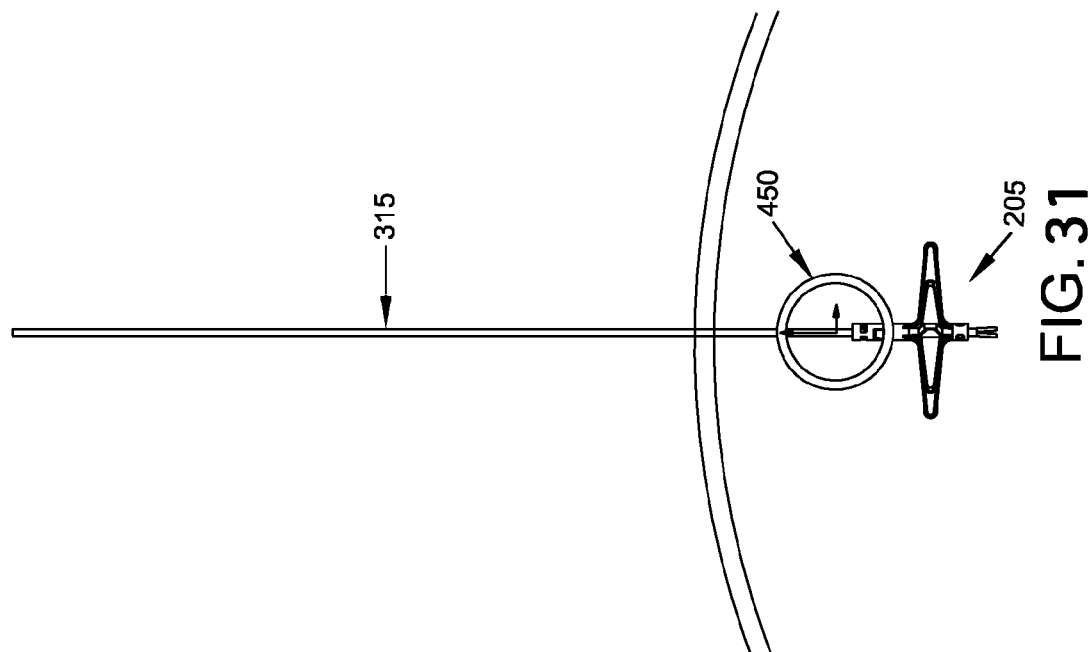
Figure 30:
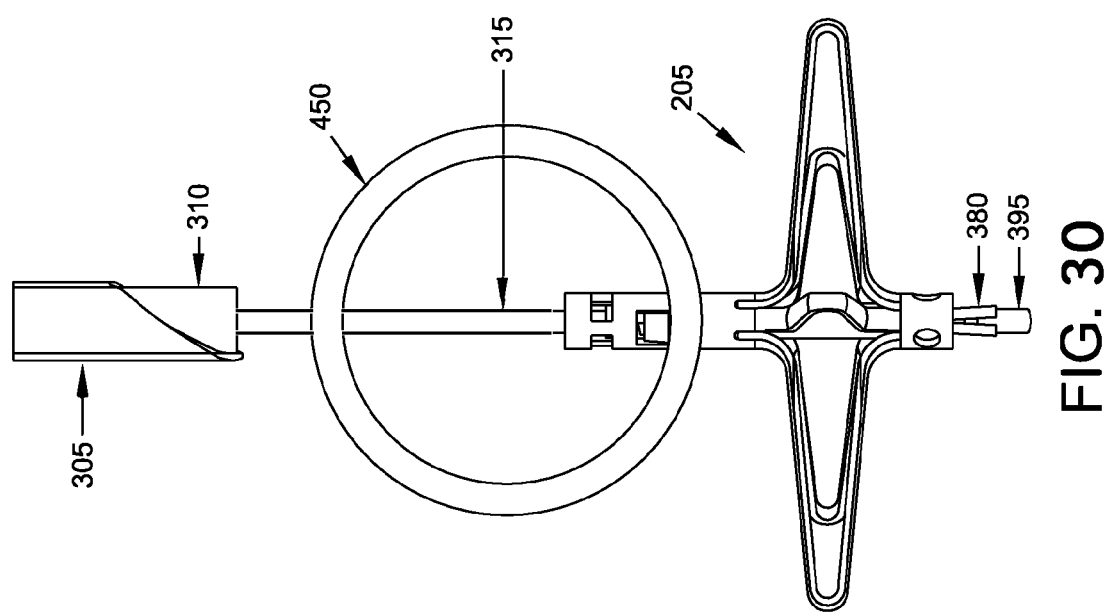
Figure 33:
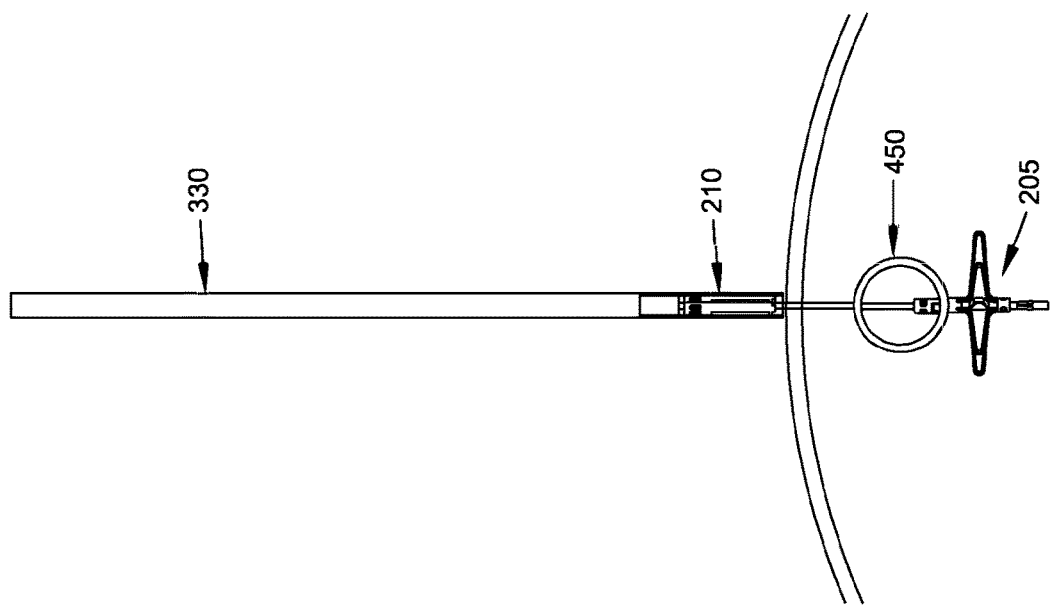
Figure 32:
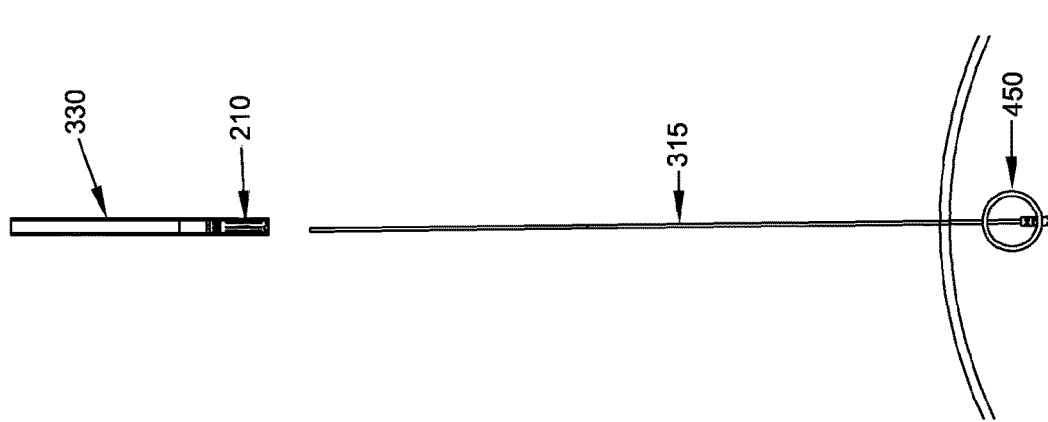
Figure 35:
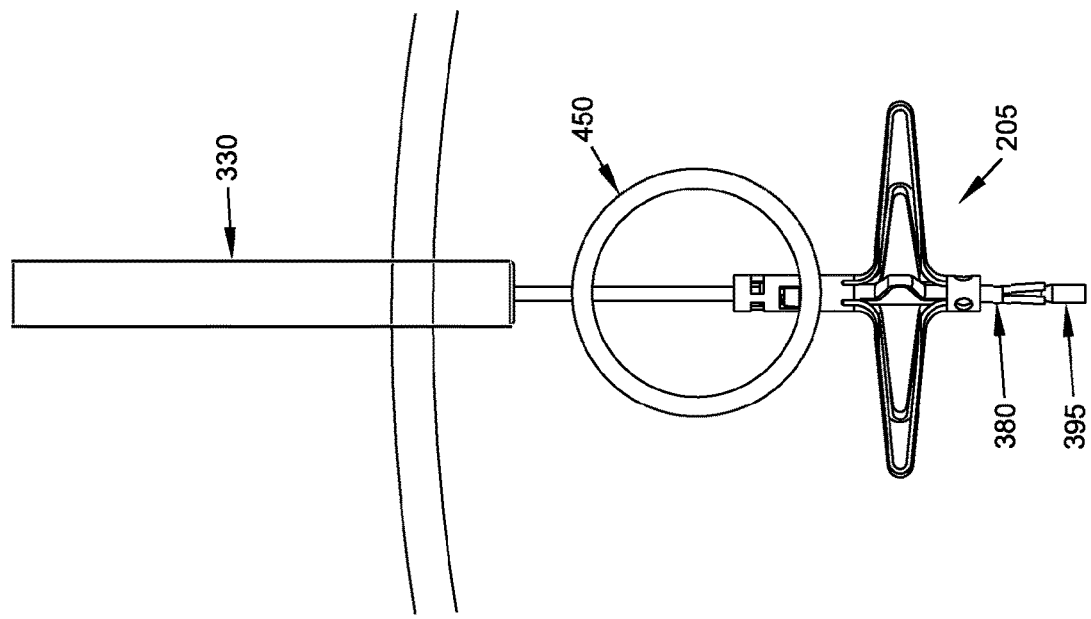
Figure 34:
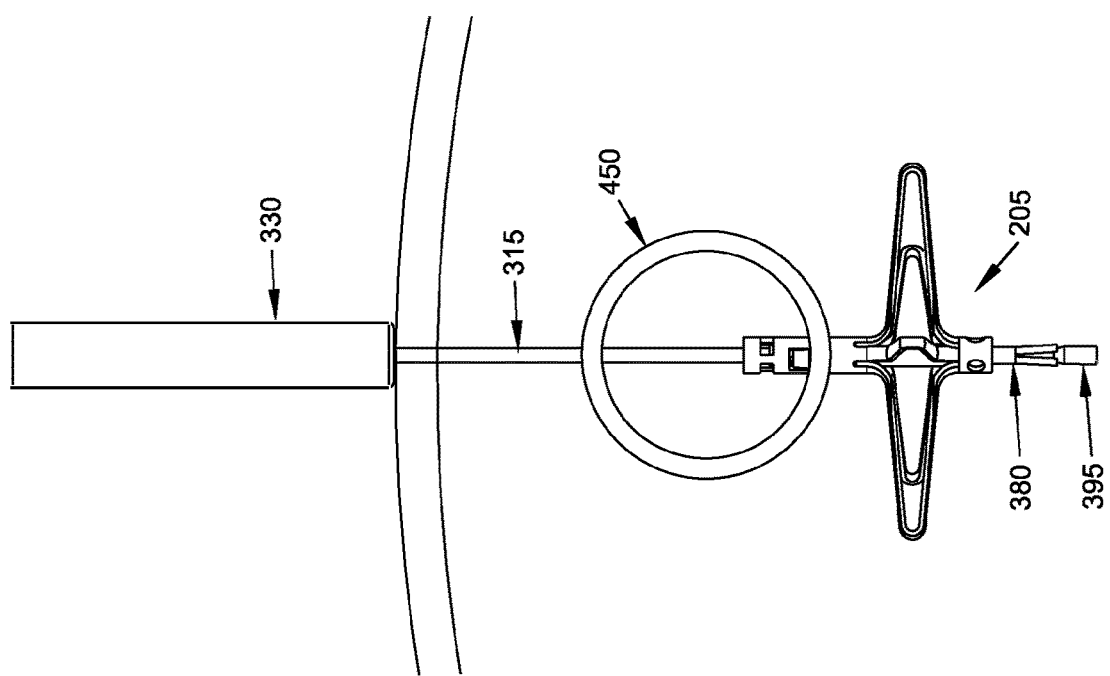
Figure 37:
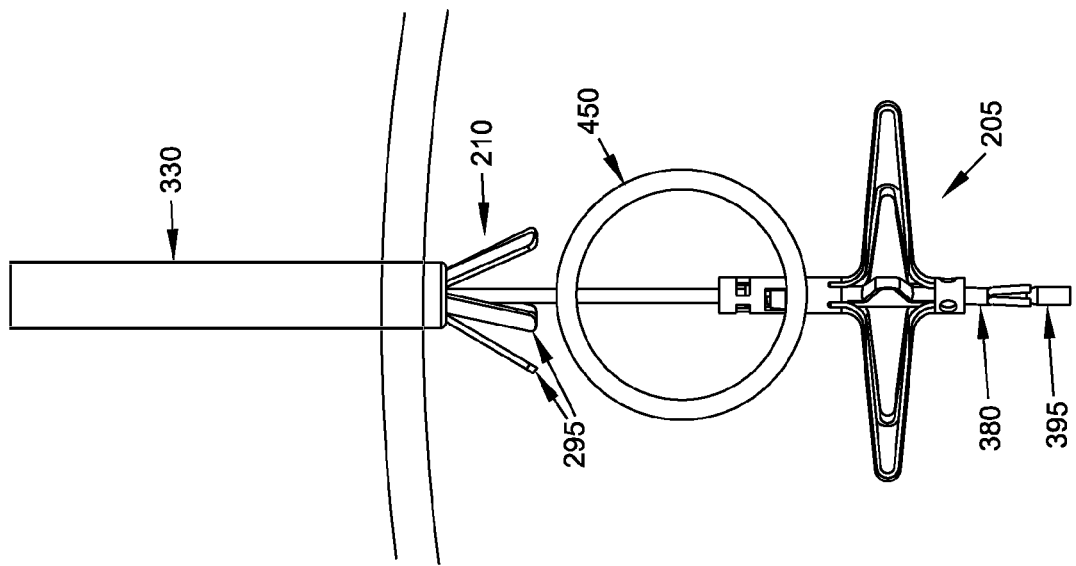
Figure 36:
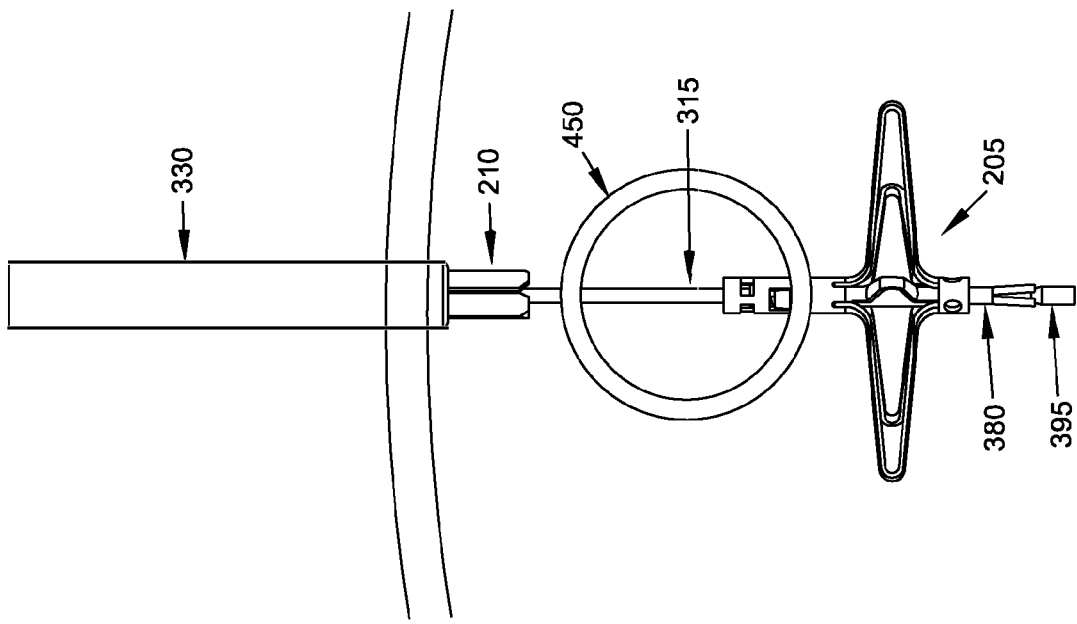
Figure 39:
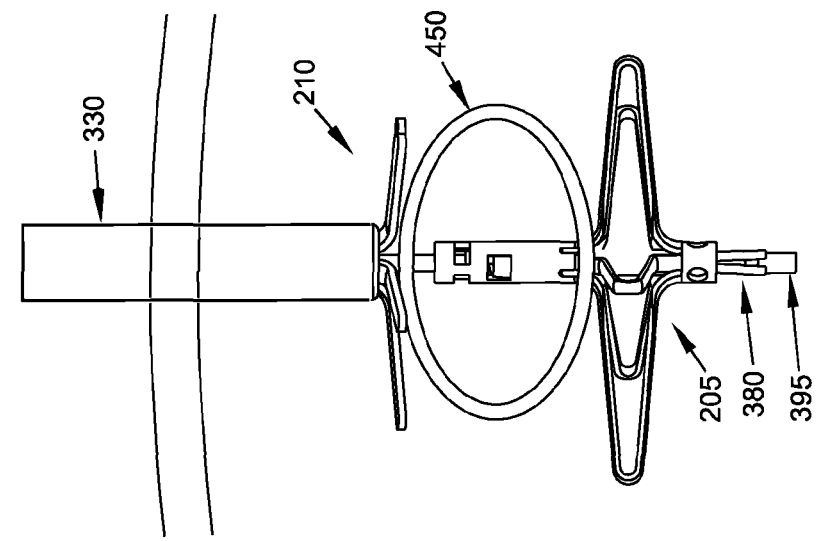
Figure 38:
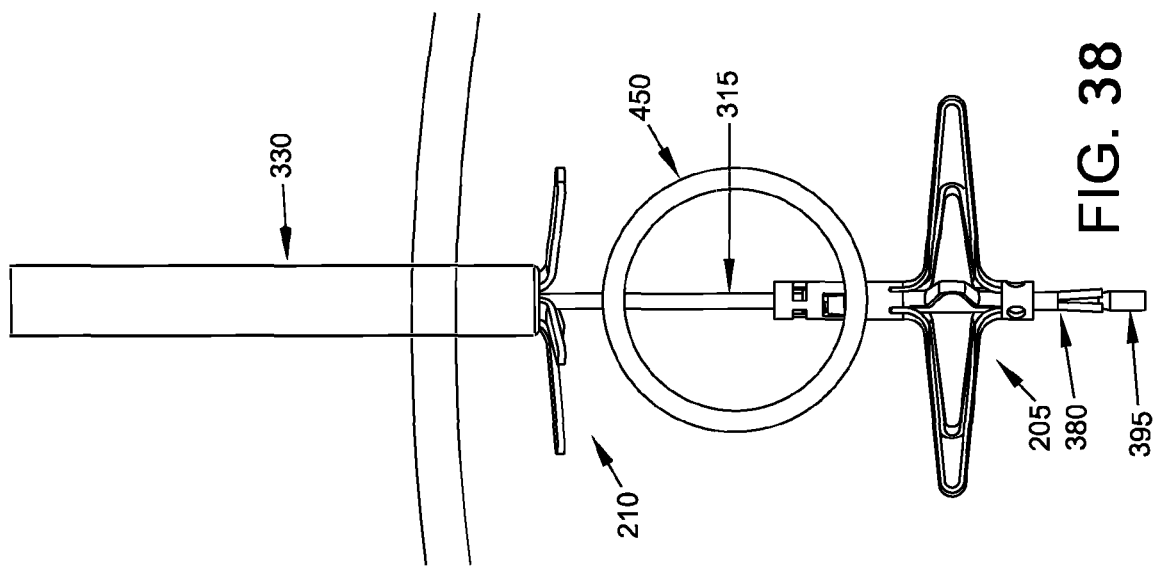

At this point, hollow needle 305, distal implant delivery tube 310 and push rod 320 may be removed (FIG. 30), leaving distal implant 205 mounted on composite guidewire 315, with the legs 235 fully deployed on the far side of the blood vessel and the proximal end of distal implant 205 extending into the interior of the blood vessel (FIG. 31).

Next, proximal implant delivery tube 330 (carrying proximal implant 210 therein) is advanced down composite guidewire 315, until the distal end of proximal implant delivery tube 330 sits just proximal to the blood vessel (FIGS. 32-35).

Then push rod 320 is used to advance the distal end of proximal implant 210 out of the distal end of proximal implant delivery tube 330. As this occurs, legs 295 are released from the constraint of proximal implant delivery tube 330 and open radially. See FIGS. 36-39.

Figure 40:
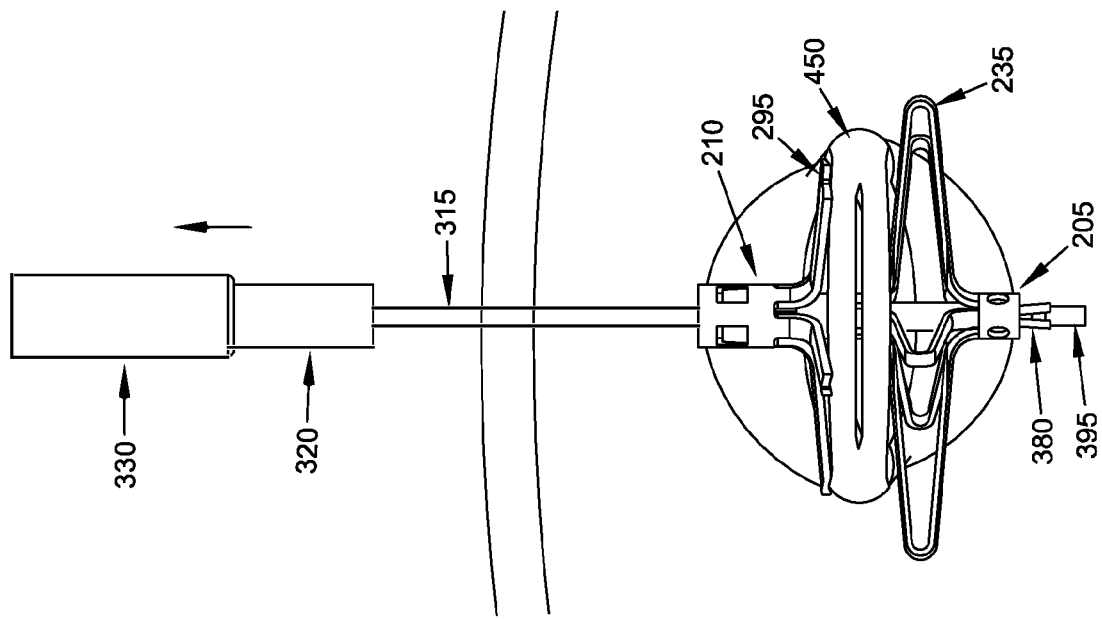

Next, using push rod 320, proximal implant 210 is pushed distally as distal implant 205 is pulled proximally using composite guidewire 315. More particularly, guidewire rod 370 is pulled proximally, which causes enlargement 395 on the distal end of guidewire rod 370 to expand guidewire sheath 380 to a size larger than lumen 262 in distal implant locking tube 220, which causes guidewire sheath 380 to move proximally, which causes proximal movement of distal implant 205. As distal implant 205 and proximal implant 210 move together, their legs 235, 295 compress the blood vessel, thereby occluding the blood vessel. Distal implant 205 and proximal implant 210 continue moving together until inwardly-projecting tangs 300 of proximal implant 210 enter windows 245 of distal implant 205, thereby locking the two members into position relative to one another. See FIG. 40.

Figure 41:
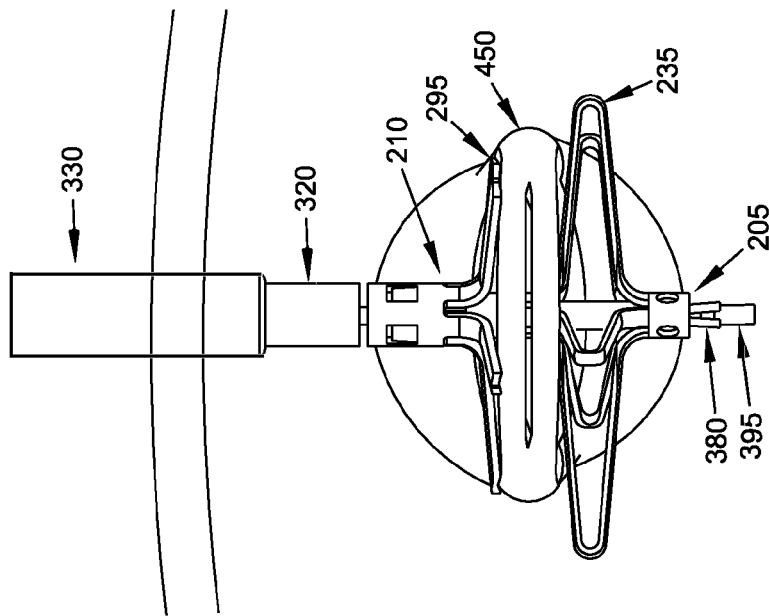

At this point push rod 320 and proximal implant delivery tube 330 are removed. See FIG. 41.

Figure 43:
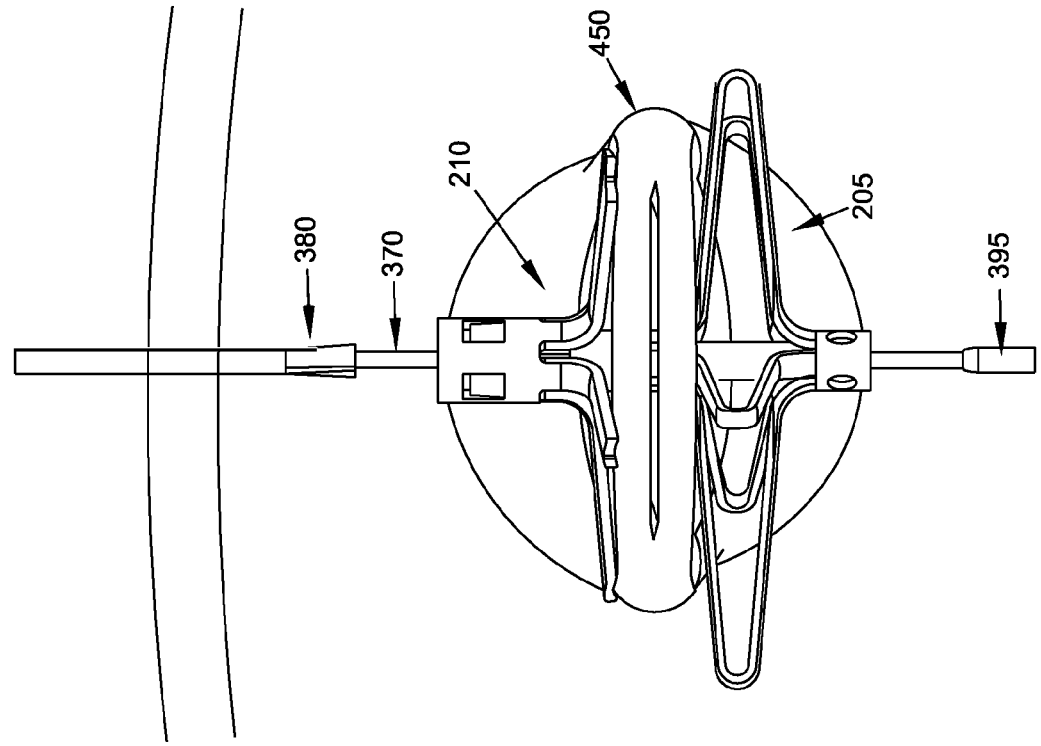
Figure 42:
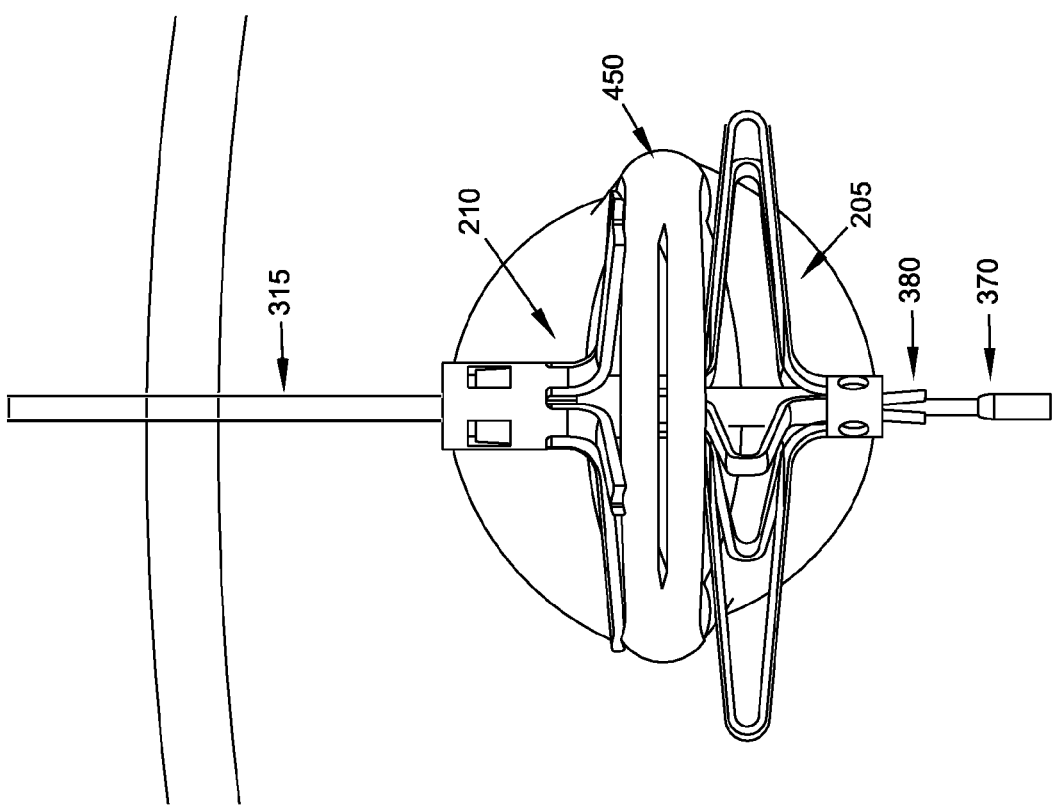
Figure 44:
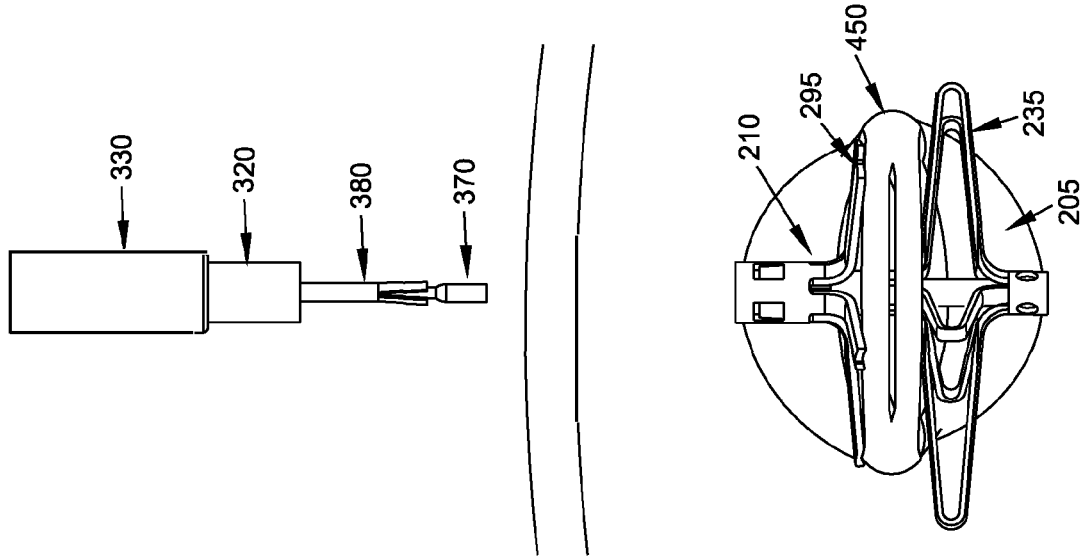

Next, composite guidewire 315 is removed. This is done by first advancing guidewire rod 370 distally (FIG. 42), which allows the distal end of guidewire sheath 380 to relax inwardly, thereby reducing its outer diameter to a size smaller than lumen 262 in distal implant locking tube 220. As a result, guidewire sheath 380 can then be withdrawn proximally through the interior of two-part fastener 200. See FIG. 43. Then guidewire rod 370 can be withdrawn proximally through the interior of two-part fastener 200. See FIG. 44.

The foregoing procedure leaves two-part fastener 200 locked in position across the blood vessel, with the opposing legs 235, 295 compressing the blood vessel, whereby to occlude the blood vessel.

Figure 47:
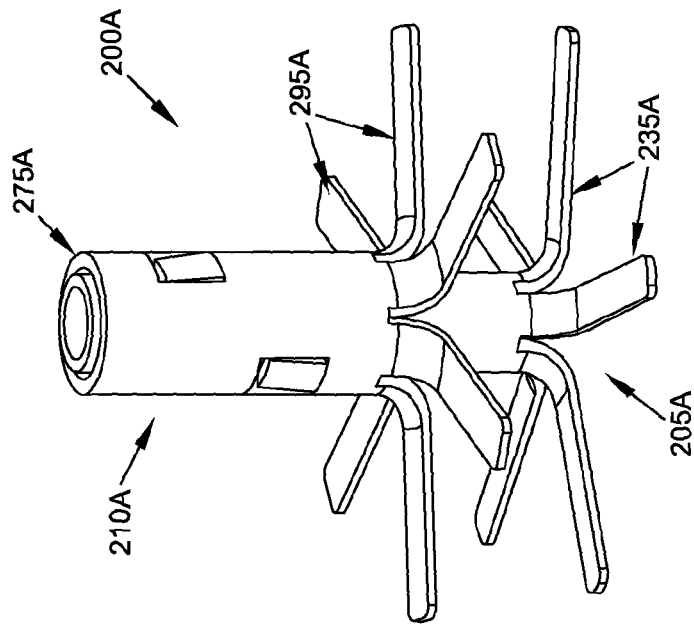
FIGS. 46-49 are schematic views showing a two-part fastener formed in accordance with the present invention.
Figure 48:
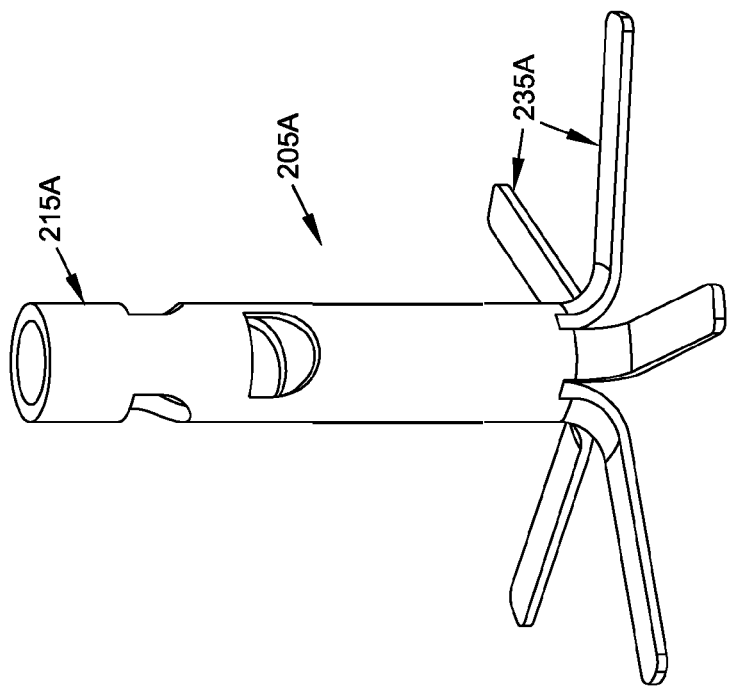
Figure 51:
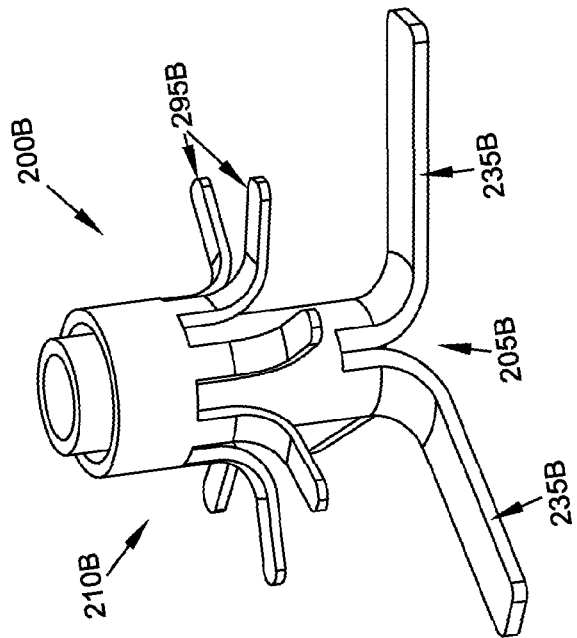
FIGS. 50-53 are schematic views showing still another two-part fastener formed in accordance with the present invention.
Figure 50:
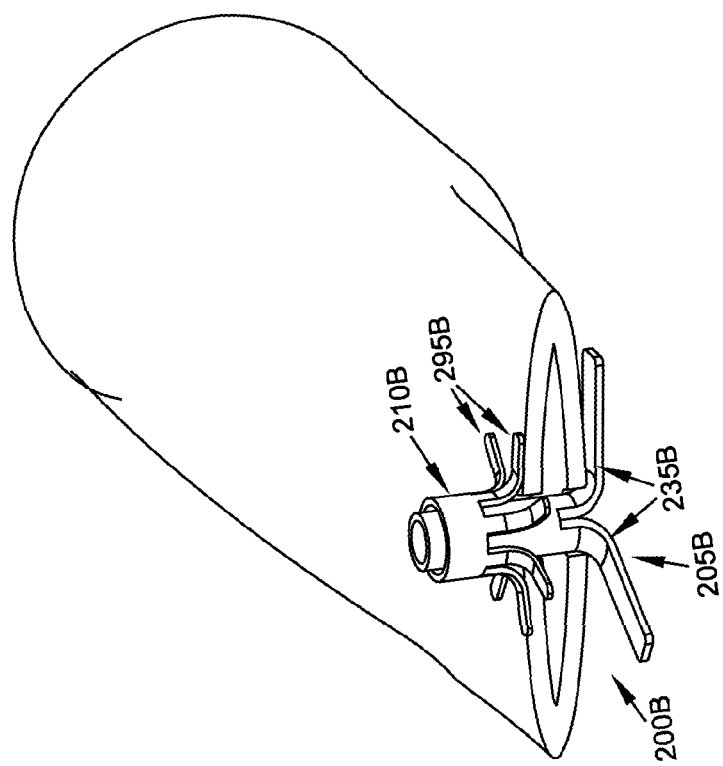
Figure 53:
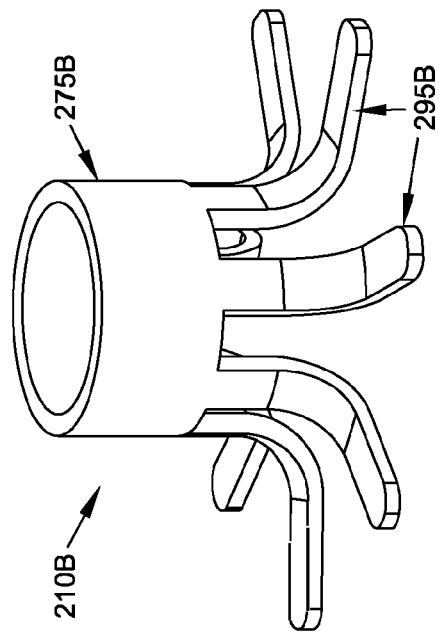
Figure 52:
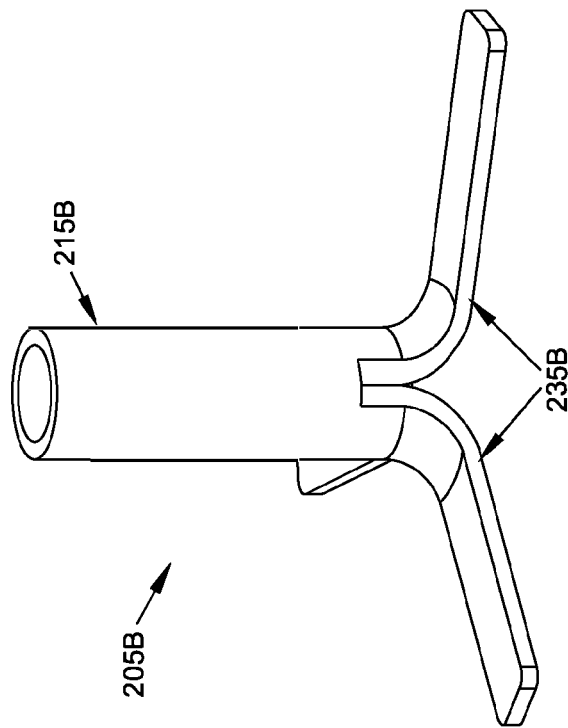

FIGS. 46-49 illustrate an embodiment of a two-part fastener 200A embodying principles of the invention. Two-part fastener 200 generally comprises a distal implant 205A and a proximal implant 210A. Distal implant 205A is shown in further detail in FIG. 48. Distal implant 205A comprises a tubular distal implant body 215A having a distal end 226A, a proximal end 227A, and a lumen 230A. The distal end of the body 215A is slit to define a plurality of legs 235A that can extend generally radially, as shown when the implant is released from its delivery tube. A set of windows 245A are formed in the tubular body. Distal implant body 215A is preferably formed out of an elastic material (e.g., a shape memory material having superelastic properties such as Nitinol or superelastic polymers, including superelastic plastics) and constructed so that its legs 235 normally project radially outwardly as shown in FIGS. 47 and 48), however, due to the elastic nature of the material used to form distal implant body 215A, legs 235A can be constrained inwardly to a tubular shape containable within the lumen of a delivery needle. When any such constraint is removed, the elastic nature of the material causes legs 235A to return to their relaxed, expanded position.

Figure 46:
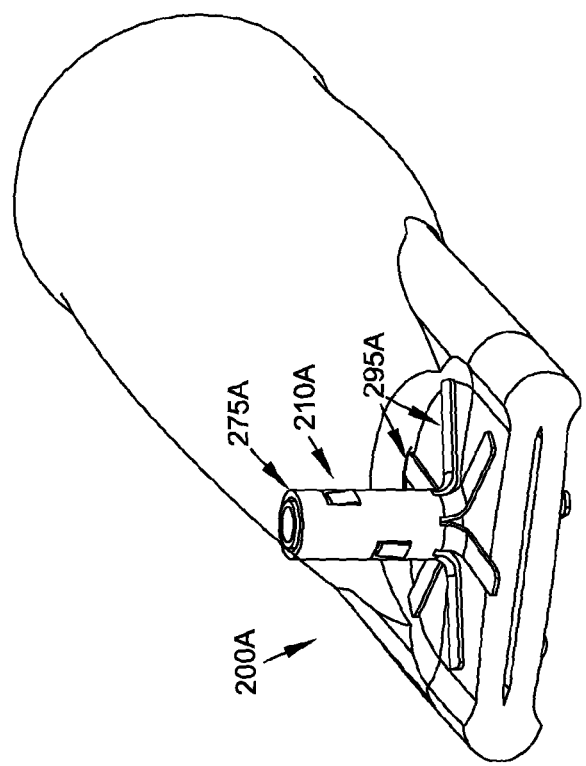
Figure 49:
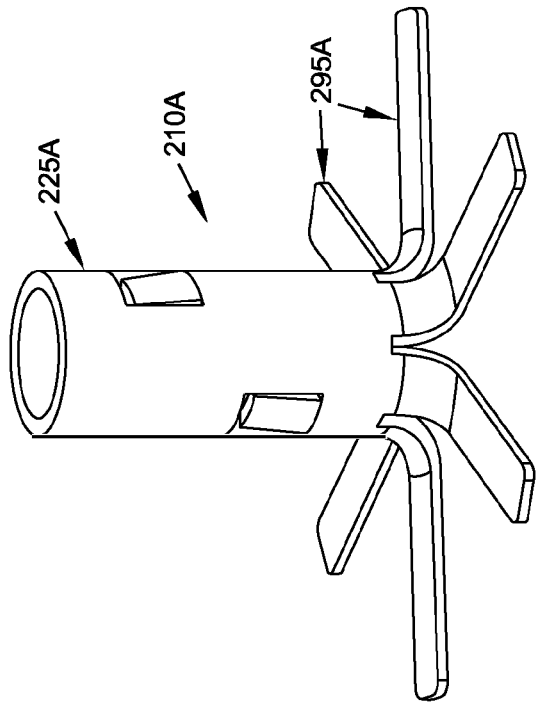

FIGS. 46, 47 and 49 show proximal implant 210A comprises a tube 275A having a distal end 280A, a proximal end 285A, and a lumen 290A. The inner diameter of the lumen 290A of the tube is greater than the outer diameter of the tubular body 215A of the distal implant so that it can receive the proximal end of the distal body as shown in FIG. 47. The distal implant also is formed from a superelastic material and is slit at its distal end to define a plurality of legs 295A that will expand to a relaxed, radially extended shape when released from a delivery tube in the same manner as the distal implant. A set of inwardly-projecting tangs 300A are formed in tube 275A and are arranged to be received in the windows 245A of the tubular body of the distal implant when the implants are brought together, this locking the implants together, as shown in FIG. 47. Tissue or non-tissue (or both) disposed between the legs of the proximal and distal legs will be clamped with the tubular body of the distal implant extending through an aperture in the tissue and/or non-tissue, transfixing them together (See FIG. 46). In this embodiment, the implants may be formed to have relatively short tubular portions to define a low-profile configuration in which the height of the tubular body of the implant is no greater than about the maximum diameter of its expanded legs.

Two-part fastener 200 may be deployed using associated installation apparatus that may comprise a hollow needle 305 (FIG. 15) for penetrating tissue, a retention guidewire 315 (FIGS. 17-22) for temporarily maintaining the position of the distal implant, a push rod 320 (FIG. 23) for controlling the position of the proximal implant Hollow needle 305 (FIG. 15) comprises a distal end 335, a proximal end 340 and a lumen 345 extending therebetween. Distal end 335 terminates in a sharp point 350. Hollow needle 305 may have a side port 355 which communicates with lumen 345.

The retention wire may be in the form of a composite guidewire 315 (FIGS. 17-22) that includes an elongated guidewire rod 370 and a guidewire sheath 380 having a lumen that receives the rod. The distal end 385 of the guidewire rod 370 terminates in an enlargement 395. The distal end 400 of guidewire sheath 380 has proximally extending slits 416 that allow the distal end of guidewire sheath 380 to expand radially when the enlarged end of the rod 370 is drawn into the slit end of the sheath. The expanded end of the sheath can engage the deployed distal implant to retain the distal implant in position while the proximal implant is deployed.

In the deployment of the fastener, hollow needle 305, loaded with the distal and proximal implants arranged in tandem, and with the retention guidewire 315 extending through the implants is advanced to the tissue site to be fastened or occluded with the needle passing through the layers (tissue and/or non-tissue) to be fastened. As this is done, any blood flowing out side port 355 can be monitored—excessive or pulsatile blood flow can indicate that hollow needle has accidentally struck an artery. With the distal tip of the needle located distally of the tissue and with the distal tip of the retention guidewire extended slightly beyond the tip of the needle and in its slightly expanded configuration, the pusher tube is maintained in its position to maintain the positions of the implants and the delivery needle is withdrawn proximally to release the distal implant from the needle and to enable the legs of the distal implant to expand. The retention guidewire maintains the distal implant in its position. Next, with the proximal implant retained within the delivery needle, the needle is withdrawn sufficiently to locate the proximal implant on the proximal side of the layers to be fastened. Then, with the pusher tube in engagement with the proximal end of the proximal implant, the needle is further withdrawn to release the proximal implant. Then, by manipulating the retention guidewire and the pusher tube the implants can be drawn together to lock the implants together and fastening the layers together between the legs of the implants. The retention guidewire then can be configured to a removable state and, together with the pusher, can be removed from the patient.

FIGS. 50-53 illustrate another two-part fastener 200B. Two-part fastener 200B is generally similar to the aforementioned two-part fastener 200A, except that distal implant 205B utilizes a friction fit to lock distal implant 205B to proximal implant 210B.

FIGS. 54-57 illustrate another two-part fastener 200C having a distal implant 205C and a proximal implant 210C. Two-part fastener 200C is generally similar to the aforementioned two-part fastener 200, except that distal implant 205C comprises a tube 225C which receives and secures the proximal ends of legs 235C. Legs 235C are preferably elongated elements (e.g., bent wires) formed out of a superelastic shape memory material so as to provide the legs 235C with the desired degree of elasticity.

The composite guidewire 315 can be replaced by an alternative guidewire which includes a mechanism for releasably binding the alternative guidewire to distal implant 205. By way of example but not limitation, such an alternative guidewire may include screw threads, and distal implant 205 may include a screw recess, so that the alternative guidewire can be selectively secured to, or released from, the distal implant 205, i.e., by a screwing action.

Looking next at FIGS. 58-61, there is shown another two-part fastener 200E formed in accordance with the present invention. Two-part fastener 200E generally comprises a distal implant 205E and a proximal implant 210E.

Distal implant 205E comprises a distal implant body 215E and a distal implant locking tube 220E. Distal implant body 215E comprises a tube 225E having a distal end 226E and an opposing proximal end. Preferably distal implant 205E has a lumen 230E extending distally from its proximal end. Lumen 230E may extend along the entire length of distal implant body 215E or it may terminate short of the distal end of distal implant body 215E. By way of example but not limitation, where two-part fastener 200E is to be set over a guidewire, lumen 230E extends along the entire length of distal implant body 215E. Tube 225E is slit intermediate its length so as to define a plurality of legs 235E. Distal implant body 215E is preferably formed at least in part out of an elastic material (e.g., a shape memory material having superelastic properties such as Nitinol or superelastic polymers, including superelastic plastics) and is constructed so that its legs 235E normally project laterally away from the longitudinal axis of tube 225E (e.g., in the manner shown in FIGS. 58-61), however, due to the elastic nature of the material used to form at least the legs 235E of distal implant body 215E, legs 235E can be constrained inwardly (e.g., within the lumen of a delivery needle, as will hereinafter be discussed) so that distal implant body 215E can assume a substantially linear disposition (in which case the distalmost tips of legs 235E converge to form the aforementioned proximal end of distal implant body 215E). However, when any such constraint is removed (e.g., when distal implant body 215 is no longer constrained within a delivery needle), the elastic nature of the material used to form at least the legs 235E of distal implant body 215E causes legs 235E to assume the position shown in FIGS. 58-61.

Figure 58:
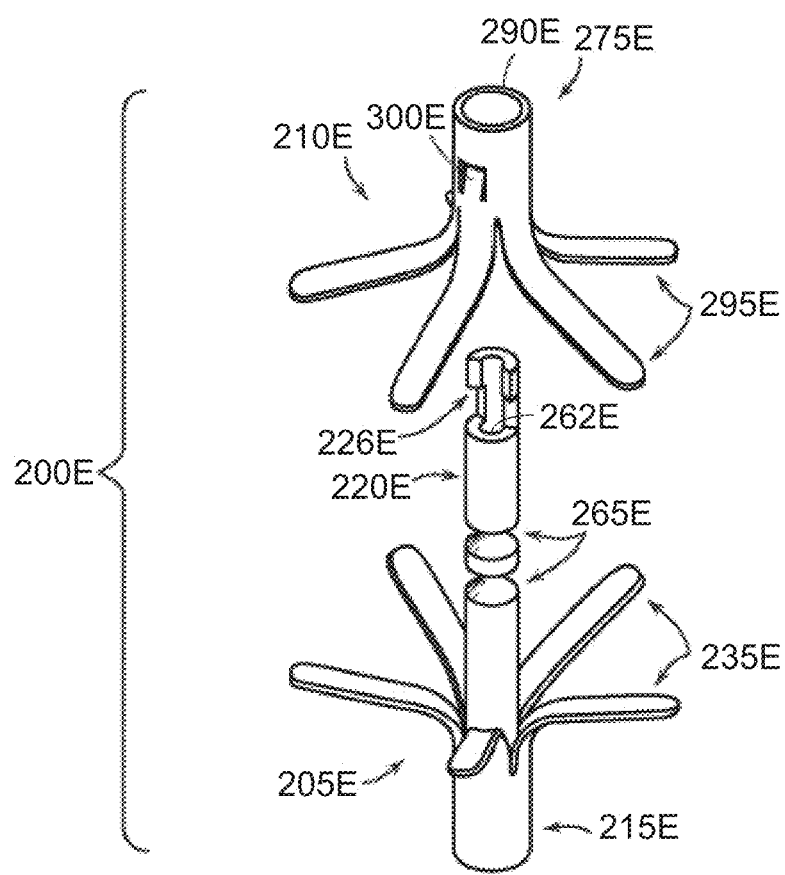
Figure 59:
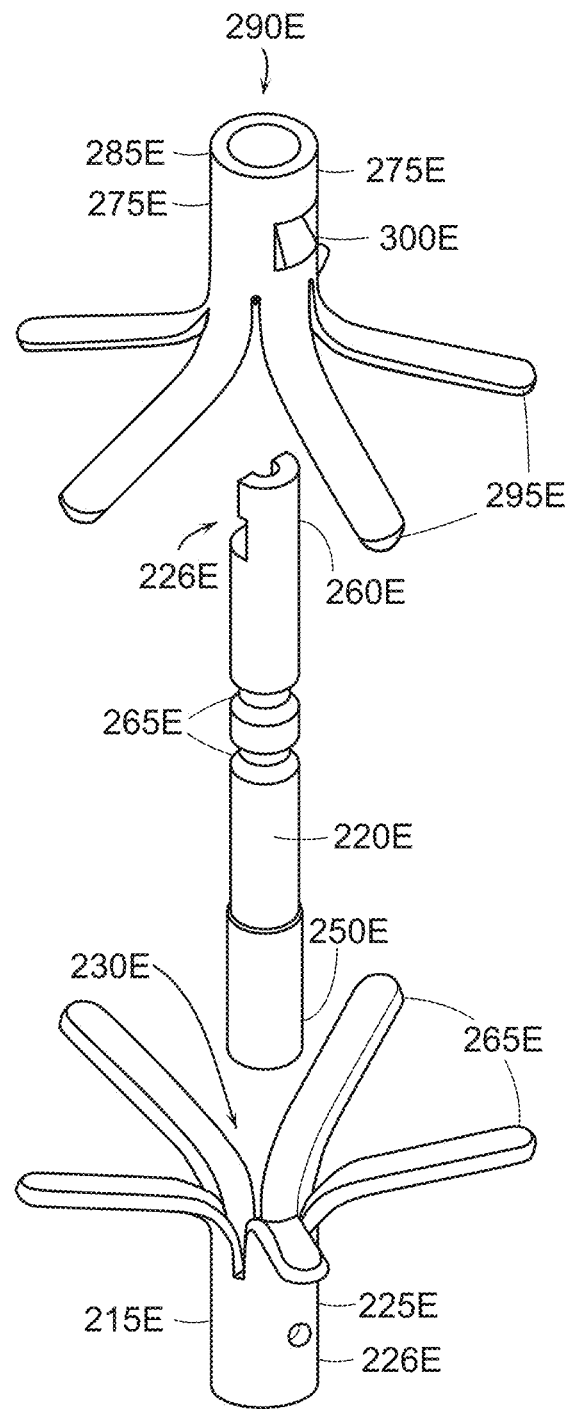
Figure 63:
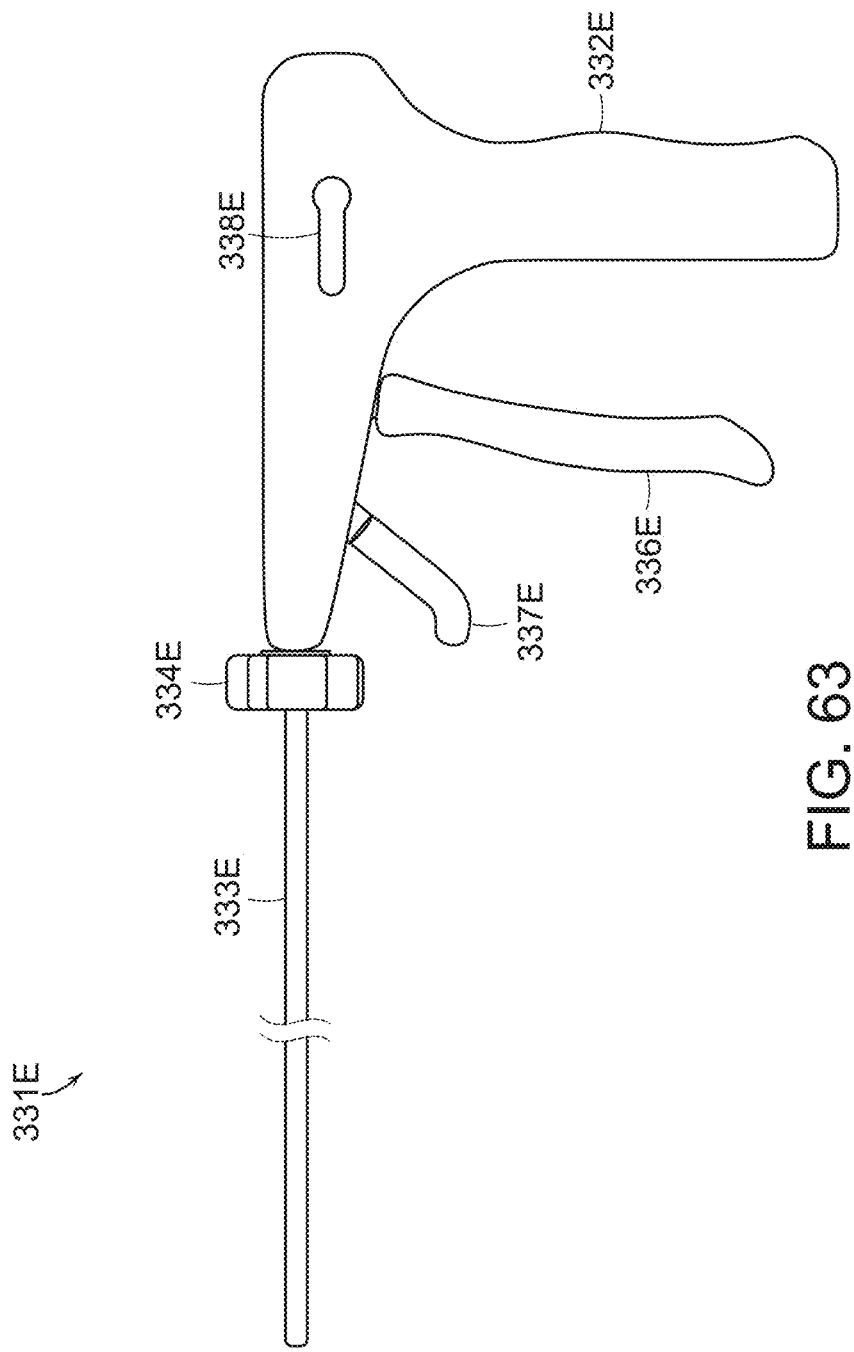

In one preferred form of the invention, and as seen in FIGS. 58-60, legs 235E of distal implant 205E extend at an acute angle to the longitudinal axis of distal implant 205E, such that legs 235E collectively define a concave region 236E.

Distal implant locking tube 220E (FIGS. 58-61) comprises a generally tubular structure having a distal end 250E and a proximal end 260E. Preferably distal implant locking tube 220E has a lumen 262E extending distally from proximal end 260E. Lumen 262E may extend along the entire length of distal implant locking tube 220E or it may terminate short of the distal end of distal implant locking tube 220E. By way of example but not limitation, where two-part fastener 200E is to be set over a guidewire, lumen 262E of distal implant locking tube 220E extends along the entire length of distal implant locking tube 220E. A set of circumferential grooves or recesses 265E are formed in distal implant locking tube 220E, with grooves or recesses 265E being disposed intermediate distal end 250E and proximal end 260E. Distal implant locking tube 220E also comprises a first half 266E of a mechanical interlock for releasably securing distal implant locking tube 220E (and hence distal implant 205E) to a distal implant delivery tube 310E (see below). Distal implant locking tube 220E is preferably formed out of a biocompatible material which is relatively inelastic along its length, whereby to minimize lengthwise stretching, although it may be somewhat flexible, whereby to allow it to be delivered over a curved path. By way of example but not limitation, distal implant locking tube 220E may be formed out of a titanium alloy such as Ti 5 AL-4V.

Distal implant locking tube 220E is disposed within, and extends proximally from, lumen 230E of distal implant body 215E. Distal implant locking tube 220E is secured to distal implant body 215E in ways well known in the art (e.g., by spot welding, adhesives, mechanical interlocks, etc.), whereby to collectively form a singular structure (see FIGS. 58-61). Note that by forming distal implant body 215E out of an elastic material, and by forming distal implant locking tube 220E out of a material which is relatively inelastic along its length, distal implant body 215E is easily deformable (e.g., so that its legs 235E can be constrained within a delivery needle) while distal implant locking tube 220E is fixed in configuration (e.g., so that it can serve to hold proximal implant 210E to distal implant 205E, as will hereinafter be discussed).

Still looking now at FIGS. 58-61, proximal implant 210E comprises a tube 275E having a distal end, a proximal end 285E, and a lumen 290E extending therebetween. Tube 275E is slit at its distal end so as to define a plurality of legs 295E. A set of inwardly-projecting tangs 300E are formed in tube 275E, between legs 295E and proximal end 285E, for engaging the aforementioned grooves or recesses 265E in distal implant locking tube 220E, as will hereinafter be discussed (note that, if desired, the locations and configurations of grooves or recesses 265E and tangs 300E can be reversed, i.e., outwardly-projecting tangs 300E can be provided on distal implant locking tube 220E and grooves or recesses 265E can be provided on the inner side wall of tube 275E, or other means can be provided for connecting tube 275E of proximal implant 210E to distal implant locking tube 220E of distal implant 205E). Proximal implant 210E is preferably formed at least in part out of an elastic material (e.g., a shape memory material having superelastic properties such as Nitinol) and constructed so that its legs 295E normally project laterally away from the longitudinal axis of tube 275E (e.g., in the manner shown in FIGS. 58-61), however, legs 295E can be constrained inwardly (e.g., within the lumen of a delivery needle, as will hereinafter be discussed) so that proximal implant 210E can assume a substantially linear disposition (with the distal ends of legs 295E collectively forming the distal end of proximal implant 210E). However, when any such constraint is removed, the elastic nature of the material used to form at least the legs 295E of proximal implant 210E causes legs 295E to return to the position shown in FIGS. 58-61.

In one preferred form of the invention, and as seen in FIGS. 58-061, legs 295E of proximal implant 210E extend at an obtuse angle to the longitudinal axis of proximal implant 210E, such that legs 295E collectively define a concave region 301E.

Note that the concavity of concave region 236E of distal implant 205E is the reverse of the concavity of concave region 301E of proximal implant 210E (in other words, and as seen in FIGS. 58-61, the concavity of concave region 236E of distal implant 205E faces the concavity of concave region 301E of proximal implant 210E).

As will hereinafter be discussed, distal implant 205E and proximal implant 210E are configured and sized so that distal implant locking tube 220E of distal implant 205E can be received in lumen 290E of proximal implant 210E, with the expanded legs 235E of distal implant 205E opposing the expanded legs 295E of proximal implant 210E (see, for example, FIGS. 60 and 61), whereby to impose a clamping action on the side walls of a blood vessel (e.g., vein) disposed therebetween and thereby occlude the blood vessel, as will hereinafter be discussed in further detail (or, as an alternative, the opposing expanded legs of the proximal and distal implants may interdigitate so as to further enhance the clamping action. Furthermore, distal implant 205E and proximal implant 210E are configured and sized so that they may be locked in this position, inasmuch as inwardly-projecting tangs 300E of proximal implant 210E will project into circumferential grooves or recesses 265E of distal implant locking tube 220E of distal implant 205E, whereby to secure proximal implant 210E to distal implant 205E. Note that the positions of circumferential grooves or recesses 265E of distal implant locking tube 220E and inwardly-projecting tangs 300E of proximal implant 210E are coordinated so that when inwardly-projecting tangs 300E of proximal implant 210E are disposed in circumferential grooves or recesses 265E of distal implant locking tube 220E, legs 235E of distal implant 205E and legs 295E of proximal implant 210E are sufficiently close to ensure adequate clamping of a blood vessel (or other tubular structure) disposed therebetween.

Two-part fastener 200E is intended to be deployed using associated installation apparatus. In one preferred form of the invention, such associated installation apparatus preferably comprises a hollow needle 305E (FIG. 66) for penetrating tissue, a distal implant delivery tube 310E (FIG. 67) for delivering distal implant 205E through hollow needle 305E to the far side of the blood vessel (or other tubular structure) which is to be occluded, and a proximal implant delivery tube 330E (FIG. 67) for delivering proximal implant 210E for mating with distal implant 205E, as will hereinafter be discussed.

If desired, the associated installation apparatus may be provided in the form of a laparoscopic device 331E as shown in FIGS. 62-70. Laparoscopic device 331E comprises a handle 332E, an outer sheath 333E, a knob 334E, a first trigger 336E, a second trigger 337E and a release lever 338E, with the functionality hereinafter described.

More particularly, hollow needle 305E (FIG. 66) comprises a distal end 335E, a proximal end (not shown, but contained within laparoscopic device 331E) and a lumen 345E extending therebetween. Distal end 335E of hollow needle 305E terminates in a sharp point 350E.

Distal implant delivery tube 310E (FIG. 67) comprises a distal end 360E and a proximal end (not shown, but contained within laparoscopic device 331E). Distal end 360E of distal implant delivery tube 310E also comprises a second half 361E of a mechanical interlock for releasably securing the distal end of distal implant delivery tube 310E to the proximal end of distal implant 205E, i.e., by the releasable interconnection of the first half 266E of the mechanical interlock (carried by the proximal end of distal implant locking tube 220E) with the second half 361E of the mechanical interlock (carried by the distal end of distal implant delivery tube 310E).

Proximal implant delivery tube 330E (FIG. 67) comprises a distal end 435E, a proximal end (not shown, but contained within laparoscopic device 331E) and a lumen 445E extending therebetween.

Two-part fastener 200E and its associated installation apparatus (e.g., laparoscopic device 331E) are preferably used as follows.

First, hollow needle 305E is passed to the occlusion site, preferably while needle 305E is contained within sheath 333E of laparoscopic device 331E (FIG. 64. Then sheath 333E is retracted, e.g., by turning knob 334E (FIG. 65), and hollow needle 305E is passed across the blood vessel (e.g., a vein) which is to be occluded (or passed across another tubular structure which is to be occluded, or passed through tissue or objects to be secured to one another, such as a solid organ, or layers of tissue, etc.).

Next, hollow needle 305E is retracted proximally, back across the blood vessel, e.g., via first trigger 336E (FIG. 66). This action allows legs 235E of distal implant 205E to expand radially on the far side of the blood vessel. At this point, distal implant locking tube 220E extends proximally through the blood vessel.

Figure 67:
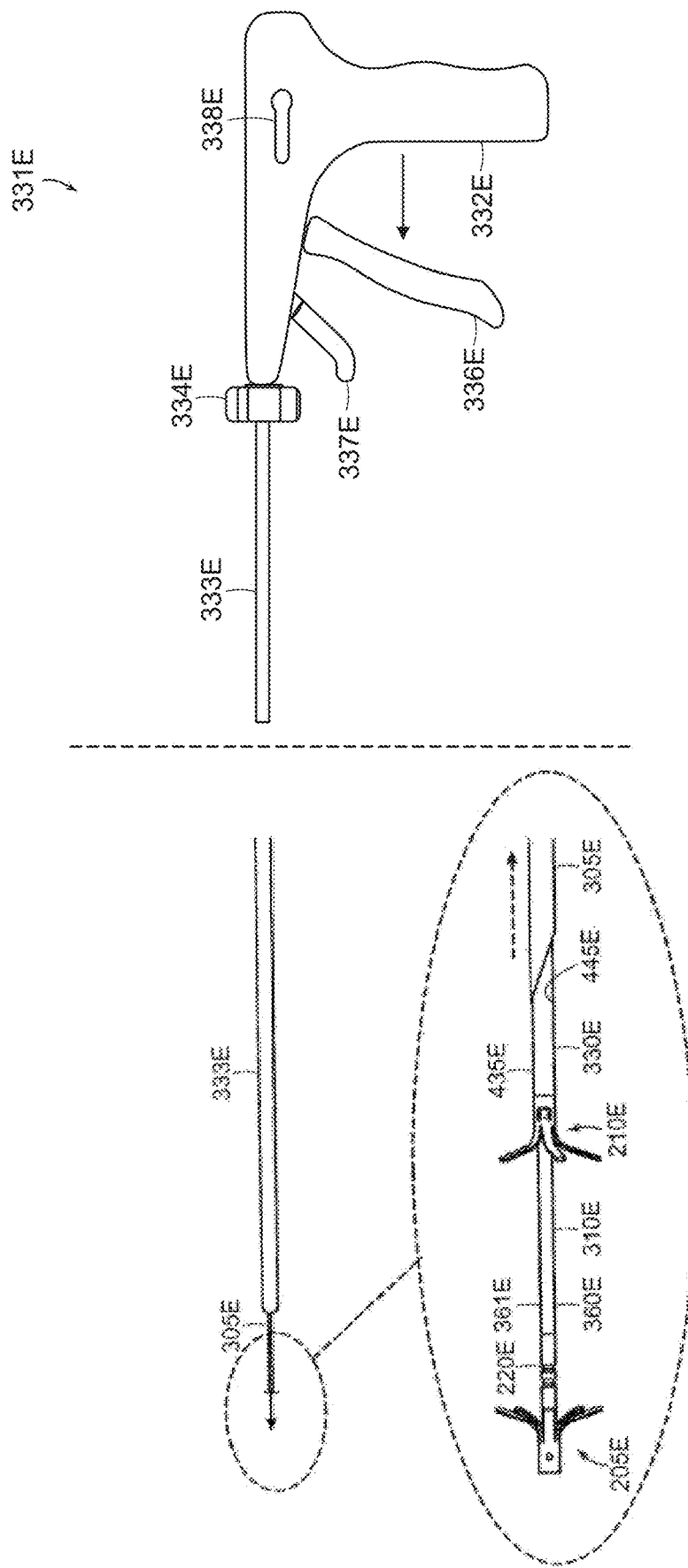
Figure 69:
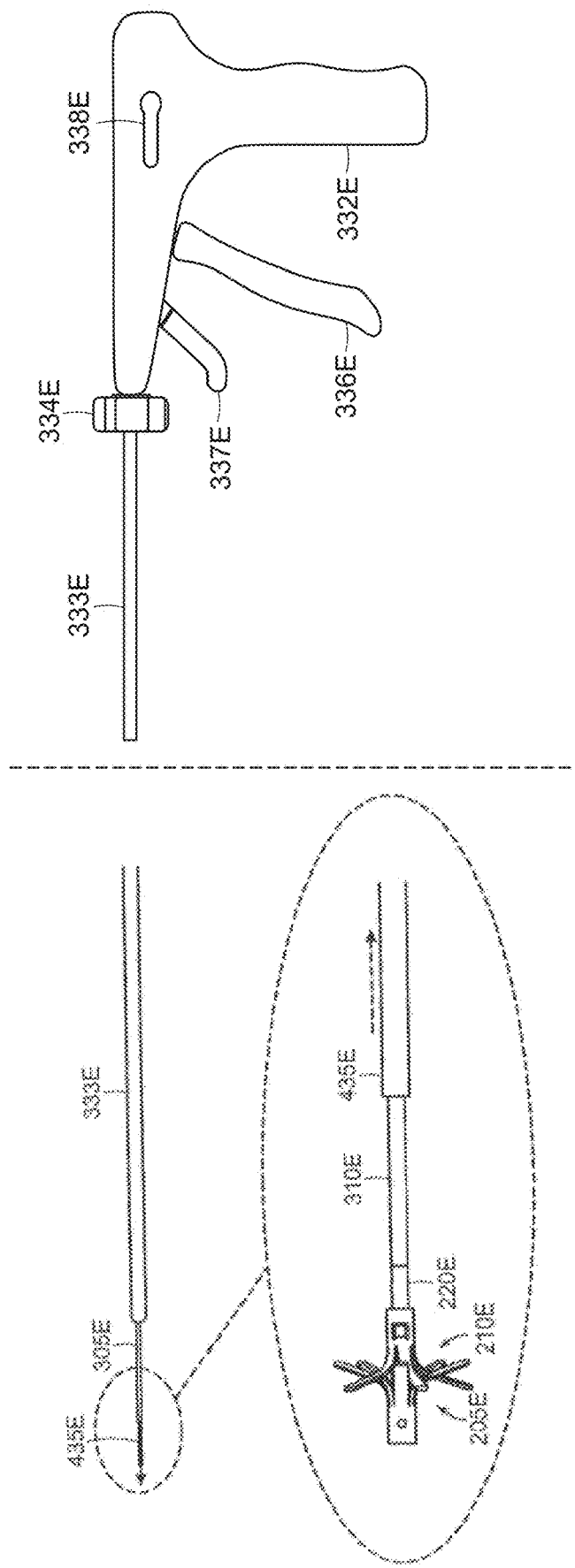

Then, with distal implant delivery tube 310E held in place via distal implant delivery tube 310E and its interlock with distal implant locking tube 220E (and hence distal implant 205), hollow needle 305E is withdrawn further proximally (e.g., via first trigger 336E) until proximal implant 210E is no longer constrained within hollow needle 305E (FIG. 67). As this occurs, legs 295E of proximal implant 210E are released from the constraint of hollow needle 305E and open radially.

Proximal implant delivery tube 330E is then advanced distally, e.g., using second trigger 337E, until proximal implant 210E and distal implant 205E come together (FIG. 68). As distal implant 205E and proximal implant 210E move together, their legs 235E, 295E compress the blood vessel therebetween, thereby occluding the blood vessel. Distal implant 205E and proximal implant 210E continue moving together until inwardly-projecting tangs 300E of proximal implant 210E enter circumferential grooves or recesses 245E of distal implant 205E, thereby locking the two members into position relative to one another.

Figure 70:
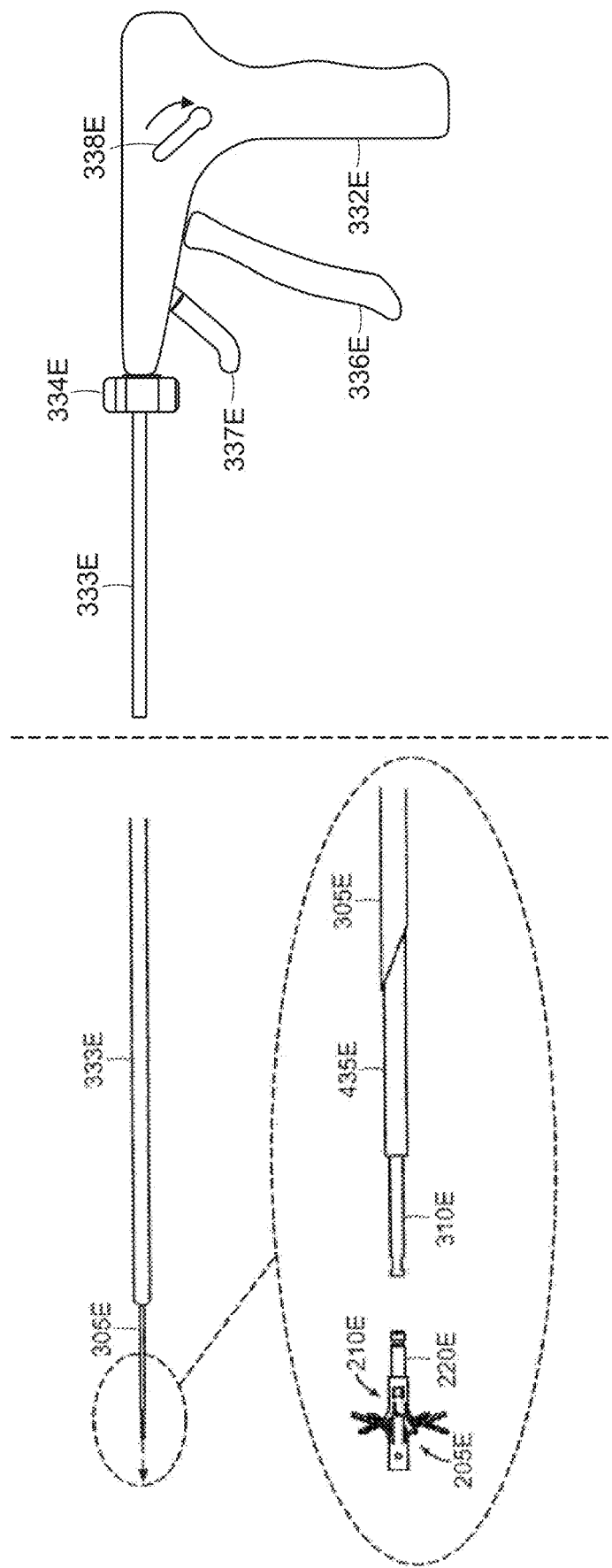
Figure 71:
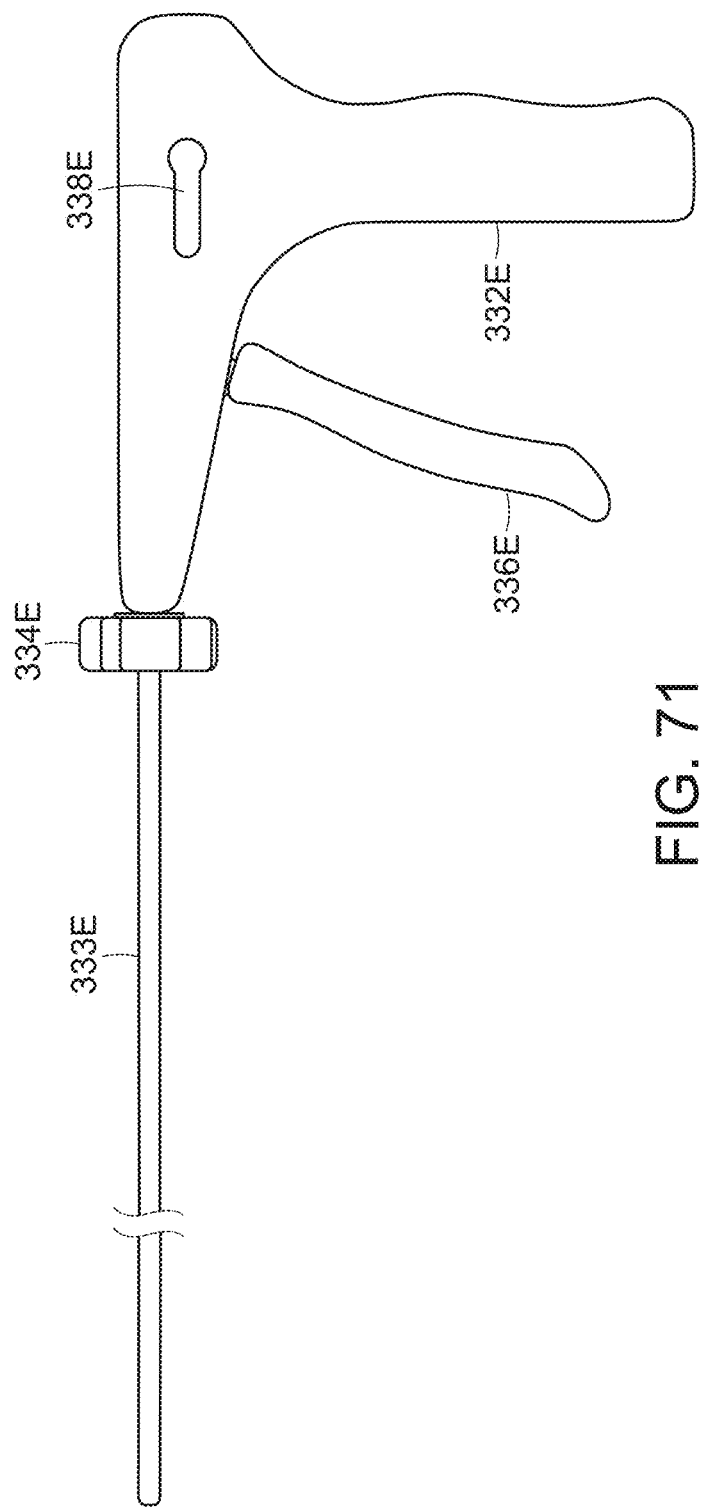
Figure 76:
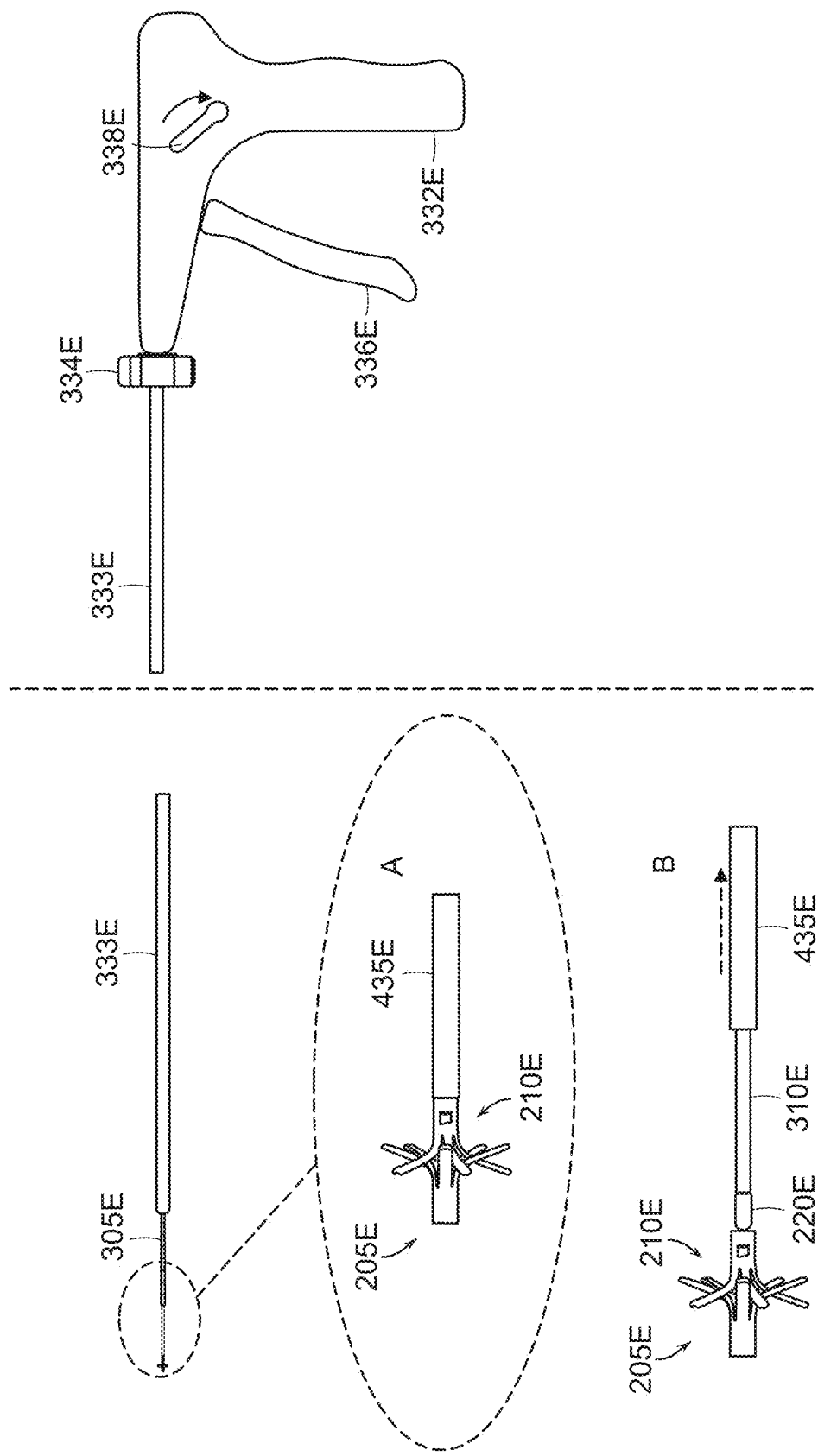

At this point, proximal implant delivery tube 330E is withdrawn (FIG. 69), distal implant delivery tube 310E is released from distal implant 205E (i.e., by using lever 338E to unlock the second half 361E of the mechanical interlock (carried by the distal end of distal implant delivery tube 310E) from the first half 266E of the mechanical interlock (carried by the proximal end of distal implant locking tube 220E), and then the installation device is withdrawn (FIG. 70).

The foregoing procedure leaves two-part fastener 200E locked in position across the blood vessel, with the opposing legs 235E, 295E compressing the blood vessel therebetween, whereby to occlude the blood vessel.

In the preceding disclosure, two-part fastener 200E is discussed in the context of using the elasticity of its legs 235E, 295E to cause its legs 235E, 295E to reconfigure from a diametrically-reduced configuration (e.g., when constrained within a delivery needle) to a diametrically-expanded configuration (e.g., when released from the constraint of a delivery needle). However, it should also be appreciated that where legs 235E, 295E are formed out of a shape memory material (e.g., Nitinol), a temperature change may be used to reconfigure legs 235E, 295E from a diametrically-reduced configuration to a diametrically-expanded configuration. By way of example but not limitation, in this form of the invention, legs 235E, 295E may be constructed so as to have a diametrically-reduced configuration when maintained at a temperature below body temperature, and legs 235E, 295E may be constructed so as to have a diametrically-expanded configuration when maintained at body temperature. As a result, by cooling two-part fastener 200E to a temperature below body temperature, inserting the two-part fastener into the body, and then allowing the two-part fastener to heat to body temperature, legs 235E, 295E can be caused to reconfigure from their diametrically-reduced configuration to a diametrically-expanded configuration.

FIGS. 71-77 show an alternative form of installation device. More particularly, FIGS. 71-77 show another laparoscopic device 331E. The laparoscopic device 331E shown in FIGS. 71-77 is generally similar to the laparoscopic device 331E shown in FIGS. 62-70, except that second trigger 337E is omitted, and lever 338E is used to both: (i) advance proximal implant delivery tube 330E until proximal implant 210E and distal implant 205E come together (FIG. 76), and (ii) release distal implant 205E from distal implant locking tube 220E (FIG. 77) (i.e., by unlocking the second half 361E of the mechanical interlock (carried by the distal end of distal implant delivery tube 310E) from the first half 266E of the mechanical interlock (carried by the proximal end of distal implant locking tube 220E)).

Figure 78:
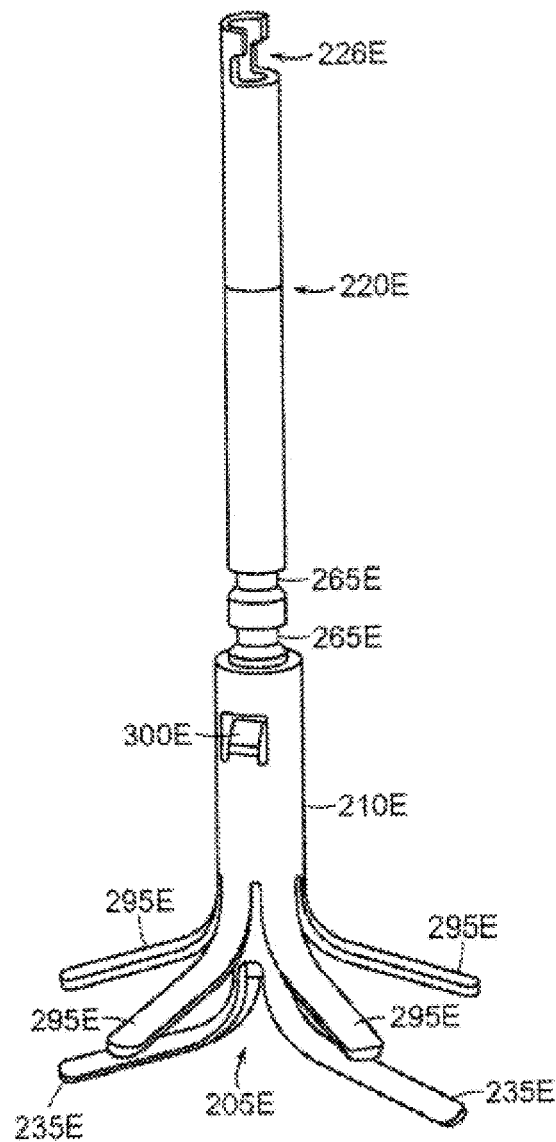
FIGS. 78-80 are schematic views showing another two-part occluder formed in accordance with the present invention.
Figure 79:
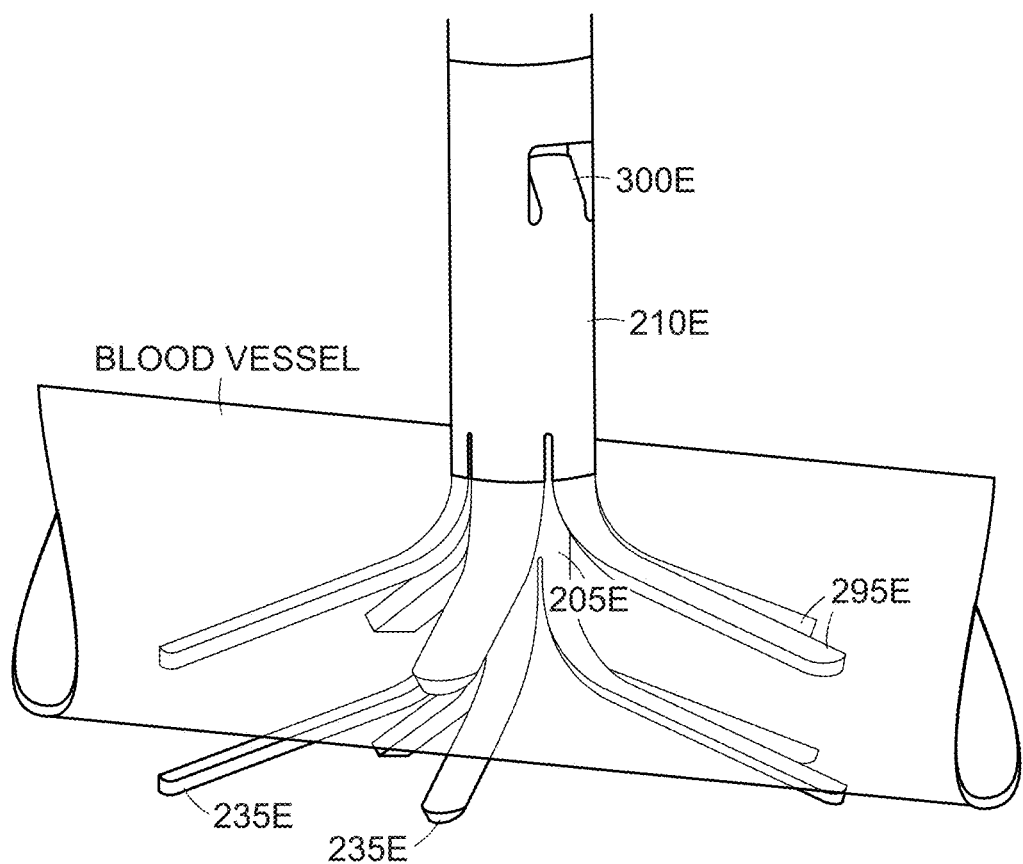
Figure 80:
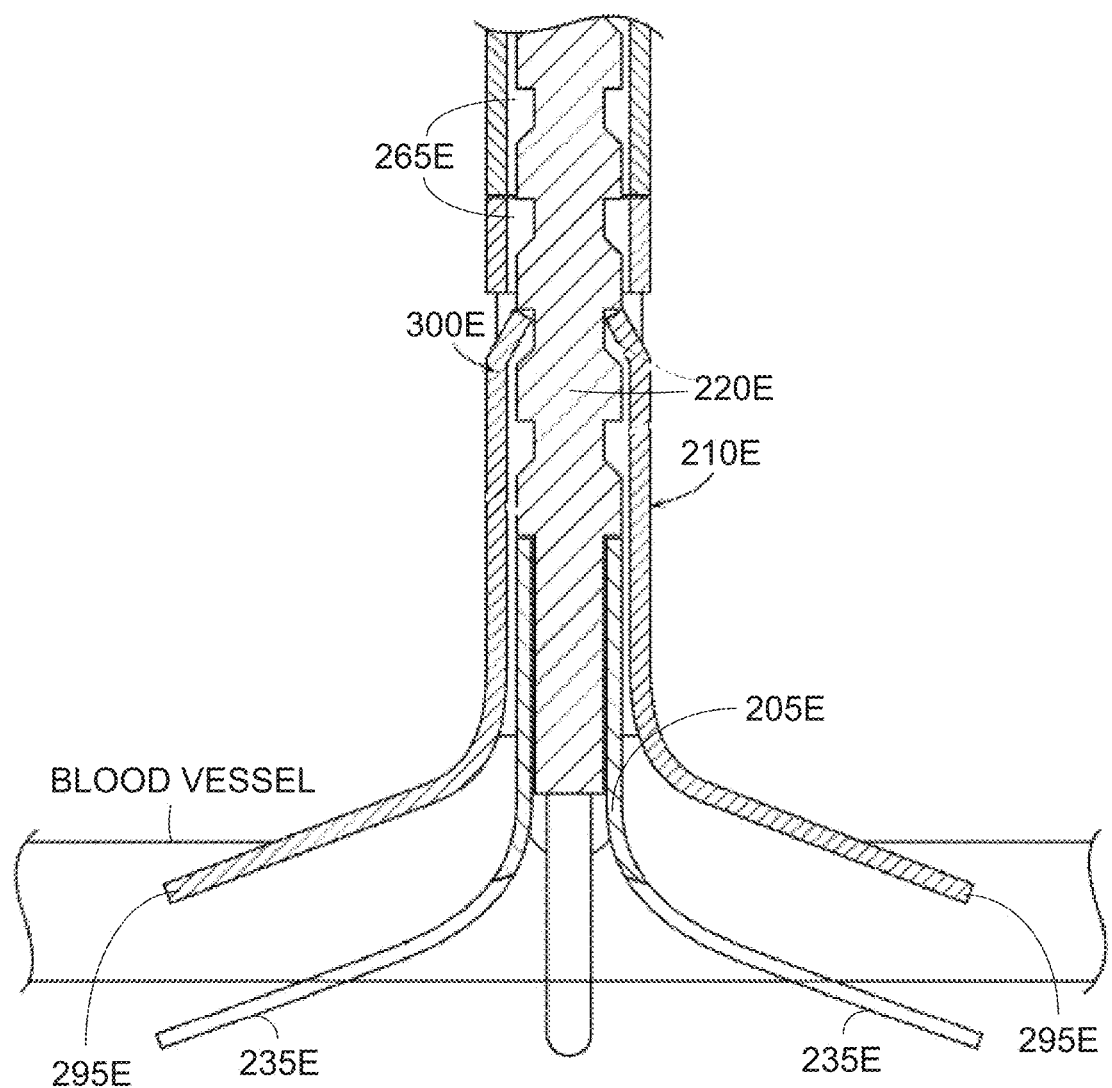

FIGS. 78-80 show another two-part fastener 200E also formed in accordance with the present invention. The fastener 200E shown in FIGS. 78-80 is substantially the same as the fastener 200E shown in FIGS. 58-77, except that legs 235E of distal implant 205E, and legs 295E of proximal implant 210E, have their concavity directed in the same direction, so that legs 235E, 295E nest with one another rather than confront one another. In addition, as seen in FIGS. 78-80, tube 225E of distal implant 205E is partially received in lumen 290E of proximal implant 210E.

Figure 81:
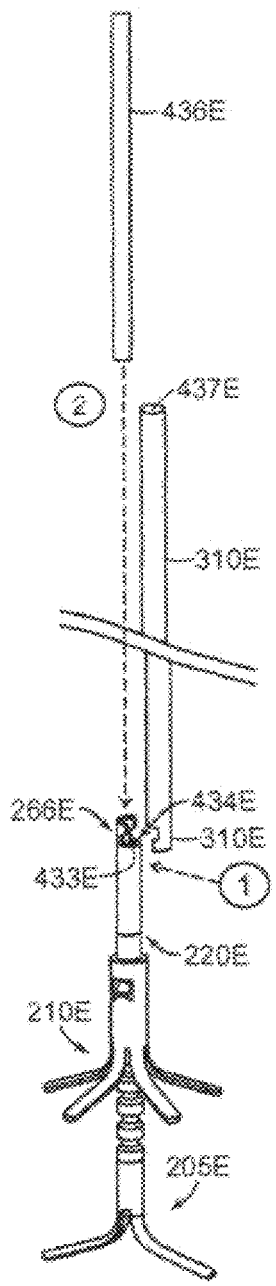
FIGS. 81-83 are schematic views showing means for securing the two-part occluder shown in FIGS. 78-80 to an installation apparatus.
Figure 82:
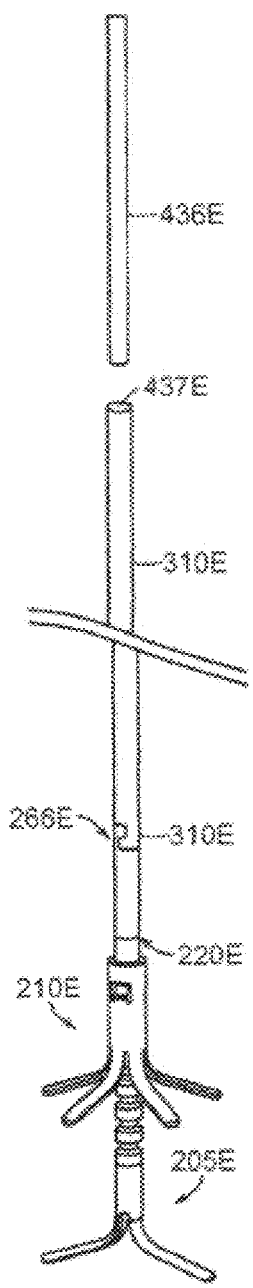
Figure 83:
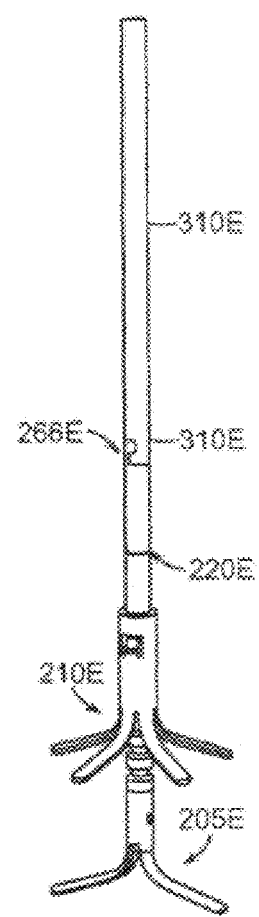

FIGS. 81-83 show one preferred construction for releasably securing distal implant 205E of the two-part fastener 200E of FIGS. 78-80 to distal implant delivery tube 310E. More particularly, in this form of the invention, and looking now at FIGS. 81-83, the first half 266E of the mechanical interlock (carried by the proximal end of distal implant locking tube 220E) comprises a stepped configuration 433E, and the second half 361E of the mechanical interlock (carried by the distal end of distal implant delivery tube 360E) comprises another stepped configuration 434E, wherein stepped configuration 433E and stepped configuration 434E are inverses of one another so as to mate together. After the second half 361E of the mechanical interlock (carried by the distal end of distal implant delivery tube 310E) has been secured to the first half 266E of the mechanical interlock (carried by the proximal end of distal implant locking tube 220E), the connection between distal implant delivery tube 310E and distal implant 205E can be enhanced, e.g., by telescopically projecting a locking rod 436E out of a central lumen 437E of distal implant delivery tube 310E and into lumen 262E of implant locking tube 220E. In this form of the invention, the installation device (e.g., laparoscopic device 331E of FIGS. 62-70, or laparoscopic device 331E of FIGS. 71-77) include appropriate control means (e.g., release lever 338E) for telescopically moving locking rod 436E out of central lumen 437E of distal implant delivery tube 310E and into lumen 262E of implant locking tube 220E. Alternatively, in another form of the invention, internal locking rod 436E may be replaced by an overtube (not shown) which telescopically projects over distal implant delivery tube 310E and distal implant locking tube 220E of distal implant 205E, whereby to enhance the connection between the members.

It should also be appreciated that other forms of mechanical interlocks may be used for releasably securing distal implant 205E of the two-part fastener 200E of FIGS. 78-80 to distal implant delivery tube 310E. By way of example but not limitation, a screw interlock may be used, e.g., the first half 266E of the mechanical interlock (carried by the proximal end of distal implant locking tube 220E) may comprise a threaded bore, and the second half 361E of the mechanical interlock (carried by the distal end of distal implant delivery tube 360E) may comprise a threaded post, wherein the threaded post carried by the distal end of distal implant delivery tube 360E may be received in the threaded bore of distal implant locking tube 220E. Alternatively, other configurations of a screw interlock may be used, or other forms of mechanical interlocks may be used.

In the constructions shown in FIGS. 58-80, a mechanical interlock (e.g., a first half 266E carried by the proximal end of distal implant locking tube 220E and a second half 361E carried by the distal end of distal implant delivery tube 310E) is used to connect distal implant locking tube 220E (and hence distal implant 205E) to distal implant delivery tube 310E. Alternatively, if desired, distal implant locking tube 220E can be formed integral with distal implant delivery tube 310E, with a weakened section disposed at their intersection, and the two members separated by a mechanical breaking action.

Figure 84:
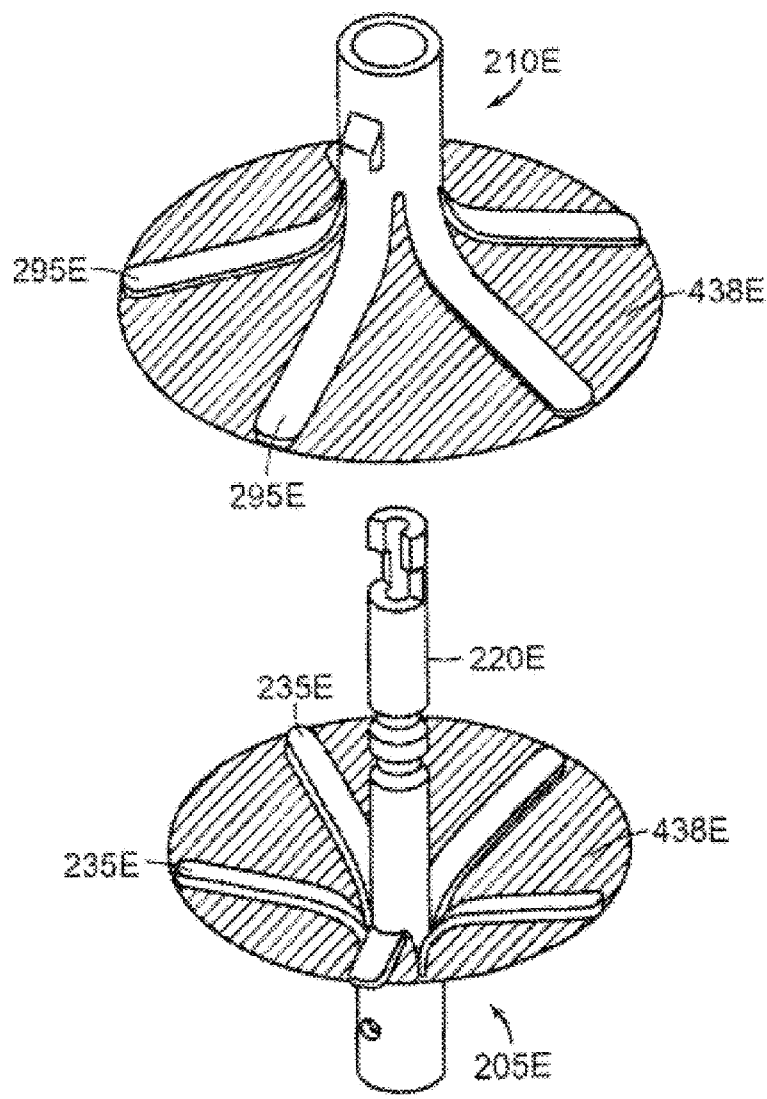
FIG. 84 is a schematic view showing another two-part occluder formed in accordance with the present invention.
Figure 85:
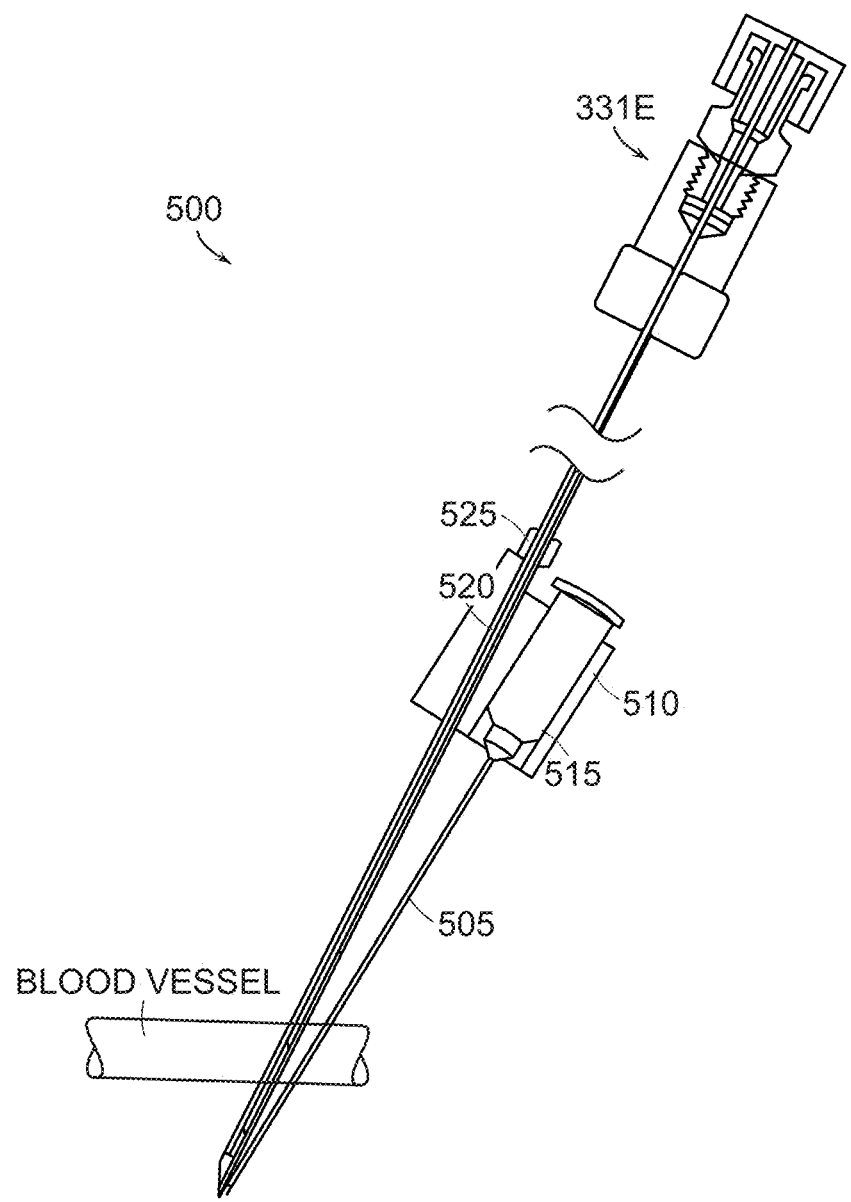
FIGS. 85-90 are schematic views showing a placement device for facilitating proper placement of an occluder so as to occlude a blood vessel (or other hollow tubular body)
Figure 86:
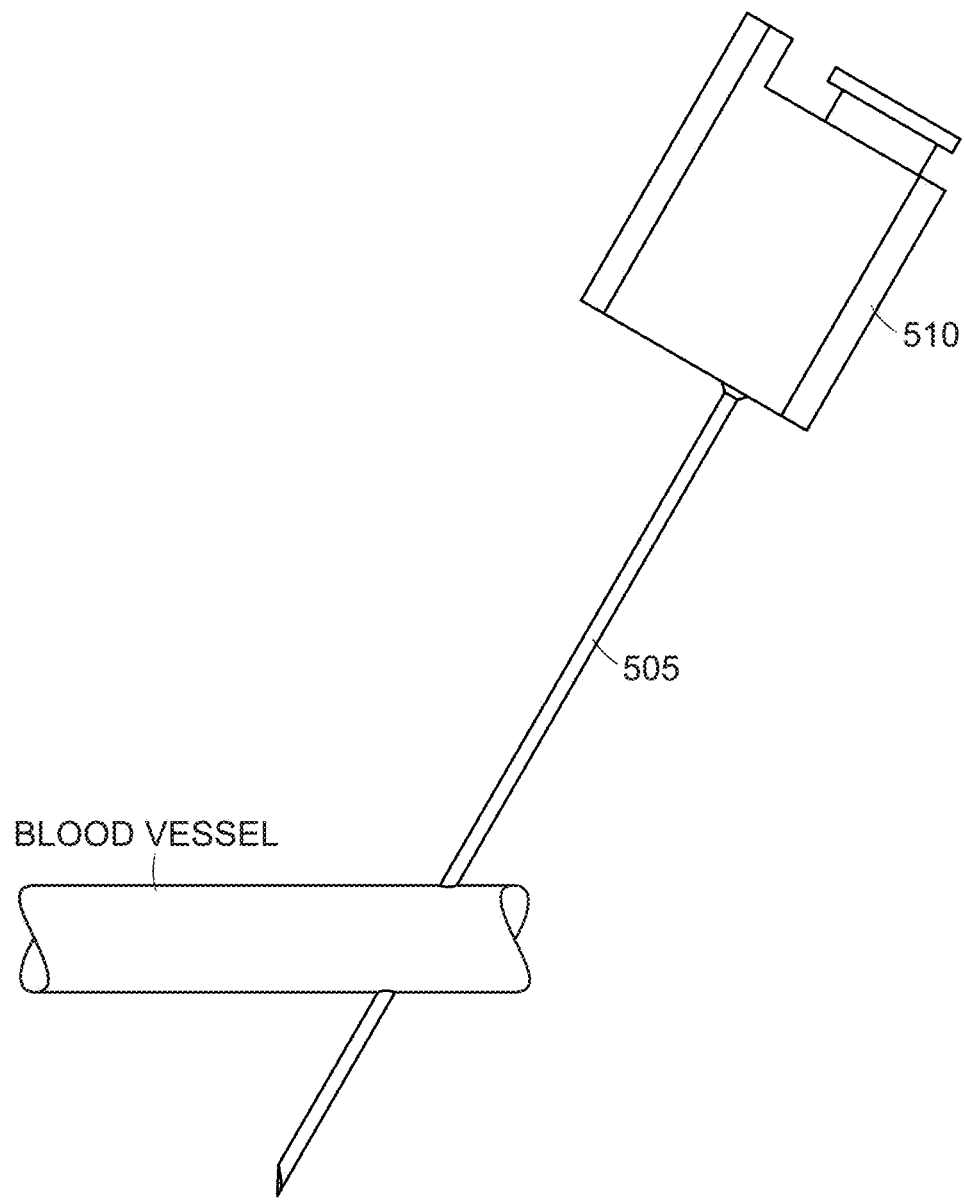
Figure 87:
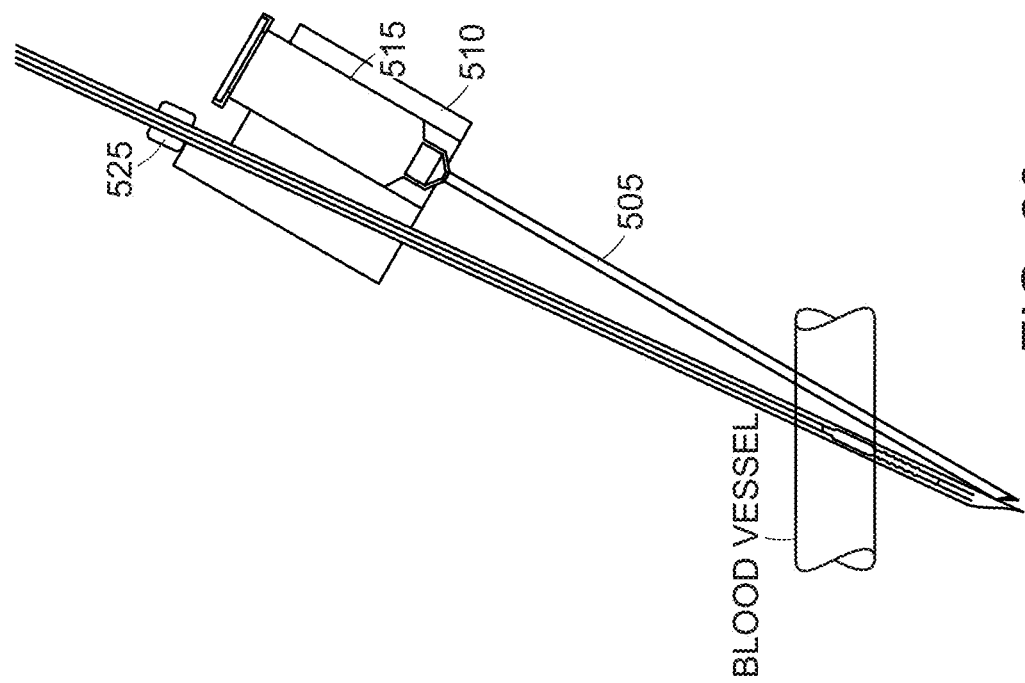
Figure 88:
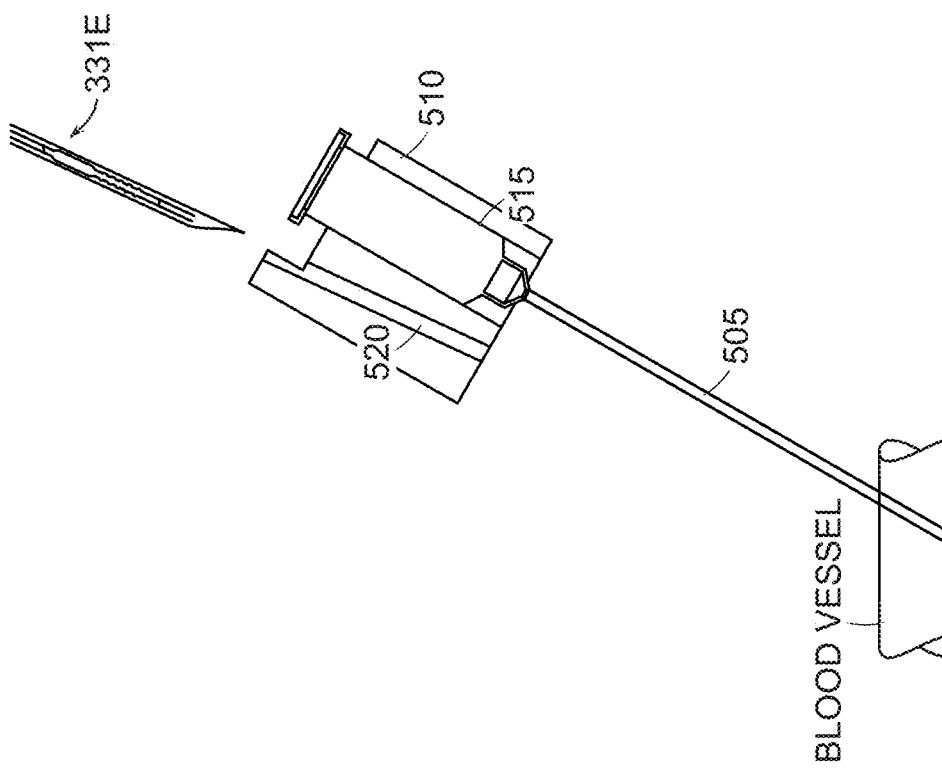
Figure 89:
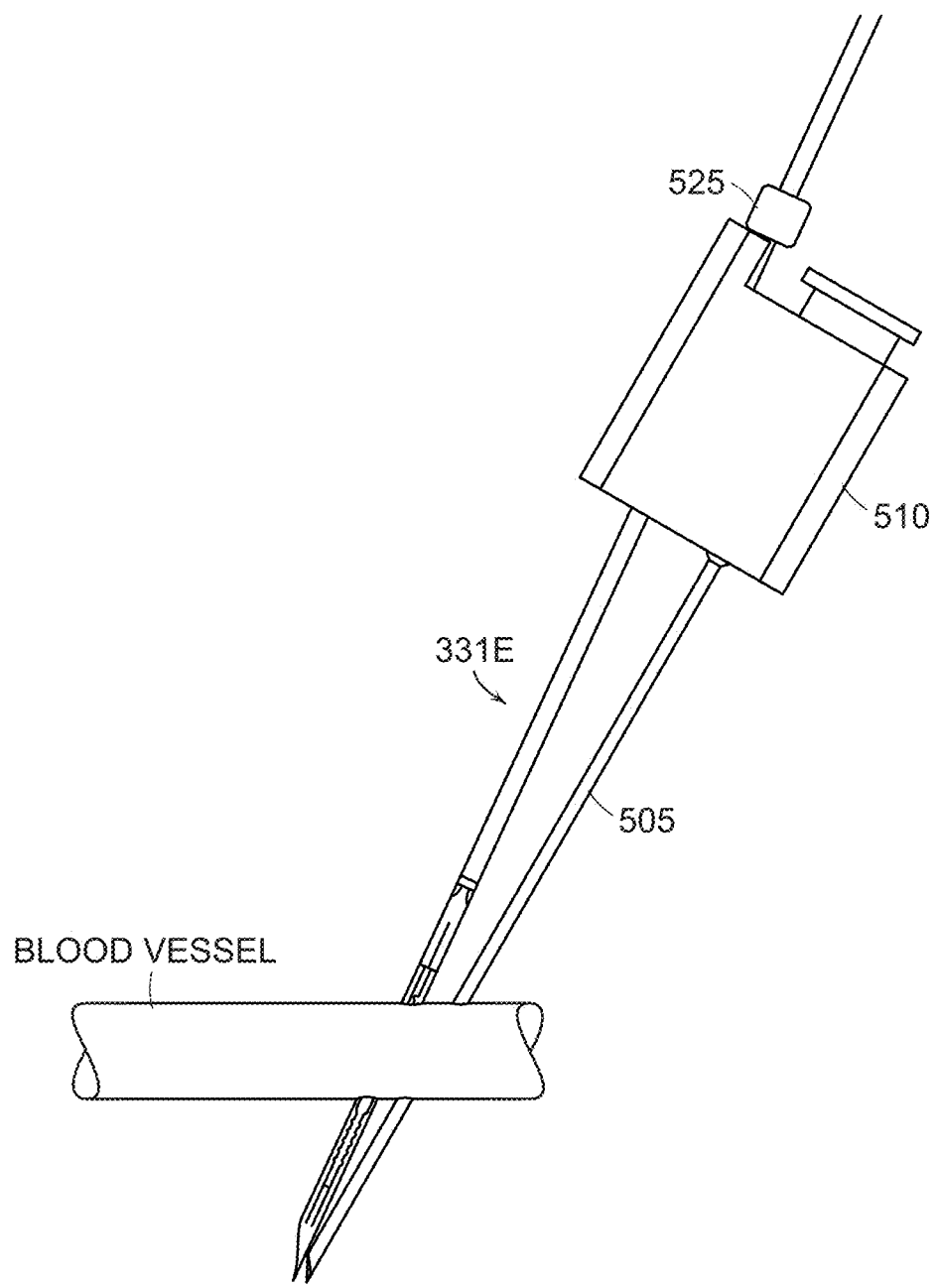
Figure 90:
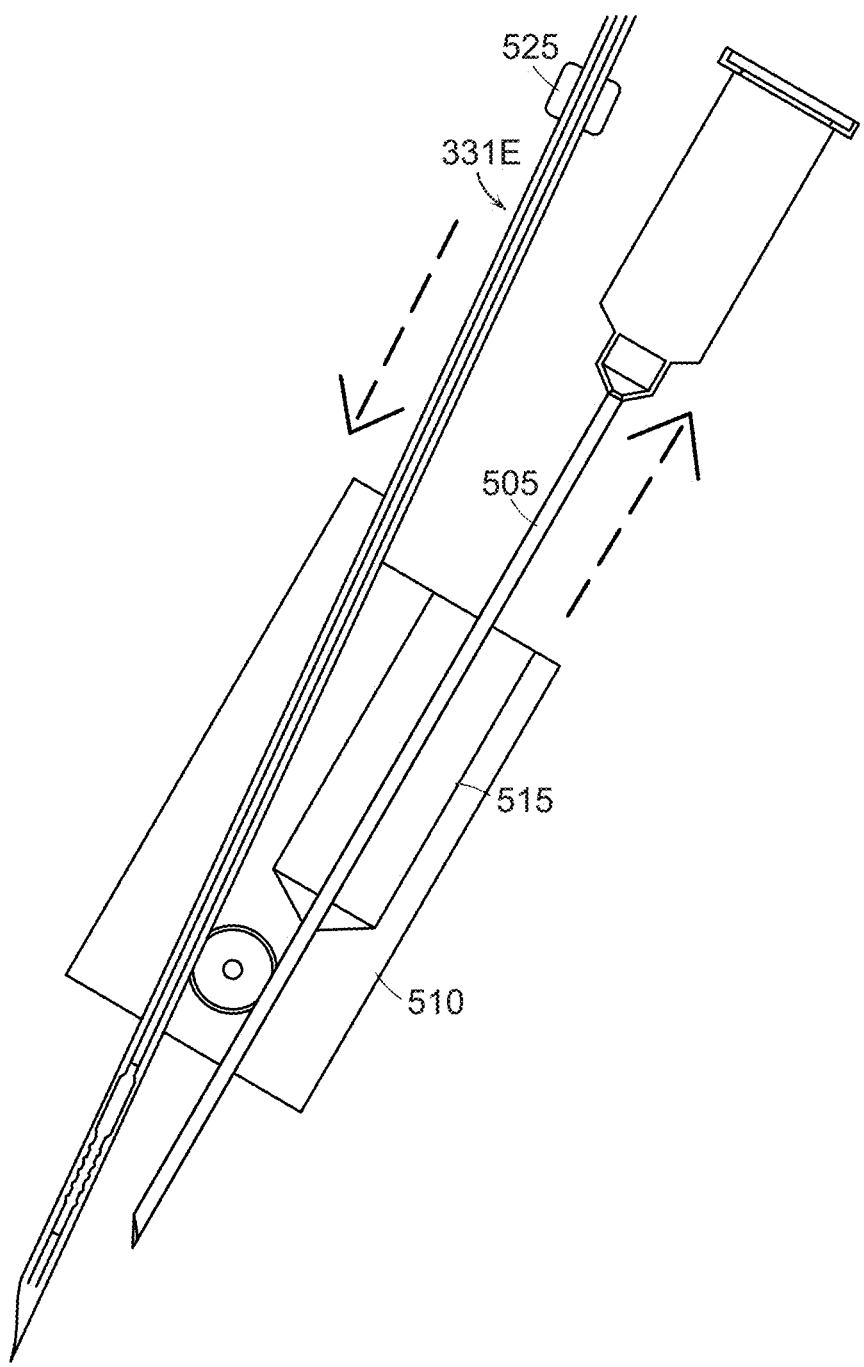

It will be appreciated that, in certain circumstances, it may be desirable to increase the surface area of those portions of the fastener which contact the tubular structure, in order to better distribute the load applied to the tissue. In this situation, it can be helpful to increase the width of the legs (e.g., legs 235E and/or legs 295E of two-part fastener 205E, etc.), and/or to provide flexible material in the zone between adjacent legs (e.g., in the manner of an umbrella) so that the flexible material can also carry load (i.e., essentially increasing the effective width of legs 235E and/or legs 295E). See, for example, FIG. 84, which shows flexible material 438E extending between legs 235E and legs 295E.

FIGS. 85-90 show a placement device 500 for the facilitating proper placement of the fastener (e.g., the two-part fastener 200E) so as to occlude a blood vessel (or other hollow tubular body). Placement device 500 generally comprises a blood vessel locator needle 505, which is a needle of relatively small diameter (e.g., 21 gauge or smaller), and a guiding component 510 (which may be manufactured from an inexpensive material such as plastic). Guiding component 510 includes a seat 515 for receiving blood vessel locator needle 505, and an opening 520 for slidably accommodating the shaft of an installation device for setting the fastener (e.g., laparoscopic device 331E of FIGS. 62-70, or laparoscopic device 331E of FIGS. 71-77, etc.).

In use, blood vessel locator needle 505 is positioned in seat 515 of guiding component 510, and then the blood vessel locator needle 505 is advanced through the target blood vessel (e.g., under ultrasound guidance). See FIG. 86. Proper placement of blood vessel locator needle 505 is confirmed as blood begins to flow out the proximal end of blood vessel locator needle 505. Next, the shaft of the installation device for setting the fastener (e.g., laparoscopic device 331E of FIGS. 62-70, or laparoscopic device 331E of FIGS. 71-77, etc.) is advanced through opening 520 of guiding component 510. See FIG. 87. Advancement occurs until a stop 525 on the shaft of the installation device engages the proximal end of guiding component 510. See FIG. 88. When stop 525 on the shaft of the installation device engages the proximal end of guiding component 510, the distal end of the shaft of the installation device will have passed through the target blood vessel. See FIG. 89. At this point, blood vessel locator needle 505 is withdrawn (see FIG. 90) and deployment of the fastener proceeds as previously discussed.

Figure 91:
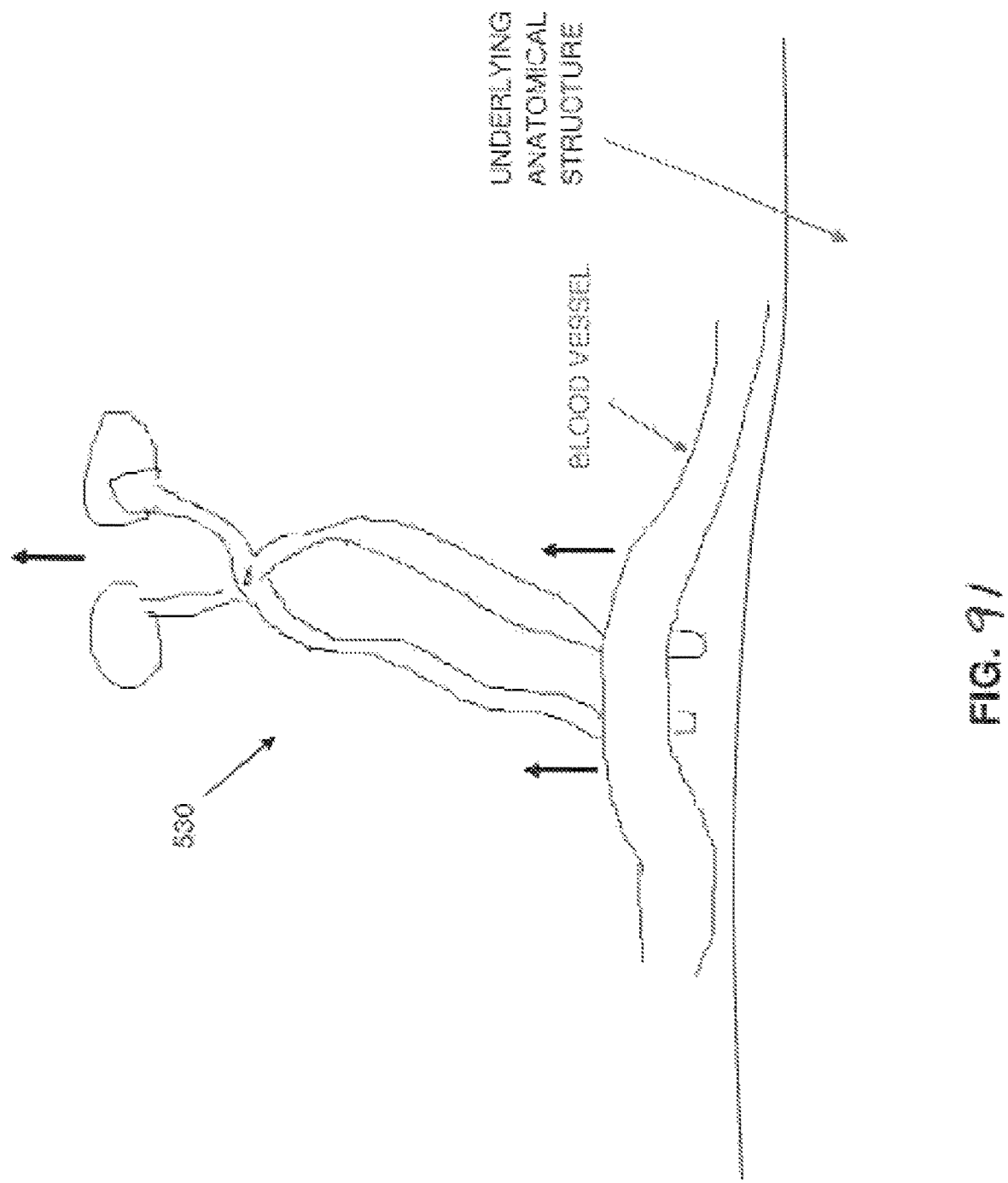
FIG. 91 is a schematic view showing a tool for lifting a blood vessel (or other hollow tubular body) away from an underlying anatomical structure so as to facilitate proper placement of an occluder.

It will be appreciated that, in certain circumstances, the blood vessel (or other tubular structure) to be occluded may be positioned close to an underlying anatomical structure, e.g., an organ, a nerve, another tubular structure, etc. In this situation, it may be helpful to lift the blood vessel (or other tubular structure) upward, away from the underlying anatomical structure, so that the sharp distal tip of the deployment needle does not engage the underlying anatomical structure, and so that the distal end of the fastener (e.g., distal implant 205E of two-part fastener 200E) does not engage the underlying anatomical structure, since any such engagement with the underlying anatomical structure could cause trauma to the underlying anatomical structure. To that end, and looking now at FIG. 91, clamping forceps 530 (or other tool having a bifurcated distal end) may be placed between the blood vessel (or other tubular structure) and the underlying anatomical structure, and then pulled upwardly, away from the underlying anatomical structure, so as to separate the target blood vessel (or other tubular structure or tissue) from the underlying anatomical structure. The fastener (e.g., two-part fastener 200E) may then be safely passed through the target blood vessel (or other tubular structure), passing between the bifurcated distal end of the tool, and deployed as previously discussed.

Using the Fastener to Occlude Tubular Structures Other than Blood Vessels

It will be appreciated that the fastener of the present invention can also be used to occlude tubular structures other than blood vessels. By way of example but not limitation, the temporary fastener of the present invention can be used to occlude other structures within the body (e.g., tubes such as fallopian tubes and/or vas deferens for temporary or permanent sterilization, ducts such as bile ducts and cystic ducts for cholecystectomy, lymphatic vessels, including the thoracic duct, fistula tracts, etc.).

Using the Fastener to Close Openings in Structures and/or for Securing at Least Two Objects Together In the foregoing disclosure, the fastener is discussed in the context of occluding a tubular structure (e.g., a blood vessel, fallopian tubes, lymphatic vessels, etc.) by clamping together opposing side walls of the tubular structure in order to occlude the tubular structure. In such an application, the fastener effectively secures one side wall of the tubular structure to the opposing side wall of the tubular structure. However, it should also be appreciated that the fastener of the present invention may be used to close openings in structures and/or to secure two or more objects together for other applications.

By way of example but not limitation, the fastener of the present invention may be used to secure two or more portions of tissue together so as to close an incision.

By way of further example but not limitation, the fastener of the present invention may be used in a "stomach stapling" procedure to bring together opposing side walls of the stomach in order to reduce the size of the stomach.

Furthermore, the fastener of the present invention may be used in an organ resection (e.g., a liver resection), so as to seal the periphery of the resected organ.

Figure 92:
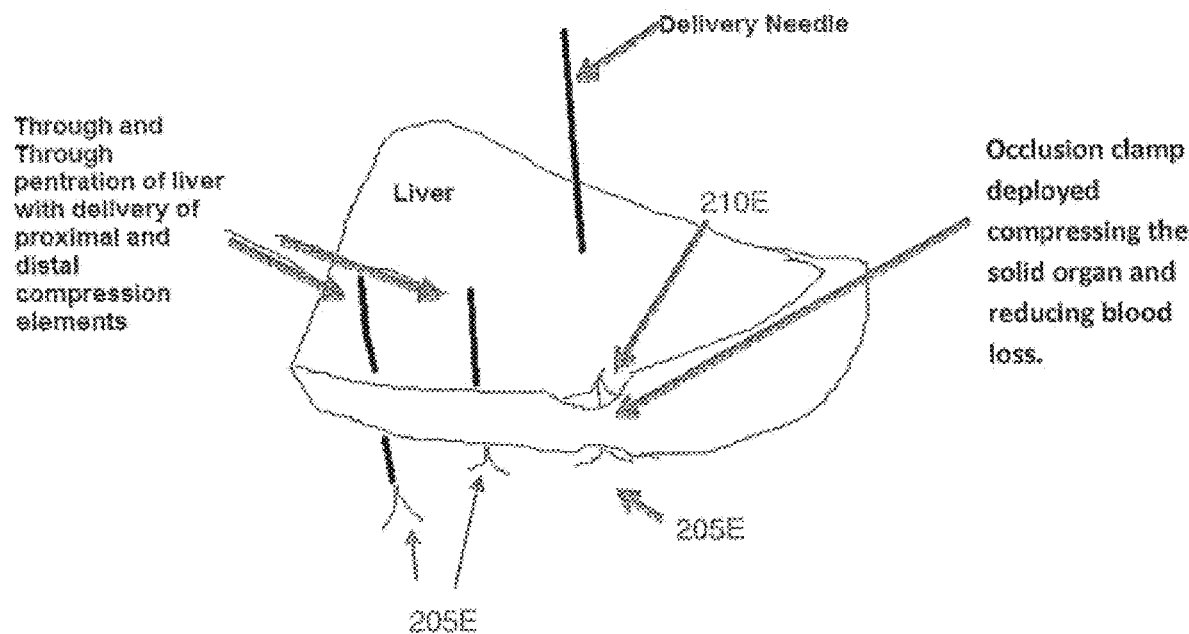
FIGS. 92-94 are schematic views showing use of an fastener for closing off an organ.
Figure 93:
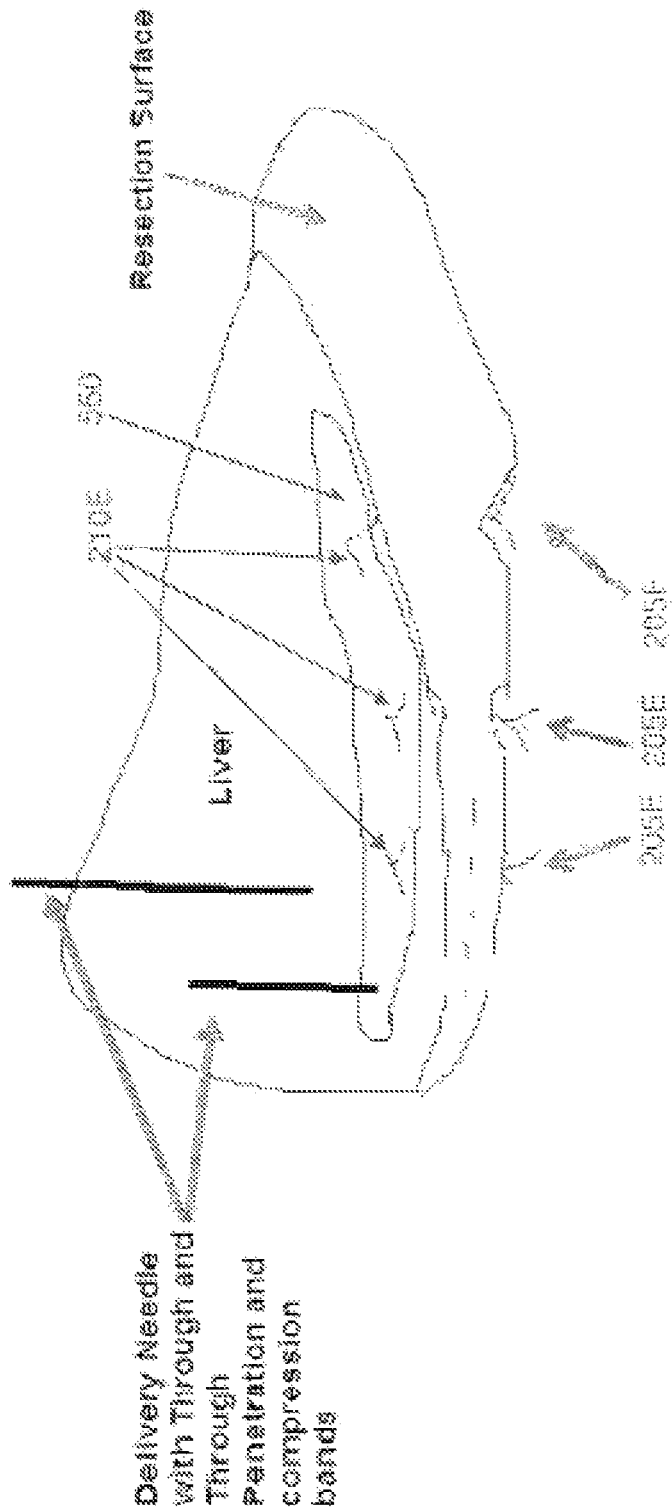
Figure 94:
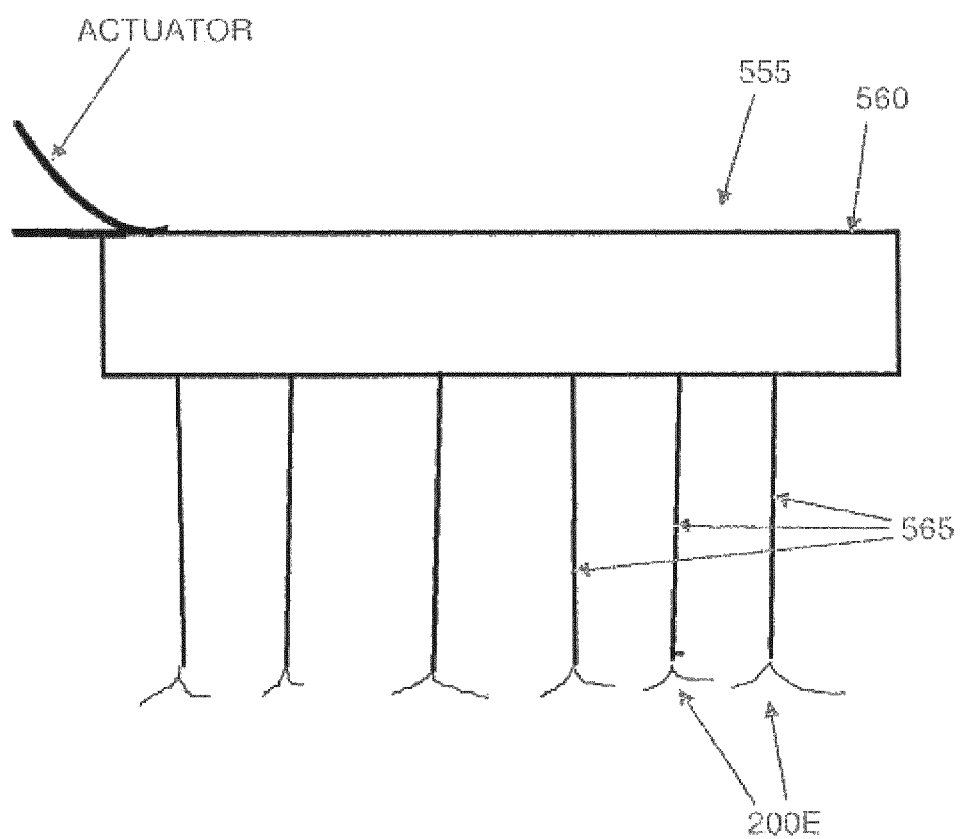

By way of further example but not limitation, and looking now at FIGS. 92-94, the fastener of the present invention can be used for selectively clamping or occluding regions of solid organs so as to selectively stop blood flow or blood loss in various regions through tissue compression. The fastener may be used in solid organ resection of the kidney or liver or other organs. Blood loss and secretion leakage (e.g., bile, urine, etc.) can be problematic in existing solid organ resection procedures. Average blood loss for a liver resection is 700-1200 ml. By clamping desired regions of the solid organ with the fastener of the present invention, it is possible to significantly reduce the amount of undesirable fluid loss (blood loss, secretion leakage, etc.). The fastener of the present invention, can be used to apply pressure selectively to broad areas of the organ and, additionally, may also be used to close off selective tubular structures and vessels connecting the organ with other regions of the body. In one embodiment and method, multiple discrete fastener elements may be individually, selectively deployed across regions of the organ. See, for example, FIG. 92, which shows multiple, single, separate puncture placements of the fastener for closing off a resected liver. Note that where multiple, single, separate puncture placements of the fastener are used, different regions of the solid organ may be compressed to different and controllable degrees.

In a novel embodiment of the present invention, the length of distal implant locking tube 220E (of distal implant 205E) remaining in the body can be determined once clamping of the fastener has been effected, by providing distal implant locking tube 220E and/or distal implant delivery tube 310E with weakened (e.g., frangible) sections, and by breaking off distal implant locking tube 220E from distal implant delivery tube 310E at a region above proximal implant 210E. This break can be achieved by incorporating selective weakened regions into the distal implant locking tube 220E and/or distal implant delivery tube 310E, so that when a selective weakened region is subjected to twists, or torques, or bending, or pulling, or selective other strains or stresses or the like, distal implant locking tube 220E will separate from distal implant delivery tube 310E at a location proximal to proximal implant 210E. Because clamping is effected across the tissue, distal implant locking tube 220E connecting distal implant body 215 and proximal implant 210E will not move, while distal implant delivery tube 310E will disconnect from distal implant locking tube 220E. Distal implant locking tube 220E, which connects distal implant body 215E and proximal implant 210E, may be solid or flexible.

In other embodiments of the present invention, distal implant locking tube 220E may be composed of multiple interlocking sections, and constrained by an encasing sheath, or once deployed, by the surrounding tissue. Once clamping of the tissue is achieved, the sheath can be retracted beyond the proximal implant, exposing an interlocking region between the distal implant locking tube 220E sections and then, with a twist, or appropriate unlocking mechanism, enable the fastener to be disconnected from the distal implant delivery tube 310E.

This construction enables the clamping distance between distal implant 205E and proximal implant 210E to be controllable, and allows for significant tissue thicknesses to be clamped.

In the embodiment shown in FIG. 93, the fasteners are delivered in conjunction with single or multiple compression bands 550, which may be polymers, or other tissue material or metals or other commonly used materials known in the art. The compression bands 550 may be rolled into the delivery needle or sheath and unfurled prior to delivery of the fasteners. The compression bands 550 extend the pressure across a broader region of the organ or tissue which receives the fasteners of the present invention.

In other embodiments, the legs of the fastener may have a thin metallic or polymeric mesh or film that is flexible, yet connects between the fingers, to enable further distribution of pressure on a clamped tissue, vessel, organ or the like.

In the embodiment of FIG. 94, multiple fasteners can be delivered in parallel to an organ, tissue, tubular structure or the like. In this form of the invention, an installation device 555, comprising a body 560 having a plurality of deployment needles 565 extending therefrom, can be used for setting the multiple fasteners. Installation device 555 can deliver either single fasteners deployed one at a time, but in a spatially-constrained way, with a pre-defined spacing between the fasteners (determined by the predefined spacing between deployment needles 565), or can deliver a plurality of fasteners all at the same time, with a single activation control. This construction can reduce the amount of time required for a procedure such as a resection, by providing for simultaneous fastener deployments.

In other embodiments of the present invention, the fasteners can be deployed across multiple tissues, or multiple folds of the same tissue, organ or tubular structure. In certain embodiments of the present invention, the distal implant locking tube 220E may be elastic, allowing for some movement of the clamped tissue, while still maintaining a desired clamping force or pressure on the tissue.

The fasteners of the above invention may also be used for bariatric surgery, or to reduce or plicate the stomach, or to create a gastrostomy sleeve.

In another embodiment of the present invention, the unreleased distal implant 205E can be used as the retractor, and retract the tissue away from any organs or tissues or major blood vessel beneath, enabling subsequent deployment of other fasteners to be placed in a manner that may enable reduction of the size of an organ, joining organs together, closing a tear in the bowel or the like. Once the other desired fasteners have been deployed, the deployment of the first fastener (i.e., unification of the proximal implant 210E with the distal fastener 205E) can be completed.

Use of the Invention Under Direct Visualization and/or Indirect Visualization

Significantly, the present invention may be practiced under direct visualization (e.g., during "open" surgery) or under indirect visualization (e.g., during laparoscopic surgery where visualization is provided through the use of a scope, or during percutaneous surgery where visualization is provided through the use of imaging apparatus such as an ultrasound imager, an X-ray imager, etc.).

Enhanced Tissue, Organ, Duct and/or Vessel Clamping or Approximation

1. Advantages of Using Two-Part Fastener

The present invention relates to, among other things, a novel two-part fastener that clamps hollow tubes, vessels and/or at least two layers of materials (i.e., biological materials or synthetic materials) together, and is an improvement over existing occlusion devices such as clamps or staples, and may connect different or similar tissues together and/or connect tissues to synthetic materials.

More particularly, the present invention relates to an apparatus and method for permanently, and controllably, bringing at least two surfaces into at least partial contact or proximity with each other. The present invention can be used for occlusion of tubular structures such as veins, arteries, bile ducts, fallopian tubes, cystic ducts, etc. The present invention can also be used to bring, attach and/or connect at least two folds (e.g., two sides of the stomach, or other parts of the legs, etc.) together so that they are connected.

The present invention can also be used to connect tissue with other materials, e.g., graft materials, hernia meshes, drug delivery materials, etc. The present invention is also intended to connect two structures together with or without the need to protect the underlying tissue layers from possible injury by the transfixing needle.

2. Drawbacks of Using Staples

The advantages of the present invention include, but are not limited to, secure clamping of vessels (or tissues) by transfixing the vessel (or tissue) so that the two-part fastener cannot be dislodged and slip off of the vessels (or tissues) with untoward consequences such as bleeding in blood vessels, and detachment of tissues, etc. Furthermore, compression of the vessel (or tissues) surrounding the puncture hole is accomplished with distributed pressure on the vessel (or tissue) from the two-part fastener preventing any leakage of blood or fluids from the occluded structure.

More particularly, two-part fastener 200 is disposed across the vessel which is to be occluded (or across the tissue(s) which are to be clamped together) such that distal implant 205 resides on one side of the vessel and proximal implant 210 resides on the other side of the vessel, with distal implant locking tube 220 passing through the vessel and connecting together distal implant 205 and proximal implant 210, whereby to generate a clamping force therebetween. This distributed pressure (i.e., compression), around the puncture hole, helps to prevent fluids (e.g., blood or bile) from leaking out of the puncture hole (i.e., the hole in the vessel where distal implant locking tube 220 passes through the vessel) after the aforementioned distal implant 205 and proximal implant 210 are brought together about the tissue to be clamped. Unlike a staple, which may produce bleeding where the legs of the staple pass through the vessel and which can "slip off" of the vessel, distal implant 205 and proximal implant 210 cannot "slip off" of the tissue. The distributed pressure around the puncture hole greatly reduces the possibility of the tissue ripping.

Bleeding, "slipping off" of tissue and ripping through tissue are common problems associated with using staples, and with using other clips (such as hemoclips) and clamps. Two-part fastener 200 of the present invention is able to hermetically close a vessel experiencing a pressure of 0 mm Hg up to, and above, 700 mm Hg (i.e., pressures at which the aforementioned issues associated with staples and prior-art clamps occur).

The novel two-part fastener 200 of the present invention also eliminates the need for an additional support material when clamping delicate tissue.

For example, one prior art medical stapling device requires the provision of additional support material when stapling fragile tissues. More particularly, this prior art medical stapling device uses an additional advanced polymer felt material placed on the tissues and stapled together with the tissues.

3. Attaching Two Objects Together Using Two-Part Fastener 200

As discussed above, two-part fastener 200 may be used for occlusion of tubular structures such as, veins, arteries, bile ducts, cystic ducts, fallopian tube, etc.). However, it should also be appreciated that two-part fastener 200 may be used to attach a non-tissue element to tissue (e.g., to attach hernia mesh to tissue, or a blood vessel stent-graft to the native vessel). Two-part fastener 200 may also be used to attach a first non-tissue element to a second non-tissue element (e.g., to attach a synthetic hernia mesh to the normal tissues surrounding edges of the hernia site, or to another segment of hernia mesh), e.g., for shaping or reconfiguring a non-tissue element.

It will be appreciated from the preceding disclosure that distal implant locking tube 220 of two-part fastener 200 passes through the tubular structure which is to be clamped, however, the entire area around distal implant locking tube 220 is compressed/closed-off so as to prevent any bleeding or leakage of fluids from occurring at the site of the entry/exit point of distal implant locking tube 220 through the side walls of the tubular structure.

Figure 96:
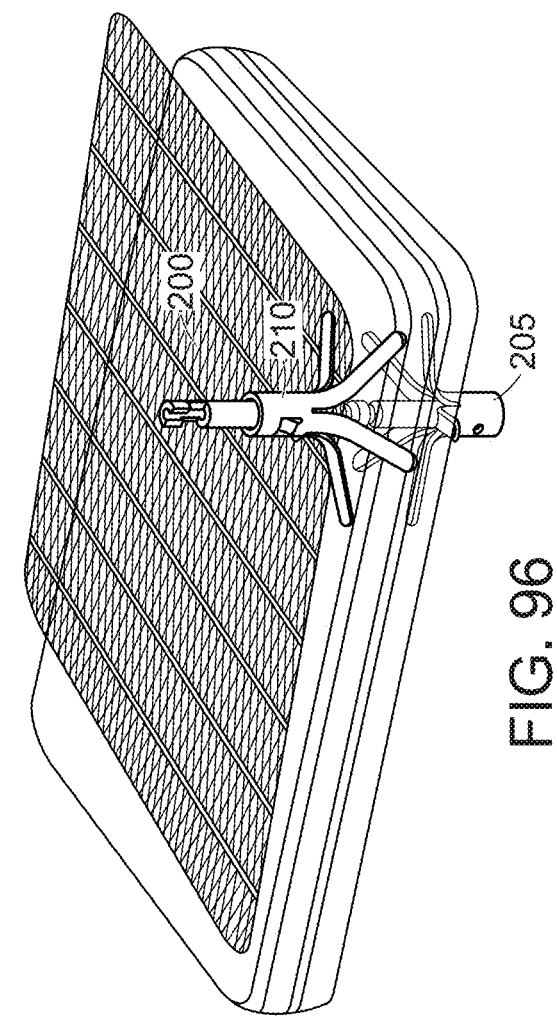
FIGS. 95 and 96 are schematic views showing the two-part fastener of the present invention being used to attach hernia mesh to tissue.
Figure 95:
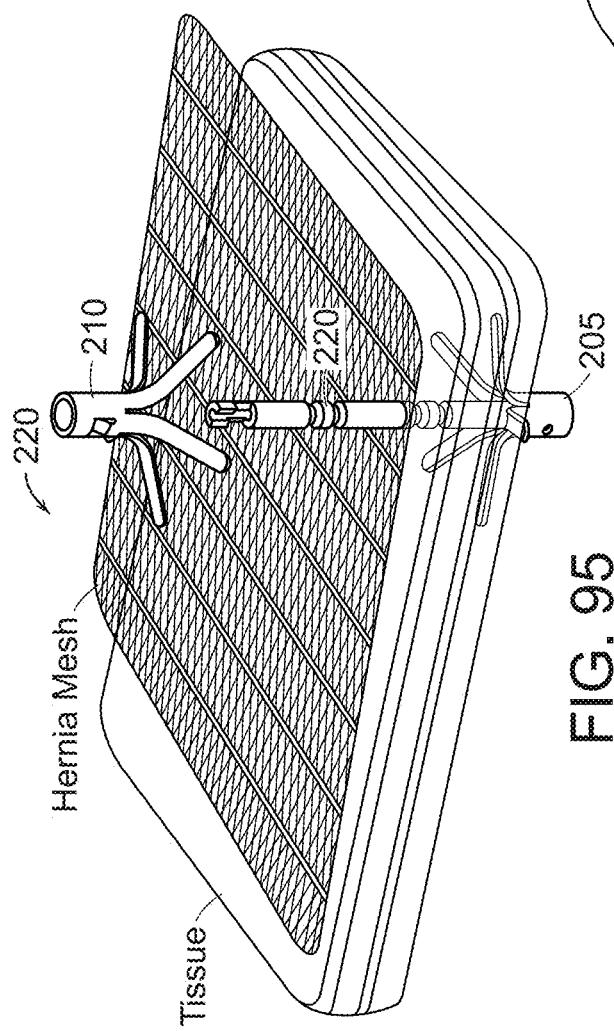

FIGS. 95 and 96 show two-part fastener 200 being used to clamp, for example, hernia mesh to tissue.

4. Two-Part Fastener 200 with Interdigitated Fingers

In addition to the foregoing advantages (over prior art clamps and staples) of using two-part fastener 200 to occlude a tubular structure, it should also be appreciated that the provision and use of a two-part fastener 200 having interdigitated legs (i.e., legs 235 of distal implant 205 and legs 295 of proximal implant 210) allows a tubular structure to be safely occluded in a way that avoids the problems associated with staples or clips (e.g., hemoclips, Ligaclips, etc.) (see above) and which allows the clamping force which is used to be adjustable.

In a preferred embodiment, the present invention generally comprises two compression elements, a proximal implant 210 for compressing the near wall of the vessel, and a distal implant 205 for compressing the far wall of the vessel. Proximal implant 210 and/or distal implant 205 may be made of a shape memory metal (e.g., Nitinol), other biocompatible metals and/or ceramics, and/or various polymers and biodegradable polymers that assume their designated configuration when two-part fastener 200 is used to occlude a vessel. Proximal implant 210 comprises a plurality of legs 295 for applying clamping pressure to the proximal side of a vessel which is to be occluded and distal implant 205 comprises a plurality of legs 235 for applying clamping pressure to the distal side of a vessel which is to be occluded.

Figure 98:
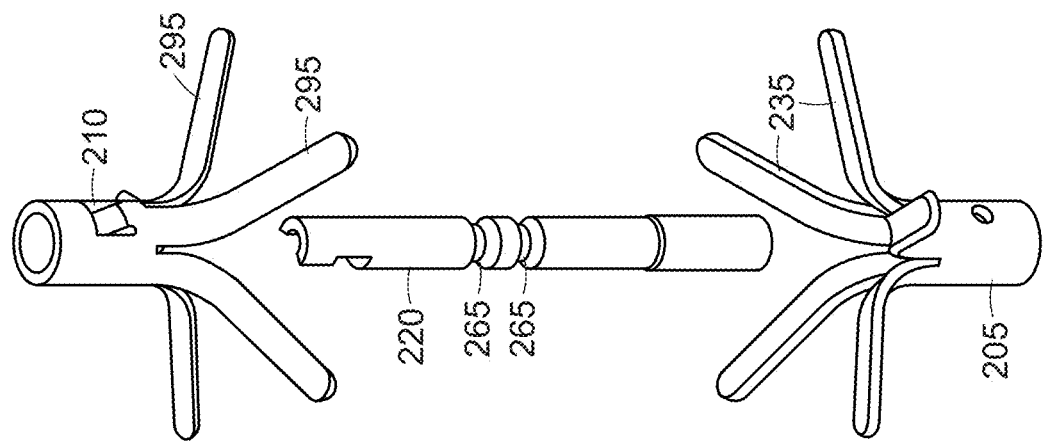
FIGS. 97-117 are schematic views showing how the distal and proximal legs of the two-part fastener may be aligned with one another, or interdigitated between one another, when the two-part fastener is deployed.
Figure 97:
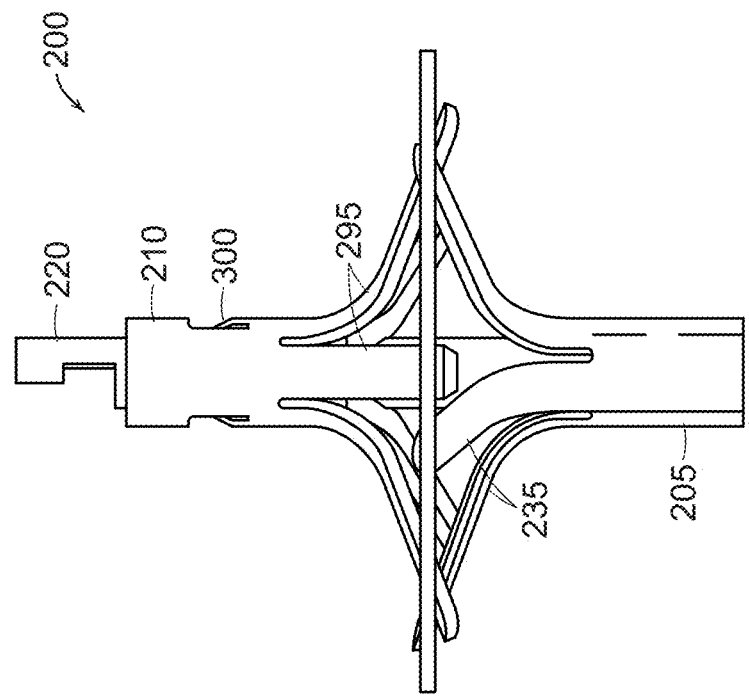

FIGS. 97 and 98 show two-part fastener 200 being used to occlude a blood vessel (or clamp tissue). In one preferred embodiment of the present invention, distal implant 205 is pre-attached to (or formed integral with) distal implant locking tube 220 (also sometimes referred to herein as the implant locking rod, which also may be made of an organic, ceramic, or biodegradable polymer). In one embodiment of the present invention, distal implant 205 is secured to distal implant locking tube 220 through welding. By way of example but not limitation, distal implant 205 may be welded to distal implant locking tube 220 using a welding material introduced at least in part into a welding hole 600 formed in distal implant locking tube 220 (see FIG. 102). In another embodiment of the present invention, distal implant 205 is secured to distal implant locking tube 220 through a mechanical locking, latching or threaded screw arrangement. In another embodiment of the present invention, distal implant 205 and distal implant locking tube 220 are formed out of one contiguous piece and material. Proximal implant 210 is preferably locked to distal implant locking tube 220 by way of inwardly-oriented flaps (i.e., inwardly-projecting tangs 300) which are formed in the body of proximal implant 210 and lock into corresponding openings (i.e., windows 265) formed in distal implant locking tube 220. It should be appreciated that, if desired, flaps (i.e., inwardly-projecting tangs 300) may be formed on distal implant locking tube 220 as outwardly projecting tangs, with corresponding openings (i.e., windows 265) being formed in proximal implant 210 (i.e., to receive the flaps formed on distal implant locking tube 220). There may be one window 265, or 2 windows 265, or 3 or more windows 265. Windows 265 may cover 1%-100% of the circumference of distal implant locking tube 220, or 1%-95% of the circumference of distal implant locking tube 220 if windows 265 are located on proximal implant 210.

Two-part fastener 200 is capable of generating an occlusion pressure (i.e., a clamping force between proximal implant 210 and distal implant 205) which is sufficient to clamp a blood vessel with a pressure of at least 100 mm Hg. In another embodiment of the present invention, two-part fastener 200 is capable of withstanding a pressure of up to 300 mm Hg, and in a further embodiment of the present invention, two-part fastener 200 is capable of supporting a pressure of over 700 mm Hg. FIG. 97 shows the interdigitation (i.e., circumferential offset) of legs 295 of proximal implant 210 and legs 235 of distal implant 205.

5. Adjustable Clamping Force

In a further embodiment of the present invention, the amount of pressure (i.e., the amount of clamping force) that two-part fastener 200 applies to the tissues, or across a blood vessel, can be variably controlled.

Figure 99:
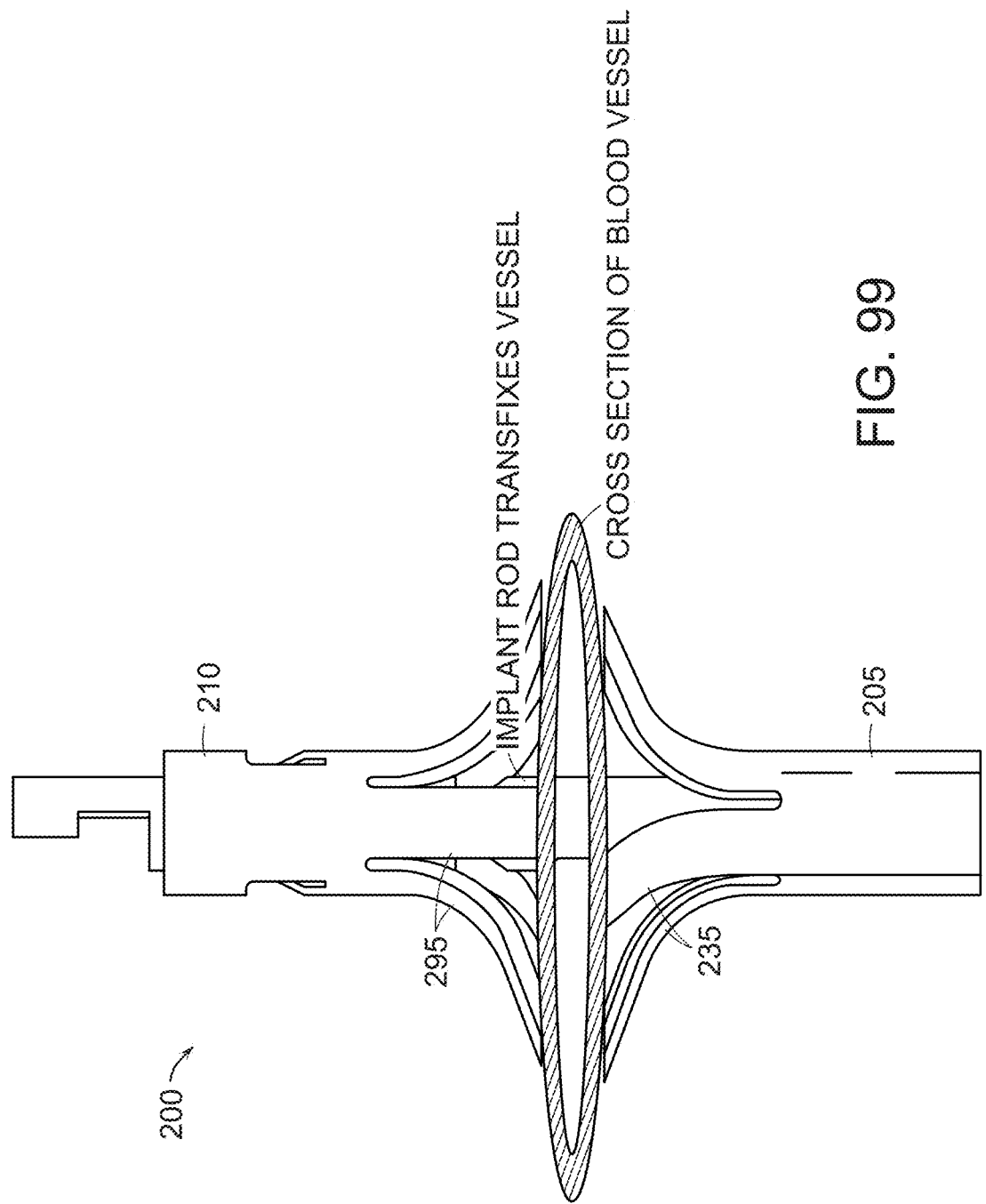

More particularly, FIG. 99 illustrates how the gap between legs 235 of distal implant 205 and legs 295 of proximal implant 210 can be controlled, effectively controlling the amount of pressure applied to the tissue being clamped, or the degree to which the aperture (i.e., lumen) of the vessel being transfixed by two-part fastener 200 is occluded.

Figure 101:
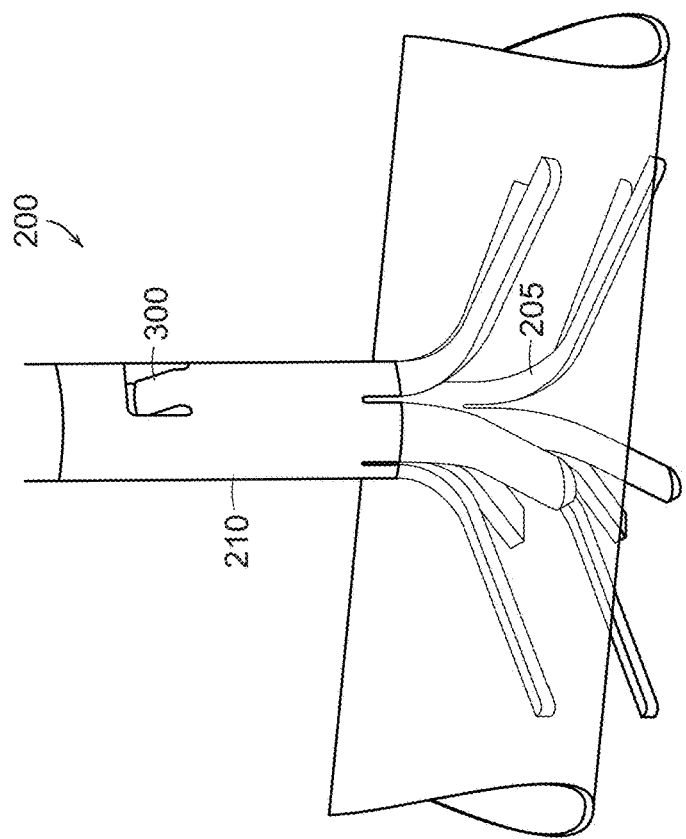
Figure 100:
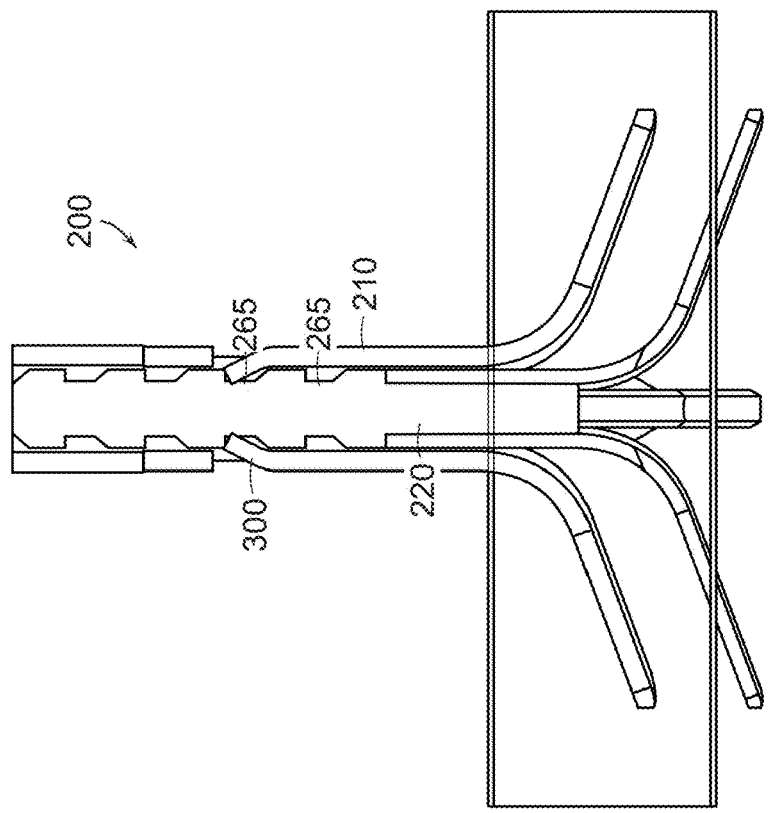

FIG. 100 shows one embodiment of the present invention wherein distal implant locking tube 220 comprises a controllable ratcheting mechanism for selectively controlling the spacing between proximal implant 210 and distal implant 205 of two-part fastener 200. In this form of the invention, legs 235 of distal implant 205 and legs 295 of proximal implant 210 are generally oriented primarily in a parallel orientation to each other, and the distal and proximal fingers are aligned so that they overlapping. FIG. 101 shows an external view of a ratcheting mechanism of the present invention which allows a variable disposition of proximal implant 210 and distal implant 205 relative to one another.

In this form of the present invention, distal implant locking tube 220 comprises a plurality of windows 265 (e.g., a plurality of circular grooves) formed along its length. Proximal implant 210 comprises a plurality of inwardly-projecting tangs 300 formed at a point along its length. As proximal implant 210 is advanced distally towards distal implant 205, inwardly-projecting tangs 300 enter into windows 265, thereby locking proximal implant 210 to distal implant 205. Inwardly-projecting tangs 300 are configured so that proximal implant 210 can only move in a single direction (i.e., distally) relative to distal implant 205. As proximal implant 210 is advanced distally relative to distal implant 205, inwardly-projecting tangs 300 can slide out of windows 265 and enter windows 265 located distally. If desired, windows 265 may comprise a chamfered distal edge to facilitate movement of inwardly-projecting tangs 300 out of windows 265 as proximal implant 210 moves distally relative to distal implant 205.

Figure 102:
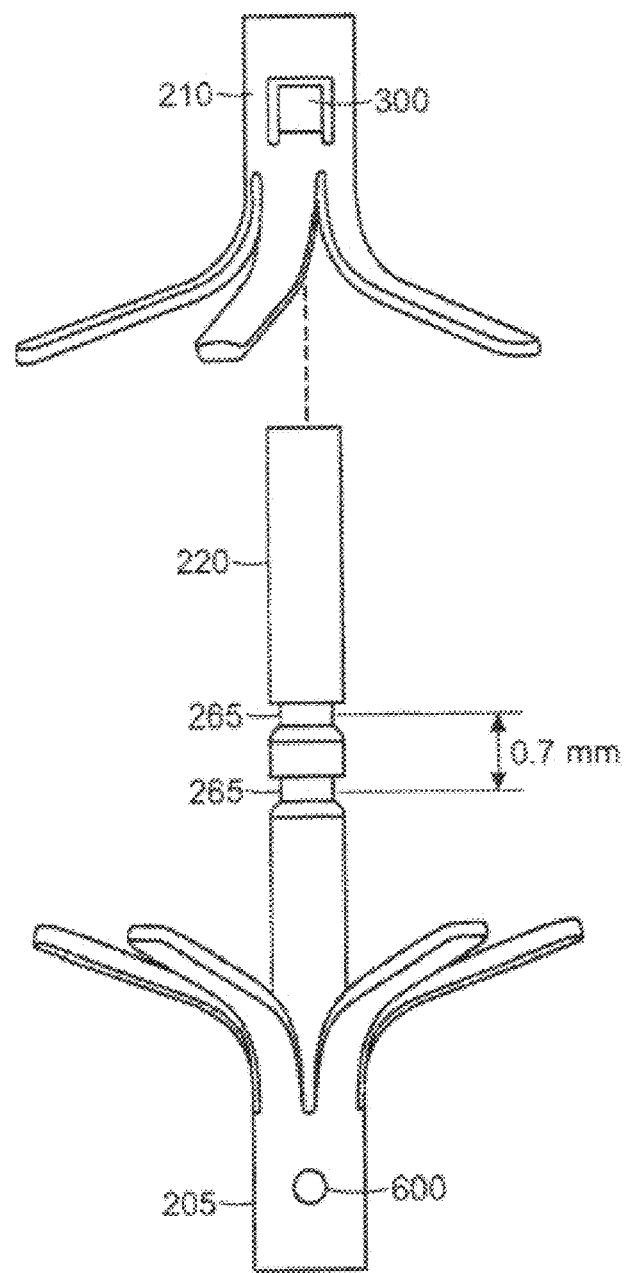
Figure 105:
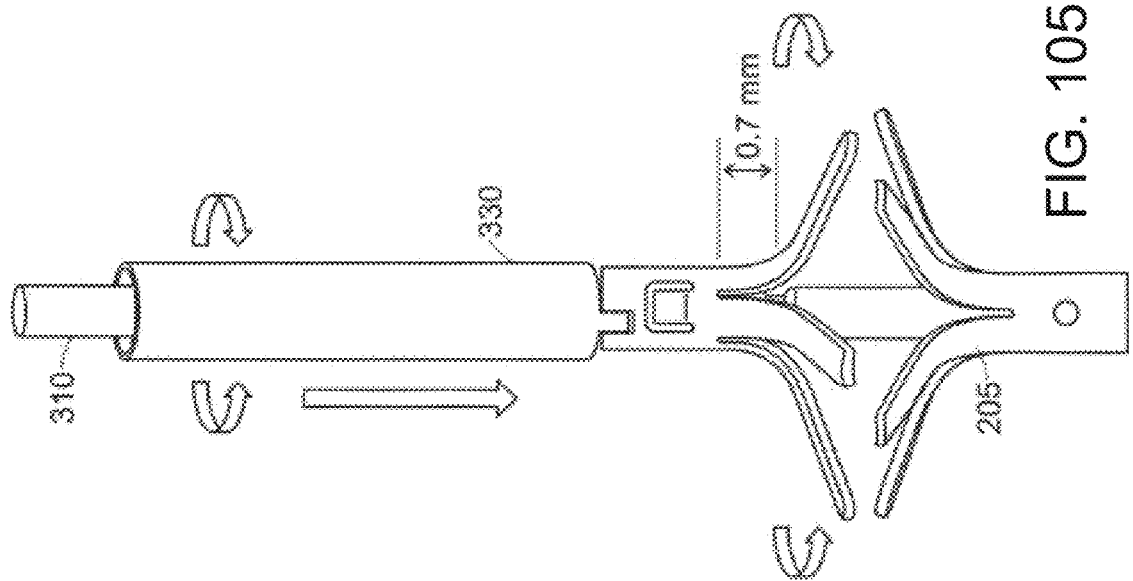
Figure 104:
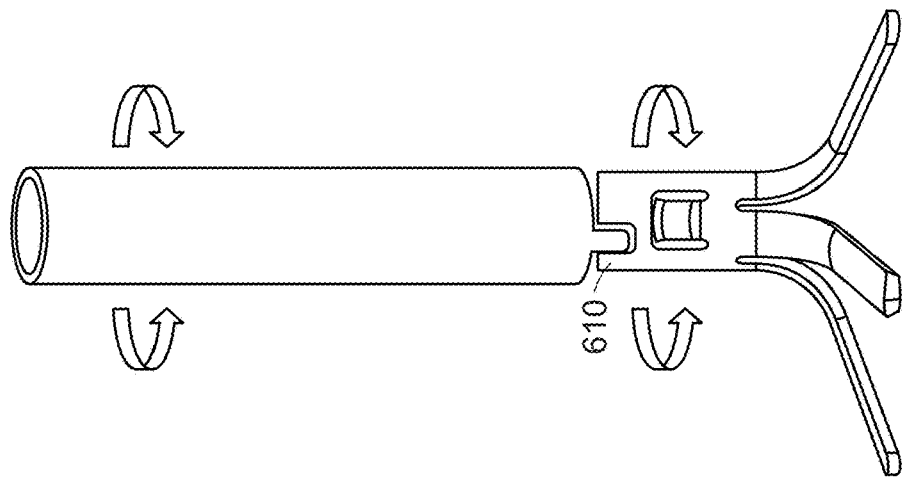

See also FIG. 102, and note the "notch-to-notch distance" (i.e., the distance between windows 265) which governs the ability to vary the degree of compression established between legs 235 of distal implant 205 and legs 295 of proximal implant 210.

The degree of overlap and/or alignment of legs 235 of distal implant 205 and legs 295 of proximal implant 210 can be controllably adjusted in several ways. First, the locking mechanism (e.g., the inwardly-projecting tangs 300 of proximal implant 210 and windows 265 of distal implant 205) may be appropriately positioned relative to one another so as to set the orientation of proximal implant 210 relative to distal implant 205 prior to locking.

Figure 103:
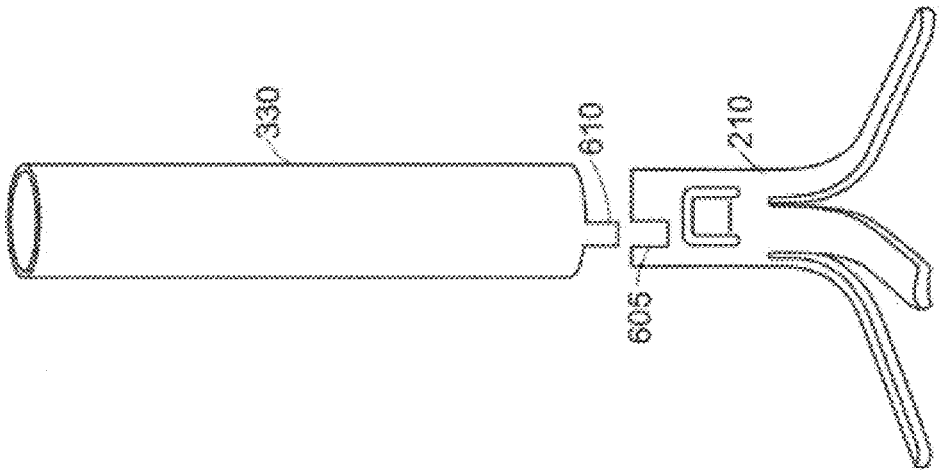
Figure 106:
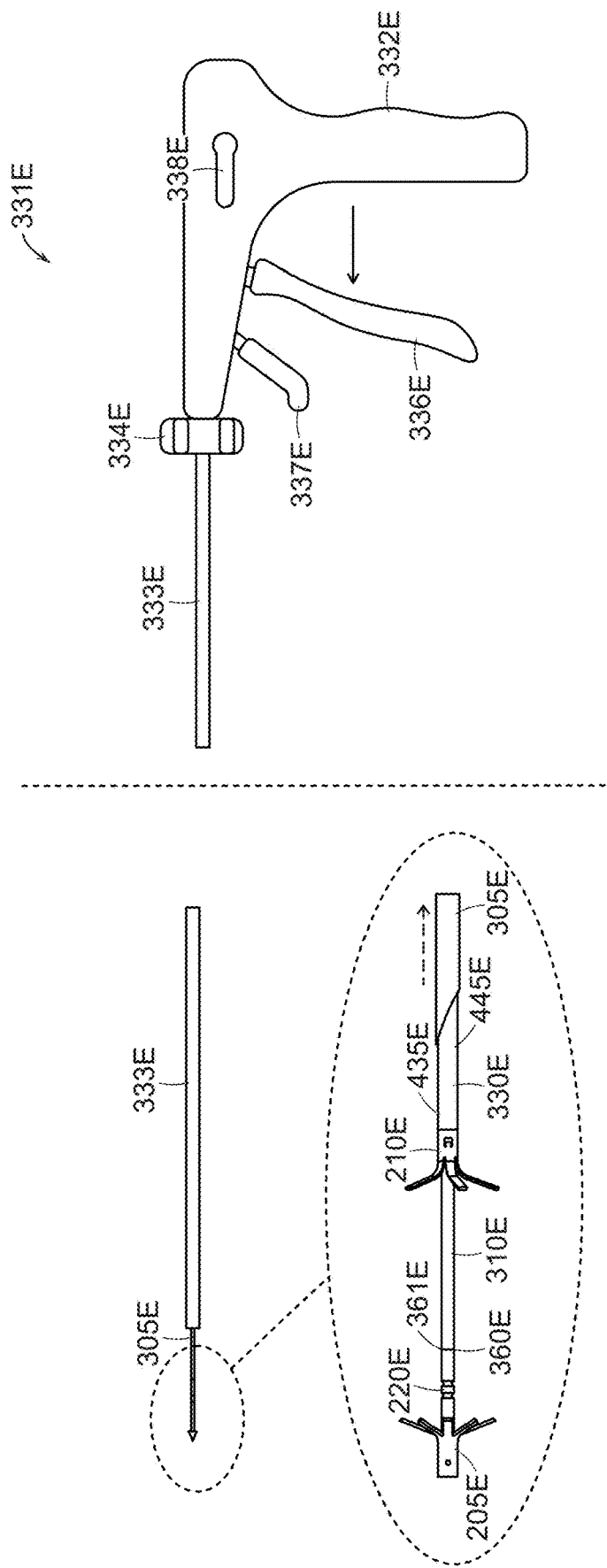

In one form of the present invention, and looking now at FIGS. 103-106, there is provided a mechanism for setting the rotational orientation of proximal implant 210 relative to distal implant 205. FIG. 103 shows the mechanism for alignment and orientation control of the proximal implant 210 through an orientation alignment groove (or notch) 605 formed in the proximal end of proximal implant 210, and a corresponding orientation alignment post (or tab) 610 formed in proximal implant delivery tube 330. If desired, multiple orientation alignment grooves 605 and multiple corresponding orientation alignment posts 610 may be provided. By controlling the degree of rotation of the proximal implant delivery tube 330 one can vary the rotational orientation of proximal implant 210 relative to distal implant 205 once proximal implant delivery tube 330 is advanced distally so as to engage proximal implant 210 and tab 610 is mated with groove 605. FIG. 106 shows how, in one form of the present invention, a rotor knob 615 may be provided which can be used to control the orientation of proximal implant 210 relative to distal implant 205. Rotor knob 615 exerts a rotary force on proximal implant tube 330 such that when rotor knob 615 is rotated, rotor knob 615 rotates implant tube 330. By way of example but not limitation, in one form of the present invention, when rotor knob 615 is rotated fully clockwise, legs 235 of distal implant 205 and legs 295 of proximal implant 210 fully overlap and are aligned. Each half-turn increment of rotor knob 615 can be configured to result in a 9-degree orientation difference between legs 235 and legs 295. Rotor knob 615 may have discrete set points (or stopping points) corresponding to each 9-degree increment of the rotor. Each one of these set points can be configured to correspond to the angles of 9-degrees, 18, 36 degrees (which is the maximal misalignment between the legs), 45, 54, 63, and 72 degrees (corresponding to full overlap of the legs) between two legs 235 and legs 295. The delivery device may have a display that indicates the angle between legs 235 and 295 that is incremented or decremented by 9-degrees depending on the half rotation of rotor knob 615 in the clockwise or counter-clockwise directions. Other discrete angle steps or increments between legs 235 and legs 295, or a continuous range of angles are also possible, depending on the particular configuration of the design of rotor knob 615.

Figure 109:
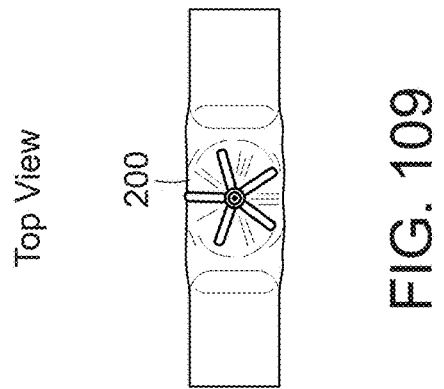
Figure 107:
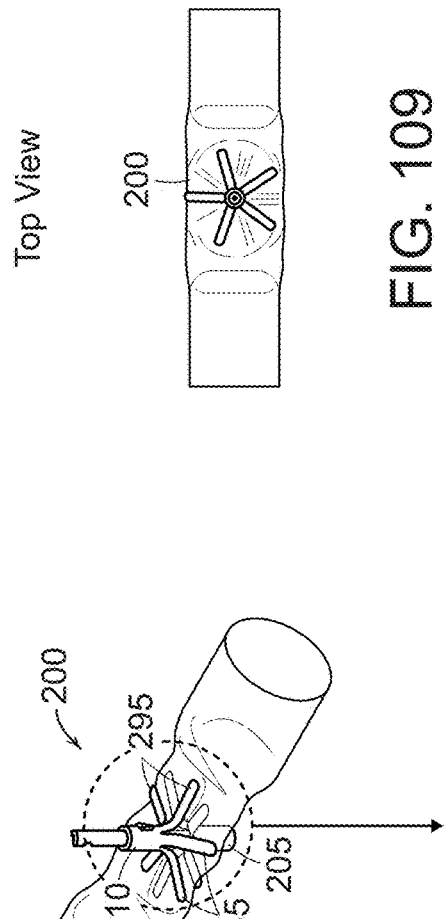
Figure 108:
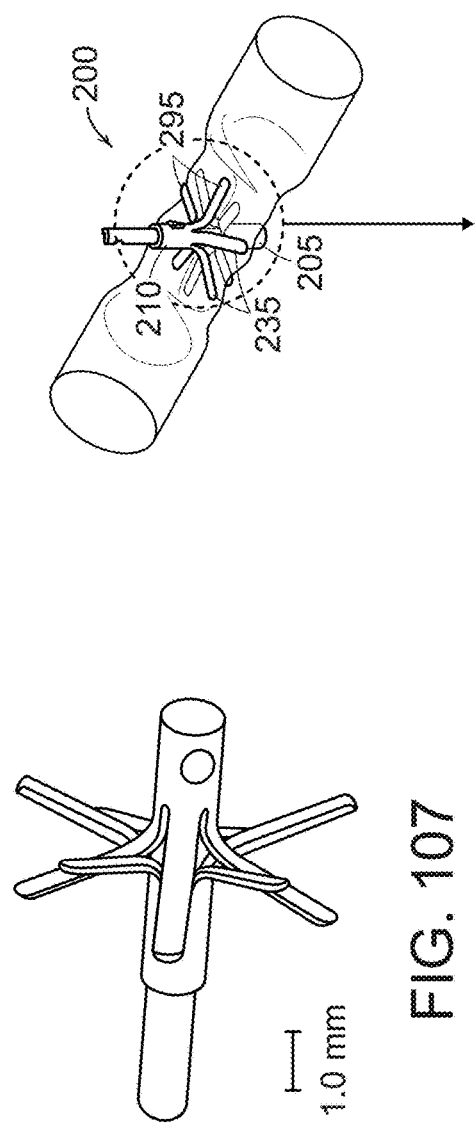
Figure 111:
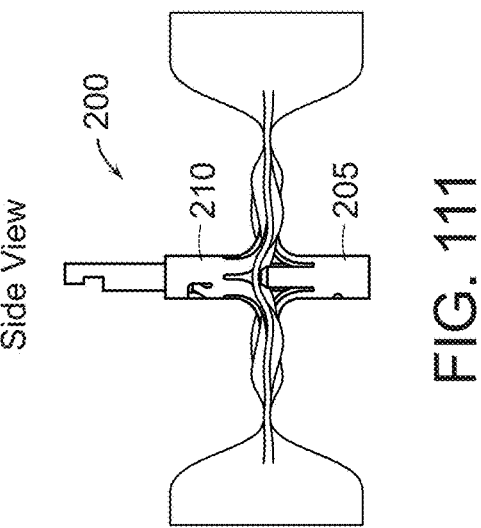
Figure 110:
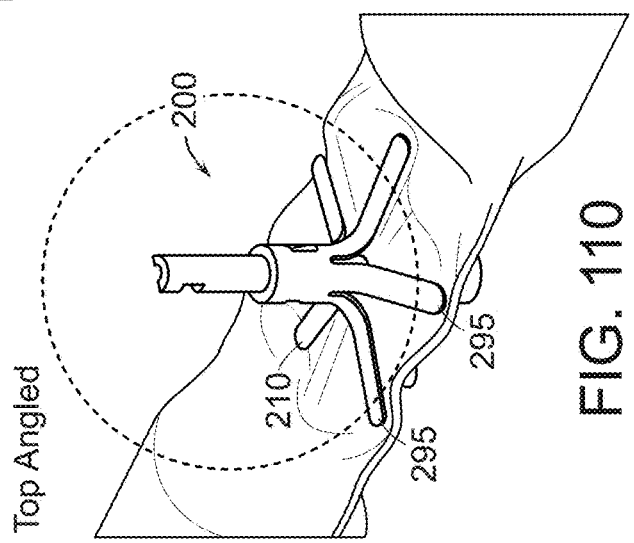

The design and mechanism of action of two-part fastener 200 is preferably such that when deployed and locked (e.g., with inwardly-projecting tangs 300 disposed in windows 265, the individual legs 295 of proximal implant 210 alternate with, and interdigitate with, the individual legs 235 of distal implant 205. FIGS. 109-111 are schematic views of a fully-deployed two-part fastener 200 (including a top view) looking down (i.e., looking distally) onto a deployed two-part fastener 200 and with the proximal and distal walls apposed. FIG. 107 is a photograph of a deployed fastener with offset legs 235 of distal implant 205 and legs 295 of proximal implant 210. Variable offset between legs 235 and legs 295 allows for the adjustment of clamping tension applied to the tissue. By way of example but not limitation, for delicate or easily damaged or torn tissue (e.g., brain tissue), or tissue that has limited elasticity, it is generally preferable that legs 235 and legs 295 substantially completely oppose one another (i.e., align with one another) so that no lateral tension is applied to the tissue. Similarly, for lung tissue, it may generally be preferable for legs 235 and legs 295 to have a substantial degree of overlap, so as to minimize the tension applied to the tissue.

On the other hand, for many vascular applications, maximum interdigitation (i.e., minimum overlap of the legs 235, 295) is generally preferred (e.g., an angle of 36 degrees between legs 235 and legs 295 may be desired) so as to maximize the tension applied to the tissue whereby to occlude the vessel.

With interdigitation of the legs 235 and legs 295 tension is projected across the tissue, with the closing force extending beyond the physical dimensions of legs 235 and legs 295 themselves.

Thus it will be seen that the disposition of legs 235 of distal implant 205 relative to the disposition of legs 295 of proximal implant 210 may be controlled so as to apply a desired clamping force according to the type and/or condition of the tissue which is to be clamped.

Figure 112:
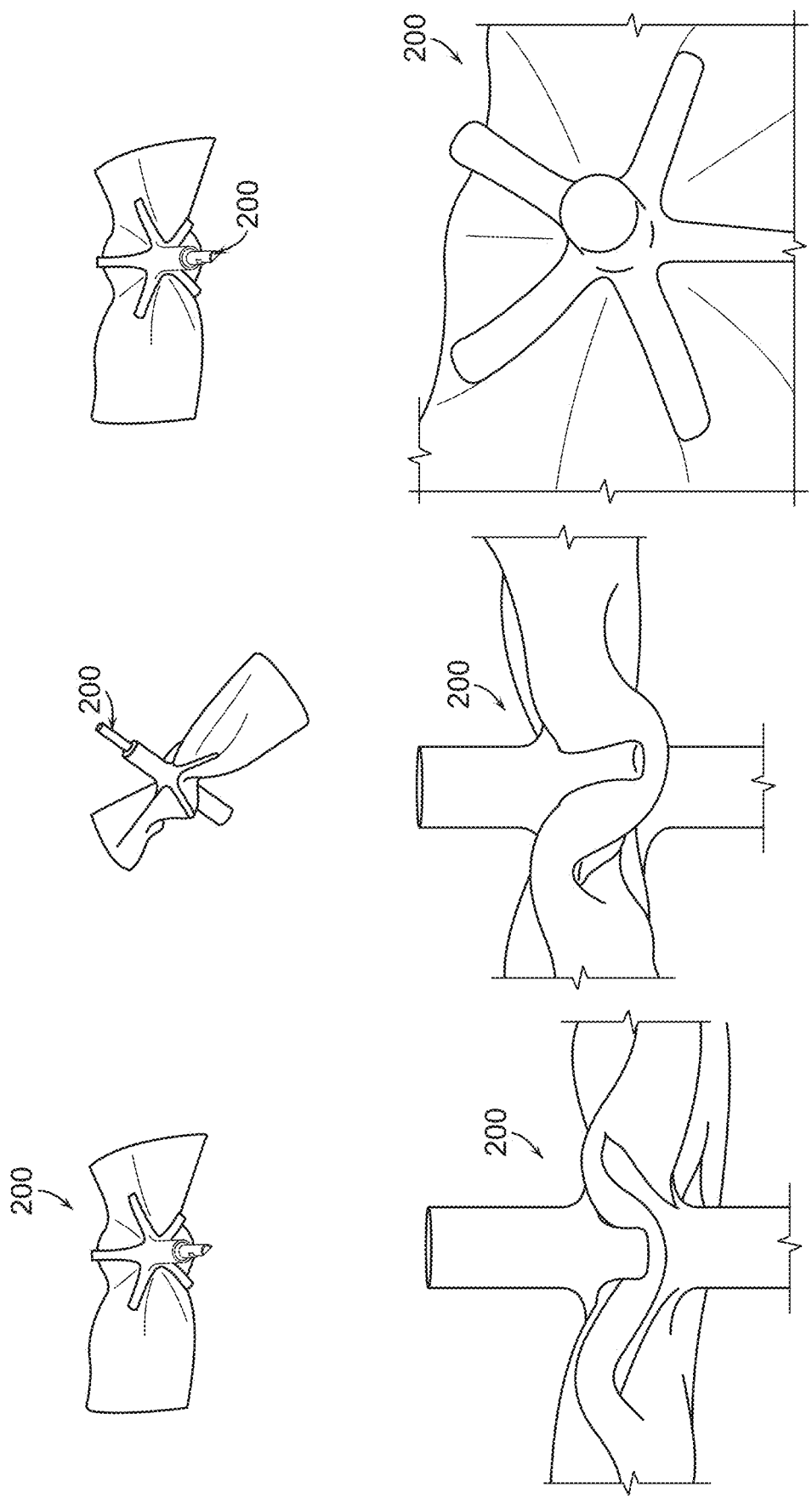

FIG. 112 shows a number of photographs that better illustrate how two-part fastener 200 effectively clamps tissue (in this case a simulated blood vessel). Legs 235 of distal implant 205 and legs 295 of proximal implant 210 are shown interdigitated. This causes ripples, or folds, in the tissue that act to extend the effective closure, and applies the closure force to the vessel well beyond the region directly contacted by the fastener legs 235, 295. By way of example but not limitation, a two-part fastener 200 having a physical occlusion diameter of 5.5 mm is able to close vessels that are over 7 mm (and even equal or greater to 1 cm) in diameter.

Figure 113:
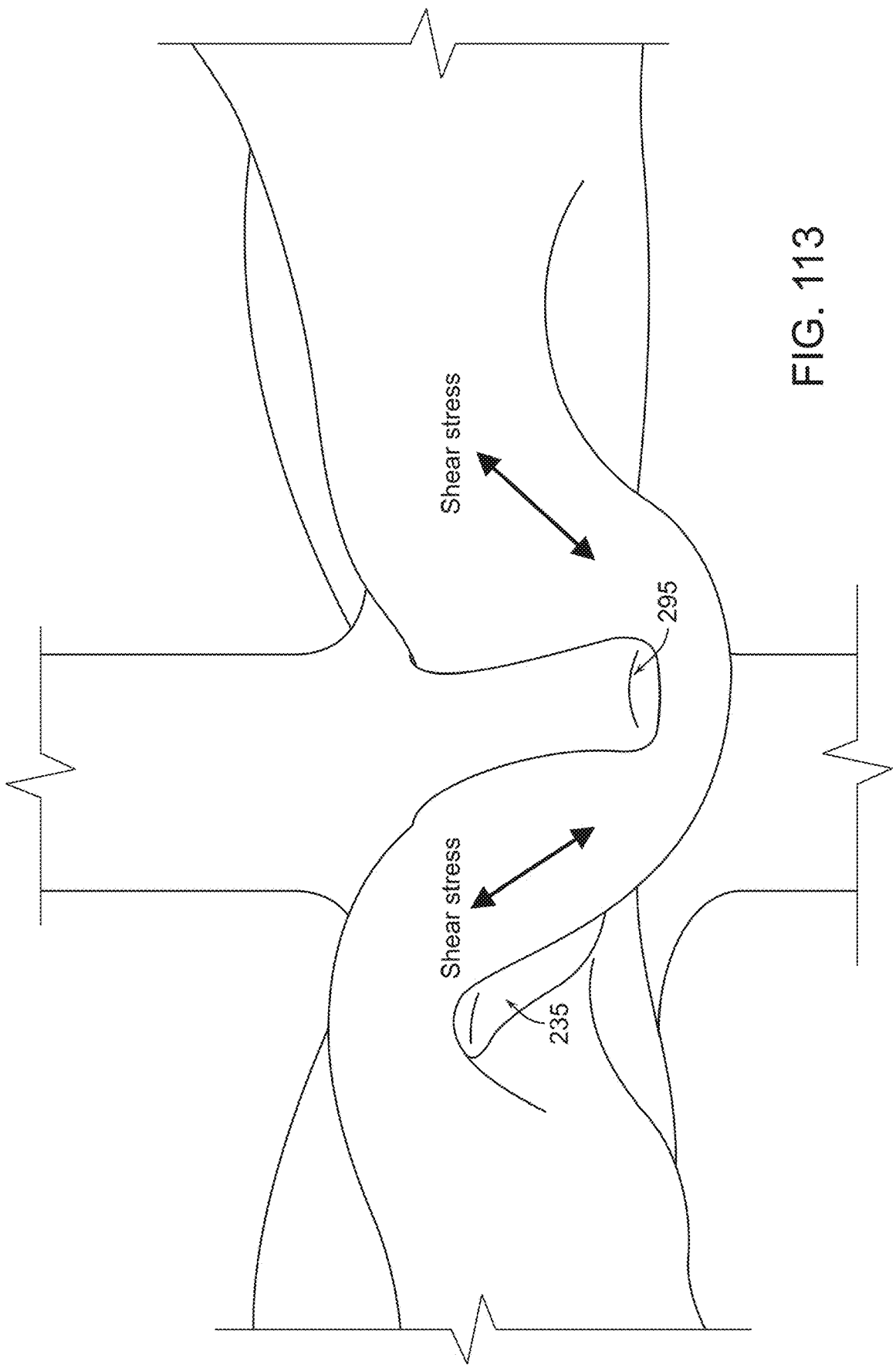

In one embodiment of the present invention, and looking now at FIG. 113, legs 295 of proximal implant 210 and legs 235 of distal implant 205 may be beveled (or rounded) so that legs 295, 235 are not sharp, and legs 295, 235 may be designed to point away from the tissue to be clamped at the free end of each leg (i.e., on the end of the leg away from the distal implant locking tube 220). This is in order to minimize any catching or damage that may be imparted on the tissue by legs 235, 295, whereby to minimize tearing or ripping of the tissue. In other embodiments of the present invention, it may be desirable to provide sharp ends to legs 235, 295 so that legs 235, 295 catch or pierce the tissue for better gripping. Legs 235, 295 may be smooth, or the surface of legs 235, 295 may be roughened, e.g., through chemical etching or mechanical means, so as to enhance the reflectivity of the implants, or to provide maximum tissue capture and gripping.

Looking at FIGS. 112 and 113, it can be seen that (i) legs 295 of proximal implant 210 and legs 235 of distal implant 205 alternate and interdigitate with one another, and (ii) the distal ends of legs 295 of proximal implant 210 pass distally of the proximal ends of legs 235 of distal implant 205, and vice versa. In effect, when fully deployed on an artery or vein, or duct, or other organ tissue, there is a predominantly circular occlusion of the vessel around distal implant locking tube 220 by legs 235, 295 of the distal implant 205 and proximal implant 210, respectively. This circular occlusion resembles, in some ways, a "pie crust" pattern in which the proximal wall and distal wall of the vessel are brought into apposition with one another, with distal implant locking tube 220 at the center of the "pie".

FIG. 113 shows the shear stress induced between the interdigitation of legs 235 and legs 295, acting to pull the tubular structure aperture closed.

Figure 114:
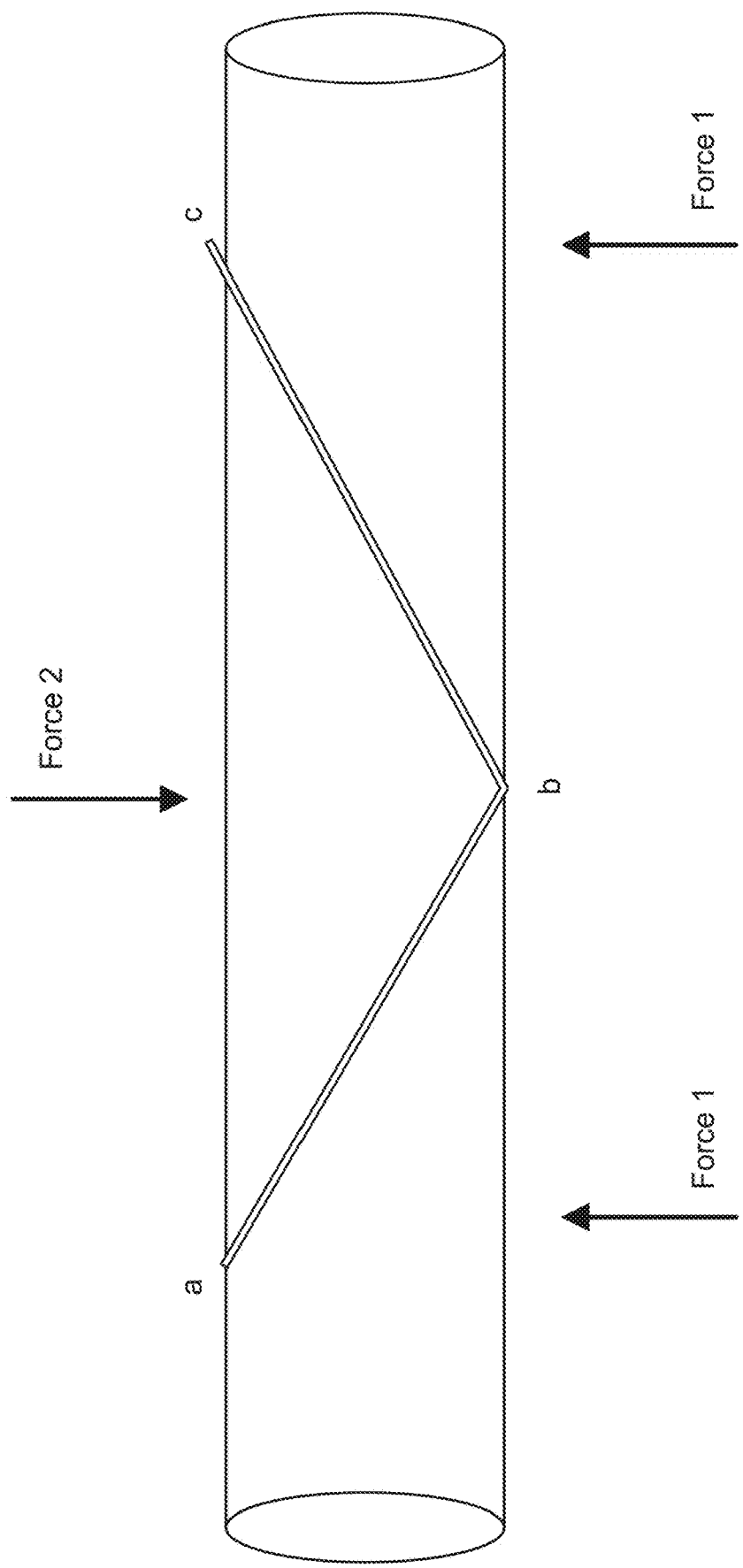

FIG. 114 shows how a plurality of forces may be applied across the vessel using the interdigitation of legs 235, 295 of two-part fastener 200 of the present invention.

Figure 115:
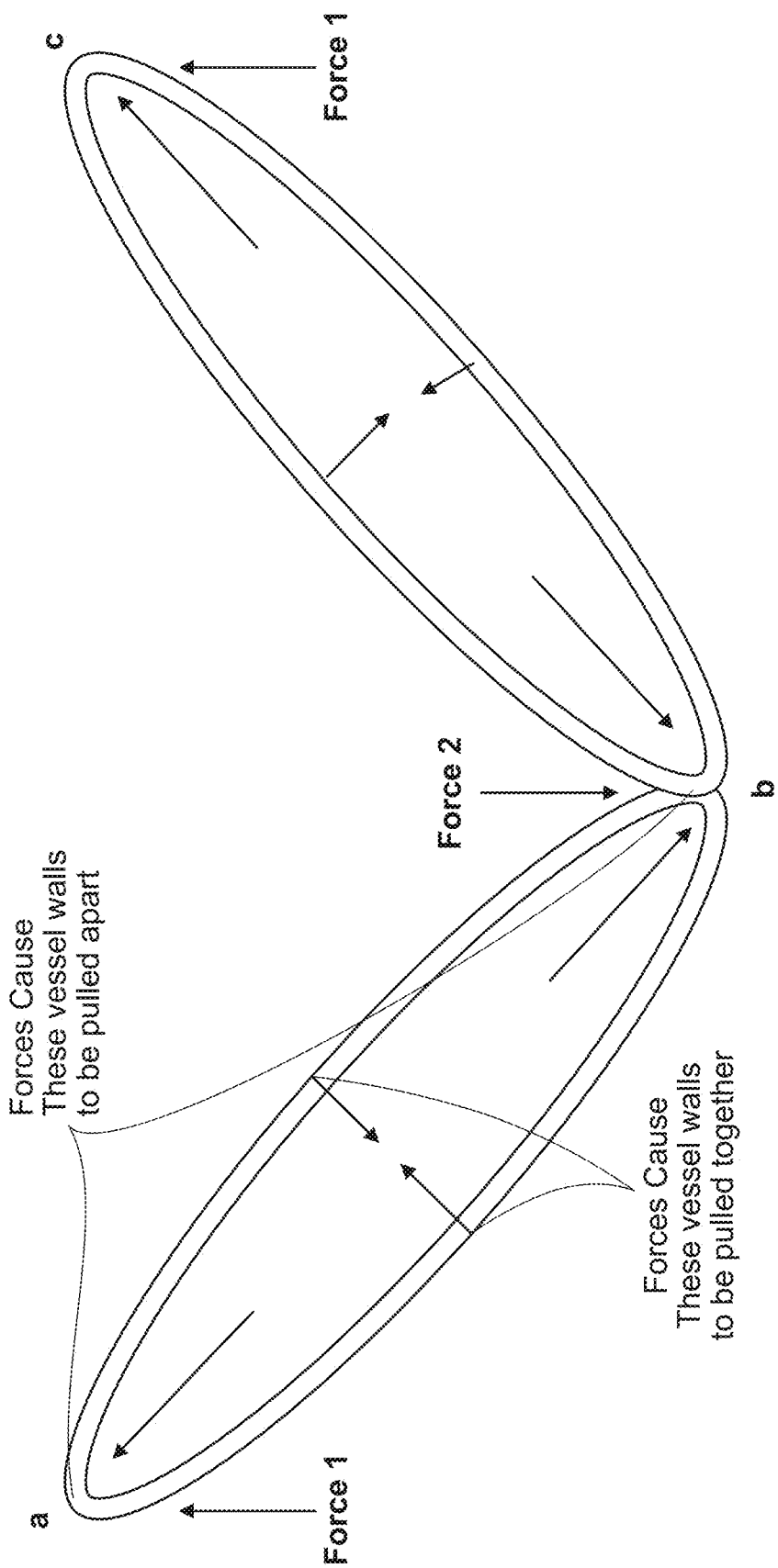

FIG. 115 shows, with the cross-sections a-b and b-c, the strains induced in a vessel by the clamping forces generated by the interdigitated legs 235, 295 of two-part fastener 200.

Figure 116:
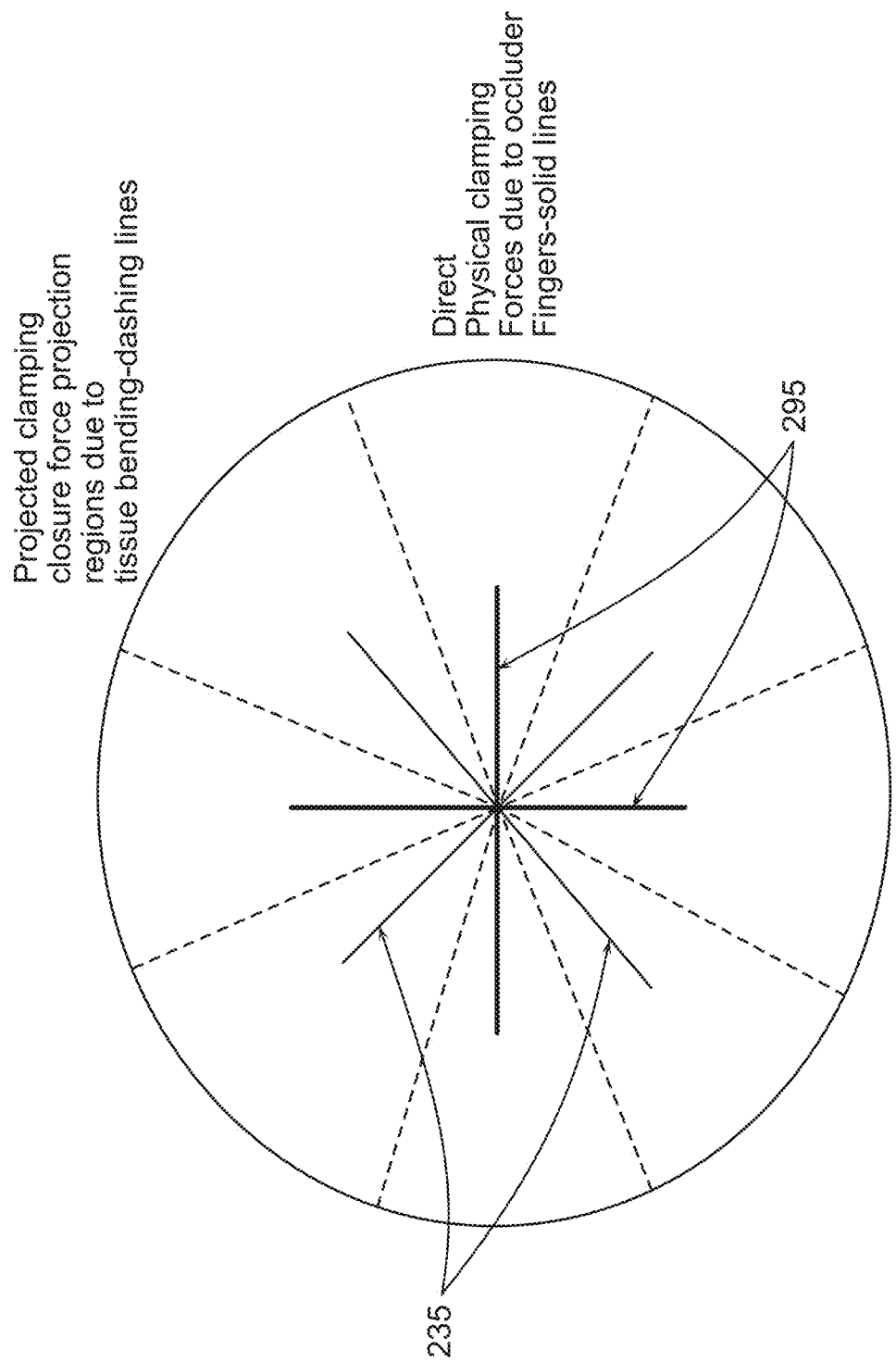

FIG. 116 is a top view showing tissue folding when legs 235 and legs 295 of two-part fastener 200 are interdigitated with one another. The dashed lines show the regions where the tissues are pulled together so as to touch. When legs 235, 295 are interdigitated, a force is applied that radiates beyond the physical length of legs 235, 295 extending the clamped tissue closure beyond the diameter of the physical legs.

Due to the interdigitated mode of operation, the estimated sum of the proximal and distal wall thicknesses of the vessel that is to be occluded does not necessarily determine whether an effective occlusion can be achieved. Since the occlusion components (i.e., legs 235 and legs 295) cross each other's plane when deployed, the proximal and distal walls of the vessel are brought into opposition with one another regardless of their summed wall thickness, i.e., 2.0 mm veins have approximately 0.2 mm wall thickness (0.4 mm combined), as compared to a 3.5 mm muscular artery having approximately 0.6 mm wall thickness (1.2 mm total combined) and even a 7.0 mm muscular artery having approximately a 1.0 mm wall thickness (2.0 mm combined). Each of these vessels, with varying dimensions, can be effectively occluded using two-part fastener 200 due to the way two-part fastener 200 ligates the vessel. The interdigitation of legs 295 of proximal implant 210 and legs 235 of distal implant 205 means effective closure can be realized even with very thin tissue, since legs 295, 235 of the fastener components cross each other's plane when two-part fastener 200 is deployed across the tissue.

In one embodiment of the present invention, where legs 295 of proximal implant 210 and legs 235 of distal implant 205 are interdigitated, the force needed to close the vessel disposed between proximal implant 210 and distal implant 205 using two-part fastener 200 is much less than the force needed to close the same vessel with a conventional ligation clip. This is due to the fact that, in the case of two-part fastener 200, interdigitated legs 295, 235 are pushing against tissue, causing the tissue waviness, bending, or folding, but are not pushing up against the full force of counter-set legs 295, 235. This means that vessel closure can be realized with a reduced level of force or pressure on the tissue.

Figure 117:
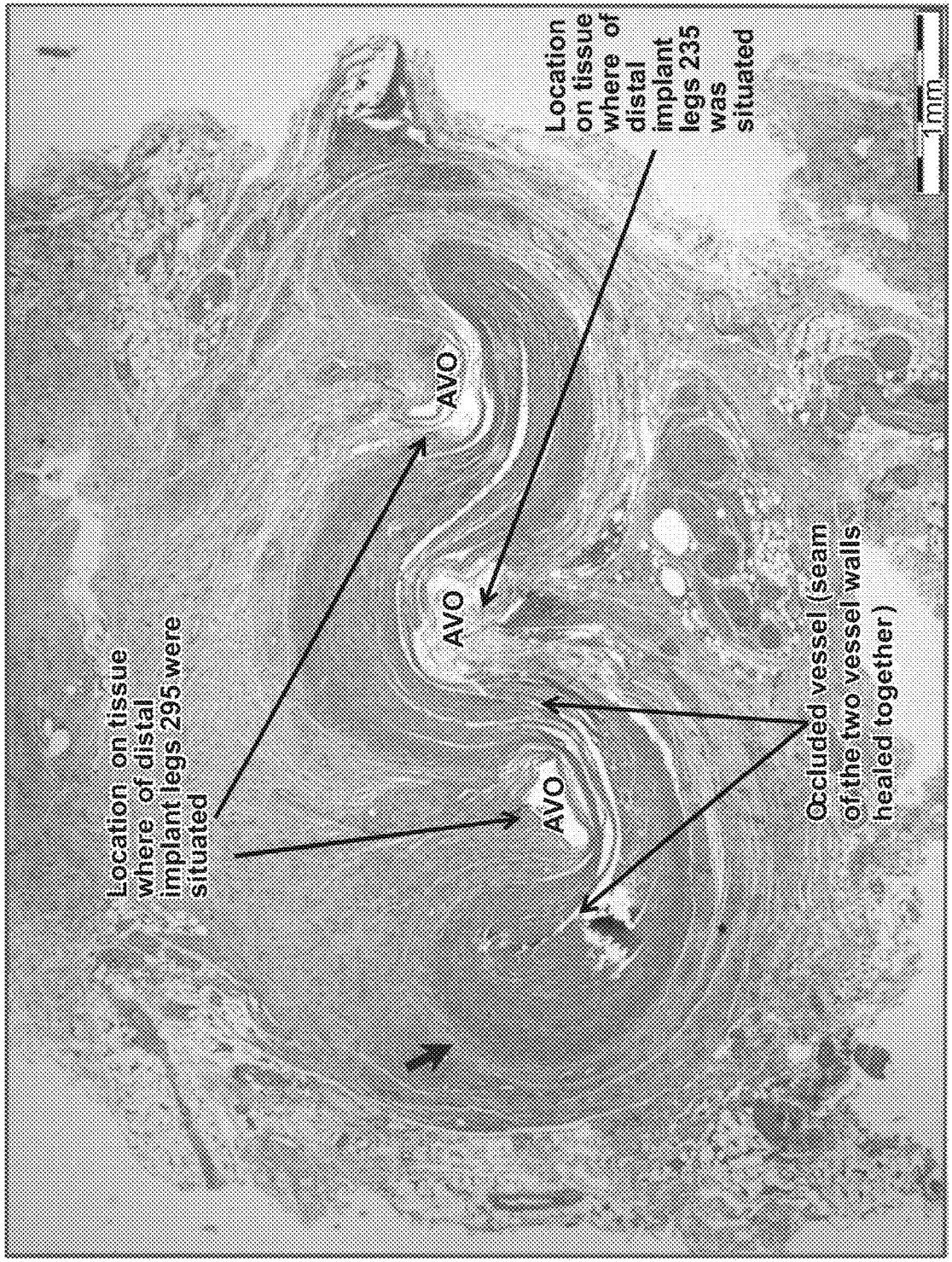

FIG. 117 is a histological section showing the residual impact on the vessel cross-section occluded by legs 295, 235 after vessel healing of up to 30 days. The vessel is completely occluded and the vessel wall tissue is compressed together and, with early healing, "healed" together. The effect of the sheer forces collapsing the vessel walls together can be seen in FIG. 117. The "pie crust" closure may be observed more clearly as well. The arrow indicates the collapsed undulating artery. AVO indicates the location of the interdigitating legs of two-part fastener 200.

The two-part fastener 200 of the present invention may be used to occlude vessels, ducts and/or to compress tissue so it is occluded/compressed at forces less than 700 grams, while the force required to seal off vessels or clamp tissue with a Ligaclip are about 10 times greater. The delivery system for two-part fastener 200 imparts a force which is transferred directly from the operator to two-part fastener 200. This reduces requirements and levering on the delivery device and the amount of force or pressure an operator may need to apply. The two-part fastener 200 of the present invention, can maintain operation in the elastic regime and does not need to be plastically deformed to realize occlusion.

6. Novel Clip with Interdigitated Fingers

It should be appreciated that the use of interdigitated legs to occlude a vessel may extend beyond use with two-part fastener 200. By way of example but not limitation, a novel clip 625 comprising interdigitated and at least in part horizontally spaced legs 630 connected at a common end 635 may be provided.

Figure 118:
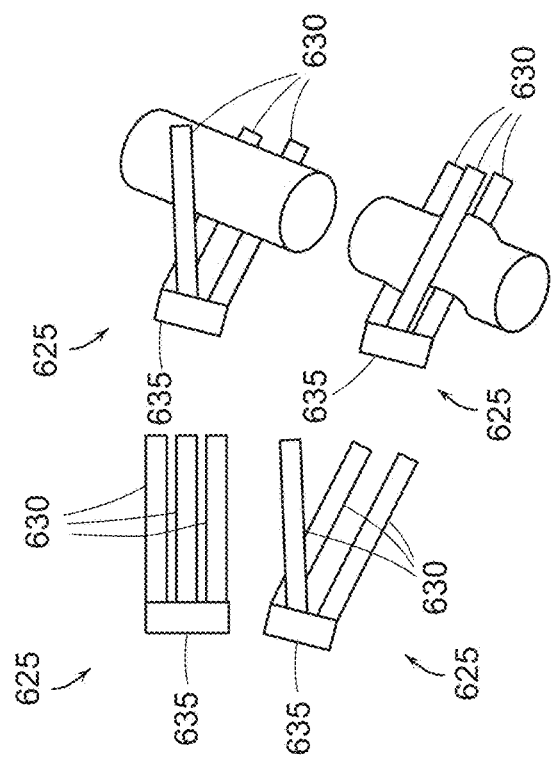
FIGS. 118-120 are schematic views showing additional ways in which the interdigitation of legs may be used to occlude a structure.
Figure 119:
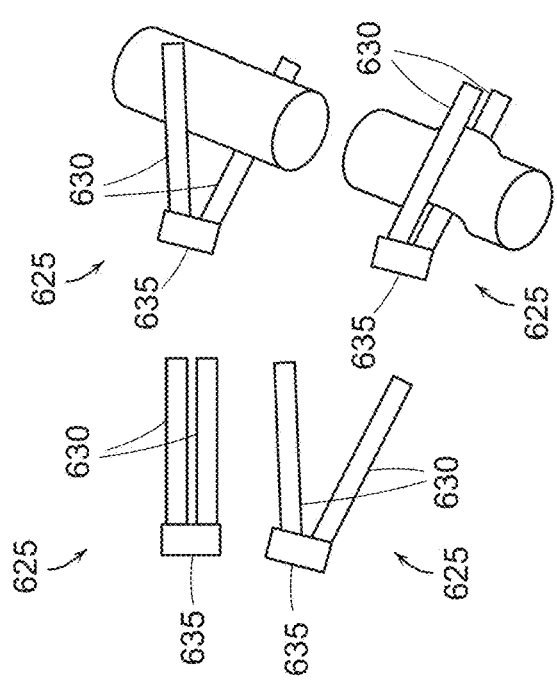
Figure 120:
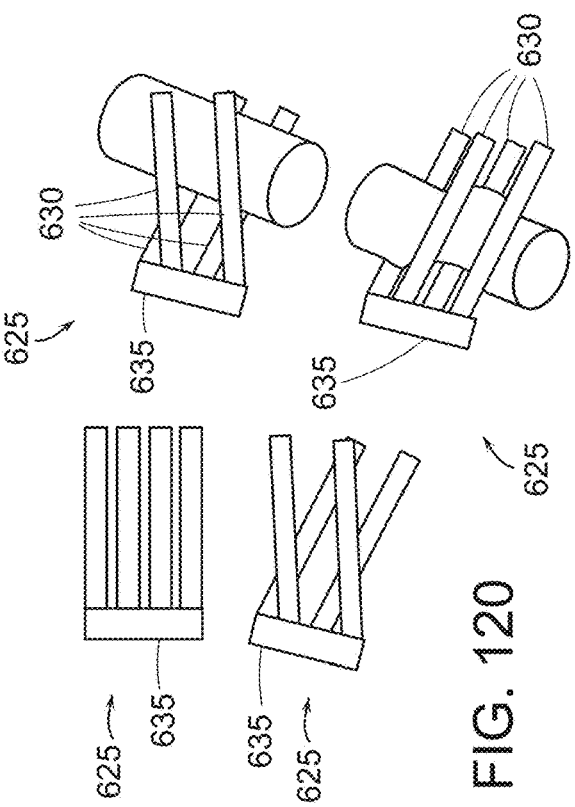

FIGS. 118-120 show a novel ligating clip 625 which uses interdigitation of legs 630 (deployed alternatingly on the proximal and distal sides of the vessel) to create vessel closure. Once again, sheer stress is induced so as to close the vessel or duct. The interdigitation of legs 630 will also reduce the likelihood that the tissue being clamped will slip out, or that the clamp will fall off. In this case, similar to a hemo-clip, legs 630 of ligating clip 625 are "squashed" together across the vessel to be occluded or tissue to be attached. In one embodiment of the invention, legs 630 are pushed so that the tips of legs 630, deployed on the distal side of the vessel, are now above the tips of legs 630 deployed on the proximal side of the vessel, crossing each others plane, so that the tissue between them is stretched closed.

7. Delivery of Multiple Two-Part Fasteners

The ability to deploy multiple two-part fasteners 200 during a procedure can be an important advantage in numerous applications. By way of example but not limitation, when treating venous reflux disease, multiple reflux sites may need to be occluded, or a certain length of vessel may need to be occluded, and it may be desirable to utilize multiple two-part fasteners 200 to achieve this. By way of further example but not limitation, when preparing a vein or artery to be used for a bypass procedure, multiple branch or tributary vessels need to be occluded, and multiple two-part fasteners 200 of the present invention may be used. By way of example but not limitation, when it is desired to isolate the region between two parts of a vessel or duct by cutting the region between the two parts (e.g., when removing a bile duct), one two-part fastener 200 may be deployed on either side of the region to be cut, so as to prevent blood loss. For example when desiring to remove a gall bladder the cystic duct needs to be ligated to prevent spillage of bile from the common bile duct or harvesting an organ, such as the kidney, for transplant or removing part or the entire organ, such as the spleen, for therapeutic considerations.

There are several ways in which multiple two-part fastener's 200 can be delivered.

8. Reusable Handle with Disposable Tip

Figure 121:
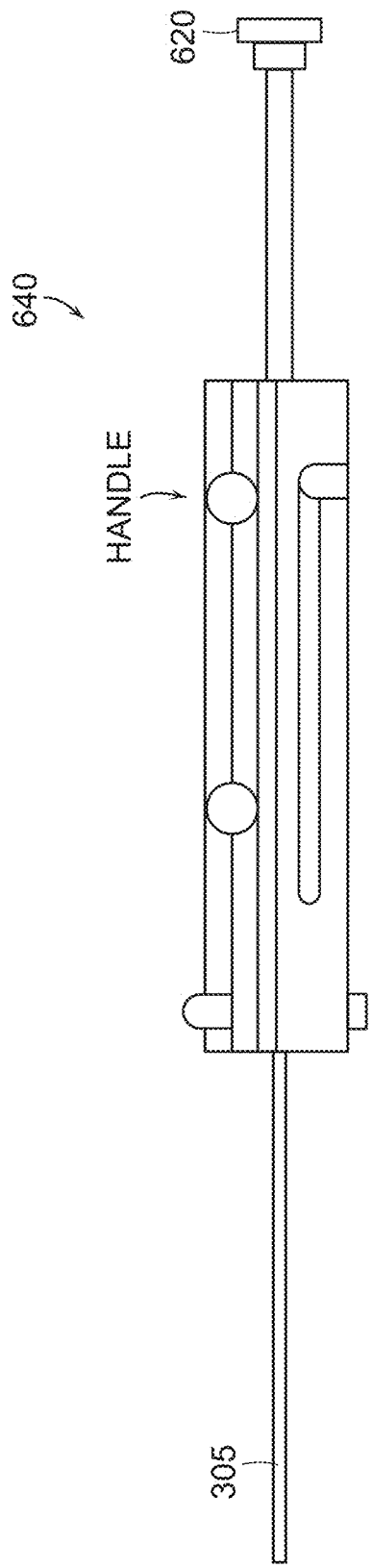
FIGS. 121-124 are schematic views showing a single use delivery device for delivering an fastener.
Figure 122:
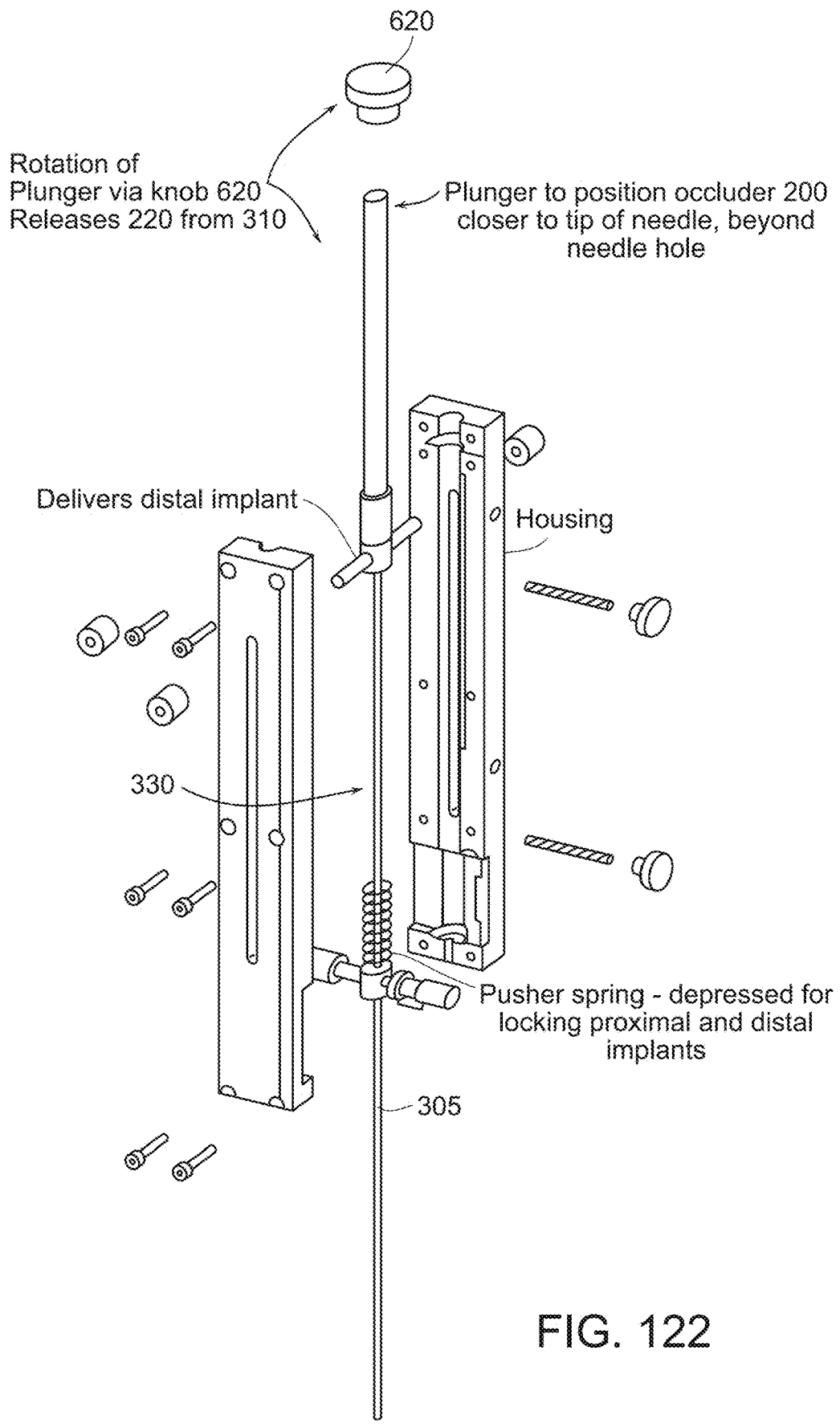

Looking next at FIGS. 121 and 122 multiple two-part fasteners 200 may be delivered using a plurality of single use disposable delivery devices 640, wherein each single use delivery device 640 contains a single two-part fastener 200. With this form of the present invention, each single use disposable delivery device 640 is used to deploy a single two-part fastener 200, and then the single use disposable delivery device 640 is disposed of after use. Multiple single use disposable delivery devices 640, each incorporating a two-part fastener 200, may be packaged as a single sterile package (e.g., 3 or 6 single use delivery devices to a sterile package). After a sterile package is opened and some (or all) of the single use delivery devices are used, all single use delivery devices must be discarded. Alternatively, each single use disposable delivery device 640 may be packaged in its own sterile package.

Figure 123:
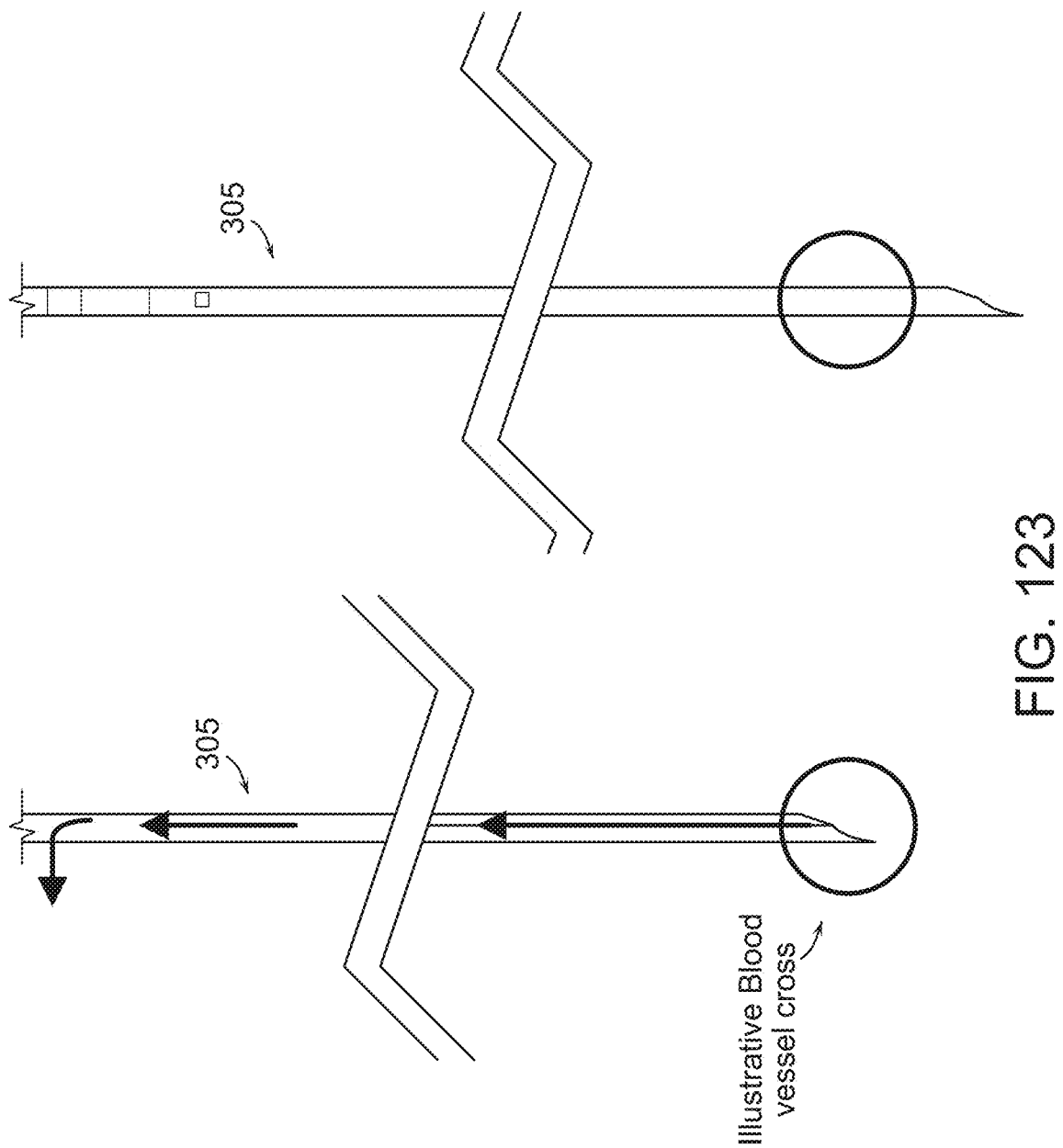
Figure 124:
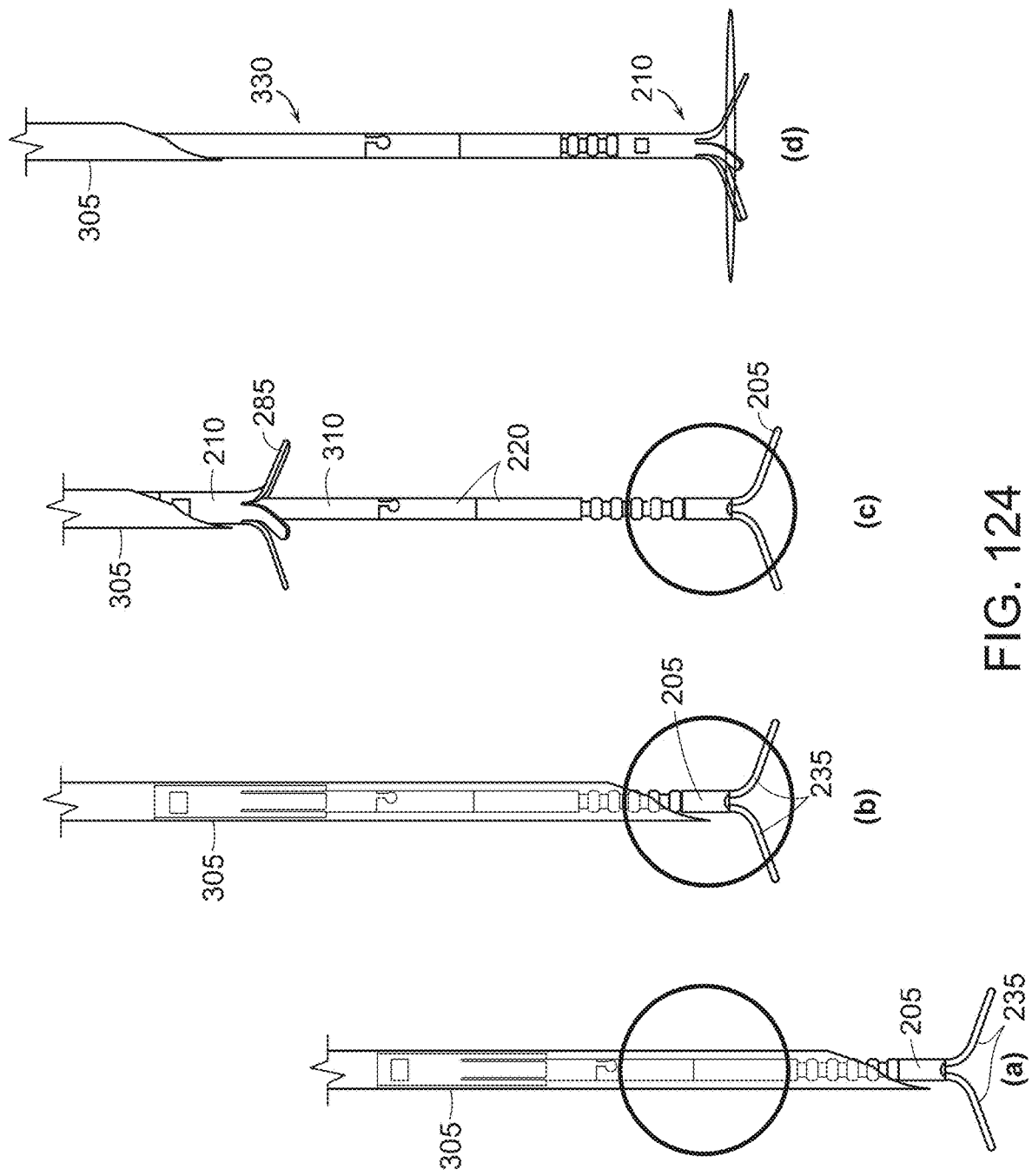

Looking now at FIG. 122, in one form of the present invention, there is provided a disposable delivery device for delivering a single two-part fastener 200. FIGS. 123 and 124 show the deployment steps for an embodiment of the delivery device. FIG. 124 shows: (a) hollow needle 305 passing through the blood vessel, (b) deployment of distal implant 205, (c) retraction of hollow needle 305 and deployment of proximal implant 210, (d) using push rod 320 to lock proximal implant 210 and distal implant 205 together. The next steps (not shown), involve retraction of proximal implant delivery tube 330. Exposing the junction between distal implant locking tube 220 and distal implant delivery tube 310, and rotating a knob 620 (FIG. 122) which rotates distal implant delivery tube 310 and releases it from distal implant locking tube 220, releasing two-part fastener 200 from the delivery device. The delivery device is then removed leaving two part fastener 200 deployed.

Figure 125:
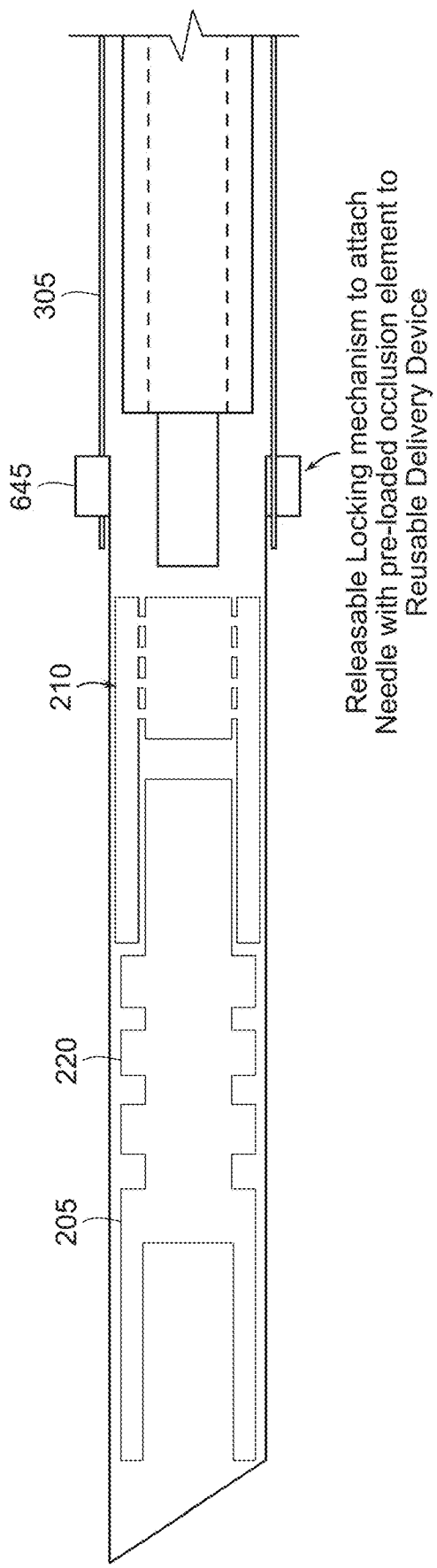
FIGS. 125-128 are schematic views showing how a reusable handle may be used to deploy a plurality of fasteners.

In another embodiment of the present invention, and looking now at FIG. 125, hollow needle 305 of the delivery device may contain two-part fastener 200, and once deployed, hollow needle 305 may be removed from the handle of the delivery device, and a new hollow needle 305 (containing a two-part fastener 200 disposed therein) may be affixed to the delivery device and used to deploy a second two-part fastener 200 during a given procedure. As such, the handle and delivery element are retained throughout the procedure, while the hollow needle 305 (and hence the two-part fastener 200 contained therein) is replaced. This form of the invention enables the delivery device to be reused multiple times during a procedure, while the individual two-part fasteners 200 are deployed and the plurality of hollow needles 305 are discarded. Hollow needle 305 can be attached to the handle (which is pre-loaded with a two-part fastener 200) prior to delivery of a two-part fastener 200, and detached following delivery of the two-part fastener 200, and replaced with a new hollow needle 305 (which is pre-loaded with another two-part fastener 200). This approach enables the delivery of multiple two-part fasteners 200 during a single procedure, and reduces the cost of the system, since the handle and delivery element is generally more costly than a hollow needle 305 which is pre-loaded with two-part fastener 200.

In one form of the present invention, the handle and delivery element can be sterilized and reused for multiple procedures.

In one form of the present invention, hollow needle 305 is configured to be threaded and screwed into the delivery device. See FIG. 125, which is a cross-section of two-part fastener 200 pre-loaded in a hollow needle 305 which is attached to the delivery device using a releasable locking mechanism 645.

Figure 126:
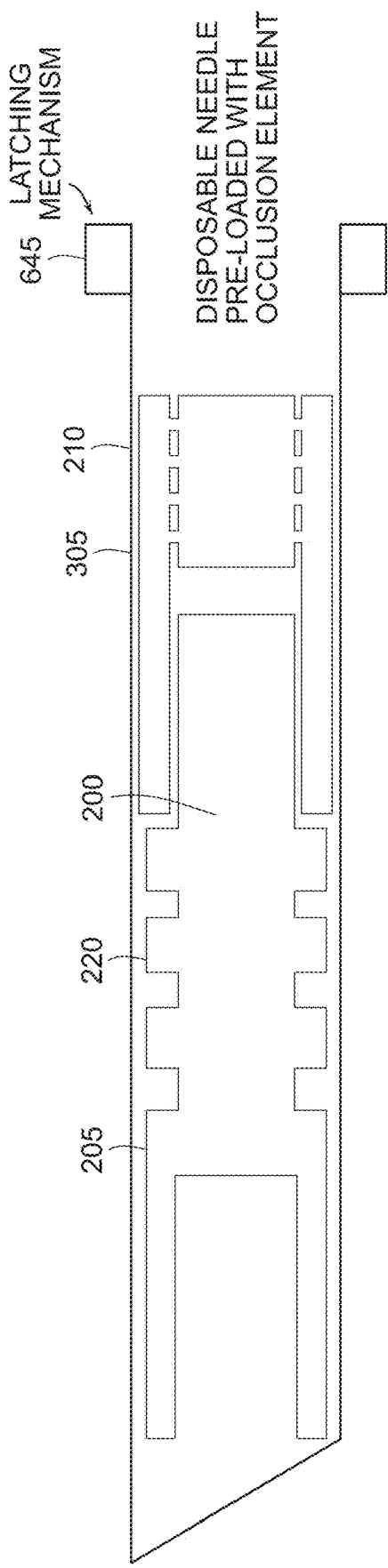
Figure 127:
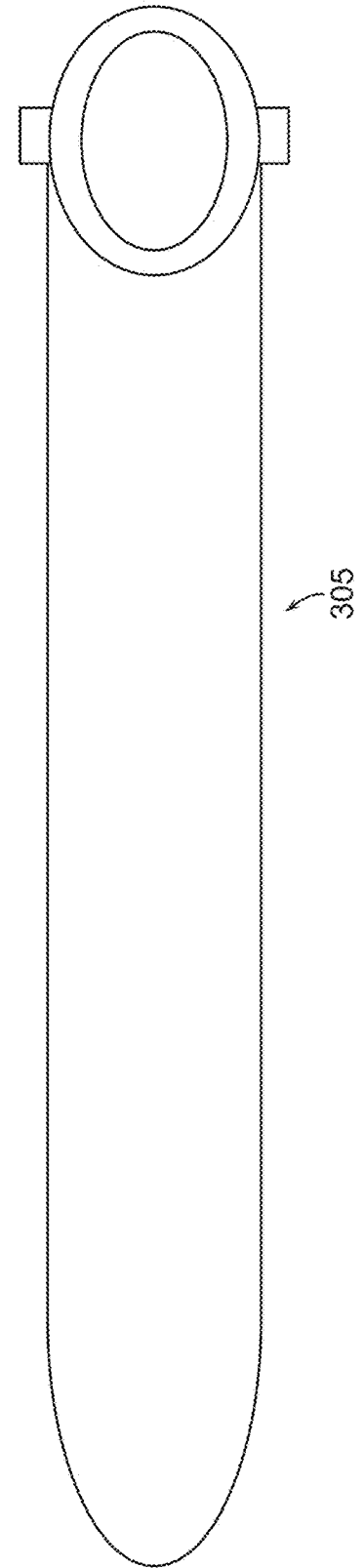
Figure 128:
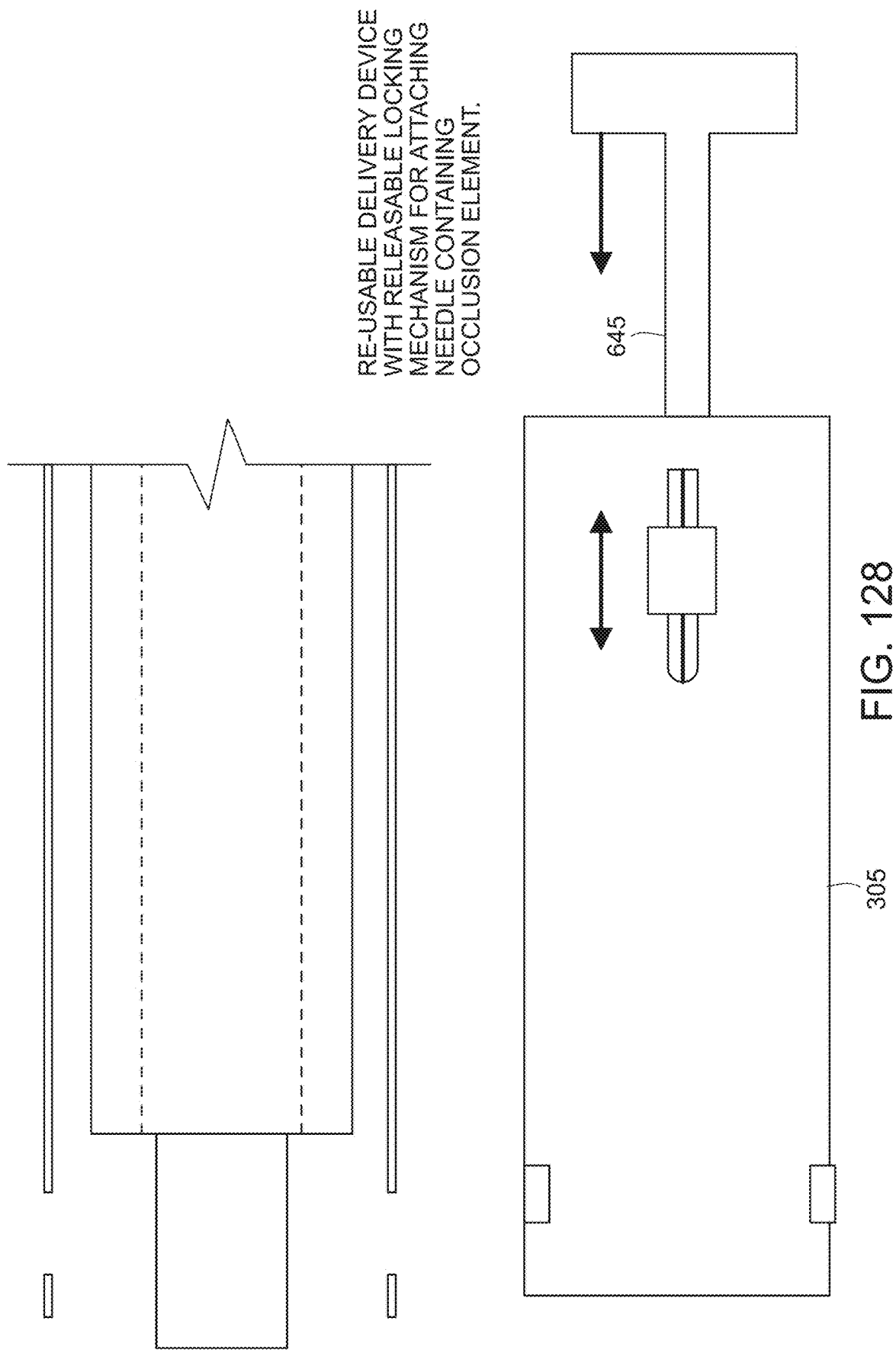
Figure 130:
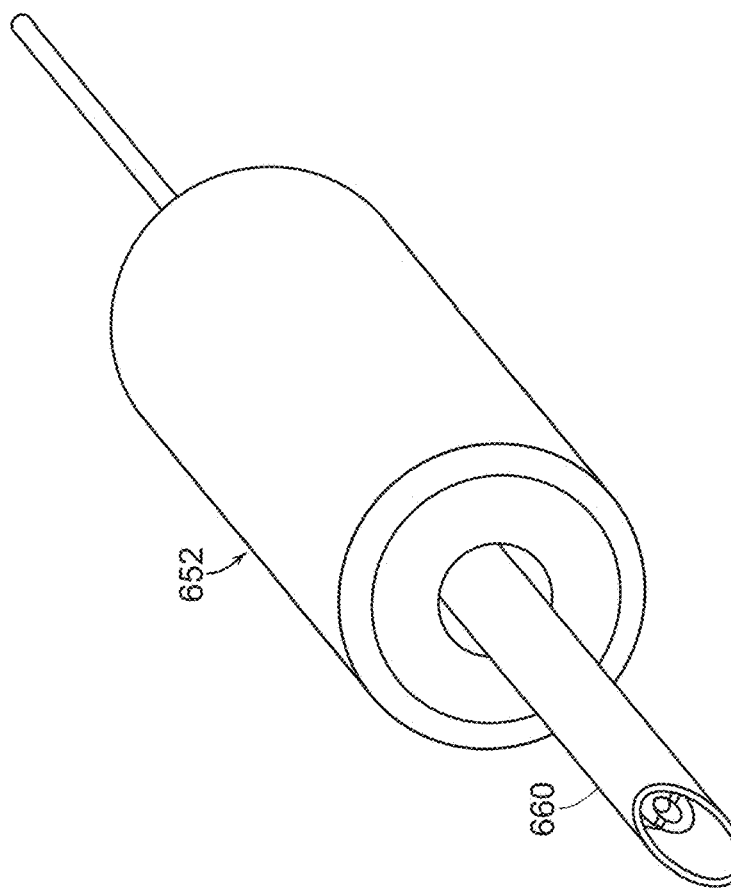
FIGS. 129-133 are schematic view showing a multiple fastener delivery device where a plurality of fasteners are disposed serially within the delivery device; schematic views showing a multiple fastener delivery device which may be used to deploy a plurality of fasteners.
Figure 129:
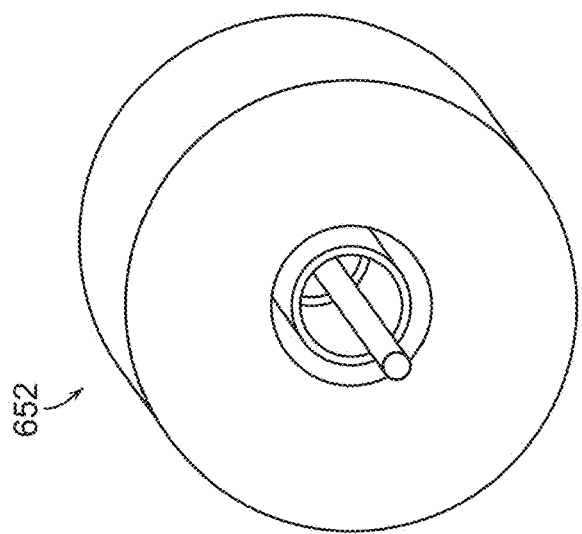
Figure 131:
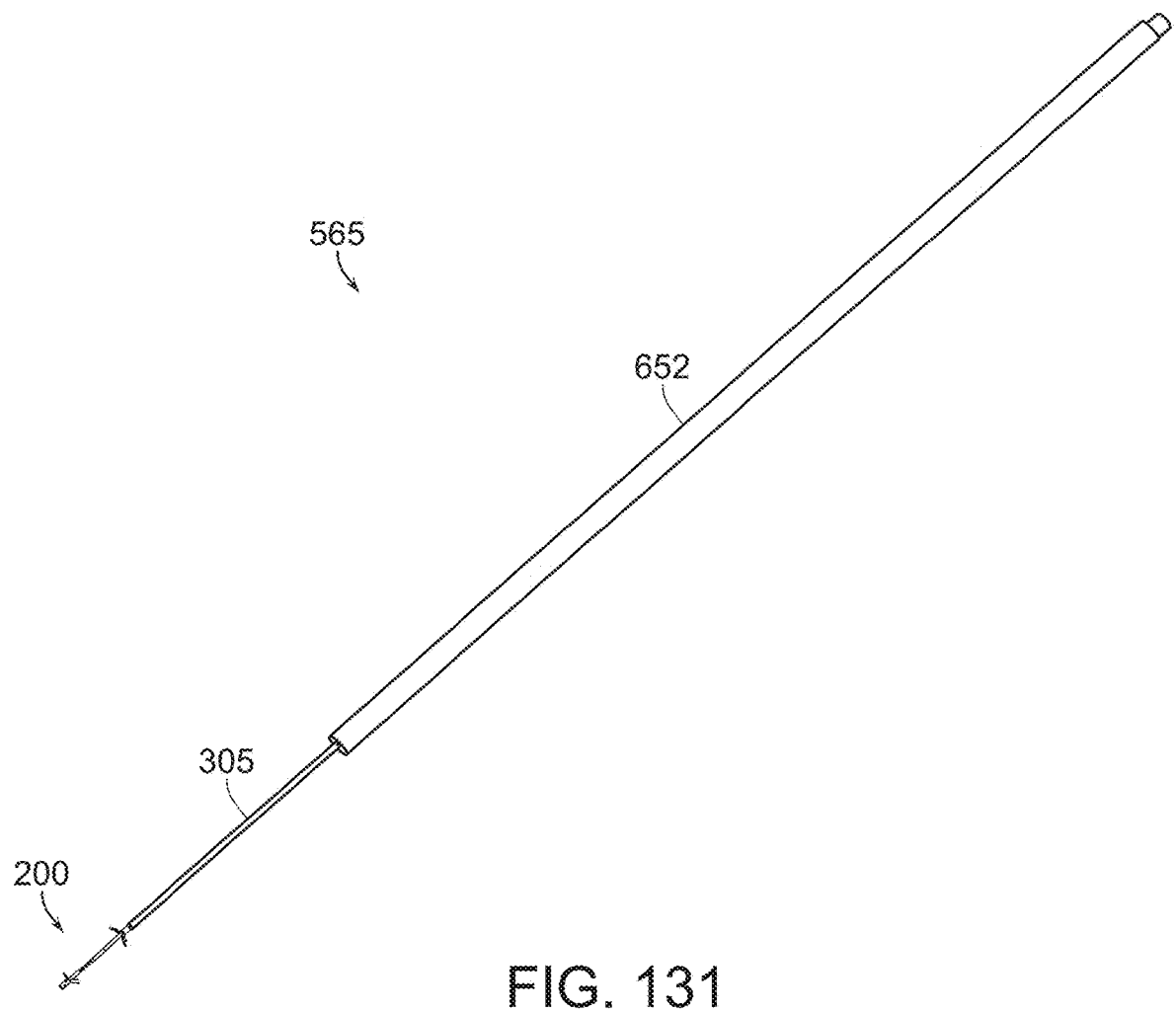
Figure 132:
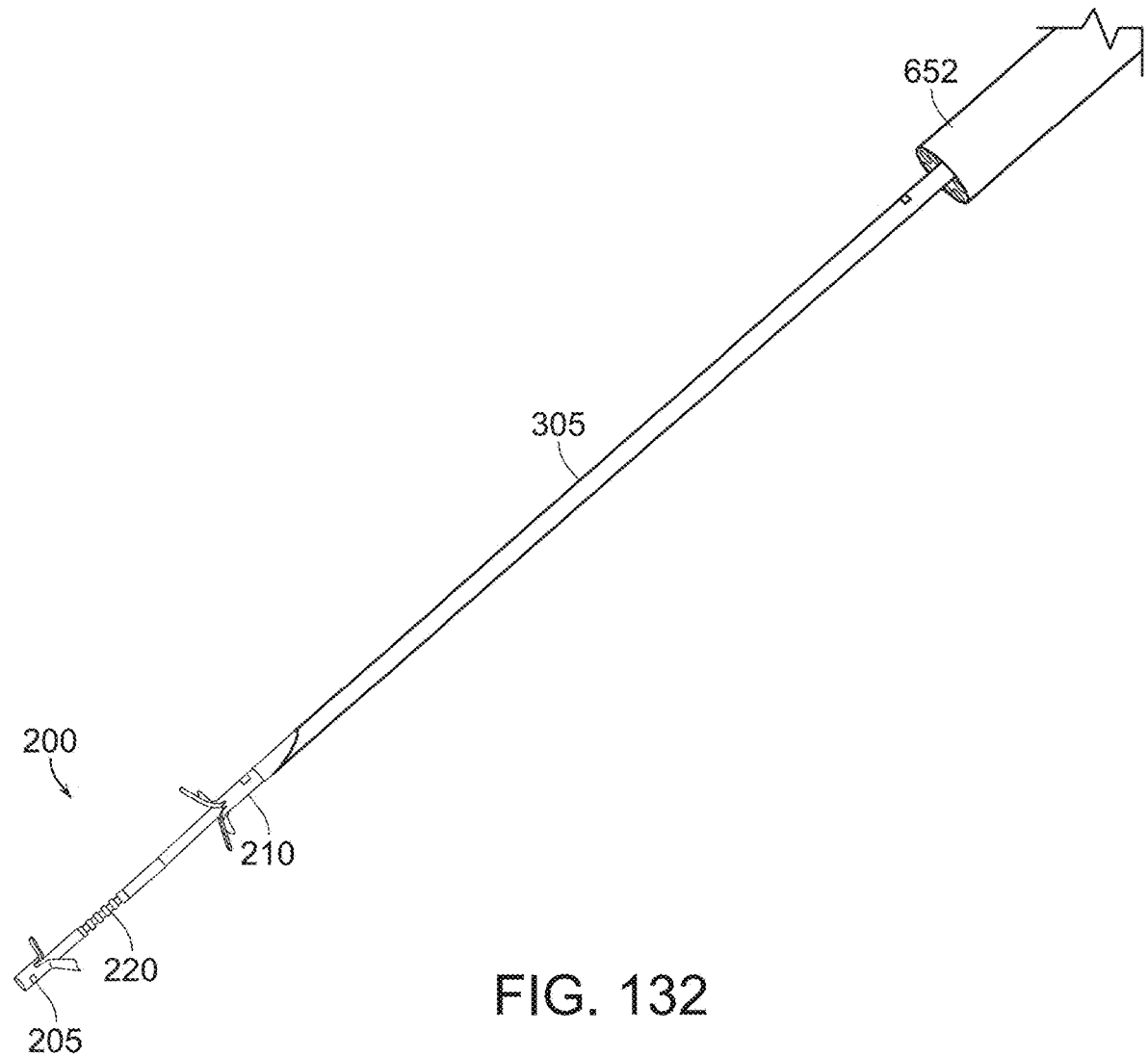

FIG. 126 shows a cross-section of hollow needle 305 with two-part fastener 200 pre-loaded inside, and a releasable locking mechanism 645 for attaching hollow needle 305 to the delivery device. FIG. 127 is an external view of hollow needle 305 showing releasable locking mechanism 645. See also FIG. 128, which shows the reusable delivery device.

9. Rotating Barrel

In still another form of the present invention, multiple two-part fasteners 200 can be disposed within a single delivery device. In one preferred form of the present invention, and looking now at FIGS. 129-139, multiple two-part fasteners 200, each contained within their own hollow needle 305, may be loaded into chambers 650 in a barrel-like cartridge 652, which in turn is mounted to a housing 665, whereby to be deployed one after another as will hereinafter be discussed. In other words, in this form of the present invention, rather than having a hollow needle 305 that is pre-loaded with a two-part fastener 200 and attached to the same delivery device, the multiple two-part fasteners 200 are each loaded into their own hollow needle 305 and into chambers 650 of cartridge 652, whereby to allow the delivery of multiple fasteners deployed one at a time, each through its own corresponding hollow needle 305.

In one preferred form of the present invention, cartridge 652 rotates, and plungers are used to first deploy the pre-loaded hollow needle 305 contained within cartridge 652 across the tubular structure (or tissue) to be occluded (or clamped), and then used to deliver the pre-loaded two-part fasteners 200 contained within the hollow needle 305.

As seen in FIGS. 129-133, in another preferred form of the present invention, multiple two-part fasteners 200 are contained within a cartridge 652 and are delivered through the same hollow needle 305. Since there is only a single hollow needle 305, the two-part fasteners 200 contained in cartridge 652 are loaded one-by-one from cartridge 652 into a single hollow needle 305 disposed in the center of the delivery device for deployment.

Figure 133:
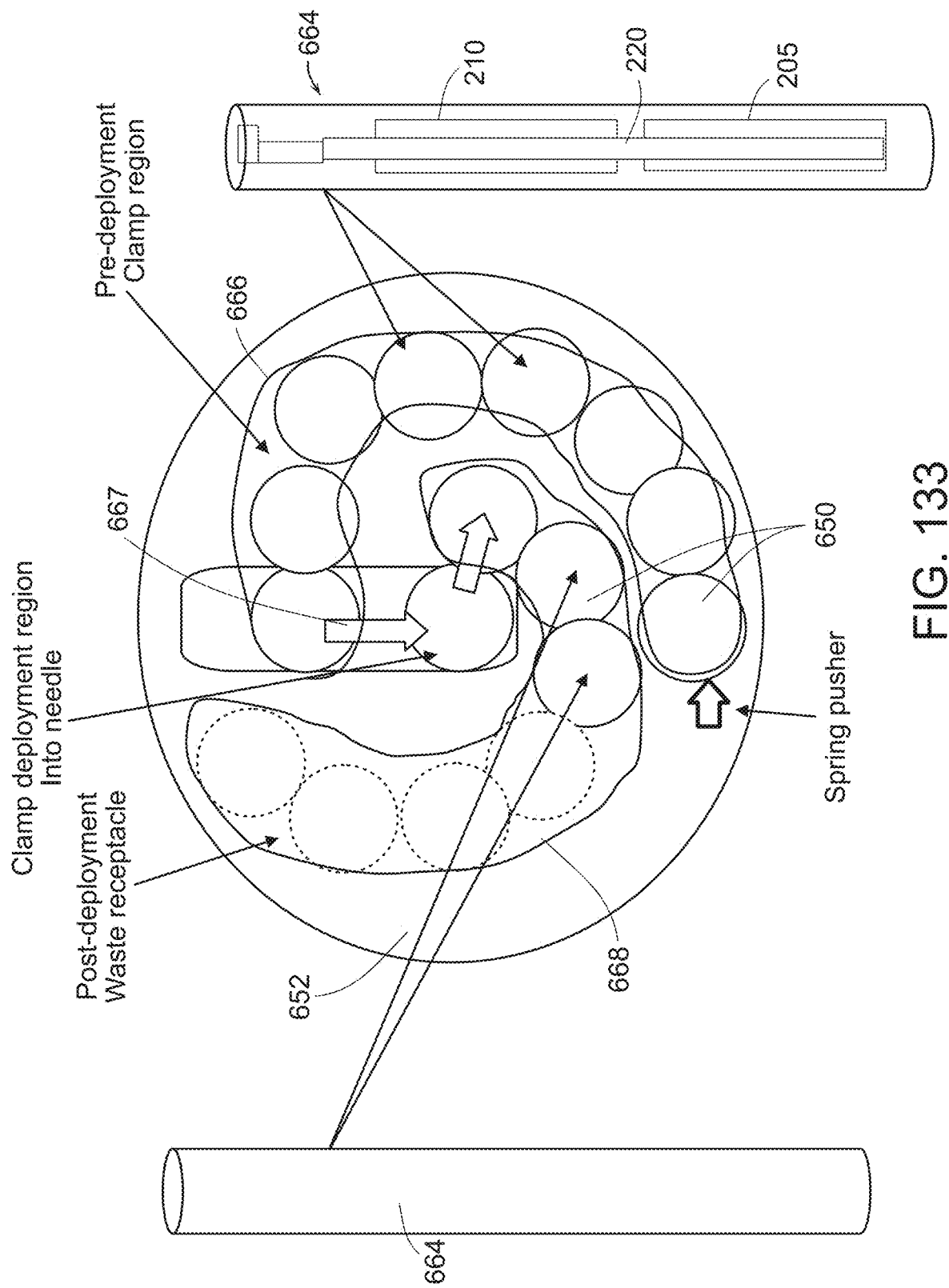
Figure 134:
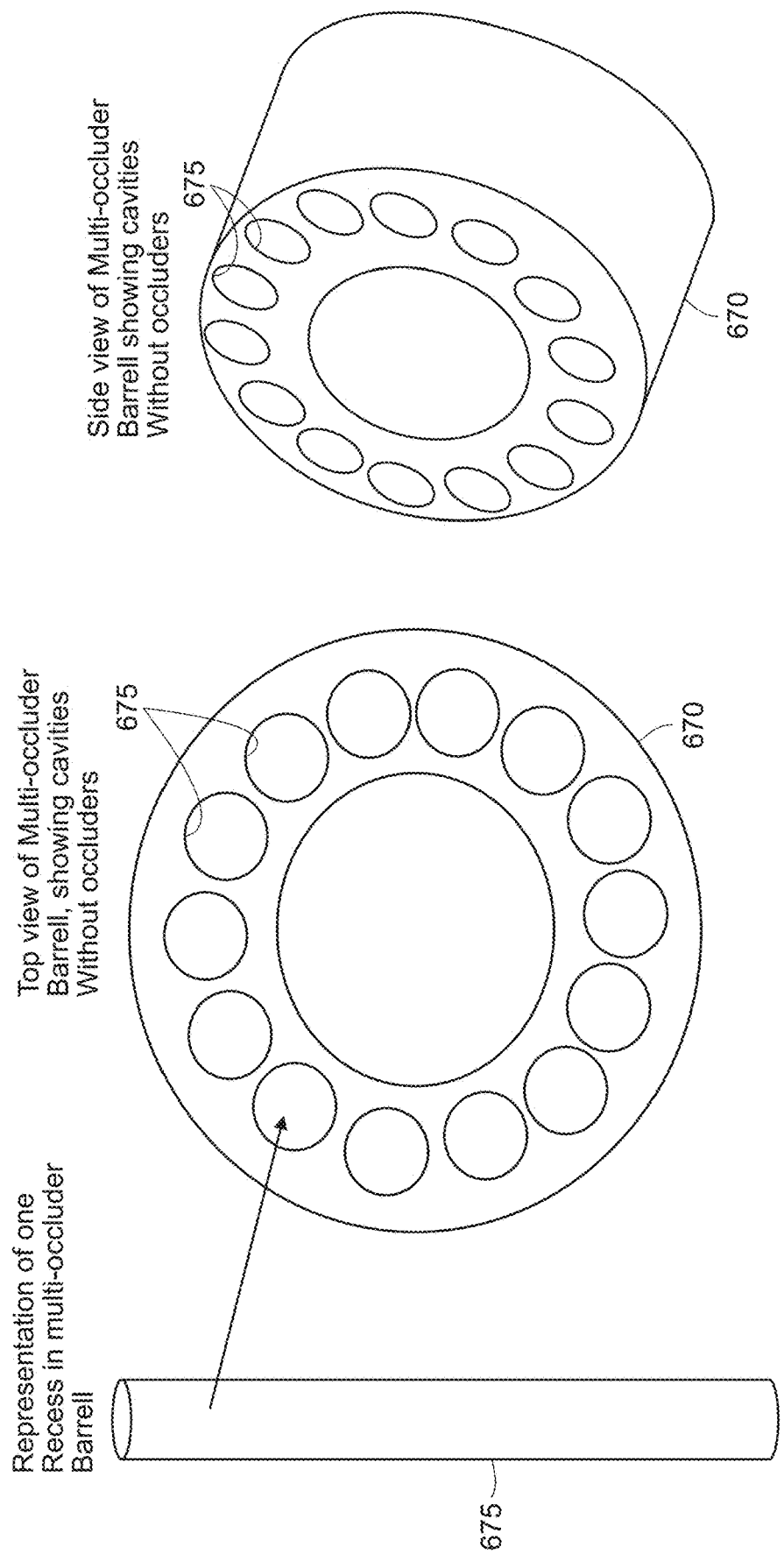

FIG. 133 shows a top view of the multi-fastener single needle device shown in FIGS. 129-132, wherein hollow needle 305 is located in the center of cartridge 652. In this form of the invention, each two-part fastener 200 is contained in a tube 664. A plurality of tubes 664, each containing a two-part fastener 200, are loaded into the cartridge 652, and into the pre-deployment clamp region 666, where a spring pushes them towards and into hollow needle 305. Once each two-part fastener 200 has been deployed, a lever or button is pressed allowing the empty container 667 to be pushed into the post deployment waste receptacle 668. The push rods to deploy two-part fastener 200 are located perpendicular to the shown clamp deployment region and can be operated in the same manner shown for the multi-needle deployment device discussed above.

FIGS. 134-157 show another operating concept of a multi-fastener delivery device formed in accordance with the present invention, wherein two-part fastener 200 is delivered through the same hollow needle 305. A barrel 670, having multiple chambers 675 which can be loaded with multiple two-part fasteners 200, is plugged into a delivery device, so that multiple two-part fasteners 200 can be delivered one after the other through a single hollow needle 305, without having to withdraw hollow needle 305 from patient body or from a laparoscopic port.

Figure 135:
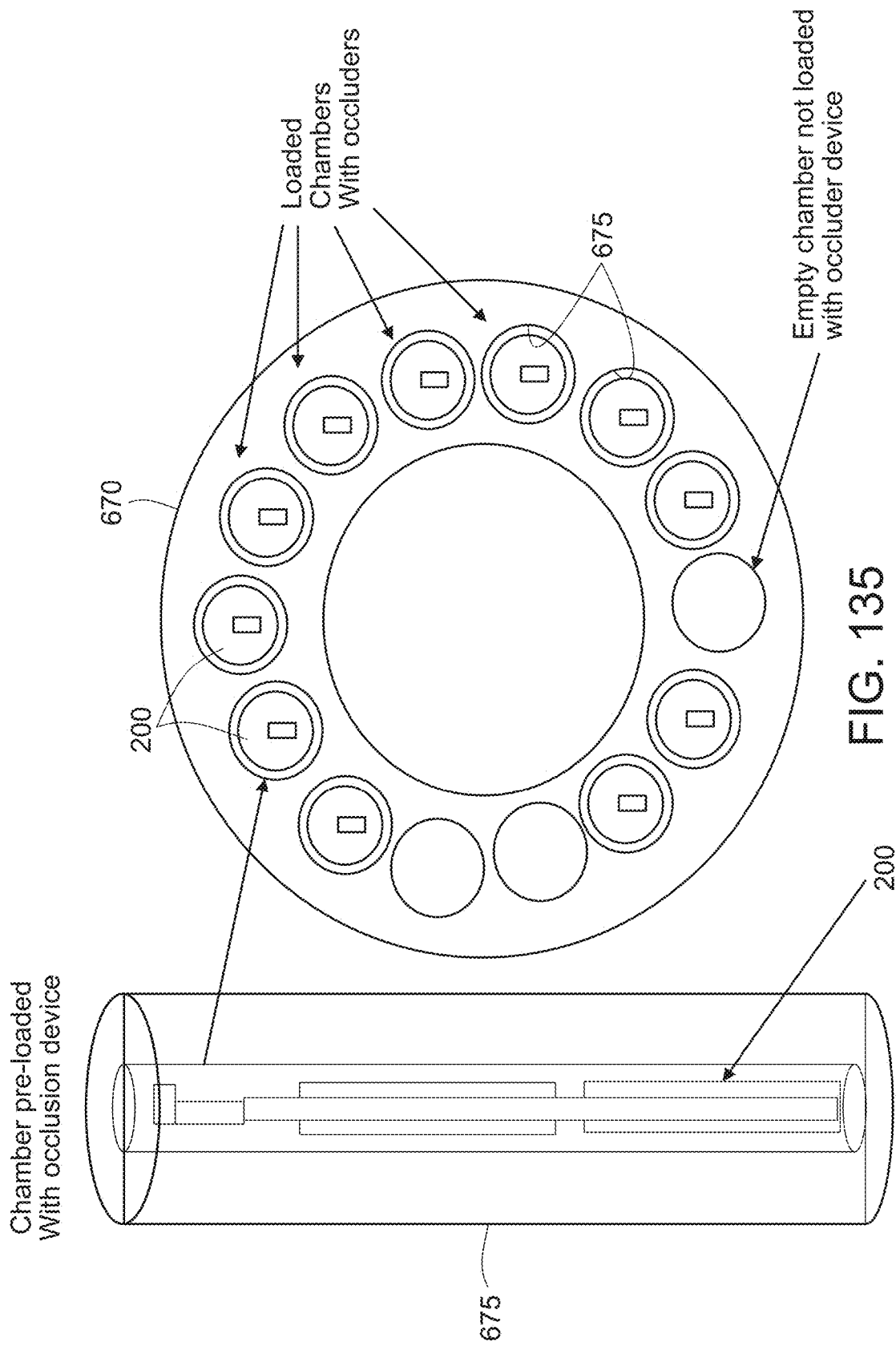
Figure 136:
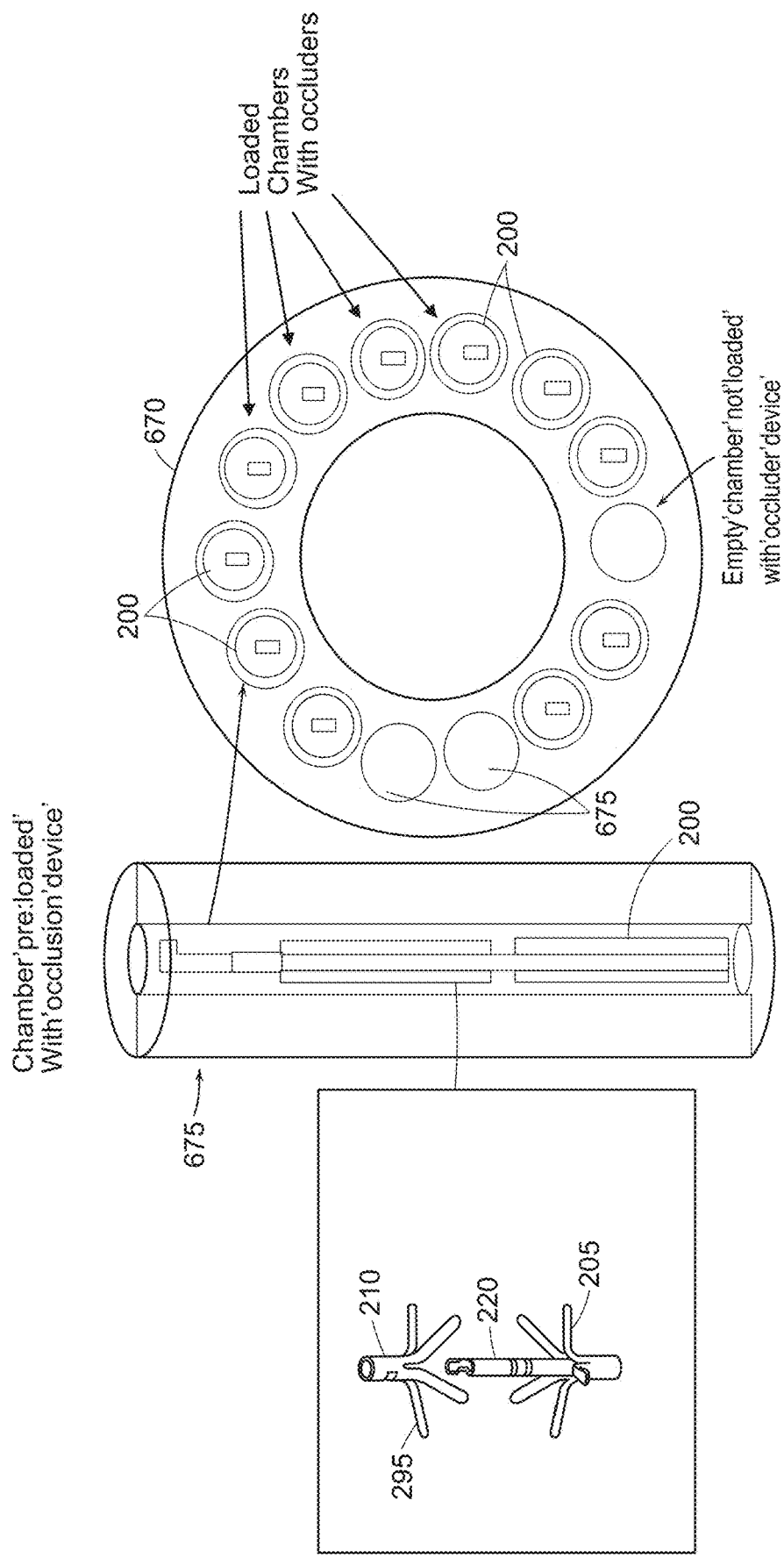
Figure 147:
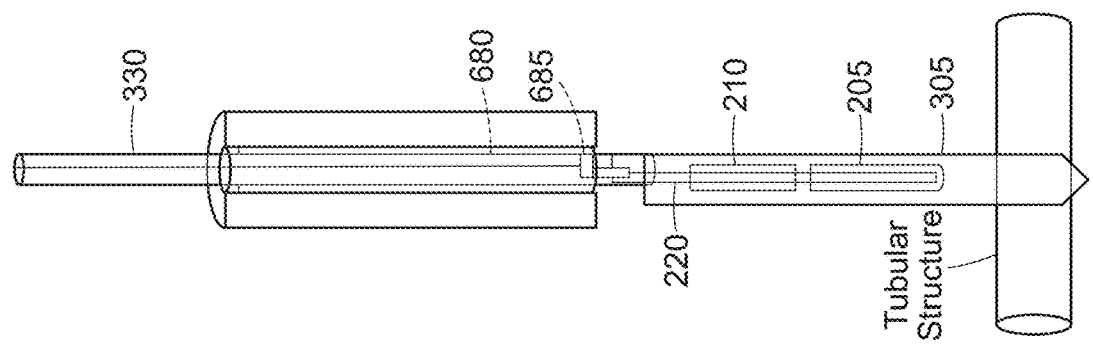
Figure 148:
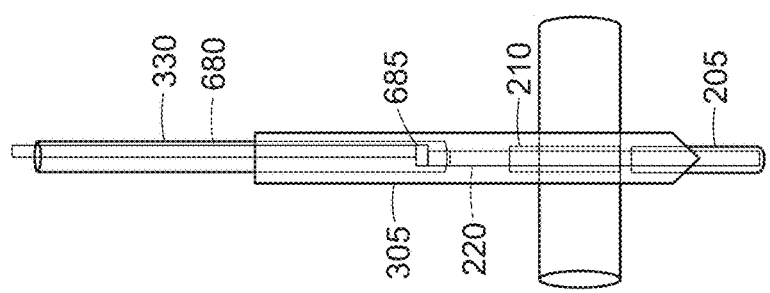
Figure 149:
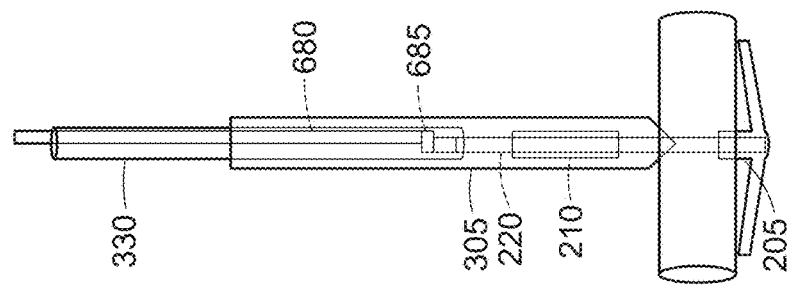
Figure 150:
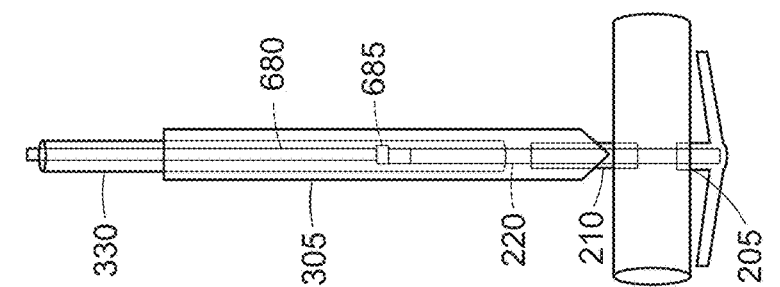

FIG. 135 shows multi-fastener barrel 670 loaded with two-part fasteners 200. The number of two-part fasteners 200, and which chambers 675 are loaded with two-part fasteners 200, may be selected and controlled by the user.

Figure 151:
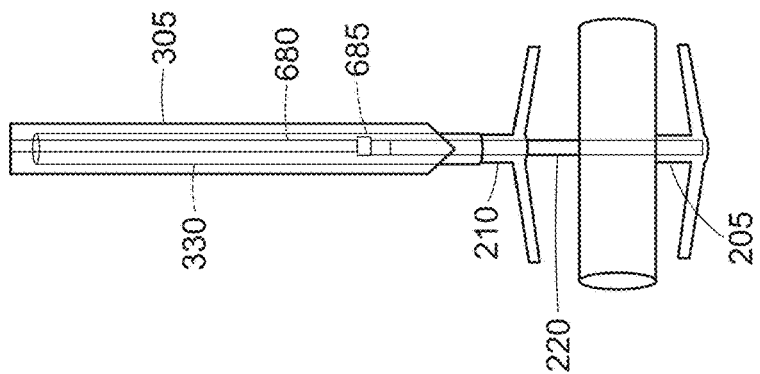
Figure 157:
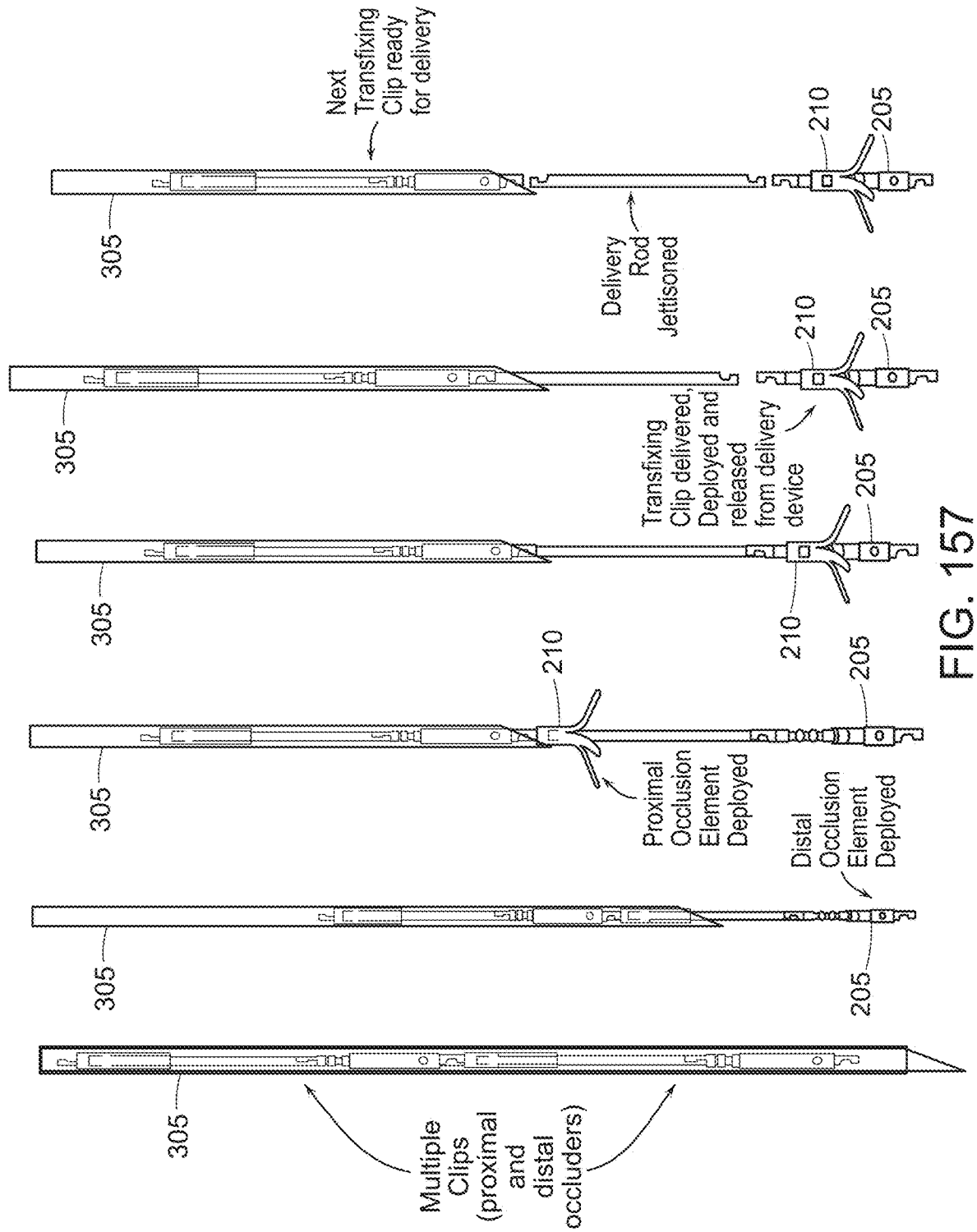

FIG. 151 shows one embodiment with two-part fasteners 200 being pre-loaded into the replaceable barrel 670 of delivery device.

FIG. 137 shows a side view of multiple fastener delivery device 665.

FIGS. 138-141 show a proximal implant delivery rod 680 and hook 685 locked onto the distal implant locking tube 220 hook of two-part fastener 200. Proximal implant delivery tube 690 covers the latching region of the two hooks, thereby securing the connection.

FIGS. 142-146 show how proximal implant delivery rod 680 and proximal implant delivery tube 690 are pushed in a coordinated fashion (e.g., together) downward (i.e., distally) so as to push two-part fastener into (and through) hollow needle 305.

FIGS. 147-151 and FIGS. 152-156 show how hollow needle 305 transfixes a tubular structure (or blood vessel or tissue) and two-part fastener 200 being deployed across a vessel or duct, in a similar manner and with similar steps to those shown in FIGS. 63-77. Once distal implant 205 is deployed, hollow needle 305 is retracted, deploying proximal implant 210. Proximal implant delivery tube 690 is then pushed down (i.e., distally), so as to push and lock proximal implant 210 onto distal implant locking tube 220, which is disposed between proximal implant 210 and distal implant 205, thereby compressing and securing the tubular structure between proximal implant 210 and distal implant 205. Proximal implant delivery tube 690 is then raised (i.e., moved proximally), exposing the clamping region between proximal implant delivery rod 680 and distal implant locking tube 220. Proximal implant delivery rod 680 is then rotated, unlocking it from the distal implant locking tube 220. The delivery device, together with hollow needle 305 is extracted, leaving the implanted transfixed two-part fastener 200 disposed across the tubular structure, blood vessel or clamped tissues.

10. Serial Deployment of Two-Part Fastener 200

In another form of the present invention, multiple two-part fasteners 200 may be disposed in the same hollow needle 305, and deployed one after another in a serial fashion. See FIG. 157.

11. Occlusion Using Asymmetric Legs 235, 295

Figure 158:
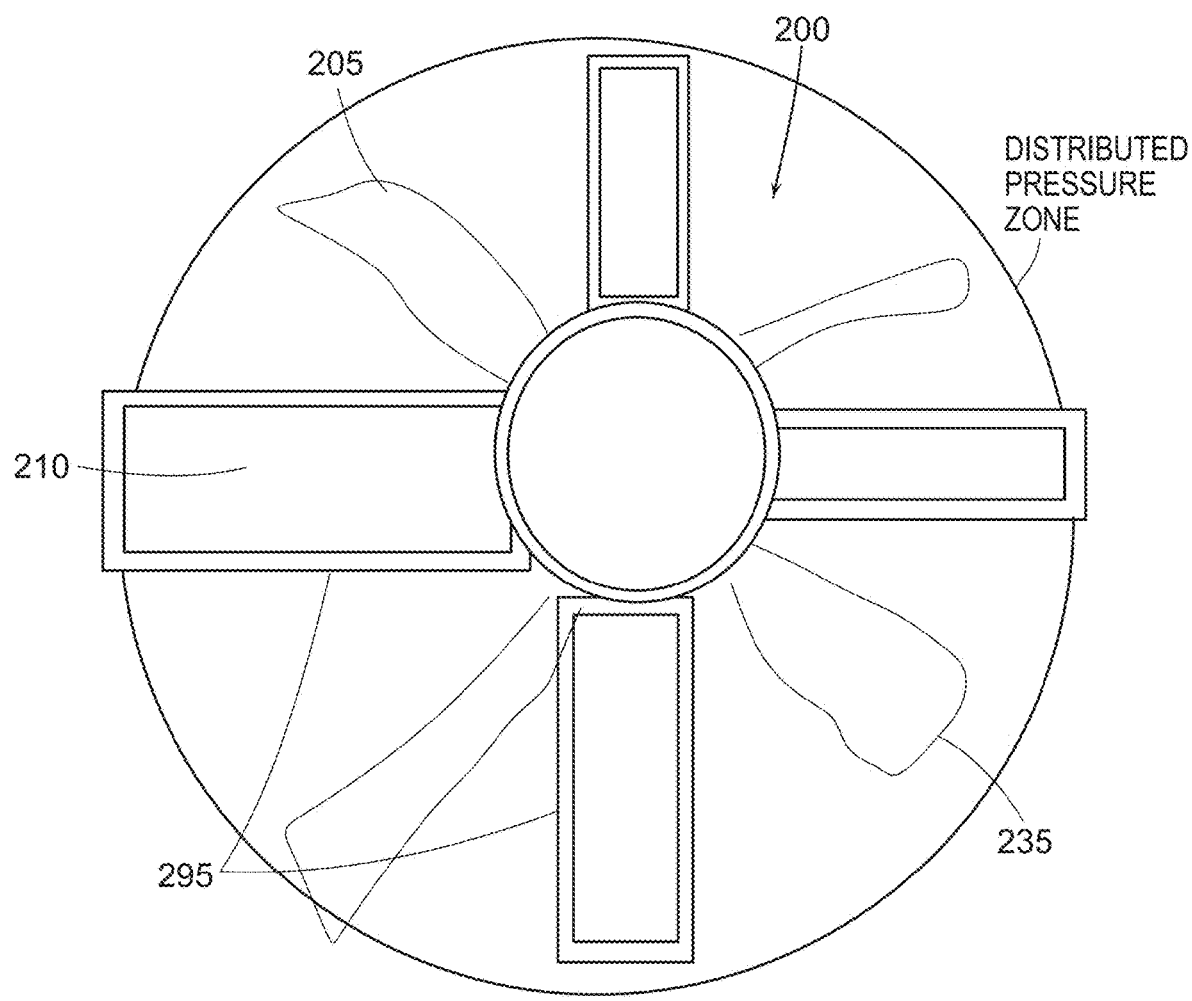
FIGS. 158-160 are schematic views showing a two-part fastener having asymmetric legs.

FIG. 158 shows the two-part fastener 200 of the present invention preventing hemorrhaging caused by the transfixing rod (i.e., distal implant locking tube 220). There are many applications for which such a device could prove useful, e.g., in aortic aneurysm repair, particularly in the thoracic aorta, where, after removal of the aneurysm, the edge of the vessel is fragile and attaching a necessary synthetic graft to close the gap in the vessel by suture is complicated by bleeding from the needle entry points. This may result in clinical failure, endangering the patient or resulting in a complications. Another example is the resection and suturing of the atrial appendage of the heart which may be resected in patients who have an anthemia with clot embolising from this appendage. Suturing the atrial appendage wall even with the buttress synthetic material often results in significant bleeding from the entry points of hollow needle 305.

FIG. 158 also shows two-part fastener 200 and the surrounding effective pressure zone. Note that the different overlaps between legs 295 of proximal implant 210 and legs 235 of distal implant 205 are controllably adjustable to provide the desired pressure zone and occlusion level.

Figure 160:
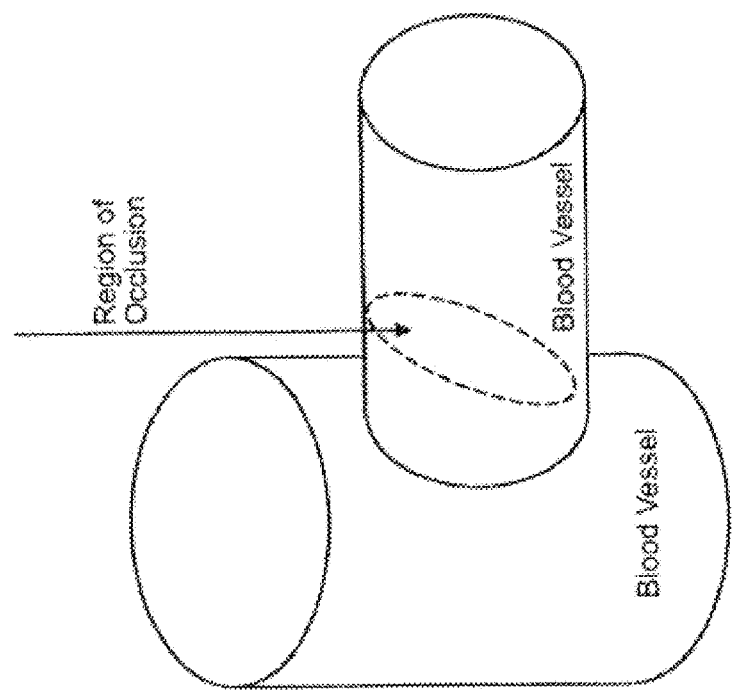
Figure 159:
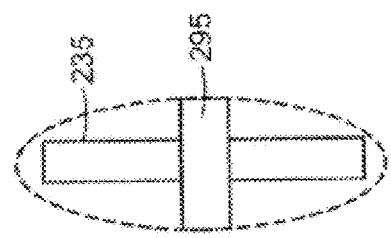

In one form of the present invention, the pressure zone generated by two-part fastener 200 is a circular area extending around the entry point of the transfixing distal locking tube 220 (FIG. 159), but in other embodiments the pressure zone may be non-circular, meaning that the lengths of legs 235 of distal implant 205 and legs 295 of proximal implant 210 are not equal along one axis relative to another, so as to permit two-part fastener 200 to be positioned proximal to a branched vessel or tissue, as shown in FIG. 160.

More particularly, FIG. 160 shows a two-part fastener 200 where the legs 235 of distal implant 205 and the legs 295 of proximal implant 210 are not symmetric, but rather are oval (i.e., shorter) in one dimension than the other, allowing placement in proximity to interconnection regions. In one form of the present invention, the orientation of the two-part fastener 200 can be determined using markings disposed on the delivery device handle (e.g., an arrow which indicates the long direction of legs 235, 295). In laparoscopic or open procedures, the orientation of two-part fastener 200 can also be visually confirmed. In percutaneous applications, ultrasound, or CT imaging can be used to further determine orientation of two-part fastener 200 relative to vessels, ducts, organs, tissue that is are to be clamped or occluded.

12. Tissue Protection

It should be appreciated that it is often desirable to stabilize (e.g., via clamping) the vessel (or other tubular structure) that is to be occluded using two-part fastener 200. In addition, it is often desirable to provide a "needle shield" under the vessel (or other tubular structure) which is to be occluded so that hollow needle 305 does not damage underlying tissue as it pierces the vessel (or other tubular structure) which is to be occluded.

FIG. 161 shows a delivery device comprising a gripper (or dissector) 695 that holds the vessel (or tissue) in place while it is transfixed, while also protecting the underlying tissue, (i.e., tissue which is not to be transfixed), via a needle stop, from being injured by hollow needle 305 as it pierces the vessel. The needle stop can also have a sharp knife-like edge, to help first dissect out the tissues to be occluded from the tissues to be protected.

13. Lift to Protect

Figure 162:
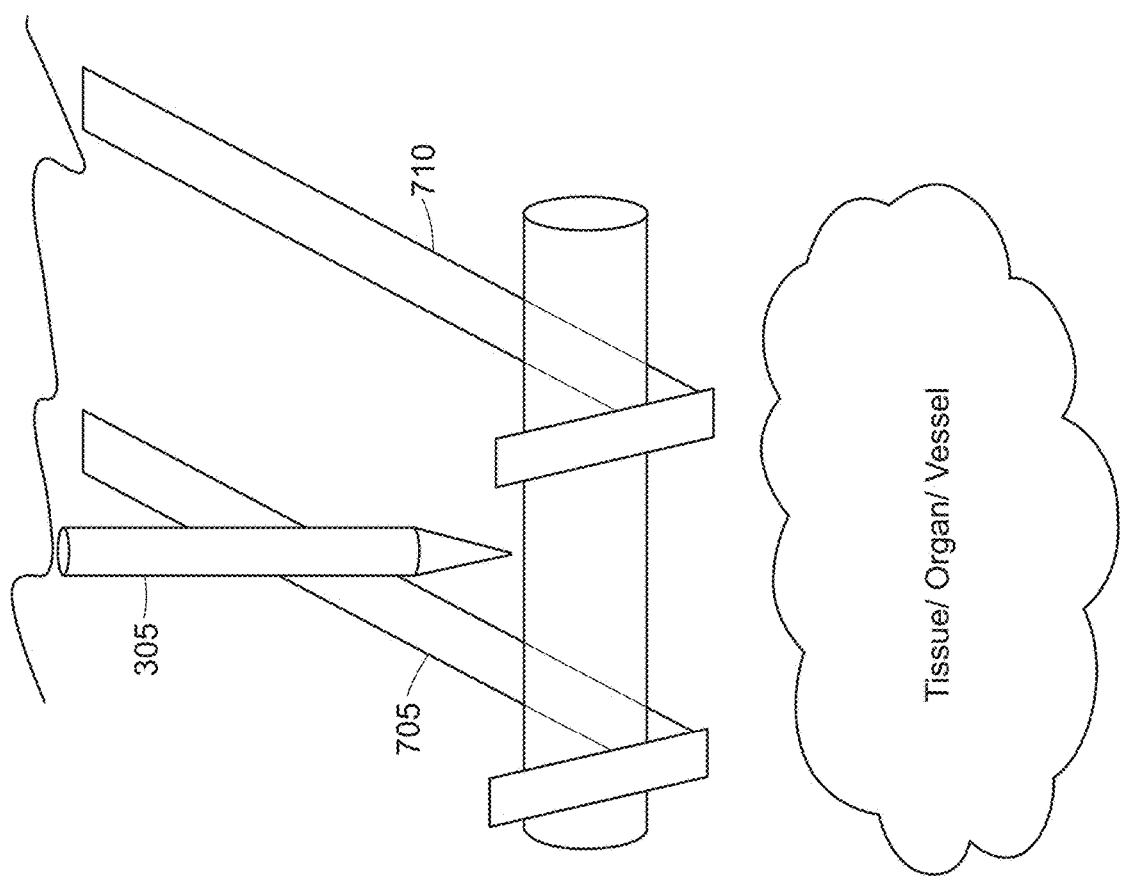
Figure 171:
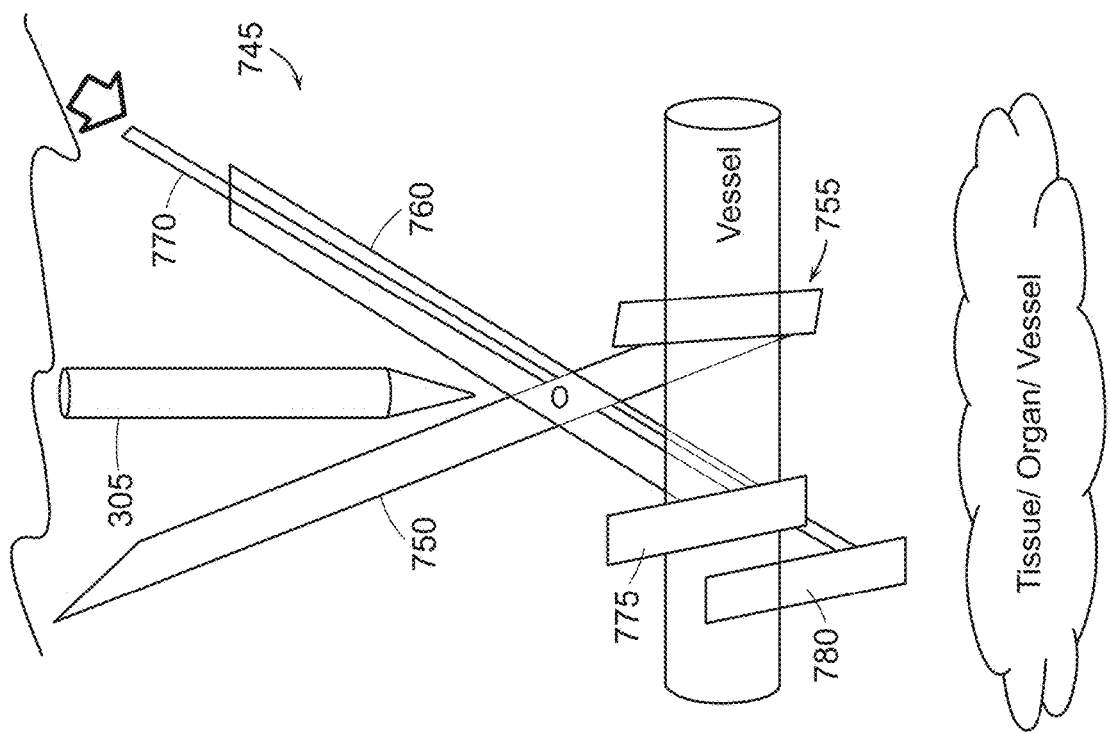

Looking next at FIGS. 162 and 171, under certain conditions (e.g., when hollow needle 305 is being used to transfix a vessel that is in proximity to tissue, organs, or other vessels) it is desirable to deploy a device 700 that can be positioned between the tip of hollow needle 305 and the vessel to protect, for example, the tissues, organs, nerves, or other biological materials and vessels that may otherwise come in contact undesirably with the tip of hollow needle 305. Other applications for which the present invention is used, may require a needle (or other sharp element) to penetrate tissues, or an organ, and the envisioned devices of the invention may act as a "shield" (or stop) to protect any tissue or biological material not desired to be penetrated beyond the desired penetration site or depth.

Figure 163:
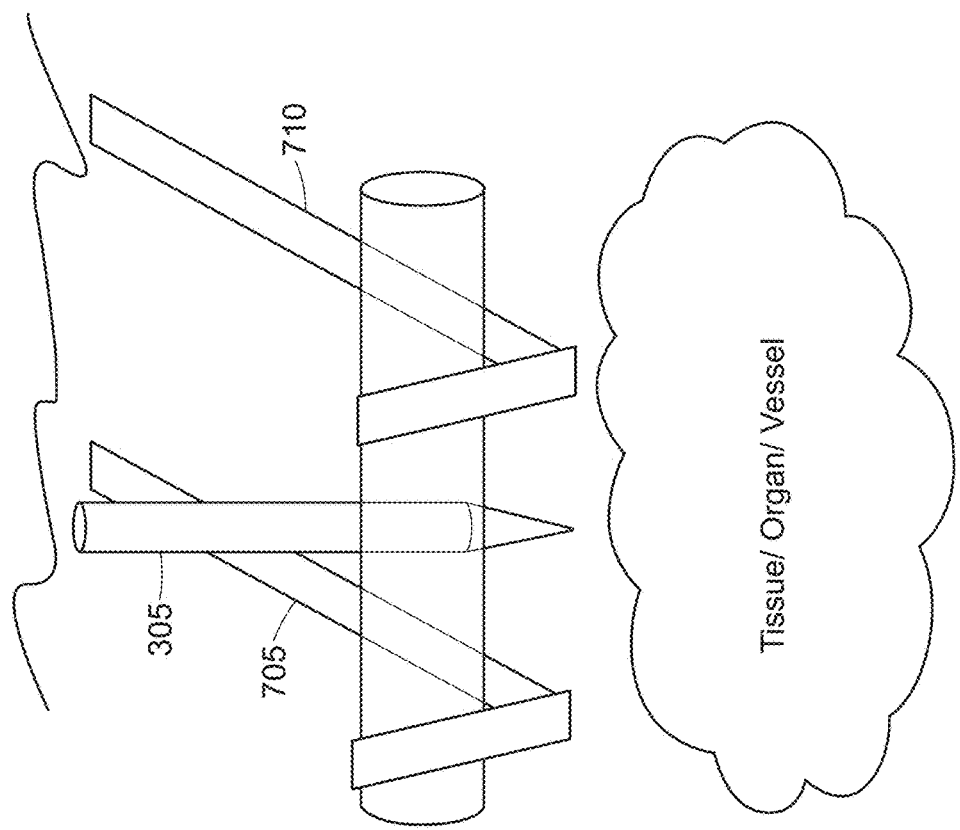

FIGS. 162 and 163 show dissection of a tubular structure which has been "lifted" so as to be free from surrounding tissue prior to penetration of the tubular structure by hollow needle 305 and delivery of two-part fastener 200. FIG. 181 shows counter traction by elevation of "dissector limbs" 705, 710 which allows easy penetration of the tubular structure by hollow needle 305 but does not control depth of penetration by hollow needle 305, thereby allowing underlying tissues to be penetrated and/or injured by hollow needle 305.

Figure 164:
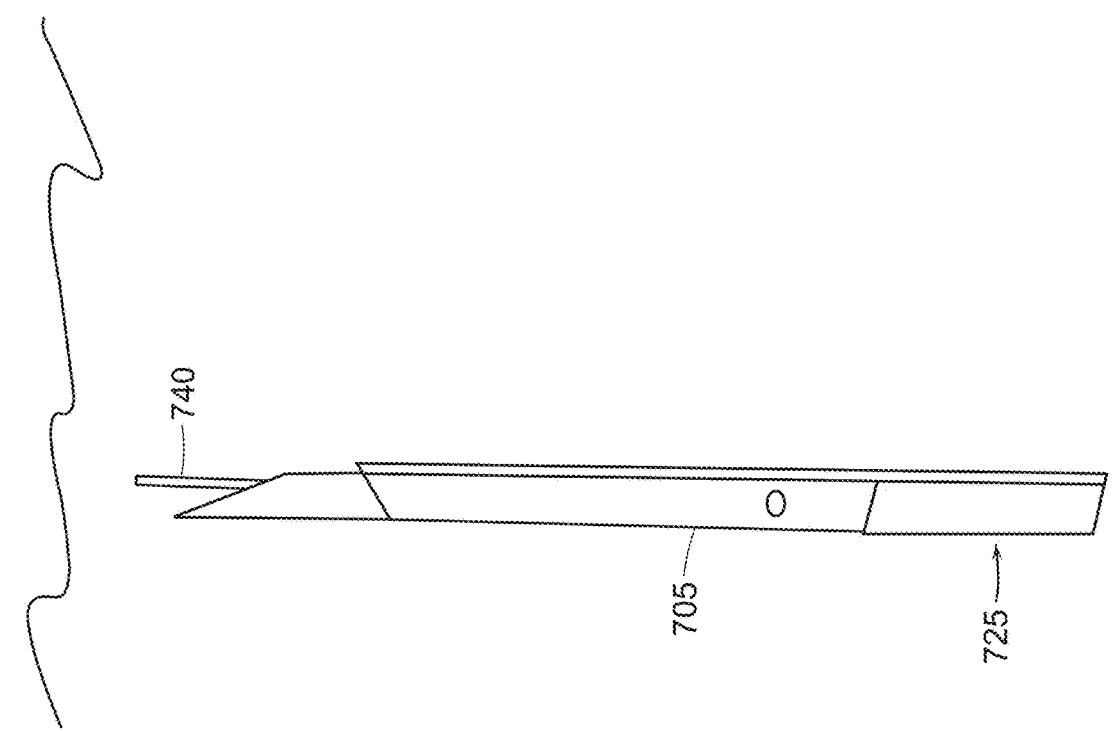
Figure 165:
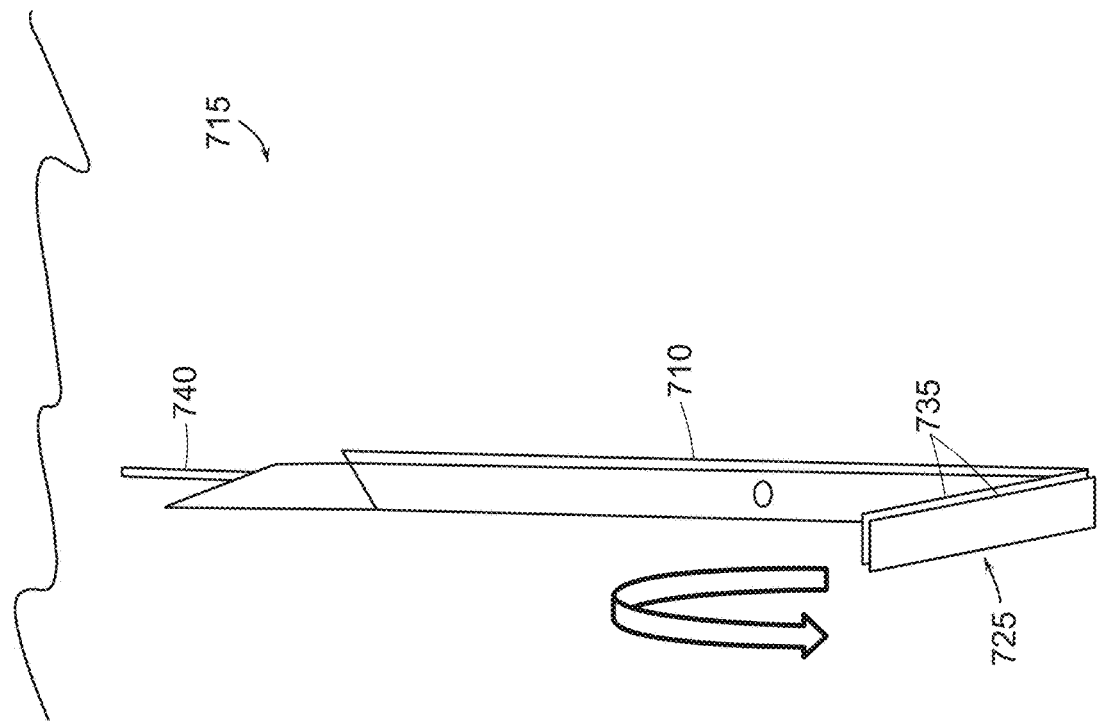
Figure 167:
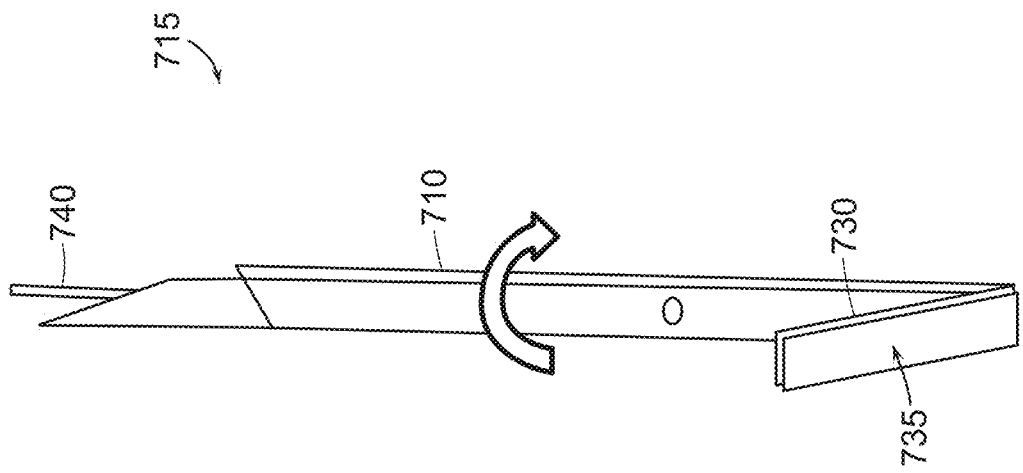

FIG. 164 shows another form of dissector formed in accordance with the present invention which may be used for dissection of the tubular structure so as to free the tubular structure from the surrounding tissues. Dissector 715 provides for elevating and counter-traction as well as providing a shield 720 to limit the penetration of hollow needle 305 into the surrounding (i.e., underlying) tissues, structure or viscera. More particularly, FIG. 164 shows dissector 715 in the closed neutral position. The dissector preferably comprises two limbs 705, 710 having curved distal tips 725. One distal tip 725 of dissector 715 comprises two superimposed curved blades 730, 735 connected to a controlling rod 740. FIG. 165 shows how depressing controlling rod 740 moves the two curved blades 730, 735 of dissector 715 apart. Rotation of controlling rod 740 rotates the movable portion of the dissector tip (i.e., curved blades 730, 735). If desired, the second limb 710 of dissector 715 has of a single, fixed curved blade 730. In another embodiment of the invention, the dissector tips 725 can be flat, and can be controllably rotated outward protruding away from the blades.

Figure 166:
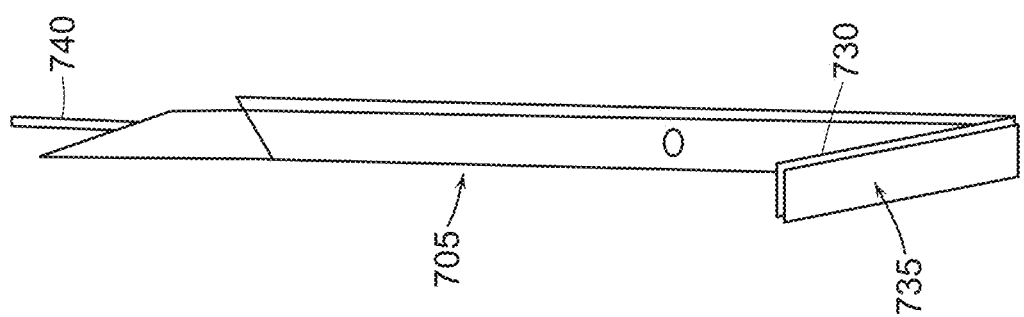

FIG. 166 shows the closed neutral position of the adjustable limbs 705, 710 wherein the two curved blades 730, 735 lie in apposition (i.e., lying on top of each other). The movable curved blade 735 is connected to controlling rod 740 which can be depressed and rotated. In this embodiment, dissector 715 is designed such that limbs 705, 710 can overlap, so that they can be easily delivered through, for example, a standard cannula for laparoscopic procedures.

Figure 185:
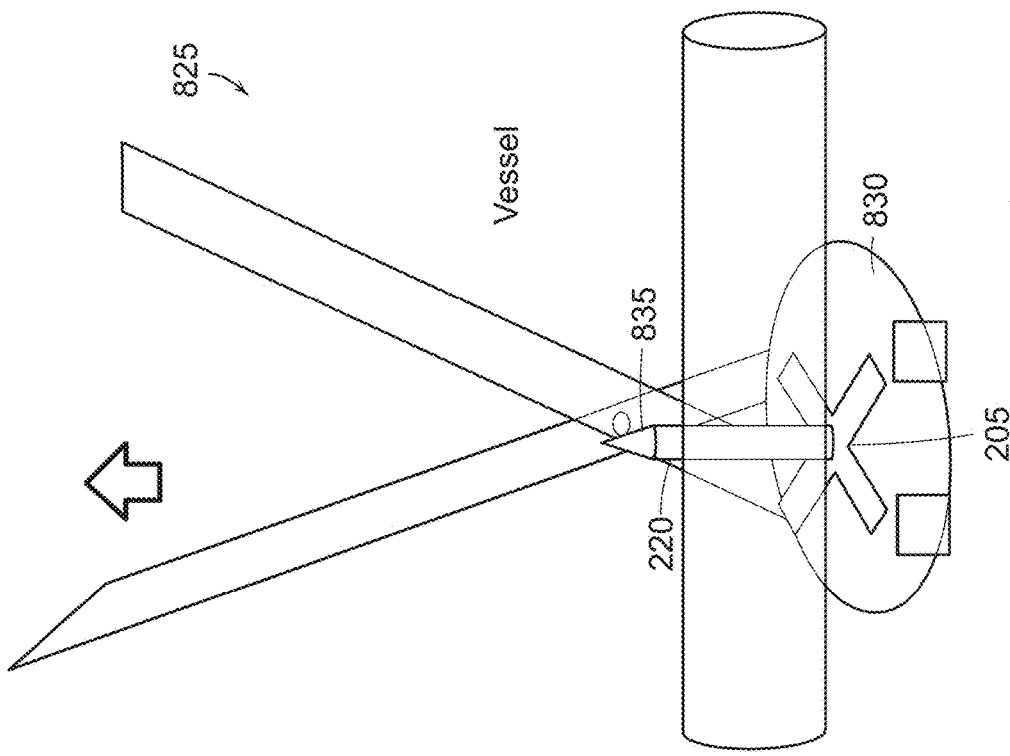

FIG. 185 shows that, by rotation of limbs 705, 710 of the dissector the dissector can be brought into an operational configuration.

Figure 169:
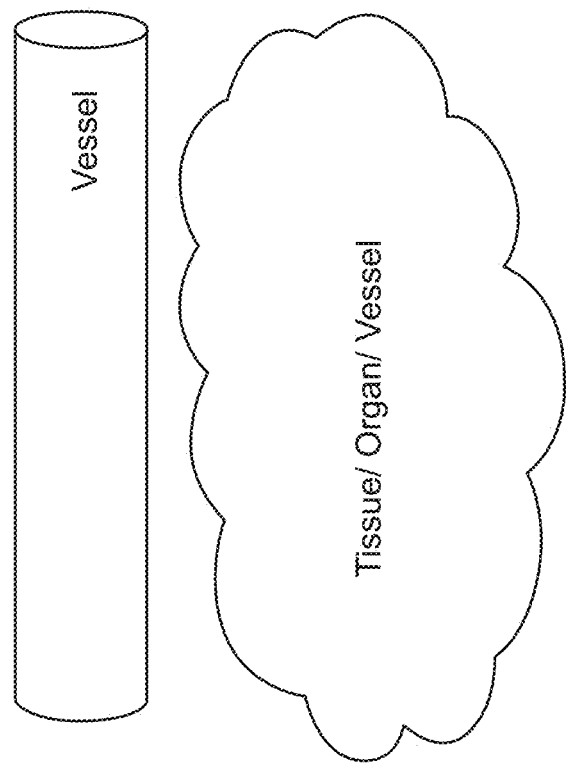
Figure 168:
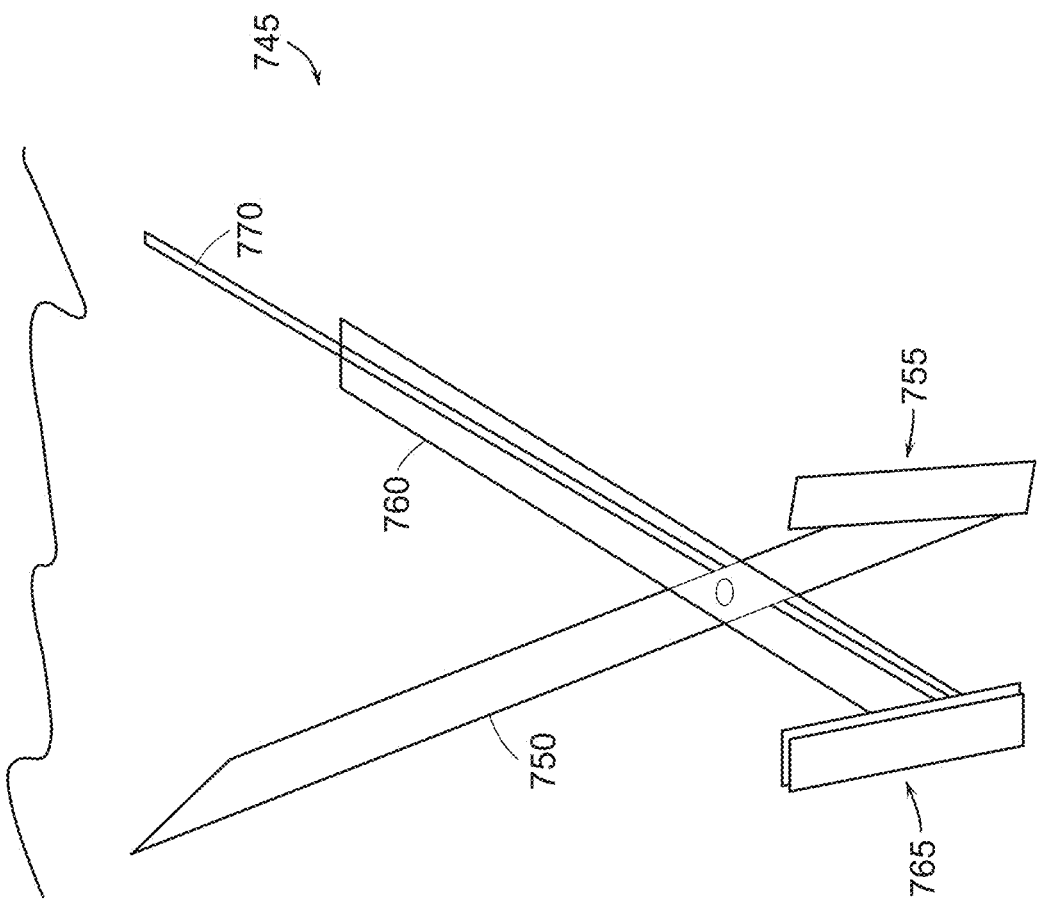

FIG. 168 shows another form of dissector 745 formed in accordance with the present invention now opened and comprising two "limbs" a first limb 750 having a single tip 755, and a second limb 760 having a double adjustable tip 765. A rod 770 is mounted to the movable component of the double dissector tip element 765. FIG. 169 shows the vessel (or tubular structure) to be penetrated by hollow needle 305 and the surrounding or underlying tissues.

Figure 170:
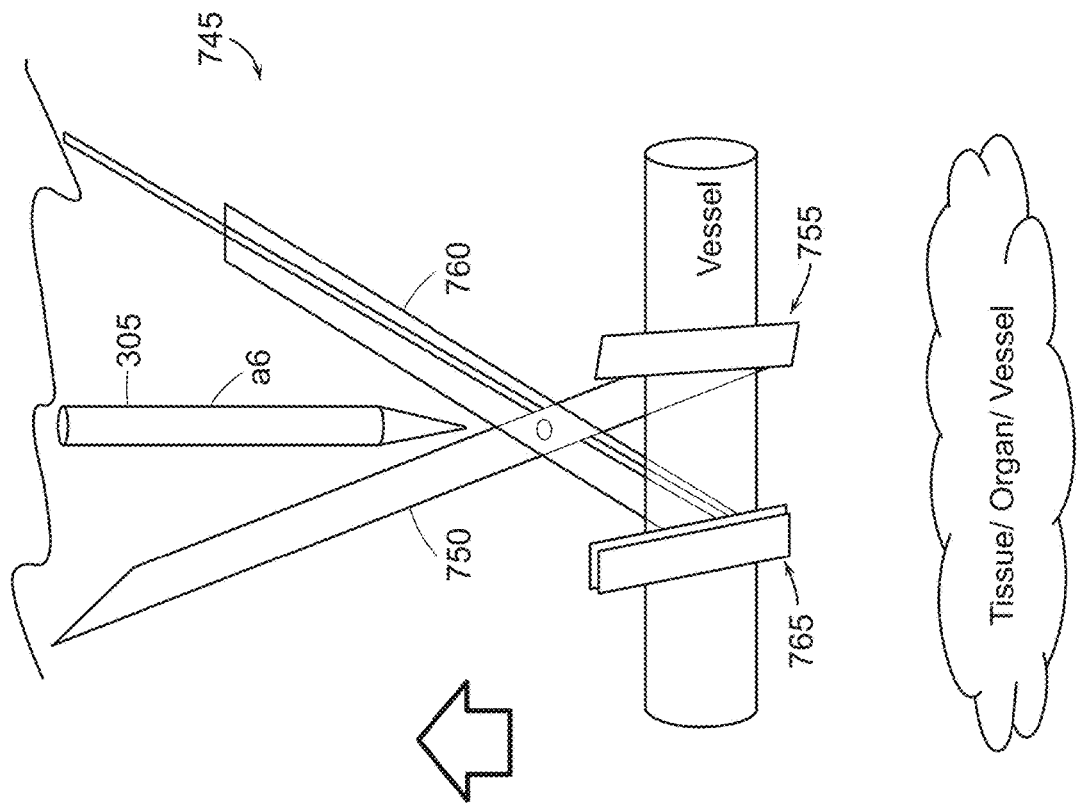

FIG. 170 shows the vessel (or tubular structure) has been dissected from the surrounding tissues and elevated by the two distal tips (or blades) 755, 765 and the hollow needle 305, is being readied to penetrate the vessel (or tubular structure).

FIG. 171 shows rod 770 being depressed and separating the two elements 775, 780 of double adjustable tip 765.

Figure 172:
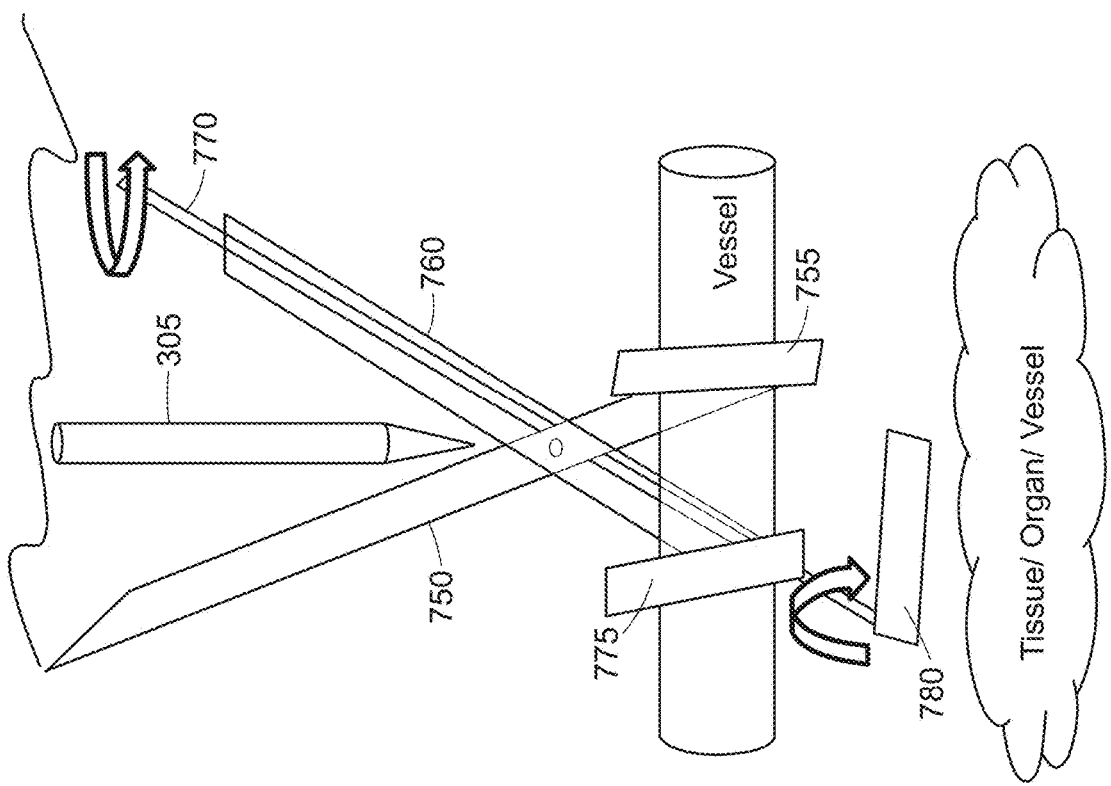

FIG. 172 shows the extended distal blade (shield) 780 of the dissector tip being rotated by rotating rod 770 so that the extended distal blade points toward the second dissector tip 755.

Figure 173:
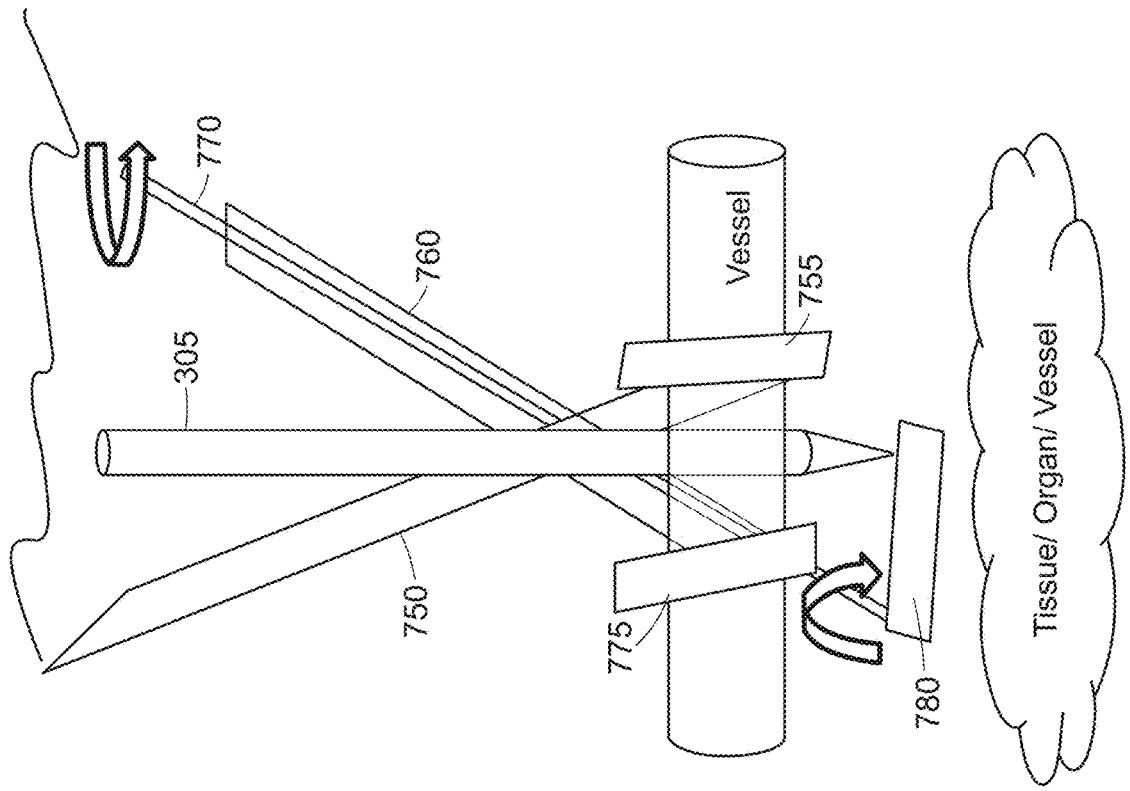
Figure 191:
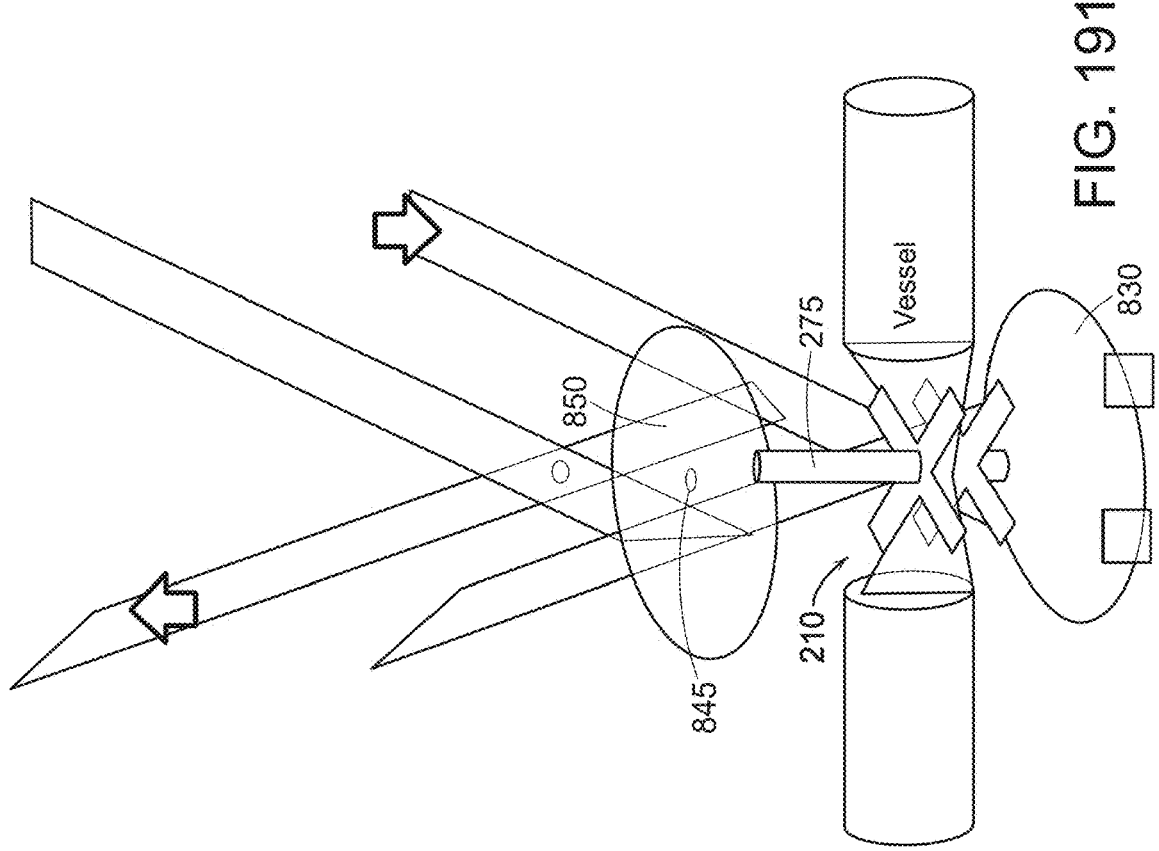

FIG. 173 shows shield 780 in place as hollow needle 305 penetrates the vessel (or tubular structure). Shield 780 limits the distal penetration of hollow needle 305 and protects the surrounding tissues, organs and structures (e.g., nerves, arteries, veins, etc.). While the embodiment of FIG. 191 shows the needle separate from the dissector 745, in another embodiment of the present invention, the needle may be connected to dissector 745 in a way that, once dissector 745 is deployed and shield 780 is positioned, the hollow needle 305 can be positioned to transect the vessel, tissue, duct or organ for deployment of the two-part fastener 200 that clamps the vessel, tissue, duct, organ.

14. Dissector

Figure 176:
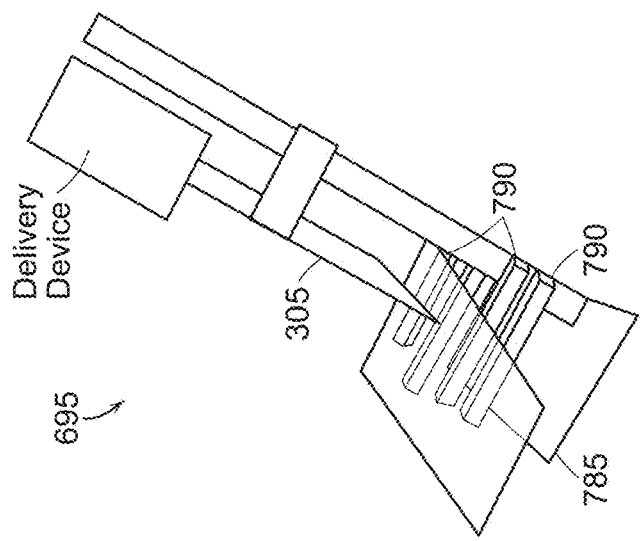
Figure 175:
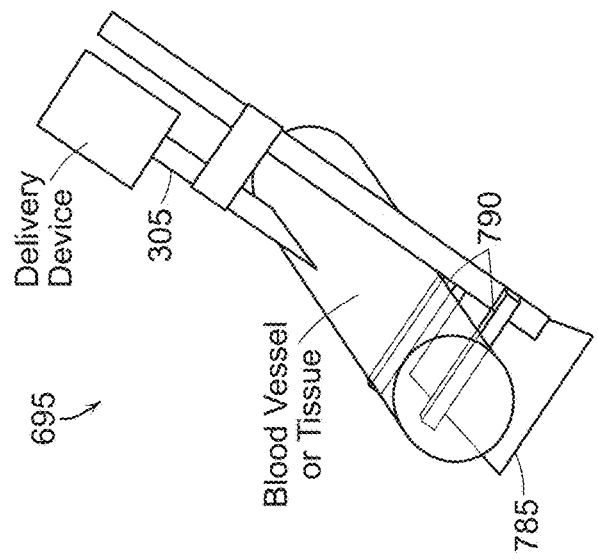
Figure 174:
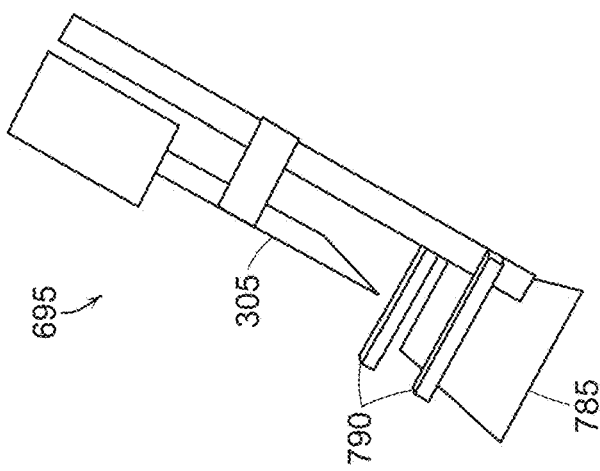
Figure 179:
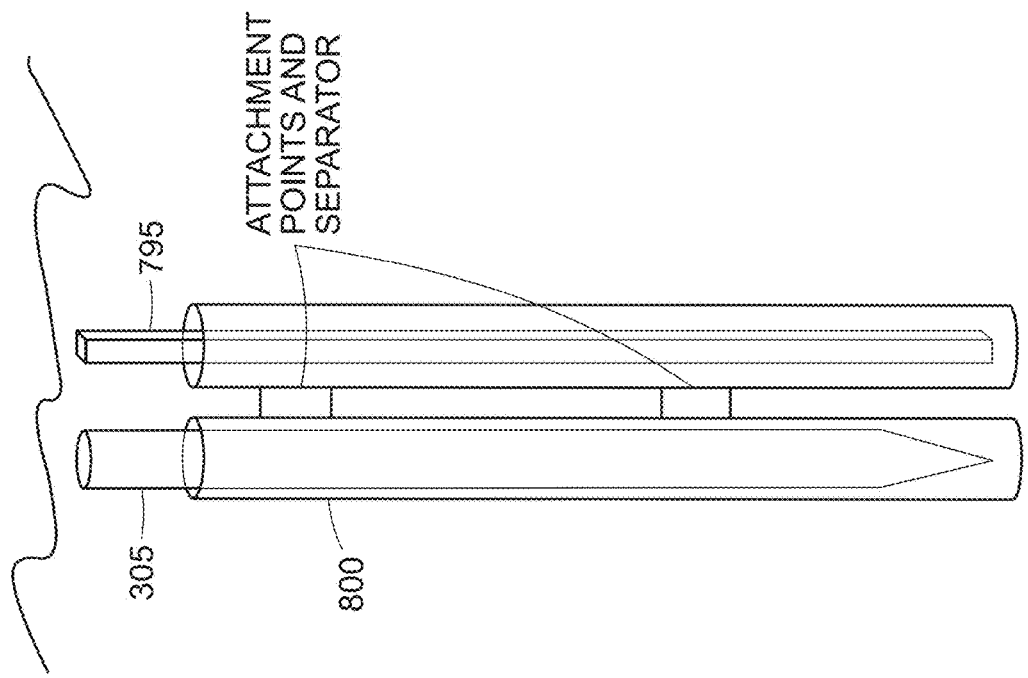
Figure 178:
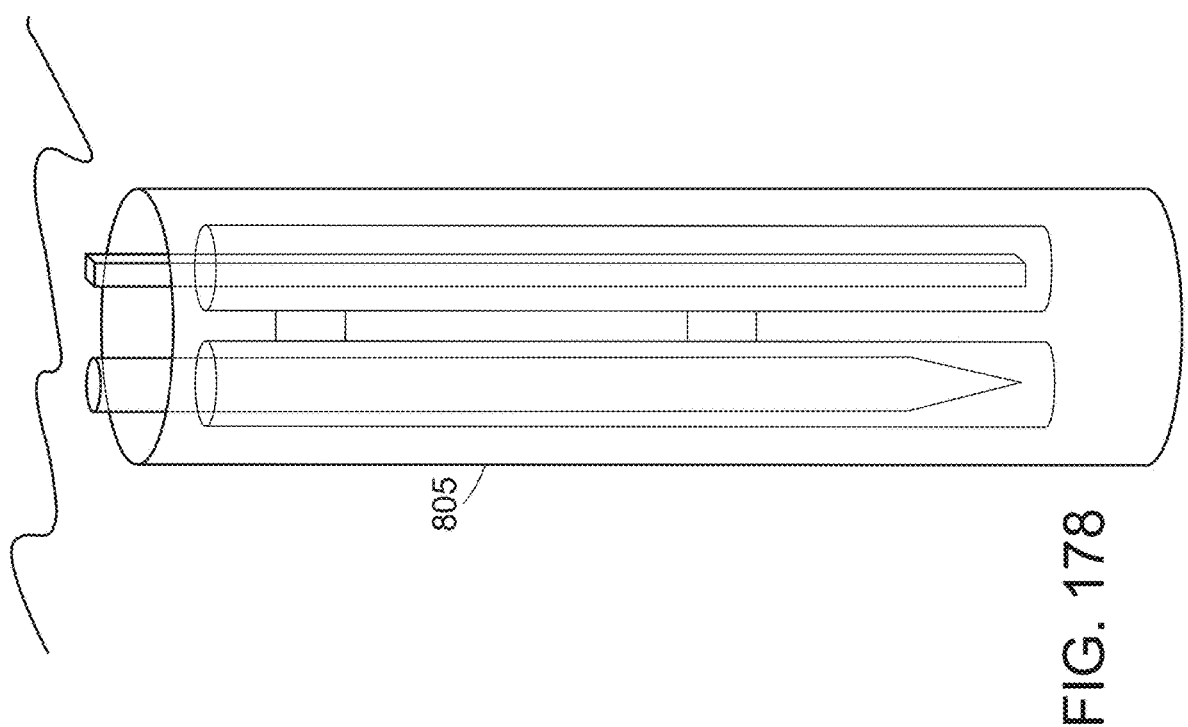

In yet another form of the present invention, and looking now at FIGS. 174-176, a needle stop (or "shield") 785 may comprise an integral part of dissector 695 support, and the two-part fastener 200 delivery device, and/or hollow needle 305 of the delivery device, may be attached to dissector 695 support. Needle stop 785 may be sharp so that needle stop 785 functions as a dissector, separating tissue located above the stop from tissue located below the stop. In one embodiment of the present invention, supports 790 are provided on dissector 695 for supporting the tissue so that it is elevated above needle stop 785. The gap between needle stop 785 and the supports 790 is preferably 1 cm or more, in another embodiment of the present invention, the gap between needle stop 785 and supports 790 is equal to, or greater than, 0.25 cm; and in another embodiment, needle stop 785 is movable and/or controllable to the point of having needle stop 785 and supports 790 in contact.

FIG. 174 shows hollow needle 305 attached to dissector 695. If desired, needle stop 785 can serve as a dissector, and may be configured to "fold up" (or roll up, in a similar way to dissector shown in FIGS. 164 and 165 so as to minimize the cross-section of needle stop 785 prior to deployment (e.g., so that needle stop 785 can be delivered via a cannula).

FIG. 175 shows a vessel or tissue held in place by supports 790 which create a gap between the vessel and needle stop 785. By virtue of the foregoing construction, in one embodiment of the invention, dissector 695 may be used to provide sufficient space for deploying two-part fastener 200.

FIG. 176 shows another embodiment of the present invention, wherein additional supports 790 are provided, and further wherein supports 790 are movable relative to one another, whereby to act as clamps to compress the tissue together and thereby facilitate penetration of the vessel by hollow needle 305.

In yet another form of the present invention, where the tissue holder element and the protective stop can be pulled together (or pushed apart) so as to create a gap sufficient for hollow needle 305 to be delivered past the vessel, organ or tissue to be penetrated by hollow needle 305, distal implant 205 may be deployed into the gap. The protective stop and tissue holder can be sized so as to easily pass through a laparoscopic cannula.

FIG. 171 shows one embodiment of the present invention wherein the protective needle stop 785 may be used as a dissector, whereby to separate a biological element of interest from other biological material, and wherein the protective needle stop 785 can serve to protect the biological material from being penetrated by hollow needle 305 when hollow needle 305 is used to deliver two-part fastener 200. The gap between protective needle stop 785 and the tissue holder is preferably adjustable, and can be controlled by pushing down or pulling up lever 786, which either (i) moves needle stop 785 distally when lever 786 is pushed distally, in either a discrete or continuous manner, so as to increase the gap between the tissue holder element and protective needle stop 785, or (ii) reduces the gap between the tissue holder element and protective needle stop 785 when lever 786 is pulled proximally.

15. "J"-Shaped Needle Stop Deployed Parallel to Hollow Needle 305

In another form of the present invention, and looking now at FIGS. 172-175 hollow needle 305 and a novel needle stop 795 contained in a sheath 800 may be configured to run parallel to each other such that, once hollow needle 305 is deployed out of a sheath 805, needle stop 795 can bend and align under hollow needle 305, whereby to prevent contact between hollow needle 305 and the tissue underneath needle stop 795. In one embodiment of the present invention, hollow needle 305 and needle stop 795 are used in conjunction with forceps (or a dissector) that supports the tissue to be transfixed by hollow needle 305.

FIG. 172 shows how hollow needle 305 and needle stop 795 may be deployed using a cannula (e.g., a laparoscopic cannula) 810 so as to facilitate delivery through a laparoscopic port. This approach may be used in conjunction with separate dissectors (not shown) and may also comprise a housing rather than a cannula.

FIG. 173 shows another embodiment of the present invention, wherein hollow needle 305 and needle stop 795 comprise a deformable material or a shape memory material or a material that has been cut so as to allow needle stop 795 to curve (e.g., stainless steel that has been laser machined). Needle stop 795 may comprise a tubular structure, ribbon or solid rod.

FIG. 174 shows deployment of needle stop 795. Once at the desired location, the needle stop is pushed out of its sheath 800 and delivered, deploying underneath the structure which is to be pierced by hollow needle 305 (to set two-part fastener 200). The depth, length and rotation angle of needle stop 795 is typically pre-set so as to locate needle stop 795 under and around where the tip of hollow needle 305 will be located.

FIG. 175 shows how, once transfixion is completed, hollow needle 305 is first removed from the vessel (i.e., withdrawn proximally) and then needle stop 795 is removed. In another embodiment of the present invention, needle sheath 805 and the needle stop sheath 800 are not connected together.

As discussed above, hollow needle 305 and needle stop 795 are preferably disposed as two separate parallel elements, with needle stop 795 attached to a hollow tube (or entirely made from the hollow tube) preferably comprising a shape memory or superelastic material (e.g., Nitinol). However, it should also be appreciated that, if desired, needle stop 795 and hollow needle 305 may be arranged, at least in part, co-axially.

17. Two-Part Fastener which Pierces Vessel from Bottom

In the foregoing disclosure, two-part fastener 200 is delivered through a hollow needle 305 that pierces the vessel (or other tubular structure which is to be occluded). More particularly, with two-part fastener 200, distal implant 205 is delivered through hollow needle 305 such that when distal implant 205 is disposed on the distal side of the vessel (or other tubular structure) which is to be occluded, distal implant locking tube 220 extends through the vessel (or other tubular structure) which is to be occluded when hollow needle 305 is retracted proximally. However, if desired, hollow needle 305 may by omitted and distal implant locking tube 220 may be configured to pierce the vessel which is to be occluded in a distal-to-proximal direction (i.e., so as to pierce the tissue from the distal side of the vessel to the proximal side of the vessel).

Figure 182:
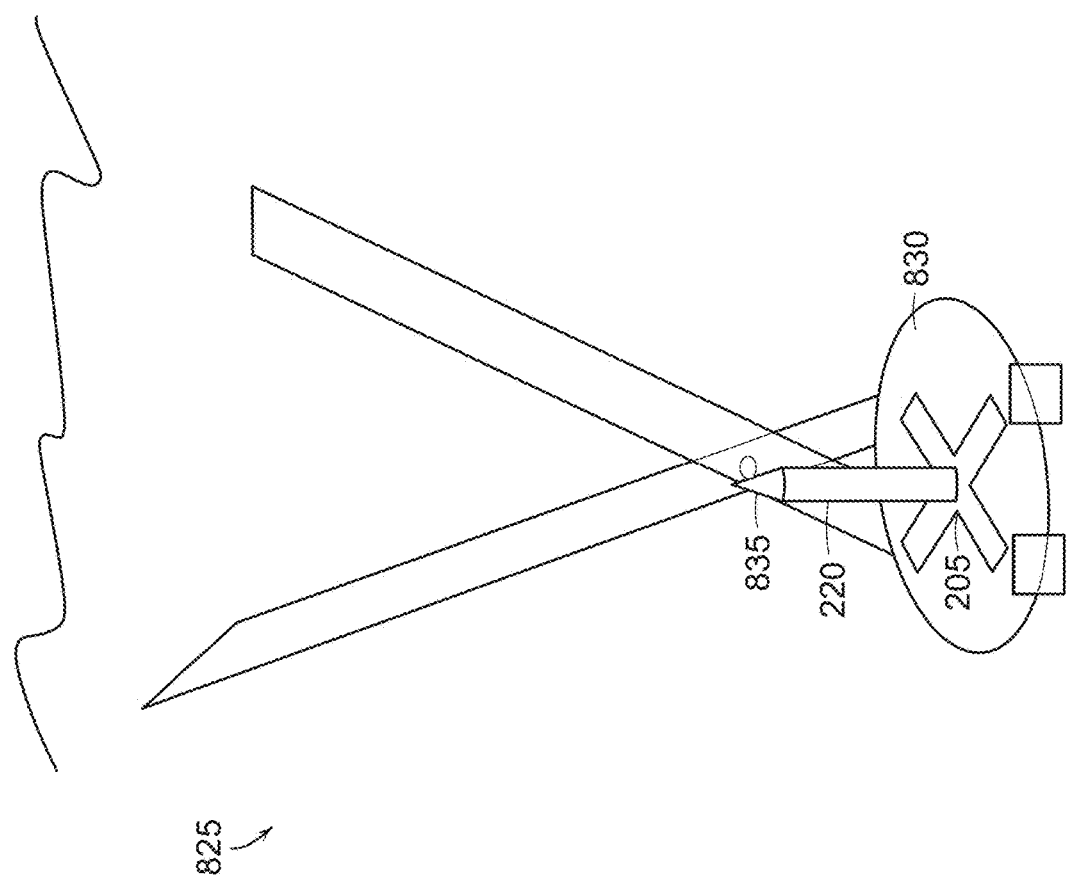

Another embodiment of the present invention is shown in FIG. 182. In this form of the present invention, a delivery device 825 comprises a holder 830 for distal implant 205, and proximal implant 210 is then slid down on top of distal implant 205 after distal implant 205 has been deployed such that distal implant locking tube 220 pierces the vessel (or other tubular structure) which is to be occluded, as will hereinafter be discussed. In this form of the invention, distal implant 205 comprises a distal implant locking tube 220 having a sharp end 835 which pierces the vessel (or other tubular structure) which is to be occluded, while proximal implant 210 comprises a cap 840 that caps sharp end 835 and protects adjacent tissue from inadvertent injury due to the sharp end 835 of distal implant locking tube 220. This configuration of two-part fastener 200 is especially advantageous for use in open surgical procedures, but may also be used in laparoscopic and other procedures.

Figure 183:
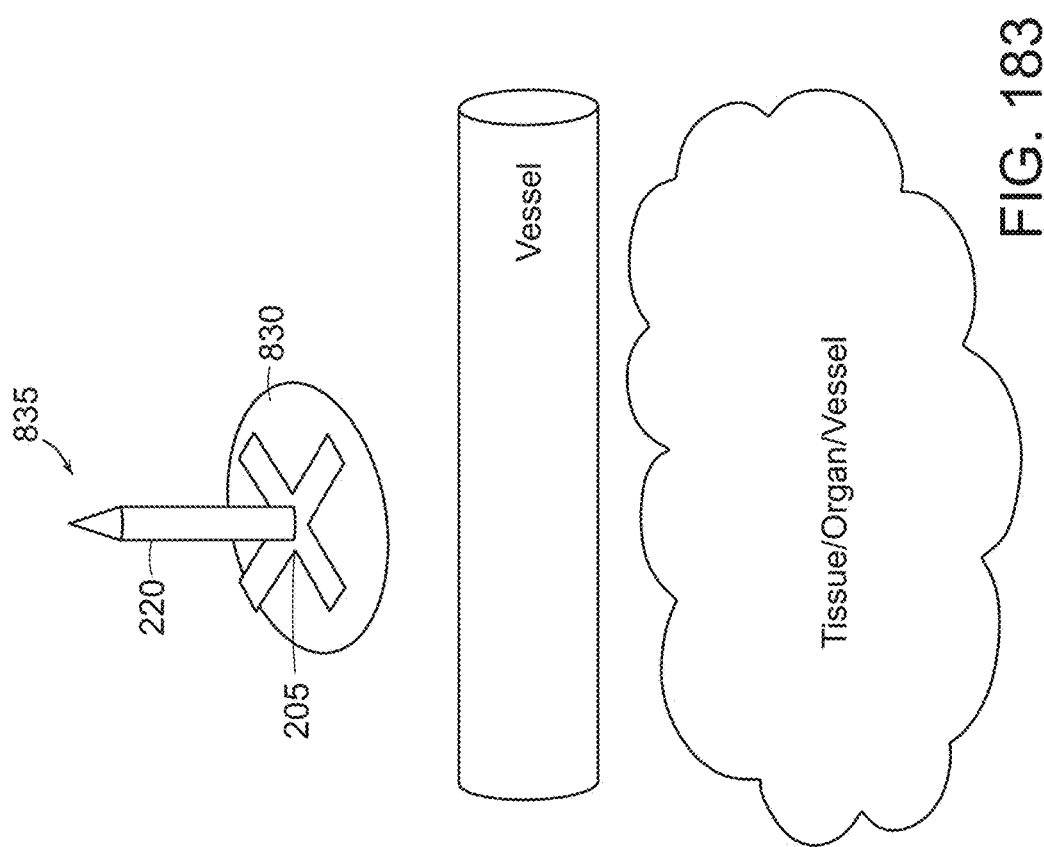
FIGS. 182-192 are schematic views showing another novel fastener formed in accordance with the present invention.

More particularly, FIGS. 182 and 183 show distal implant 205 having a spiked distal implant locking tube 220 (i.e., a distal implant locking tube having a sharp end 835) and mounted onto deployment delivery device 825 (e.g., a clamp or forceps).

Figure 184:
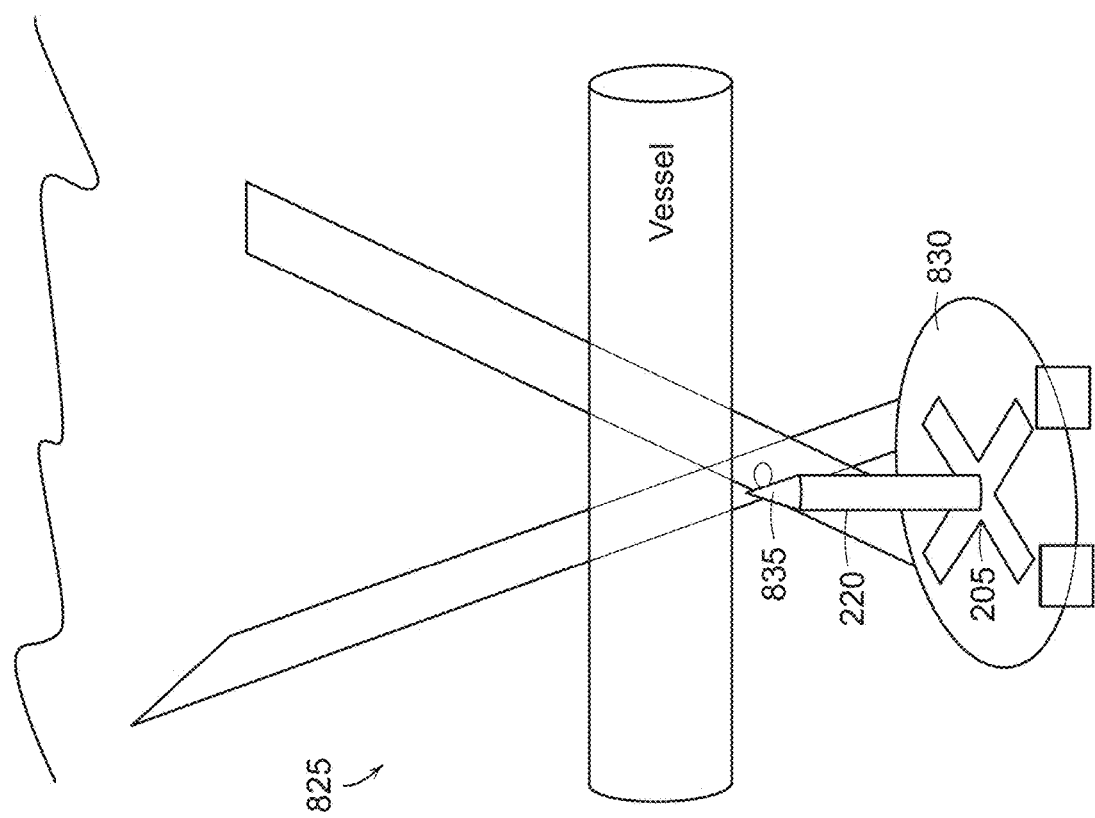

FIGS. 184 and 185 show delivery device 825 and distal implant 205 being positioned beneath the vessel to be occluded, and shows the delivery device when delivery device 825 is moved into contact with vessel so that distal implant locking tube 220 pierces the vessel from the distal side of the vessel in a distal-to-proximal direction and distal implant locking tube 220 penetrates through the vessel, whereby to exit the far (i.e., proximal) wall of the vessel (or other tubular structure), or the tissue to be clamped, so that the sharp end 835 of distal implant locking tube 220 is exposed on the proximal side of the vessel.

Figure 187:
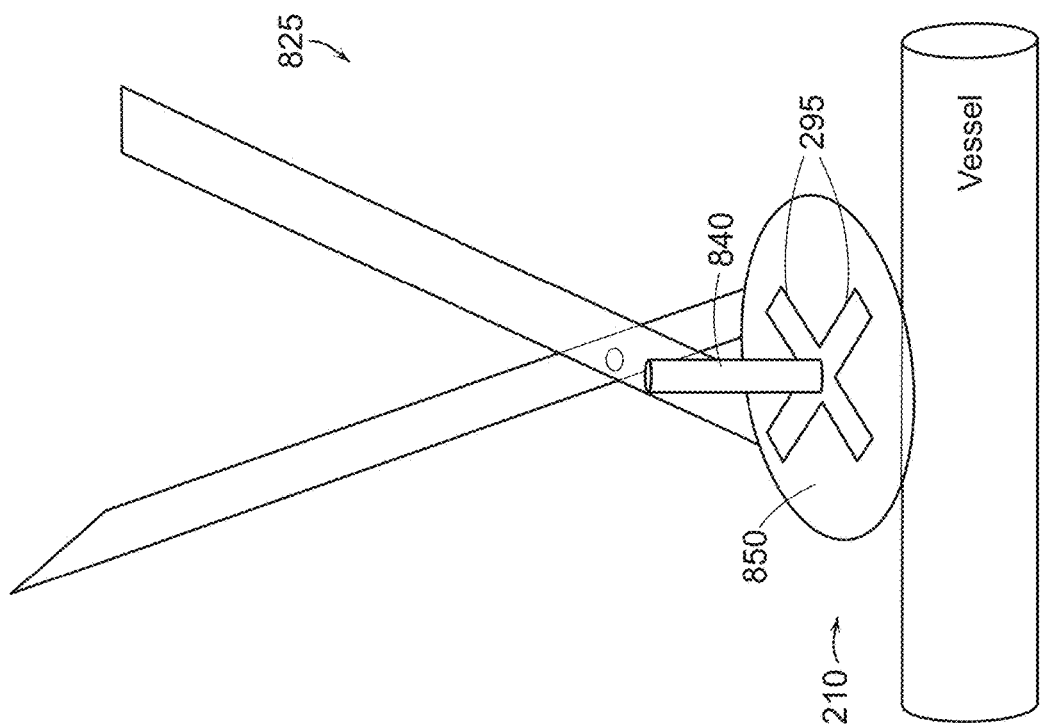
Figure 186:
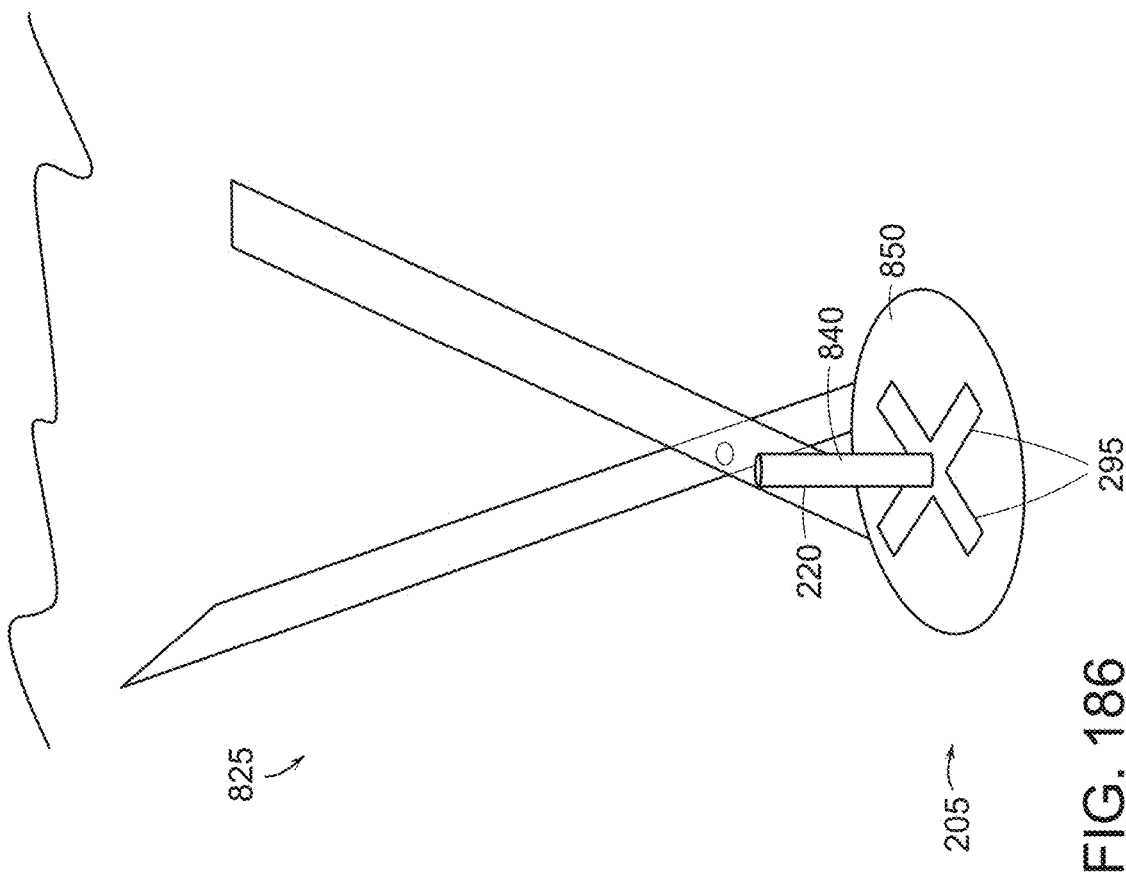

FIGS. 186 and 187 show a proximal implant 210 mounted to delivery device 825 with cap 840 extending through a hole 845 formed in a holder 850, such that proximal implant 210 is releasably retained on the distal side of holder 850. Note that proximal implant 210 comprises a locking shaft (i.e., tube 275) extending somewhat perpendicular to legs 295 of proximal implant 210. Tube 275 also comprises cap 840 for locking proximal implant 210 to distal implant locking shaft 220.

Figure 189:
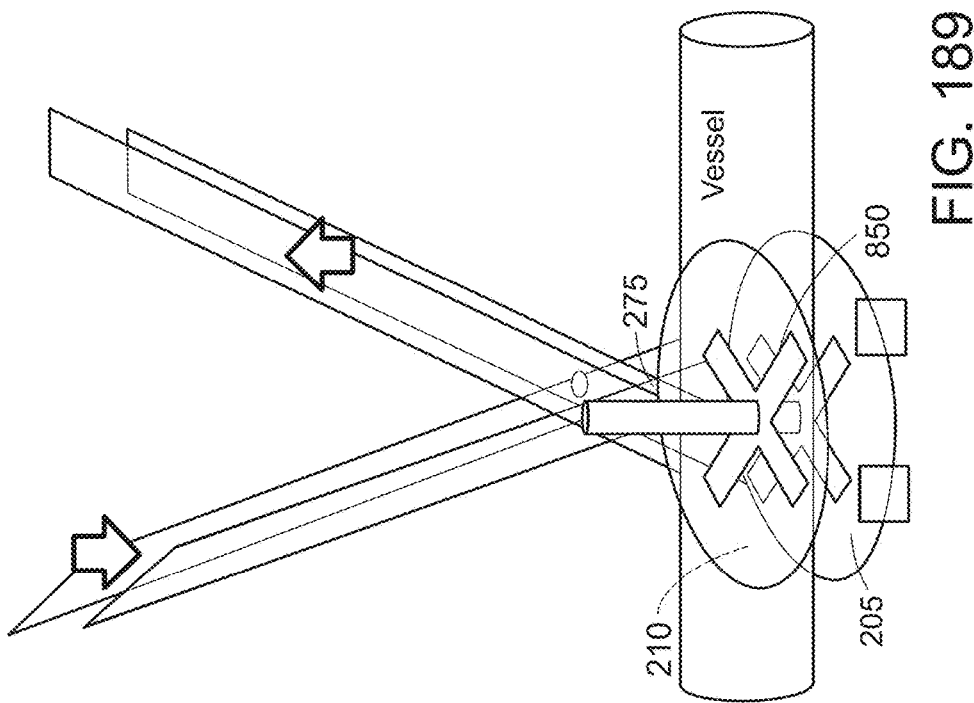
Figure 188:
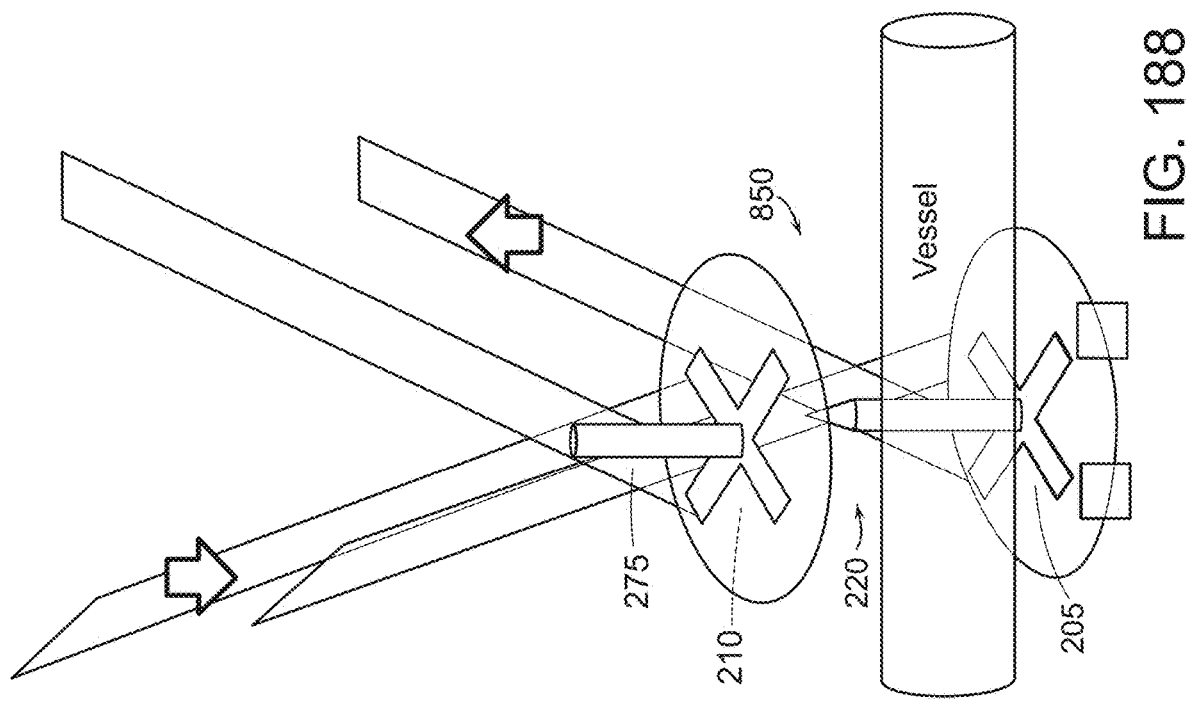

FIGS. 188 and 189 show proximal implant 210 and distal implant 205 being brought into contact with one another by aligning distal implant 205 and proximal implant 210. Tube 275 (and cap 840) of proximal implant 210, which is hollow, is locked to distal implant locking tube 220 (which may or may not be hollow) of distal implant 205. Tube 275 (and cap 840) and distal implant locking tube 220 may be made of different materials (e.g., titanium and stainless steel) or the tube 275 (and cap 840) and distal implant locking tube 220 may be made of the same material. If desired, distal implant locking tube 220 and proximal tube 275 may be configured such that they are contiguous with legs 235 of distal implant 205 and legs 295 of proximal implant 210, respectively.

Figure 190:
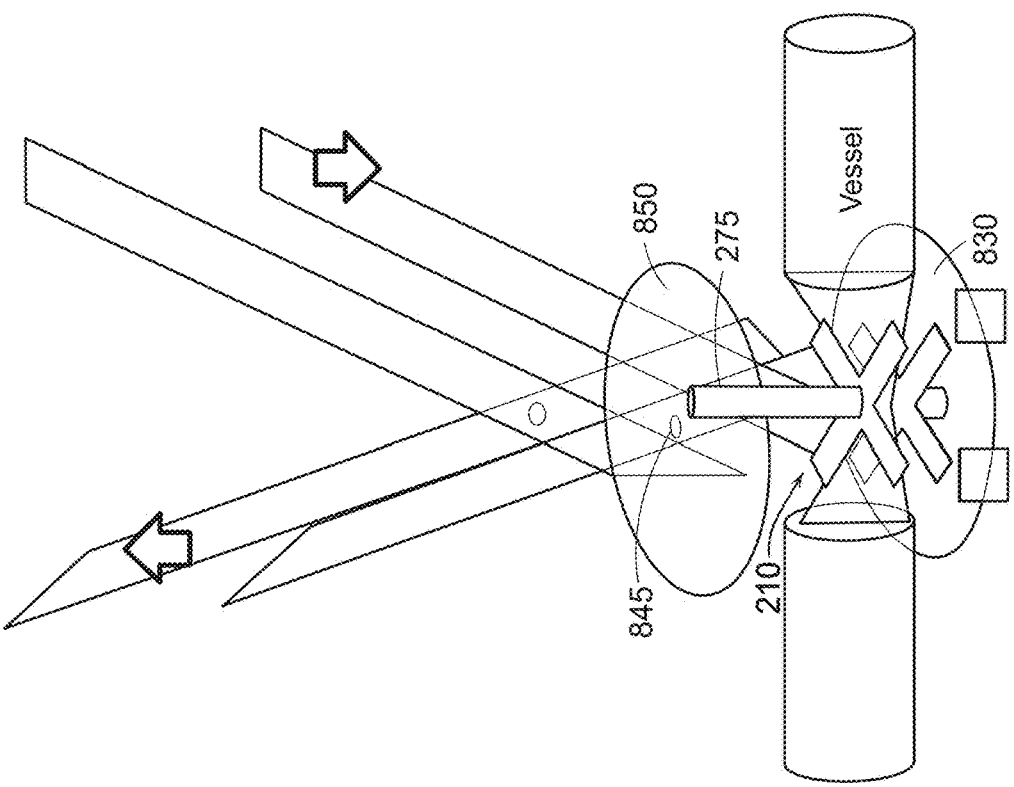

FIGS. 190 and 191 show how delivery device 825 is removed after distal implant 205 and proximal implant 210 are locked together.

Figure 192:
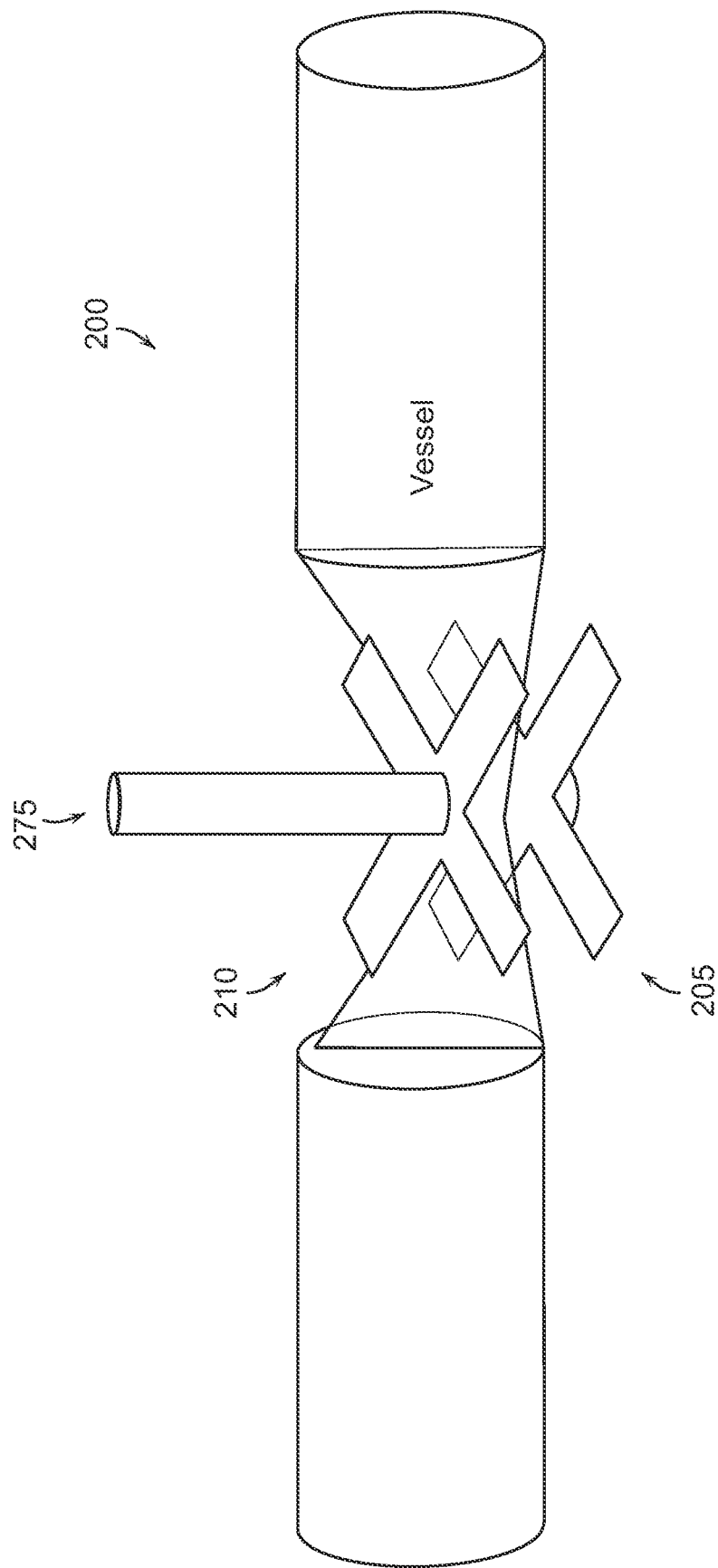

More particularly, FIG. 192 shows the delivery devices removed, leaving the vessel occluded using two-part fastener 200. Tube 275 (which may be only part of proximal implant 210, and made of Nitinol or titanium or other metals) of proximal implant 210 not only serves to lock with distal implant locking tube 220 of distal implant 205, but also protects surrounding tissue by covering the sharp end 835 of distal implant locking tube 220.

18. Exemplary Uses of the Two-Part Fastener

By way of example but not limitation, two-part fastener 200 of the present invention may be used for, and in, procedures such as left arterial appendage occlusion. It should also be appreciated that the two-part fastener 200 may be used in cardio-thoracic-vascular applications such as internal mammary artery bypass surgery where the secure ligation of branches is critical to the prevention of bleeding and for the treatment for dissecting aneurysms of the aorta (which is generally performed by sewing patches onto the native artery so as to allow suture attachment to an interposition graft). With such a procedure, one problem is typically bleeding through the needle holes of the transfixing sutures. The present invention can be used so as to pressurize the tissue around the point of transfixion and prevent bleeding.

In a similar fashion, when occluding the atrial appendage to prevent clot formation and embolization during surgery, the atrial appendage tends to bleed around the needle hole when sutured using a needle. The novel two-part fastener 200 of the present invention can mitigate this bleeding by providing sealing pressure where two-part fastener 200 pierces the atrial appendage.

It should be appreciated that two-part fastener 200 may be used as a vessel anastomotic device for mechanically joining various vessels together.

In addition, two-part fastener 200 may be used so as to allow the reliable fixation of covered stents to the aortic wall in the endovascular treatment of aortic aneurysms, particularly where the stent attachment zone is short and uneven. This may be performed percutaneously or through a catheter-directed endo-vascular approach.

It should also be appreciated that two-part fastener 200 may be used in applications involving solid organs where the use of staples may be undesirable or unacceptable.

For example, solid organs do not generally accept conventional staplers since solid organs bleed through the staple entry points. The two-part fastener 200 of the present invention avoids these issues, and is suitable for parenchymal resection of organs such as the liver, spleen, kidney and lung. The pressurized zone around the transfixing point wound prevents the bleeding that occurs with standard suture technique through the needle entry points.

For such applications, it may be desirable to modify the two-part fastener 200 of the present invention so as to form a multi-vessel fastener capable of deploying a row of clips simultaneously, and/or to apply clips laterally to the solid tissue edges.

The two-part fastener 200 of the present invention may also be used for other applications. By way of example but not limitation, the two-part fastener 200 of the present invention may be used in general surgical applications, e.g., occlusion of the spermatic cord as an alternative to vascectomy in male sterilization; cystic and bile duct occlusion; bowel fistula or other fistulous tracts, etc. Or the present invention may be used for attachment of tissues, e.g., during hernia repair where synthetic materials (e.g., hernia mesh) are used to reinforce the site of the hernia repair. The two-part fastener 200 of the present invention may also be used for secure ligation of the fallopian tube for sterilization procedures. This can be accomplished by the simple application of the two-part fastener 200 of the present invention to the fallopian tube, using open, laparoscopic or robotic surgery.

It should also be appreciated that two-part fastener 200 may be used for orthopedic applications, e.g., as anchors in joint surgery or repair of tendons or ligaments.

And two-part fastener 200 may be used for interventional radiologically-directed procedures performed under imaging (e.g., ultrasound, CT, fluorosocopy, etc.), including, but not limited to, the ligation of tubular or vascular structures or the coaptation of tissues When using conventional staples, it is common to also use a buttress, integrating tissue stapling with a buttress provides surgeons with both greater functionality and efficiency. The present invention does not require the use of a buttress, or support material, as in the case of the Endo GIA product, thereby simplifying two-part fastener 200, avoiding the need for additional materials in the body, and reducing the cost and complexity of these procedures. If desired, however, in certain instances, the present invention could also be used in conjunction with similar supporting or buttressing materials.

The present invention can be used in a fashion similar to a stapler for open surgery procedures (e.g., an open anastomosis).

By way of example but not limitation, two-part fastener 200 may be used for the prevention of, or treatment of, blood clot embolization in the pulmonary or peripheral systemic circulation. The present invention may be used to percutaneously (or laparoscopically or even in open surgery) occlude a vein, in the presence of a vein (superficial or deep) that has a clot where there is the possibility of propagation and dislodgment of the clot into the blood stream in the large veins returning the blood to the heart and lungs. Two or more two-part fasteners 200 can be placed on either side of the clot, thereby trapping and containing the clot, or the occlusion elements may be deployed upstream from the clot, thus preventing propogation of the clot toward the heart or lungs.

20. Two-Part Fastener Utilizing Electro/RF Cautery

In another form of the present invention, a modified form of two-part fastener 200 may be used to cauterize a vessel, tubular structure, and/or to bond different tissues. More particularly, in this form of the present invention, at least a portion of two-part fastener 200 connects to an electrical cauterizing unit (e.g., monopolar, bipolar, etc.) which is preferably built into the delivery device.

In one form of the present invention, two-part fastener 200 is connected to an energy source (or energy sources) and the vessel or duct or tissues may be occluded (or attached, fused, or connected to each other) by the application of RF energy. The RF energy may be applied between two-part fastener 200 and an electrode located in, or on, the patient at another location (e.g., a patient return electrode), or an electrode located between proximal implant 210 and distal implant 205 of two-part fastener 200. The same potential may be applied to both proximal implant 210 and distal implant 205 in a monopolar electro-surgery mode, or a potential difference may be applied between the proximal implant 210 and distal implant 205 in a bipolar electrosurgery mode. The energy source may produce an RF current, where the currents and voltages may be monitored and controlled and with controllable duty cycles at frequencies from 200 Khz-3.3 MHz that, so as to optimize the attachment of the tissues or occlusion of the vessels and ducts, and/or the denaturing of collagen and other proteins to produce fusion or binding, or coagulation or blending. Once the energy is delivered to the tissues, the occlusion elements (e.g., distal implant 205 and proximal implant 210) and the delivery device are removed. See FIG. 202 In one form of the invention, distal implant 205 and proximal implant 210 may be held at the occlusion site for a controllable amount of time after application of the energy and before removal, so as to help ensure better occlusion. Distal implant 205 and proximal implant 210 approximate the various tissues to a controllable degree, whereby to reduce the amount of energy needed to be imparted to the tissues and vessels, thus reducing damage and maximizing binding. In this form of the invention, distal implant 205 comprises a plurality of legs 855, and proximal implant 210 comprises a plurality of legs 860. Legs 855 of distal implant 205 and legs 860 of proximal implant 210 provide significant surface area, or contact area, between an occlusion element electrode and the tissue. As such, binding or sealing or connecting of tissue or occlusion of vessel or duct can occur over a large surface area. This area can be much larger than the cross-section of the delivery element probe or device that penetrates the patient skin. See FIGS. 199 and 200. In one embodiment of the present invention, the effective ratio of the diameter of distal implant 205 and proximal implant 210 to the diameter of the delivery element probe or device may be greater or equal to 2:1 (and may be up to 10:1 or more). Furthermore, the surface area of tissues that can be connected can be large, depending upon the dimension of legs 860 of proximal implant 210 and legs 855 of distal implant 205. These legs are the functional equivalent of legs 235 and 295 of the two-part fastener 200.

When distal implant 205 and proximal implant 210 are removed, a hole may remain which is sealed around the edges in the segment of the occluded vessel duct or tissue. However, if desired, various coagulants or sealants or glues (e.g., cyanoacrylate) may be injected through the needle or delivery device or a separate different delivery device (injected through a second needle placed near the site) so as to close the hole in the tissue, and/or to promote healing.

In one embodiment of the present invention, distal implant 205 and proximal implant 210 are extracted through the same hollow needle 305 that delivered them.

In one form of the present invention, distal implant 205 and proximal implant 210 may be decoupled from the electrical energy source once they have delivered the electrical energy to the tissue, and then locked together and decoupled from the delivery device so as to remain implanted, sandwiching the tissue that has been treated with RF energy. This approach may transform (or enhance) the integrity of the tissue (e.g., in bowel or stomach tissue) so as to reduce the likelihood that two-part fastener 200 will migrate through the tissue.

Figure 193:
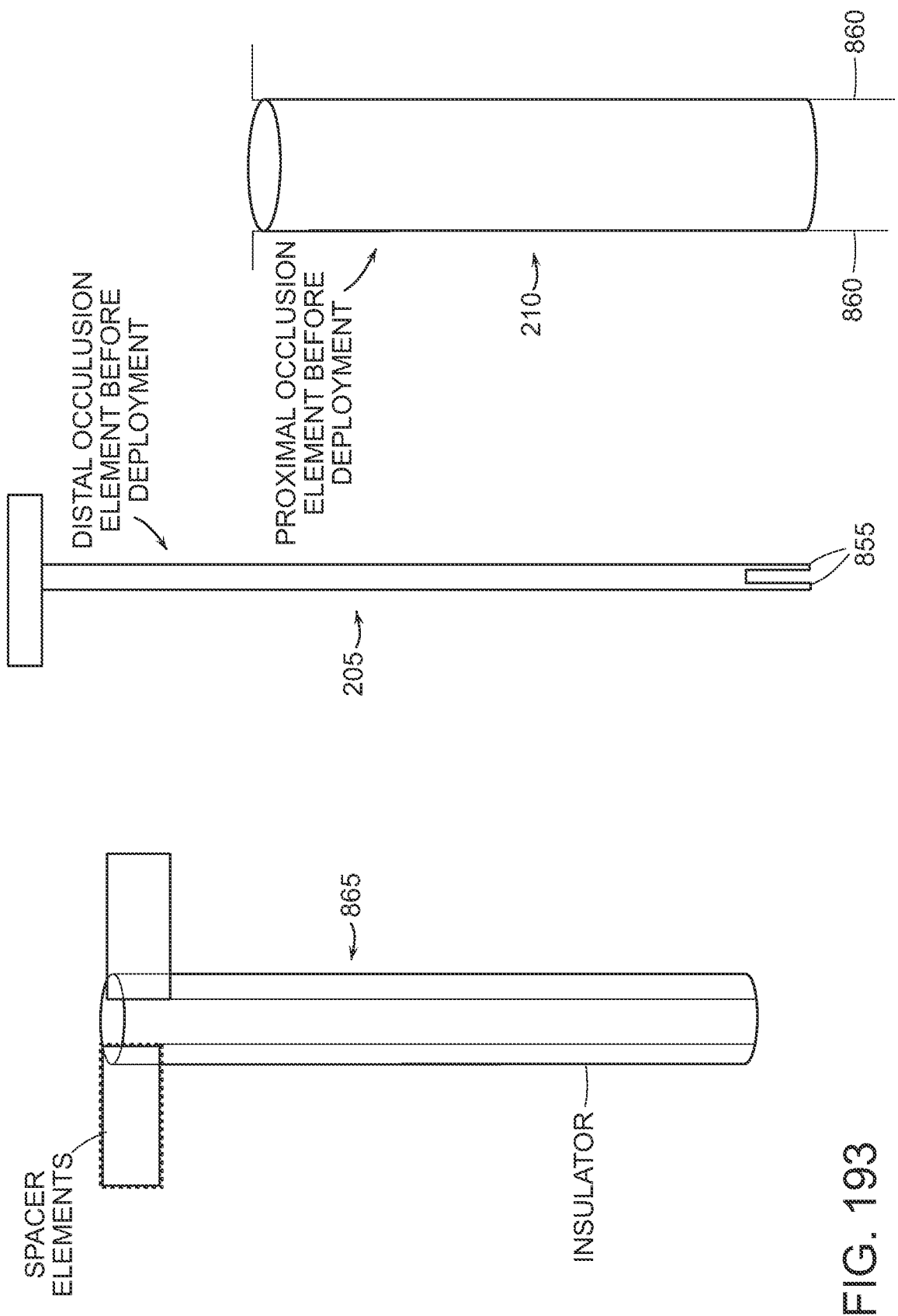
Figure 194:
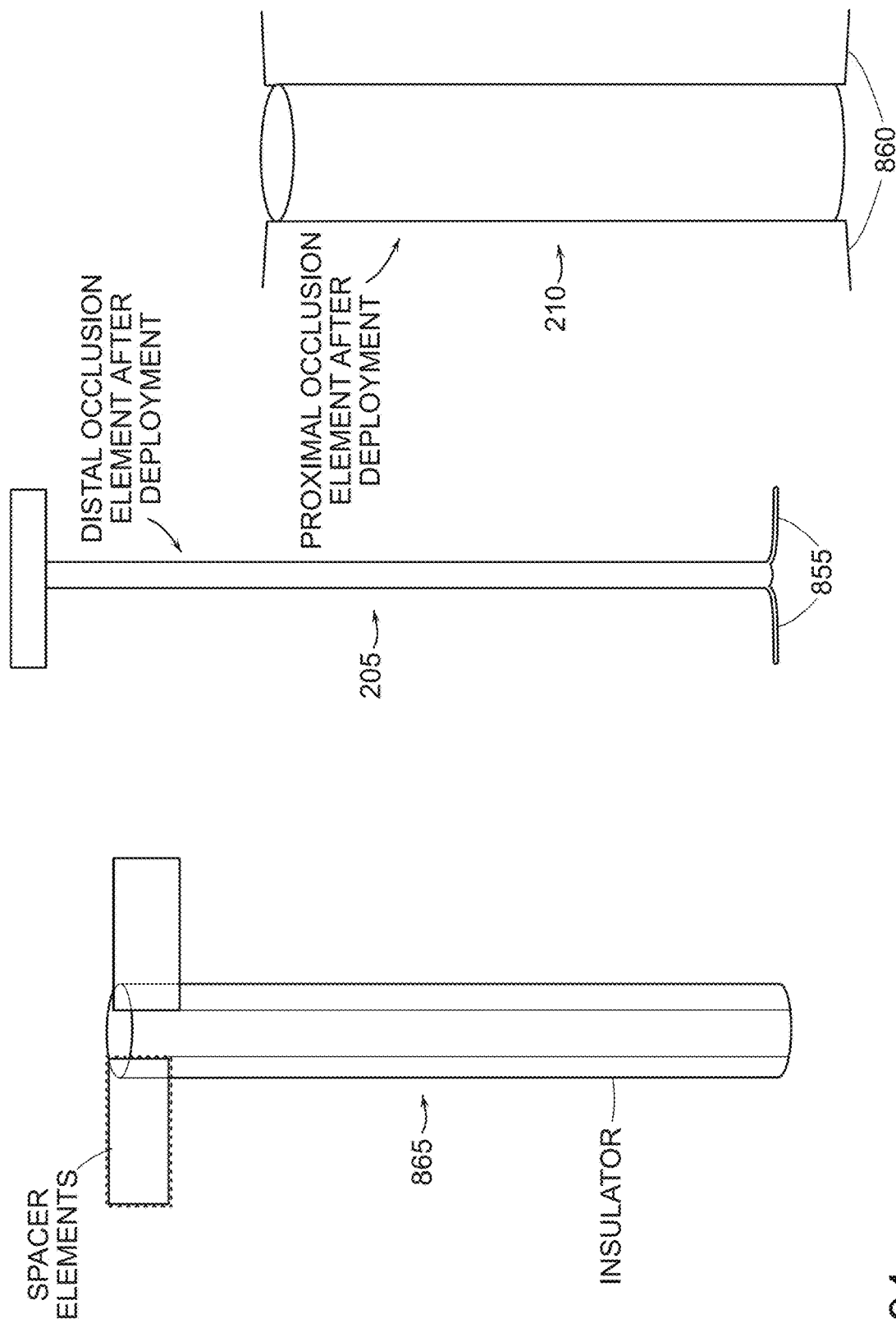
Figure 196:
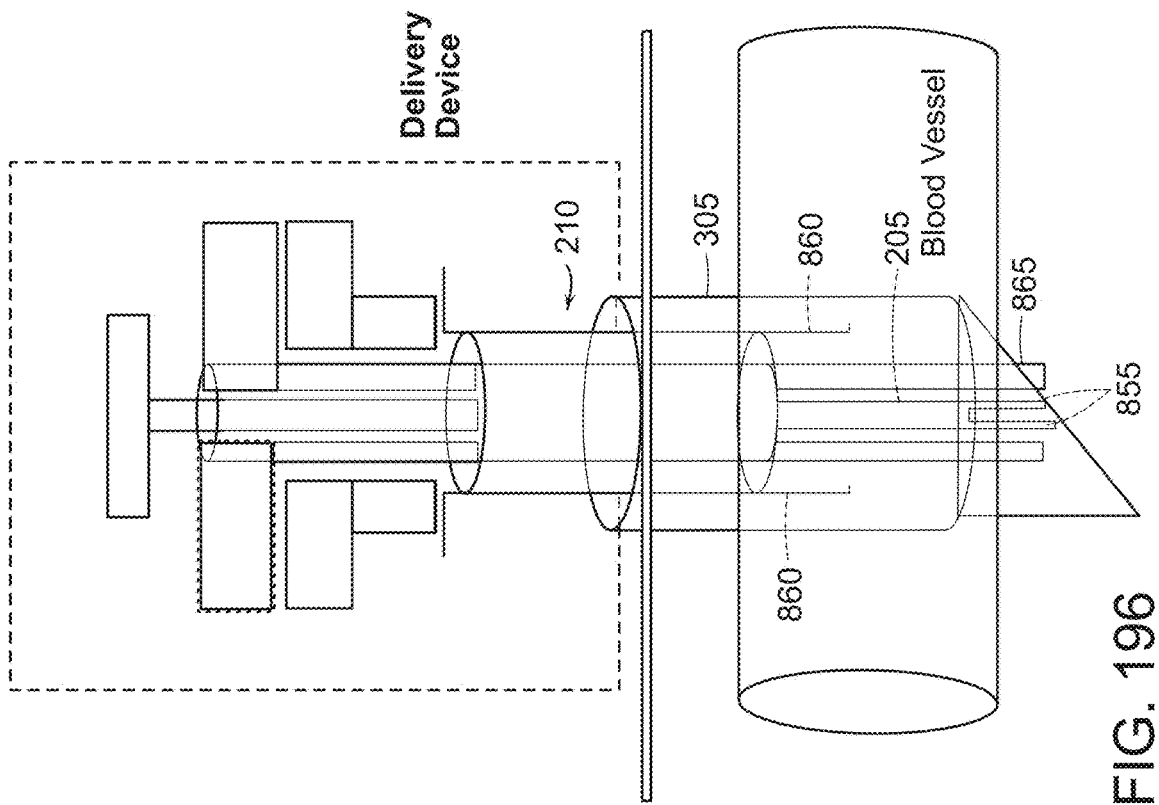
Figure 195:
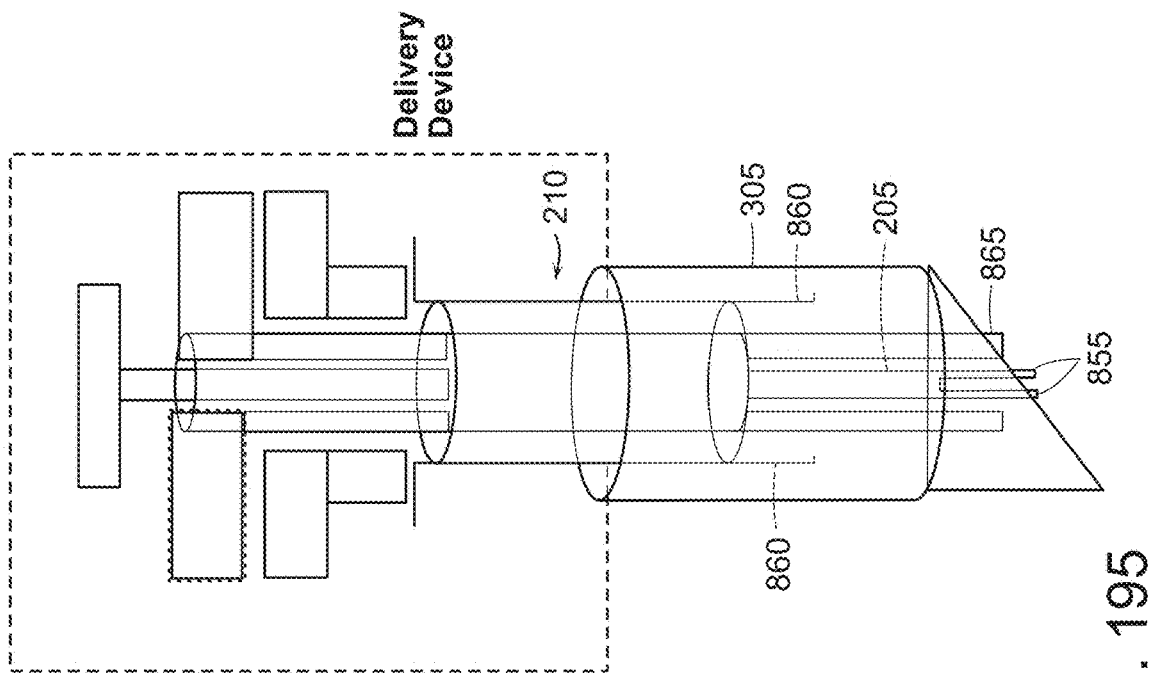

FIG. 193 shows a preferred embodiment of the present invention with the distal implant 205, proximal implant 210 and the insulating element 865 being shown before being deployed. FIG. 194 shows an embodiment of the present invention where the occlusion elements are deployed. All three elements are generally contained within a delivery device and a needle (e.g., hollow needle 305) that controls their deployment and delivery of two-part fastener 200 through multiple tissue layers or a vessel, duct or fallopian tube.

More particularly, FIG. 193 shows individual electrode elements (i.e., distal implant 205 and proximal implant 210) and insulating element 865, prior to deployment.

And FIG. 194 shows distal implant 205 and proximal implant 210 and the insulating element 865 after deployment.

FIG. 219 shows the delivery device with hollow needle 305 attached.

FIG. shows the delivery device with hollow needle 305 penetrating through a vessel or tissues.

Figure 197:
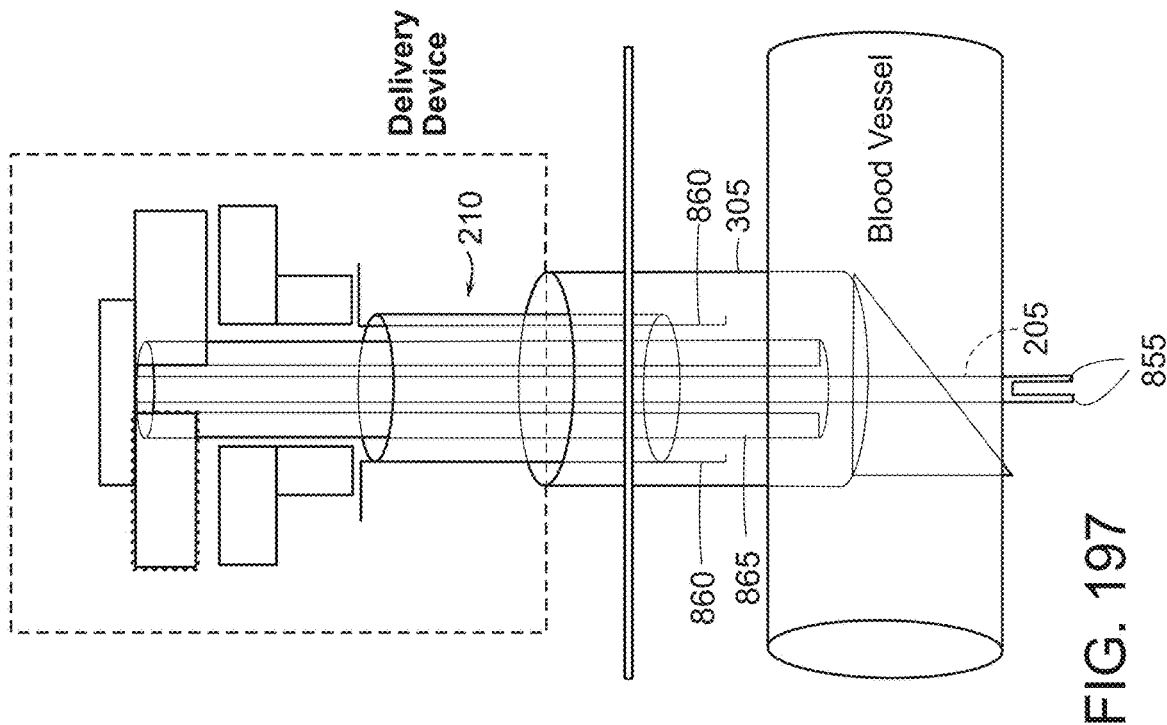

FIG. 197 shows advancement of distal implant 205.

Figure 198:
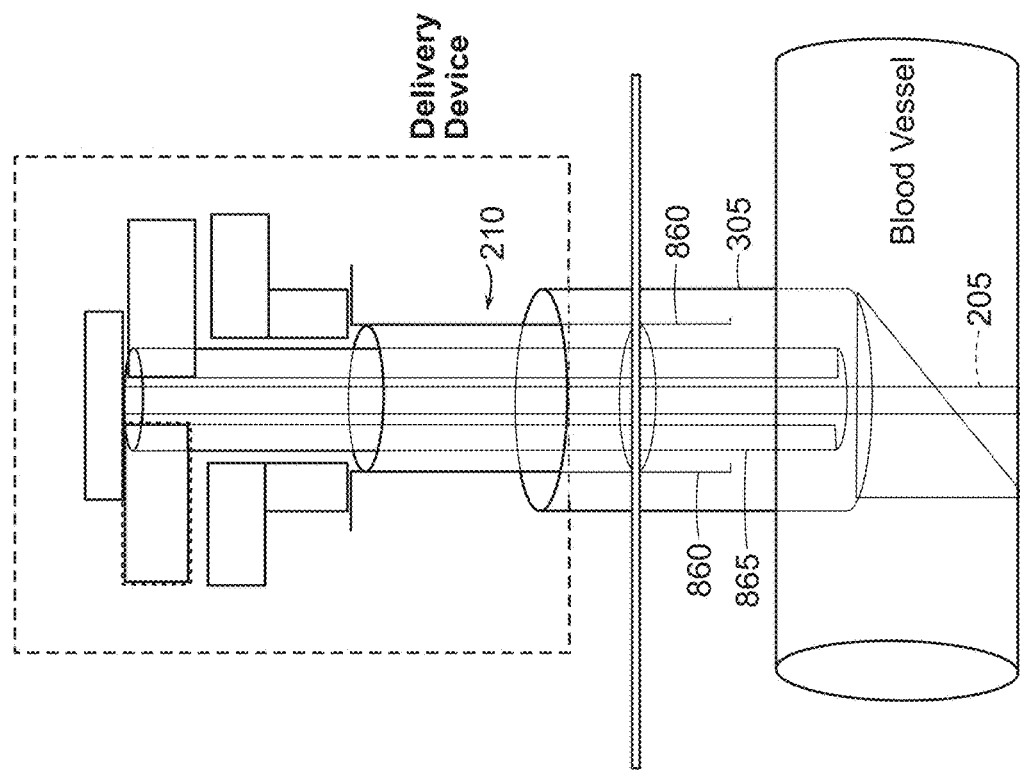

FIG. 198 shows deployment/opening of distal implant 205 so as to cause legs 855 of distal implant 205 to extend radially outward.

Figure 199:
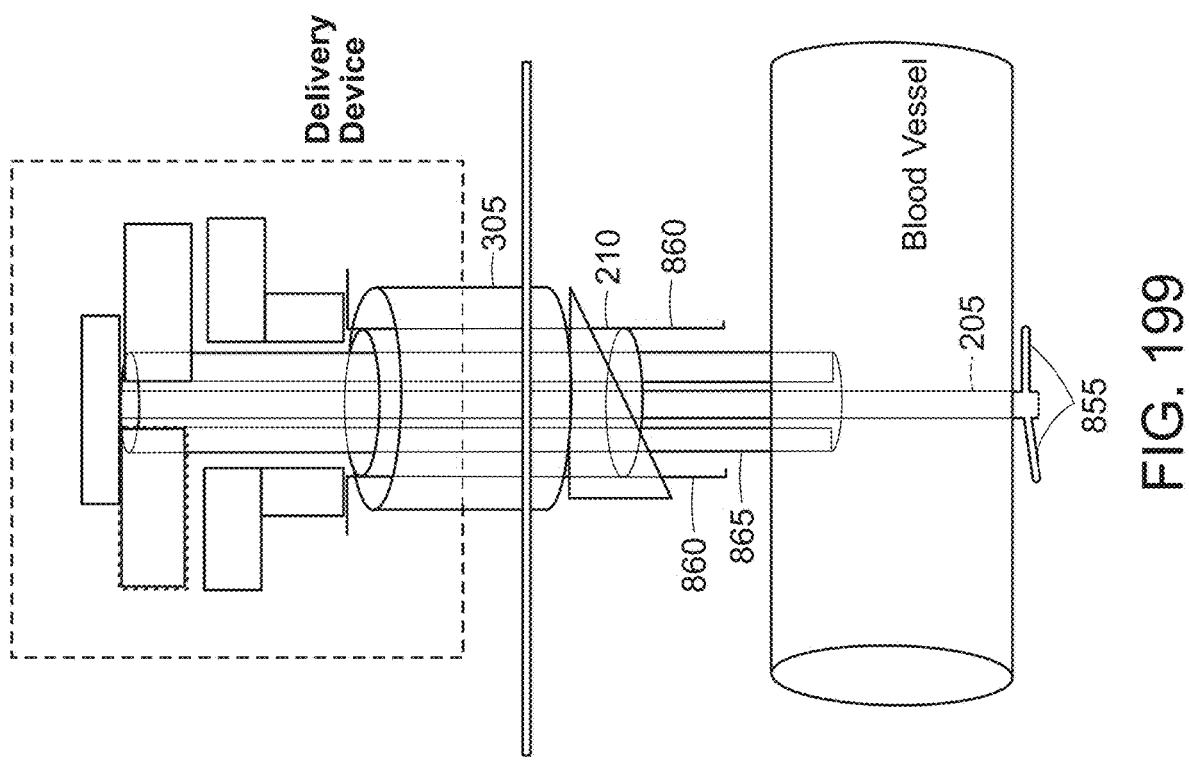

FIG. 199 shows raising of hollow needle 305 and deployment of proximal implant 210 beyond the tip of hollow needle 305.

Figure 200:
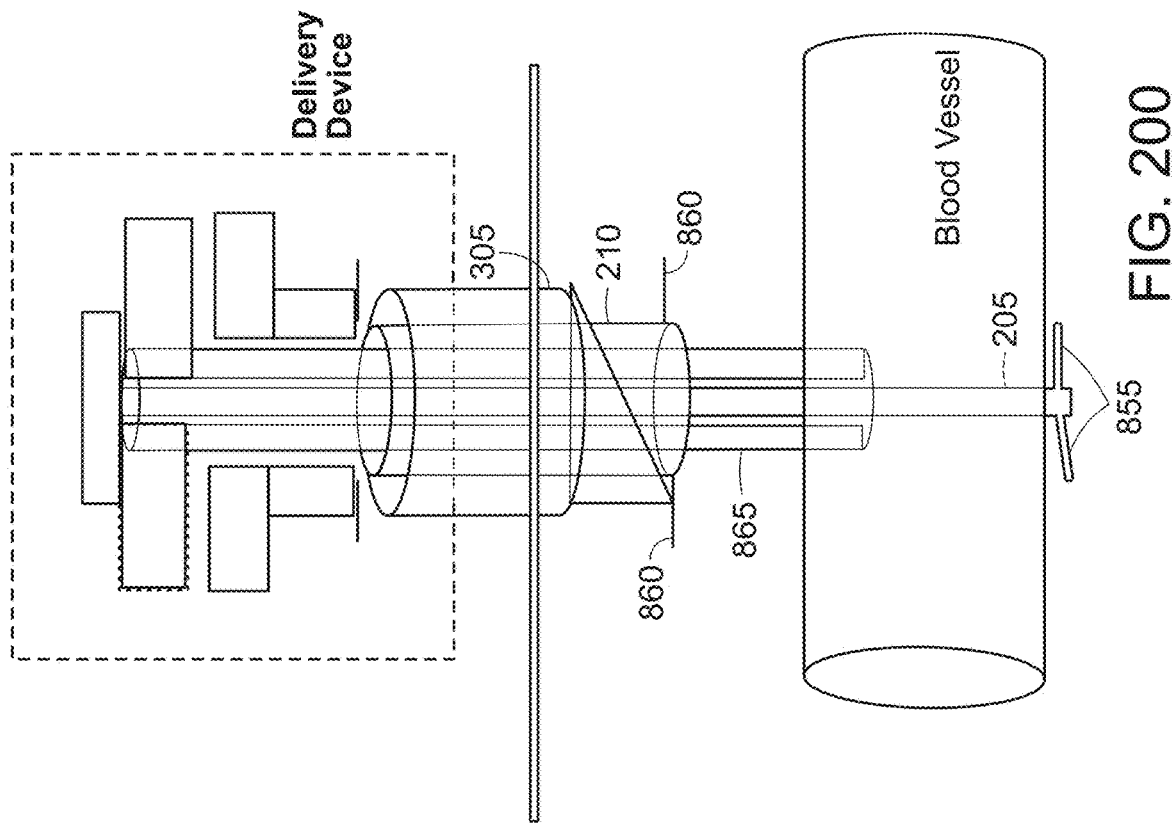

FIG. 200 shows legs 860 of proximal implant 210 opening (or in its open condition) once released from hollow needle 305.

Figure 201:
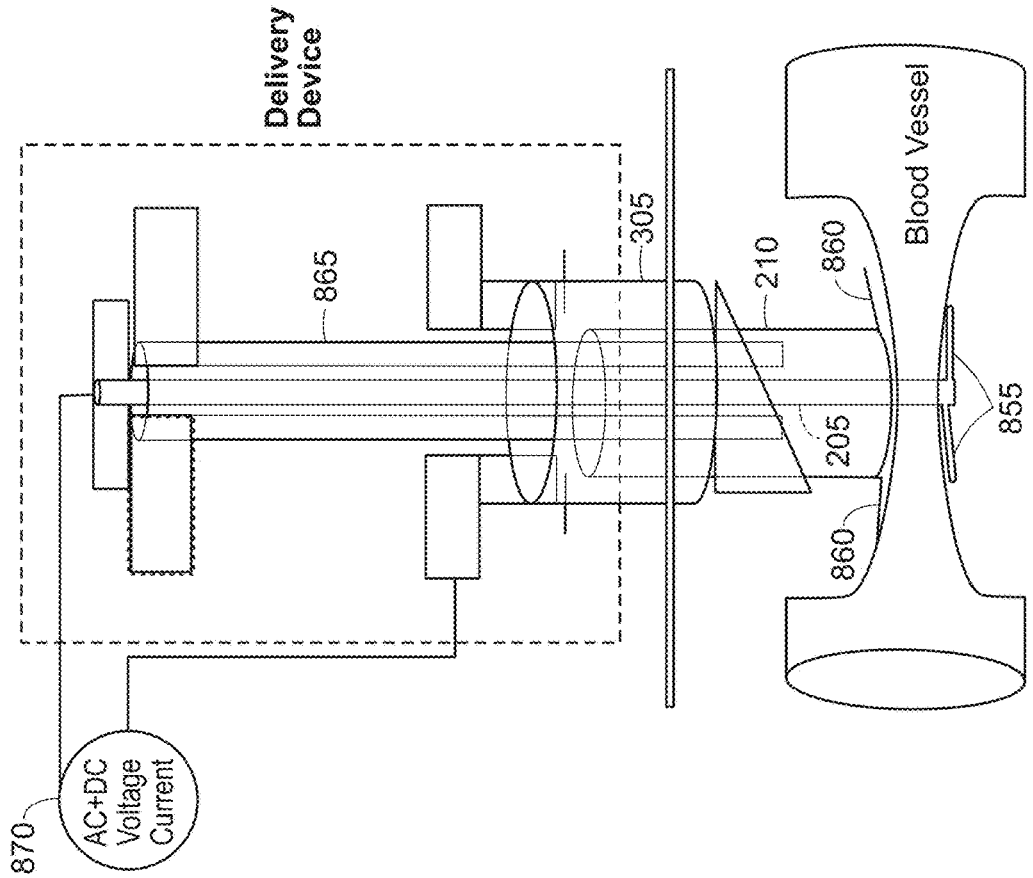

FIG. 201 shows proximal implant 210 and distal implant 205 being connected to an electrical energy source 870. In the embodiment shown in FIG. 201, there is a potential difference between the proximal implant 210 and distal implant 205. In other embodiments of the present invention, the potential difference between both proximal implant 210 and distal implant 205 may be the same, and another electrode may be placed in or on the patient.

Figure 202:
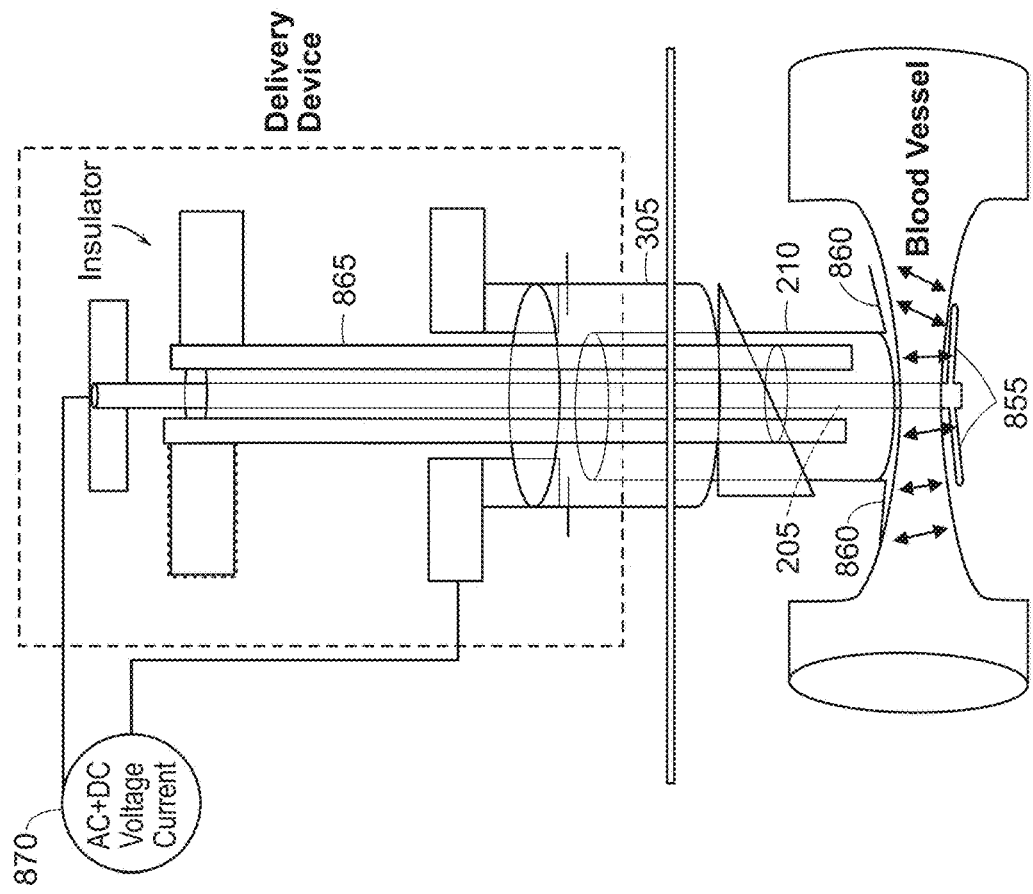

FIG. 202 shows the application of energy to tissue, e.g., by the application of radio-frequency (RF) current and voltage between the electrodes (i.e., legs 855 of distal implant 205 and legs 860 of proximal implant 210) which penetrates through the tissue. The duty cycle and frequency of the RF energy can be adjustably controlled so as to optimize sealing of the tissue or vessel, while minimizing any burning of the tissue.

Figure 203:
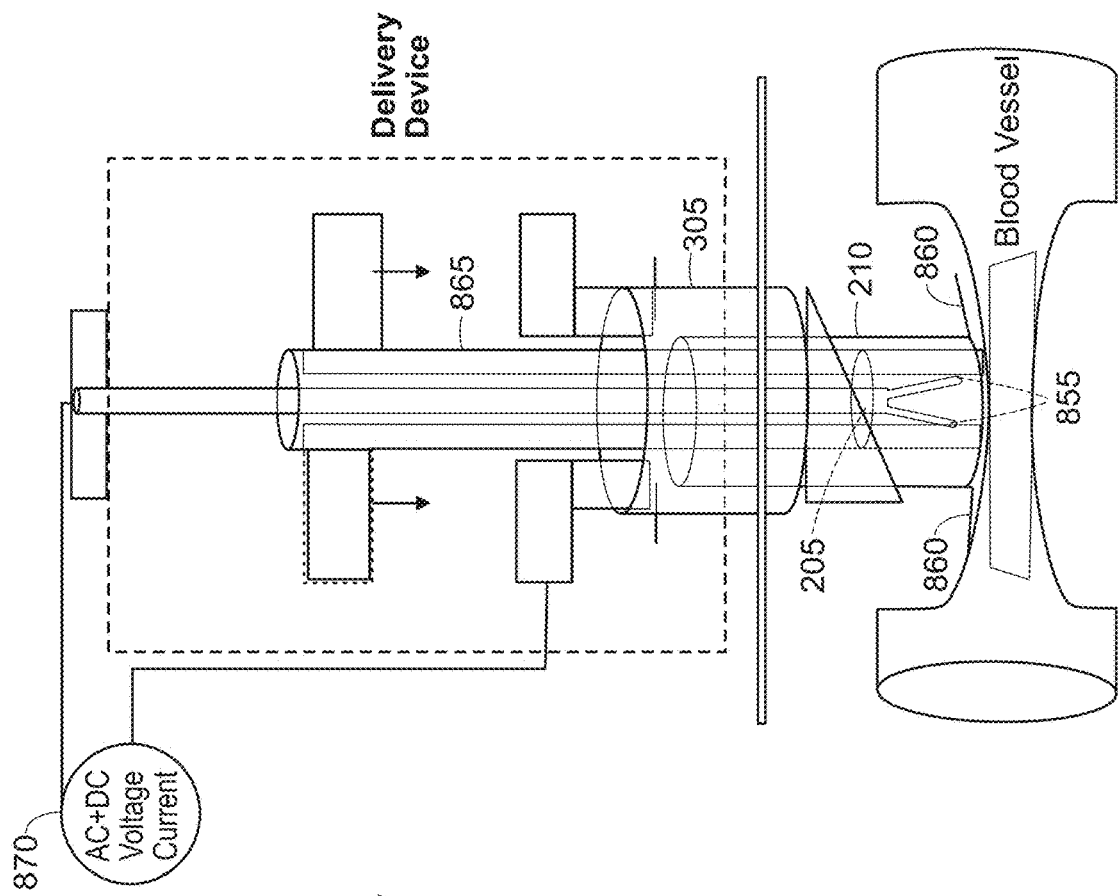
Figure 204:
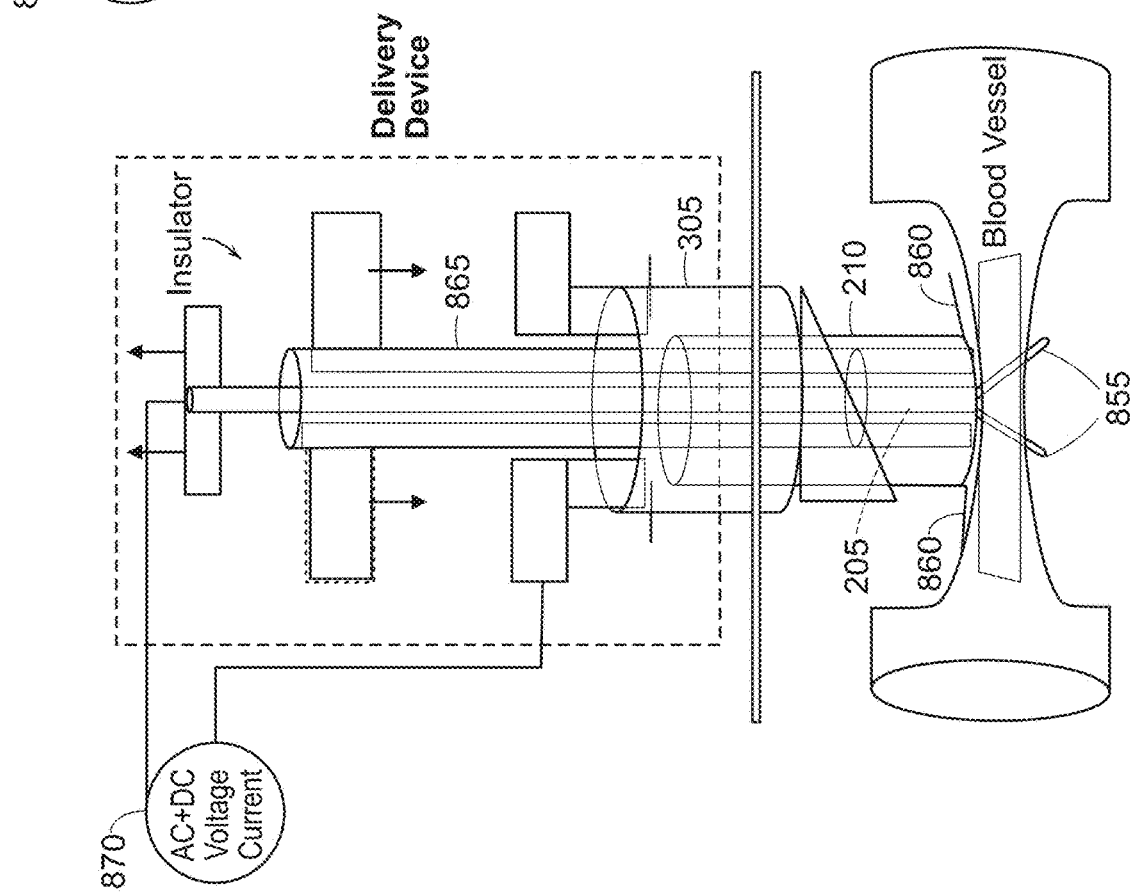

FIG. 203 shows that, after application of the RF energy to the sandwiched tissue, distal implant 205 is retracted first. In this case, distal implant 205 is retracted into the insulating element 865.

FIG. 228 shows the fully retracted distal implant 205.

Figure 205:
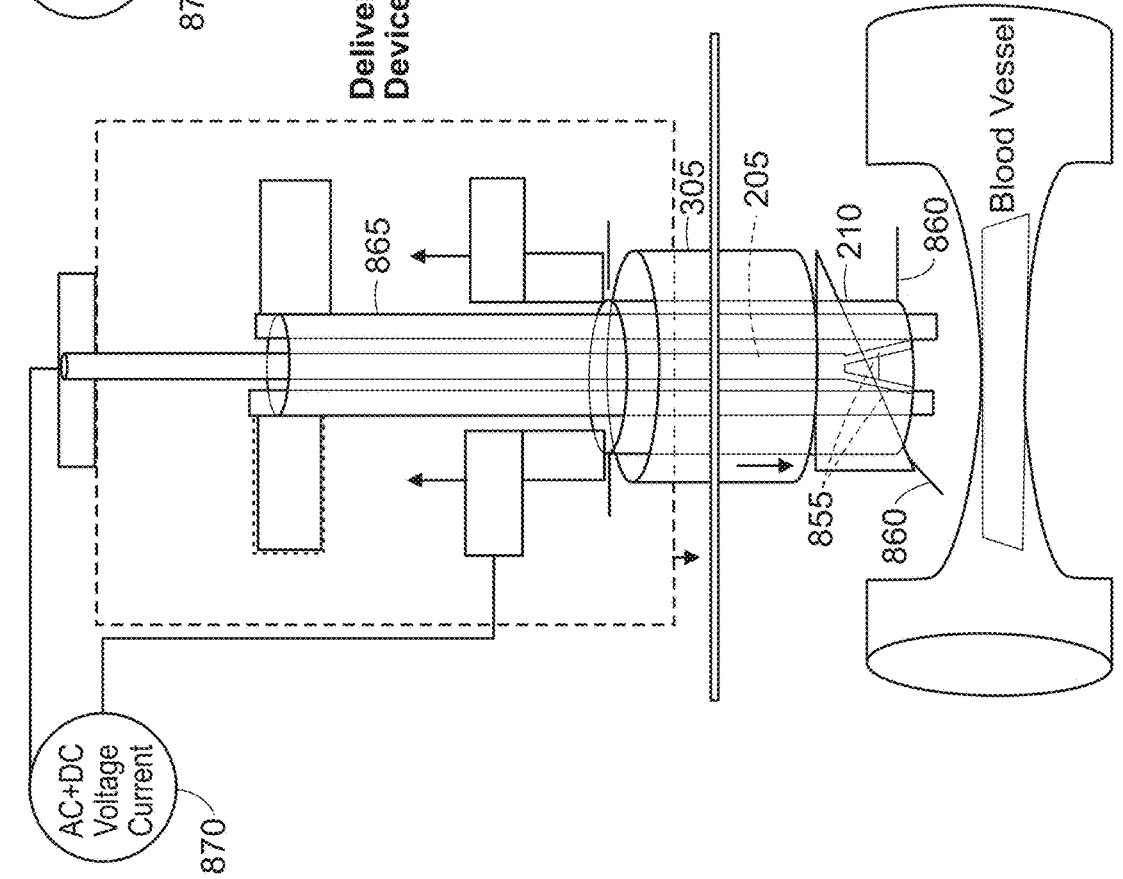

FIG. 205 shows the assembly being raised a little relative to the tissue, with hollow needle 305 being pushed down so that it begins to compress legs 860 of proximal implant 210.

Figure 206:
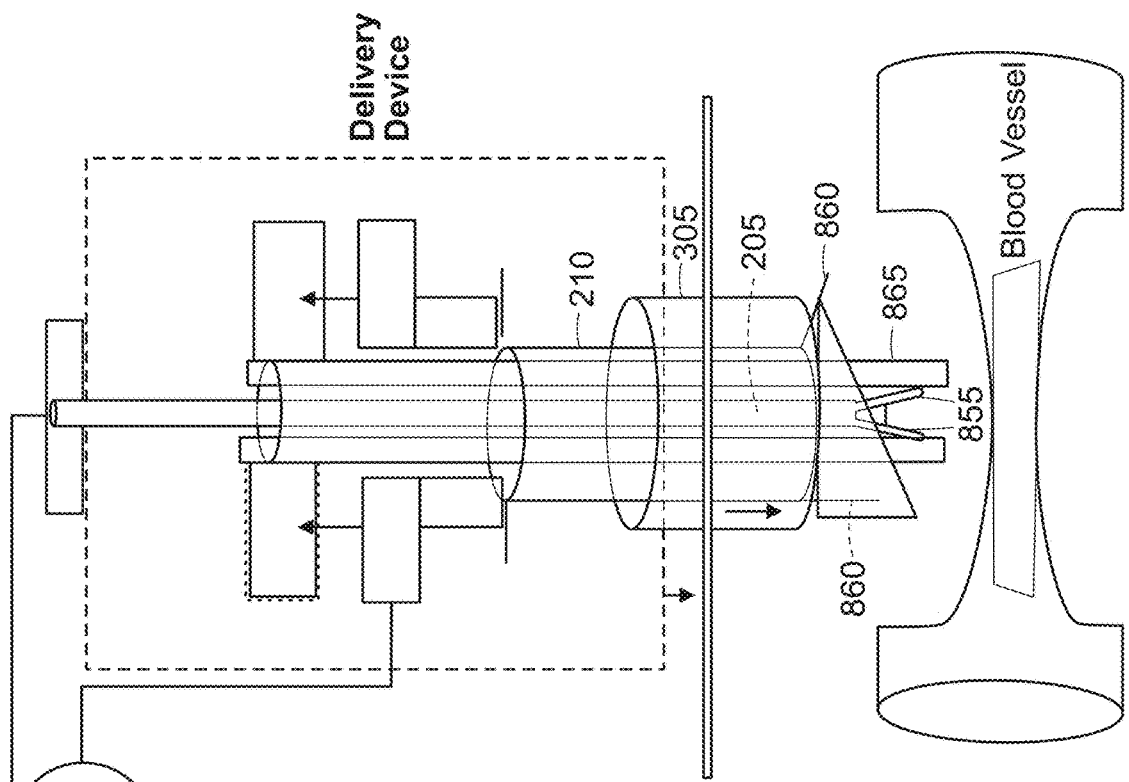

FIG. 206 shows how hollow needle 305 compresses the legs 860, or fingers (e.g., legs 295) of proximal implant 210, while proximal implant 210 is raised relative to hollow needle 305.

FIG. 207 shows how hollow needle 305 (and assembly) are extracted from the body, leaving the vessel or tissue sealed.

Figure 208:
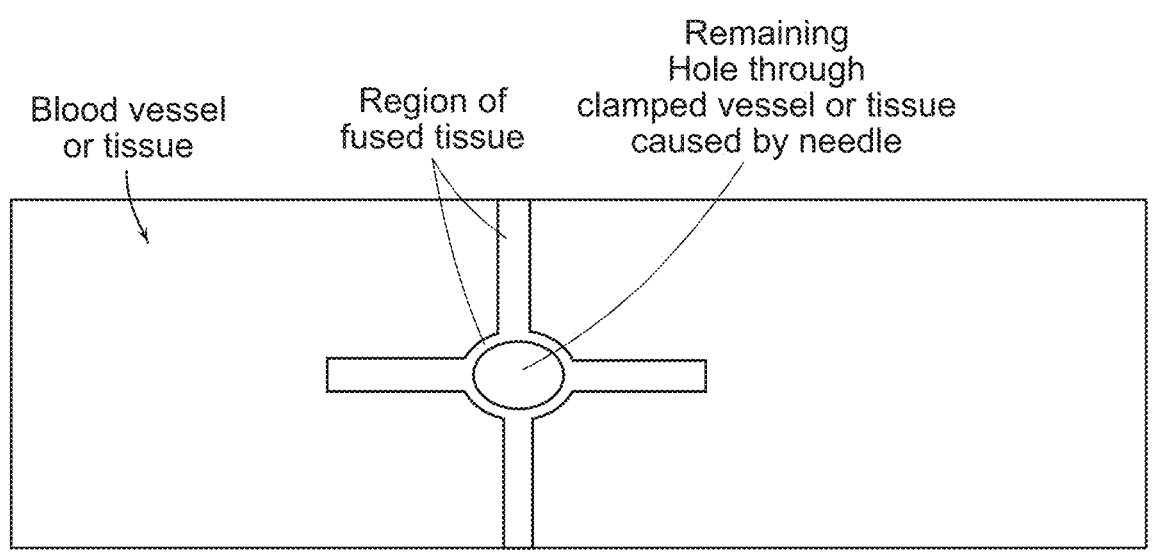

FIG. 208 shows the sealed tissue region, with the possible needle hole sealed around its perimeter.

In another embodiment of the present invention, legs 235 of distal implant 205 are placed at the tip of hollow needle 305, and then opened and deployed by withdrawal of hollow needle 305, while distal implant 205 remains in the same location.

In another embodiment of the present invention, two-part fastener 200 is used in conjunction with a robotic arm for robotic surgery. The ability to deliver two-part fastener 200 through a needle reduces the number of steps and maneuvers that the surgeon must perform, thereby simplifying occlusion of vessels and/or attachment or approximation of tissues. Also, the amount of surrounding tissue required to be cleared around the vessel is reduced.

21. Novel Handle

The sequence of events required to deliver the occlusion device, as described above, may be automated using a system of motors and springs, and may be powered by a power supply or battery that may or may not be rechargeable. It should also be appreciated that, if desired, the device may be powered by a solar cell built into the system. In one embodiment of the invention, the entire delivery may be activated through a single button.

Figure 209:
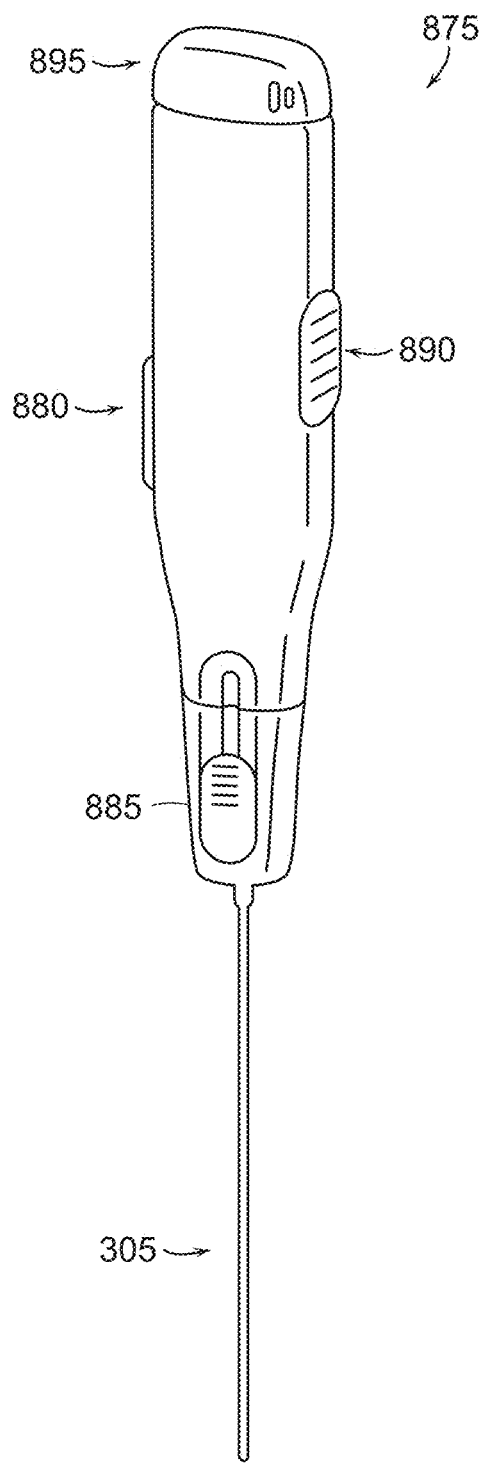

FIG. 209 shows an ergonomic design for a novel handle 875 formed in accordance with the present invention that may contain a battery (not shown) in order to provide the necessary energy to seal tissue or automate various delivery device actions or alternatively, the present invention could be connected to a transformer and/or electrical outlet. In other embodiments, the present invention is simply a mechanical device and not connected to any energy source such as AC or DC voltage and current.

Figure 211:
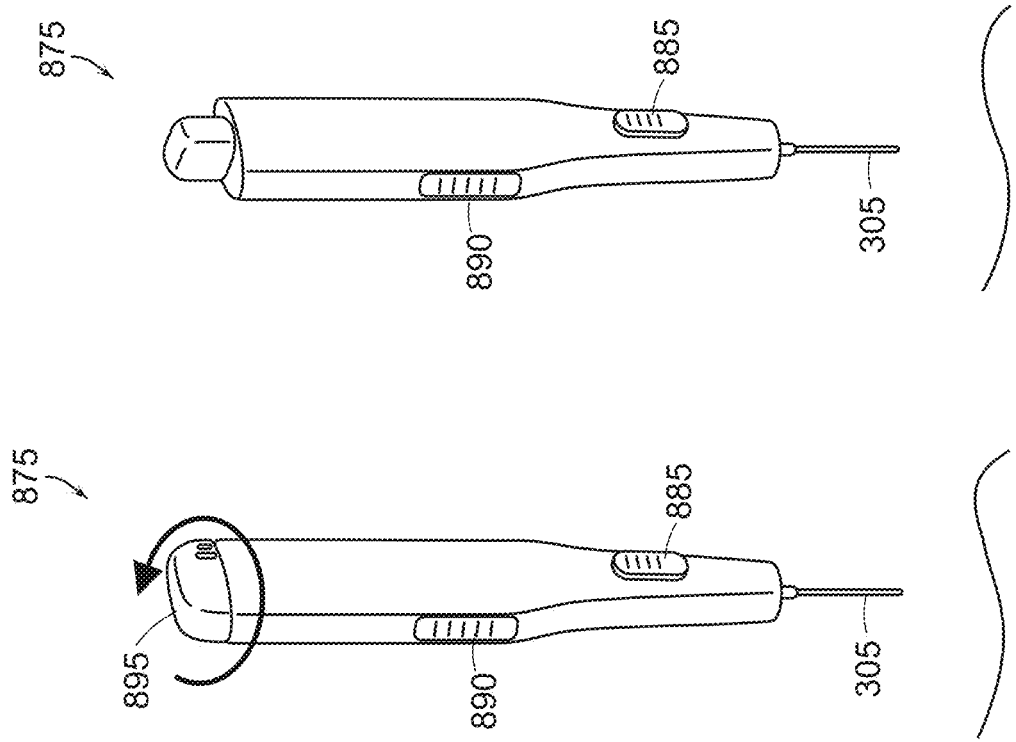

FIGS. 210 and 211 show a refined handle design of a delivery device for fastener implant 200. The refined handle design uses sliders to actuate deployment of proximal implant 210 and distal implant 205 and lock them together.

In practice, a vessel is occluded by sliding handle 875 aside, and then sliding it all the way down, as seen in FIG. 210. This brings proximal implant 210 and distal implant 205 together, whereby to occlude the vessel.

Figure 212:
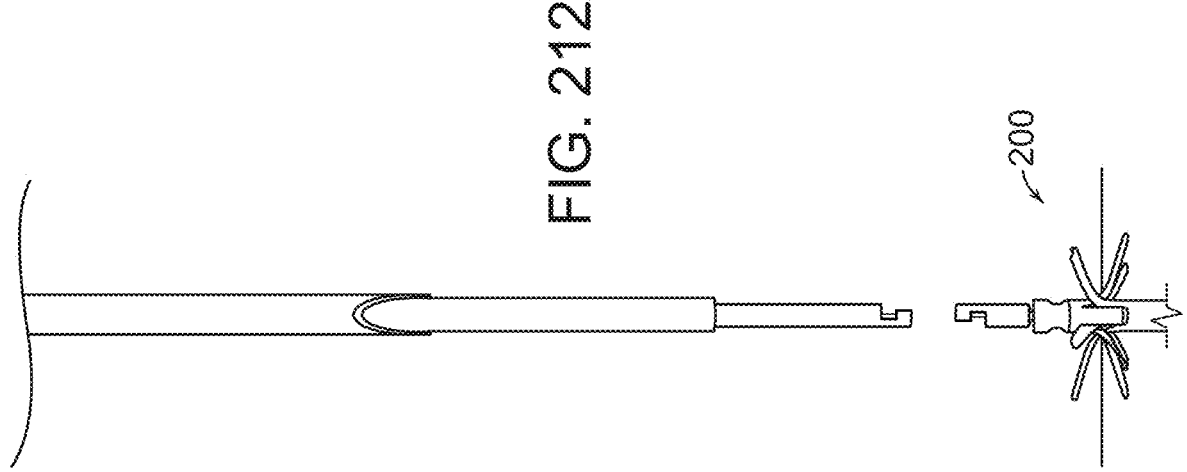

Removal of the delivery device is accomplished by rotating handle 875 counterclockwise, until the delivery device detaches from the clip, as shown in FIG. 211. The delivery device is then withdrawn and retrieved (FIG. 212).

Among other things, (i) handle 875 is designed to provide tactile feedback upon closing of the clip; (ii) the ratcheted control of two-part fastener 200 deployment provides precise and controlled deployment of two-part fastener 200; and (iii) the design of handle 875 provides stability and secure holding of two-part fastener 200, and the solid feel provides physician comfort.

Modifications of the Illustrative Embodiments

It should be understood that many additional changes in the details, materials (e.g., shape memory polymers that are permanent or that dissolve over time, or carbon nanotube based), steps and arrangements of parts, which have been herein described and illustrated in order to explain the nature of the present invention, may be made by those skilled in the art while still remaining within the principles and scope of the invention.

The invention claimed is:

1. An apparatus for securing a tissue layer to another tissue or non-tissue layer together comprising:
   a distal implant comprising a distal body and a plurality of legs which may assume (i) a diametrically reduced delivery configuration and (ii) a diametrically expanded deployed configuration in which the legs are extended radially of the distal body; and a proximal implant, separate from the distal implant, the proximal implant comprising a proximal body and a plurality of legs configured to assume (i) a diametrically reduced delivery configuration and (ii) a diametrically expanded deployed configuration in which the legs are extended radially of the proximal body;

wherein the proximal and distal implants are connectible together, the radially extended configuration of the plurality of legs of the proximal and distal implants being constructed and arranged so that when the proximal and distal implants are connected together, the plurality of legs of the proximal and distal implants are interdigitated in the absence of the tissue and the another tissue or non-tissue layers between the proximal and distal implants; and the proximal and distal implants being deployable separately of each other.

2. The apparatus of claim 1, wherein the proximal and distal implants comprise a shape memory material such as nitinol and where the plurality of legs of each of the proximal and distal implants self-expand upon release of each implant from its delivery configuration.

3. The apparatus of claim 1 wherein the legs of at least one of the proximal and distal implants, when diametrically expanded, together define a concave configuration.

4. The apparatus of claim 1, wherein the distal implant legs together form a concave configuration when diametrically expanded, and the proximal implant legs together form a concave configuration when diametrically expanded.

5. The apparatus of claim 4 wherein the concave configuration of the legs of the proximal implant faces the concave configuration of the distal implant.

6. The apparatus of claim 1, wherein the tissue layer and the another tissue or non-tissue layer comprise the opposed walls of a mammalian body lumen.

7. The apparatus of claim 6, wherein when connected together, at least one of the proximal body and the distal body transfixes the tissue layer and the another tissue or non-tissue layer at a transfixion site.

8. The apparatus of claim 7, wherein the plurality of legs of the distal implant and the plurality of legs of the proximal implant together create an area of compression that circumscribes the transfixion site.

9. The apparatus of claim 7 wherein the plurality of legs of the deployed and connected proximal and distal implants having sufficient stiffness to constrain layers disposed between the plurality of legs of the proximal and distal implants in a serpentine configuration that circumscribes the transfixion site to effect a sealed region about the transfixion site.

10. The apparatus of claim 1, further comprising a delivery tube comprising a needle or a catheter having a distal outlet opening, wherein the delivery tube contains the distal implant in its diametrically-reduced configuration and the proximal implant in its diametrically-reduced configuration in readiness to be ejected, serially, from the delivery tube.

11. The apparatus of claim 10, wherein the delivery tube is configured to advance the distal implant in its diametrically-reduced configuration through the tissue layer and the another tissue or non-tissue layer before the distal implant is ejected from the delivery tube.

12. The apparatus of claim 11, further comprising a mechanism for maintaining the position of the distal implant after ejection out of the delivery tube, thereby to facilitate retraction of the delivery tube to deploy the proximal implant.

13. The apparatus of claim 12, wherein the mechanism comprises a retention member configured to selectively engage with the distal implant to hold the distal implant in place while the proximal implant is deployed.

14. The apparatus of claim 13, wherein the distal body has a lumen and wherein the retention member is configured to fit axially through the lumen in the distal body, the retention member further comprising a selectively expandable locking region configured to interfere with the lumen of the distal body to maintain the position of the distal implant, the locking region being selectively configurable to a low profile to release the distal implant and enable removal of the retention member through the lumen of the distal body.

15. The apparatus of claim 12 wherein the proximal implant has a proximal end and further comprising a push rod engageable with the proximal end of the proximal implant to maintain the position of the proximal implant proximally of the tissue layer and the another tissue or non-tissue layer while the delivery tube is withdrawn to deploy the proximal implant.

16. The apparatus of claim 15 wherein the mechanism for maintaining the position of the distal implant comprises a retention member configured to selectively engage with the distal implant to hold the distal implant whereby the retention member and the push rod can be manipulated to draw the deployed proximal and distal implants toward each other to connect them together.

17. The apparatus of claim 12 wherein the mechanism for maintaining the position of the distal implant comprises a locking tube secured to the distal body and extending in a proximal direction, the proximal end of the locking tube having a first portion of an interlock mechanism;

a distal implant retention tube having proximal and distal ends with a second portion of the interlock mechanism at the distal end, the first and second portions of the interlock mechanism being mateable to releasably connect with each other, the proximal end of the distal implant retention tube being receivable through the proximal body of the proximal implant, the interlock mechanism enabling the position of the distal implant to be maintained while the delivery tube is withdrawn proximally.

18. The apparatus of claim 17 where the first and second portions of the interlock mechanism are complementary and separable from each other.

19. The apparatus of claim 18 further comprising a supplemental lock for the interlock mechanism to temporarily prevent separation of the first and second portions of the interlock mechanism.

20. The apparatus of claim 19 wherein the supplemental lock comprises an elongate wire removably disposed through the distal implant retention tube and passing through the interlock mechanism to engage the interlock mechanism and prevent separation of the first and second portions of the interlock mechanism.

21. The apparatus of claim 1 further comprising:

the proximal body of the proximal implant comprising a proximal tube having proximal and distal ends, the distal end of the proximal tube having a plurality of longitudinally extending slits extending through the distal end of the proximal tube and defining the plurality of legs of the proximal implant, the plurality of legs of the proximal implant extending distally and having free distal ends, the proximal tube being formed from a material having a shape memory in which the legs extend radially outward about the proximal tube axis, the legs being confinable into a tubular shape within a delivery tube in readiness to self-expand when released from the delivery tube, the proximal portion of the proximal tube having a first locking element.

22. The apparatus of claim 21 further comprising:
the distal body of the distal implant comprising a distal tube having proximal and distal ends, the proximal end of the distal tube having a plurality of longitudinally extending slits extending through the proximal end of the distal tube and defining the plurality of legs of the distal implant, the plurality of legs of the distal implant extending proximally and having free proximal ends, the distal tube being formed from a material having a shape memory in which the legs extend radially outward about the distal tube axis, the legs being confinable into a tubular shape within a delivery tube in readiness to self-expand when released, the distal implant having a proximal portion having a second locking element engageable with the first locking element of the proximal implant to lock the connected proximal and distal implants together.

23. The apparatus of claim 21 further comprising:
the distal body of the distal implant comprising a distal tube having proximal and distal ends, the distal end of the distal tube having a plurality of longitudinally extending slits extending through the proximal end of the distal tube and defining a plurality of distally extending legs having free proximal ends, the distal tube being formed from a material having a shape memory in which the legs extend radially outward about the distal tube axis, the legs being confinable into a tubular shape within a delivery tube in readiness to self-expand when released, the distal implant having a proximal portion having a second locking element engageable with the first locking element of the proximal implant to lock the connected proximal and distal implants together.

24. The apparatus of claim 1 further comprising:
the distal body of the distal implant comprising a distal tube formed from a material having a shape memory and having proximal and distal ends with a plurality of circumferentially spaced, longitudinally extending slits formed between its ends that define a plurality of radially extendable legs, the legs being extendible radially outward about the distal tube axis in response to axial compression of the ends of the distal tube, the legs having a tubular shape memory,
a locking tube attached to and extending proximally from the distal portion of the distal tube and being receivable in the proximal end of the distal tube when the distal tube is axially compressed, the locking tube and the proximal portion of the locking tube having cooperative locking elements to secure the distal implant in an axially compressed configuration in which the legs extend radially.

25. The apparatus of claim 24 further comprising:
the proximal implant having a locking element in the proximal body;
the proximal portion of the locking tube being receivable in the proximal body, the locking tube having an additional locking element engageable with the locking element of the proximal implant.

26. The apparatus of claim 1 wherein the plurality of legs of the proximal and distal implants have free ends and, when deployed, the plurality of legs of the proximal and distal implants can engage tissue substantially along the lengths of the legs.

27. The apparatus of claim 1 wherein the proximal and distal implants are connectible by locking elements that are disposed on the proximal and distal bodies and are independent of the plurality of legs of the proximal and distal implants.

28. The apparatus of claim 1 wherein the proximal implant is deployable only after the distal implant has been deployed.

29. The apparatus of claim 1 wherein the distal implant can be deployed externally on the distal side of the tissue layer and the another tissue or non-tissue layer and the proximal implant can be deployed externally on the proximal side of the tissue layer and the another tissue or non-tissue layer.

30. The apparatus of claim 1 wherein the proximal and distal bodies are less than about 18 gauge.

31. The apparatus of claim 1 wherein the proximal and distal implants are connectible only after they have been deployed.

32. The apparatus of claim 1 further comprising:
the plurality of legs of the deployed and connected proximal and distal implants having sufficient stiffness to constrain layers disposed between the plurality of legs of the proximal and distal implants in a serpentine configuration that circumscribes the proximal and distal implant bodies.

33. The apparatus of claim 1 wherein the connected proximal and distal implants define an axis and wherein the plurality of legs of the deployed and connected proximal and distal implants have sufficient stiffness to constrain layers disposed between the plurality of legs of the proximal and distal implants in a serpentine configuration that circumscribes the axis.

* * * * *